(12) United States Patent
Hwang et al.

(10) Patent No.: US 7,109,293 B2
(45) Date of Patent: Sep. 19, 2006

(54) SYSTEM FOR DETECTING PROTEASE

(75) Inventors: Inhwan Hwang, Seoul (KR); Dae Heon Kim, Seoul (KR); Yong Jik Lee, Seoul (KR)

(73) Assignee: Ahram Biosystems Inc., Seoul (KR)

( * ) Notice: Subject to any disclaimer, the term of this patent is extended or adjusted under 35 U.S.C. 154(b) by 682 days.

(21) Appl. No.: 10/214,932

(22) Filed: Aug. 8, 2002

(65) Prior Publication Data

US 2003/0100707 A1    May 29, 2003

(30) Foreign Application Priority Data

Aug. 10, 2001    (KR) ............................... 2001-48123

(51) Int. Cl.
    *C07K 14/00* (2006.01)
(52) U.S. Cl. .................................................. 530/350
(58) Field of Classification Search ............... 435/69.1; 530/350

See application file for complete search history.

(56) References Cited

U.S. PATENT DOCUMENTS

| | | | |
|---|---|---|---|
| 4,644,055 A | 2/1987 | Kettner et al. | 530/330 |
| 5,171,662 A | 12/1992 | Sharma | 435/5 |
| 5,491,084 A | 2/1996 | Chalfie et al. | 435/189 |
| 5,861,267 A | 1/1999 | Su | 435/23 |
| 5,958,713 A | 9/1999 | Thastrup et al. | 435/7.4 |
| 5,989,838 A | 11/1999 | Zavada et al. | 435/7.23 |
| 6,117,639 A | 9/2000 | Germann et al. | 435/6 |
| 6,245,884 B1 | 6/2001 | Hook | 530/300 |
| 6,326,354 B1 | 12/2001 | Gross et al. | 514/12 |
| 6,333,167 B1 | 12/2001 | Quinet et al. | 435/23 |
| 2002/0025508 A1 | 2/2002 | Fechteler et al. | 435/4 |
| 2003/0049712 A1 | 3/2003 | Haugwitz | 435/23 |

FOREIGN PATENT DOCUMENTS

| | | |
|---|---|---|
| WO | WO 98/16657 | 4/1998 |
| WO | WO 98/31821 | 7/1998 |
| WO | WO-00/08469 | 2/2000 |
| WO | WO 00/73802 A1 | 7/2000 |
| WO | WO 00/79241 A2 | 12/2000 |

OTHER PUBLICATIONS

Deo, et al., "Bioluminescence Detection of Proteolytic Bond Cleavage by Using Recombinant Aequorin"; Analytical Biochemistry, vol. 281, pp. 87-94, 2000.
Ermolieff, et al.; "Proteolytic Activation of Recombinant Promemapsin 2 (Pro-β-secretase) Studied with New Fluorogenic Substrates"; Biochemistry, vol. 39, pp. 12450-12456, 2000.
Kasai, et al., "Inhibition of the Hepatitis C Virus NS3 Protease Activity by Fv Fragment of Antibody 8D4", Biochemical and Biophysical Research Communications, vol. 281, pp. 416-424, 2001.
Kuhelj, et al., "Inhibition of Human Endogenous Retrovirus-K10 Protease in Cell-free and Cell-based Assays", The Journal of Biological Chemistry, vol. 276, No. 20, pp. 16674-16682, 2001.
Song, et al., "Development of an *in vivo* Assay System Suitable for Screening Inhibitors of Hepatitis C Viral Protease", Mol. Cells, vol. 6, No. 2, pp. 183-189, 1996.
Faber, et al., "A Novel Method To Determine The Topology Of Peroxisomal Membrane Proteins *In Vivo* Using The Tobacco Etch Virus Protease", vol. 276, No. 39, Sep. 28, 2001, pp. 36501-36507.
Clontech Product Bulletin entitled "ApoAlert™ Bid Vectors: DsRed2 & EGFP", *CLONTECHniques*, Jan., 2002.
BD Biosciences Product Bulletin entitled "BD ApoAlert™ Apoptosis Detection Products", Jan., 2002.
Clontech Product Bulletin entitled "BD Clontech ApoAlert™ pCaspase3-Sensor Vector", *Clontechniques*, Apr., 2002.
Cho, et al., "In Vivo Assay for Hepatitis C Viral Serine Protease Activity Using A Secreted Protein," Journal Of Virological Methods (1998) 72: 109-115.
Hirowatari, et al., "A Novel Method for Analysis of Viral Proteinase Activity Encoded By Hepatitis C Virus in Cultured Cells," Analytical Biochemistry (1995) 225: 113-120.
Subramanian, et al., "Cytometric Analysis of an Epitope-Tagged Transit Peptide Bound to the Chloroplast Translocation Apparatus," The Plant Journal (2001) 25(3):349-363.
Hicks, et al., "The $NH_2$-Terminal Domain of Golgin-160 Contains Both Golgi and Nuclear Targeting Information," The Journal Of Biological Chemistry (2002) 277(39):35833-35839.
Kim, et al., "In Vivo Determination of Substrate Specificity of Hepatitis C Virus NS3 Protease: Genetic Assay for Site-Specific Proteolysis," Analytical Biochemistry (2000) 284:42-48.
Gillim, et al., "Development Of A Novel Screen For Protease Inhibitors," Clinical and Diagnostic Laboratory Immunology (2001) 8:437-440.
Pap, et al., "Peptide-Based Targeting Of Fluorophores To Organelles In Living Cells," Experimental Cell Research (2001) 265: 288-293.
Mitra, et al., "Fluorescence Resonance Energy Transfer Between Blue-Emitting and Red-Shifted Excitation Derivatives of the Green Fluorescent Protein," (1996) Gene 173:13-17.
Addya, et al., Targeting of $NH_2$-Terminal-Processed Microsomal Protein to Mitochondria: A Novel Pathway for the Biogensis of Hepatic Mitochondrial P450MT2, The Journal Of Cell Biology (1997) 139:589-599.

*Primary Examiner*—Karen Cochrane Carlson
(74) *Attorney, Agent, or Firm*—Edwards Angell Palmer & Dodge LLP; Peter C. Lauro, Esq.

(57) ABSTRACT

Disclosed is a system for detecting a protease inside a cell. In one embodiment, the system includes a chimeric protein that comprises as covalently linked components: 1) at least one optionally masked signal protein; 2) at least one protease-specific cleavage site; and 3) at least one detectable amino acid sequence. The invention has a wide spectrum of applications including use in the detection of novel protease inhibitors inside cells and tissue.

11 Claims, 16 Drawing Sheets

| Names | Schematic presentation | Localization |
|---|---|---|
| AtOEP7:GFP | | Chloroplast (outer envelop membrane) |
| AtOEP7:RFP | | Chloroplast (outer envelop membrane) |
| RbcS:GFP | | Chloroplast (stroma) |
| RbcS:RFP | | Chloroplast (stroma) |
| Cab:GFP | | Chloroplast (stroma) |
| RA:GFP | | Chloroplast (stroma) |
| F1-ATPase:GFP | | Mitochondria |
| GFP:SKL | | Peroxisome |
| $H^+$-ATPase:GFP | | Plasma membrane |
| GFP:PH | | PI(4,5)P2 |

| | |
|---|---|
| | GFP |
| | RFP |

SEQUENCE LISTING

```
<160> NUMBER OF SEQ ID NOS: 133

<210> SEQ ID NO 1
<211> LENGTH: 18
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 5' PCR primer for partial AtOEP7 coding
      sequence

<400> SEQUENCE: 1
gacgacgacg cagcgatg                                                 18

<210> SEQ ID NO 2
```

-continued

```
<211> LENGTH: 25
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 3' PCR primer for partial AtOEP7 coding
      sequence

<400> SEQUENCE: 2
ggatccccaa accctctttg gatgt                                          25

<210> SEQ ID NO 3
<211> LENGTH: 18
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 5' PCR primer for partial rubisco small subunit
      coding sequence

<400> SEQUENCE: 3
cctcagtcac acaaagag                                                  18

<210> SEQ ID NO 4
<211> LENGTH: 24
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 3' PCR primer for partial rubisco small subunit
      coding sequence

<400> SEQUENCE: 4
actcgaggga atcggtaagg tcag                                           24

<210> SEQ ID NO 5
<211> LENGTH: 18
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 5' PCR primer for partial chlorophyll a/b
      binding protein coding sequence

<400> SEQUENCE: 5
tagagagaaa cgatggcg                                                  18

<210> SEQ ID NO 6
<211> LENGTH: 25
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 3' PCR primer for partial chlorophyll a/b
      binding protein coding sequence

<400> SEQUENCE: 6
ggatcccgtt tgggagtgga actcc                                          25
```

```
<210> SEQ ID NO 7
<211> LENGTH: 24
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 5' PCR primer for partial rubisco acitvase
      coding sequence

<400> SEQUENCE: 7
tctagaatgg ccgccgcagt ttcc                                             24

<210> SEQ ID NO 8
<211> LENGTH: 25
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 3' PCR primer for partial rubisco acitvase
      coding sequence

<400> SEQUENCE: 8
ggatccatct gtctccatcg gtttg                                            25

<210> SEQ ID NO 9
<211> LENGTH: 18
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 5' PCR primer for partial F1-ATPase coding
      sequence

<400> SEQUENCE: 9
ctttaatcaa tggcaatg                                                    18

<210> SEQ ID NO 10
<211> LENGTH: 25
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 3' PCR primer for partial F1-ATPase coding
      sequence

<400> SEQUENCE: 10
ccatggcctg aactgctcta agctt                                            25

<210> SEQ ID NO 11
<211> LENGTH: 17
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 5' PCR primer for peroxisome targeting sequence

<400> SEQUENCE: 11
ccgtatgtta catcacc                                                     17
```

```
<210> SEQ ID NO 12
<211> LENGTH: 30
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 3' PCR primer for peroxisome targeting sequence

<400> SEQUENCE: 12
ttatagcttt gatttgtata gttcatccat                              30

<210> SEQ ID NO 13
<211> LENGTH: 18
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 5' PCR primer for H+-ATPase coding sequence

<400> SEQUENCE: 13
gagatgtcga gtctcgaa                                           18

<210> SEQ ID NO 14
<211> LENGTH: 23
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 3' PCR primer for H+-ATPase coding sequence

<400> SEQUENCE: 14
ctcgagcaca gtgtagtgac tgg                                     23

<210> SEQ ID NO 15
<211> LENGTH: 38
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 5' PCR primer for coding sequence containing
      the proteolytic site of NIa protease

<400> SEQUENCE: 15
cccggggtgt gcgcttccag ggaaaaactt cgggagcg                     38

<210> SEQ ID NO 16
<211> LENGTH: 24
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 3' PCR primer for coding sequence containing
      the proteolytic site of NIa protease

<400> SEQUENCE: 16
gagctcttat ttgtatagtt catc                                    24

<210> SEQ ID NO 17
<211> LENGTH: 27
```

```
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 5' PCR Primer for HIV-1 protease coding
      sequence

<400> SEQUENCE: 17
tctagaatgc ctcaggtcac tctttgg                                            27

<210> SEQ ID NO 18
<211> LENGTH: 27
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 3' PCR Primer for HIV-1 protease coding
      sequence

<400> SEQUENCE: 18
ctcgagtcaa aaatttaaag tgcaacc                                            27

<210> SEQ ID NO 19
<211> LENGTH: 46
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 5' PCR Primer for coding sequence containing
      the proteolytic site of HIV-1 protease

<400> SEQUENCE: 19
cccgggtagc caaaattacc ctatagtggg aaaaacttcg ggagcg                       46

<210> SEQ ID NO 20
<211> LENGTH: 46
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 5' PCR Primer for coding sequence containing
      the proteolytic site of HIV-1 protease

<400> SEQUENCE: 20
cccgggtgca agagttttgg ctgaagcagg aaaaacttcg ggagcg                       46

<210> SEQ ID NO 21
<211> LENGTH: 46
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 5' PCR Primer for coding sequence containing
      the proteolytic site of HIV-1 protease

<400> SEQUENCE: 21
cccgggtgct accataatga tgcagagacc aaaaacttcg ggagcg                       46

<210> SEQ ID NO 22
```

```
<211> LENGTH: 46
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 5' PCR Primer for coding sequence containing
      the proteolytic site of HIV-1 protease

<400> SEQUENCE: 22
cccgggtaga caggctaatt ttttaggggg aaaaacttcg ggagcg                46

<210> SEQ ID NO 23
<211> LENGTH: 46
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 5' PCR Primer for coding sequence containing
      the proteolytic site of HIV-1 protease

<400> SEQUENCE: 23
cccgggtcca gggaattttc ttcagagcgg aaaaacttcg ggagcg                46

<210> SEQ ID NO 24
<211> LENGTH: 41
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 5' PCR Primer for coding sequence containing
      the proteolytic site of HIV-1 protease

<400> SEQUENCE: 24
cccgggtagc gtgcctcaaa taggaaaaaa cttcgggagc g                     41

<210> SEQ ID NO 25
<211> LENGTH: 46
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 5' PCR Primer for coding sequence containing
      the proteolytic site of HIV-1 protease

<400> SEQUENCE: 25
cccgggtact ttaaattttc ccattagcgg aaaaacttcg ggagcg                46

<210> SEQ ID NO 26
<211> LENGTH: 46
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 5' PCR Primer for coding sequence containing
      the proteolytic site of HIV-1 protease

<400> SEQUENCE: 26
cccgggtgca gaaaccttct atgtagatgg aaaaacttcg ggagcg                46
```

```
<210> SEQ ID NO 27
<211> LENGTH: 46
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 5' PCR Primer for coding sequence containing
      the proteolytic site of HIV-1 protease

<400> SEQUENCE: 27
cccgggtagg aaagtactat ttttagatgg aaaaacttcg ggagcg                46

<210> SEQ ID NO 28
<211> LENGTH: 24
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 3' PCR Primer for coding sequence containing
      the proteolytic site of HIV-1 protease

<400> SEQUENCE: 28
ctcgagttat ttgtatagtt catc                                        24

<210> SEQ ID NO 29
<211> LENGTH: 192
<212> TYPE: DNA
<213> ORGANISM: Arabidopsis thaliana
<220> FEATURE:
<221> NAME/KEY: CDS
<222> LOCATION: (1)..(192)
<223> OTHER INFORMATION: Partial AtOEP7, a homologue of pea OEP14,
      comprising a chloroplast (outer envelop membrane) targeting
      sequence
<300> PUBLICATION INFORMATION:
<308> DATABASE ACCESSION NUMBER: GenBank/NM_115102
<309> DATABASE ENTRY DATE: 2002-01-10

<400> SEQUENCE: 29 atg gga aaa act tcg gga gcg aaa cag gcg act gtg gtg gtc gca gcg    48
Met Gly Lys Thr Ser Gly Ala Lys Gln Ala Thr Val Val Val Ala Ala
1               5                   10                  15 atg gcg tta gga tgg tta gcc ata gag atc gct ttc aag cct ttc ctc    96
Met Ala Leu Gly Trp Leu Ala Ile Glu Ile Ala Phe Lys Pro Phe Leu
            20                  25                  30 gat aaa ttc cgc tcc tca atc gac aaa tct gac cca acc aaa gac ccc    144
Asp Lys Phe Arg Ser Ser Ile Asp Lys Ser Asp Pro Thr Lys Asp Pro
        35                  40                  45 gat gac ttc gac acc gcc gct act gca acc aca tcc aaa gag ggt ttg    192
Asp Asp Phe Asp Thr Ala Ala Thr Ala Thr Thr Ser Lys Glu Gly Leu
    50                  55                  60

<210> SEQ ID NO 30
<211> LENGTH: 64
<212> TYPE: PRT
<213> ORGANISM: Arabidopsis thaliana

<400> SEQUENCE: 30

Met Gly Lys Thr Ser Gly Ala Lys Gln Ala Thr Val Val Val Ala Ala
1               5                   10                  15

Met Ala Leu Gly Trp Leu Ala Ile Glu Ile Ala Phe Lys Pro Phe Leu
            20                  25                  30

Asp Lys Phe Arg Ser Ser Ile Asp Lys Ser Asp Pro Thr Lys Asp Pro
```

```
                        35                  40                  45
Asp Asp Phe Asp Thr Ala Ala Thr Ala Thr Thr Ser Lys Glu Gly Leu
    50                  55                  60

<210> SEQ ID NO 31
<211> LENGTH: 237
<212> TYPE: DNA
<213> ORGANISM: Arabidopsis thaliana
<220> FEATURE:
<221> NAME/KEY: CDS
<222> LOCATION: (1)..(237)
<223> OTHER INFORMATION: Partial rubisco small subunit comprising a
      chloroplast (stroma) targeting sequence
<300> PUBLICATION INFORMATION:
<308> DATABASE ACCESSION NUMBER: GenBank/NM_105379
<309> DATABASE ENTRY DATE: 2002-01-10

<400> SEQUENCE: 31 atg gct tcc tct atg ctc tct tcc gct act atg gtt gcc tct ccg gct     48
Met Ala Ser Ser Met Leu Ser Ser Ala Thr Met Val Ala Ser Pro Ala
  1               5                  10                  15 cag gcc act atg gtc gct cct ttc aac gga ctt aag tcc tcc gct gcc     96
Gln Ala Thr Met Val Ala Pro Phe Asn Gly Leu Lys Ser Ser Ala Ala
                 20                  25                  30 ttc cca gcc acc cgc aag gct aac aac gac att act tcc atc aca agc    144
Phe Pro Ala Thr Arg Lys Ala Asn Asn Asp Ile Thr Ser Ile Thr Ser
             35                  40                  45 aac ggc gga aga gtt aac tgc atg cag gtg tgg cct ccg att gga aag    192
Asn Gly Gly Arg Val Asn Cys Met Gln Val Trp Pro Pro Ile Gly Lys
         50                  55                  60 aag aag ttt gag act ctc tct tac ctt cct gac ctt acc gat tcc        237
Lys Lys Phe Glu Thr Leu Ser Tyr Leu Pro Asp Leu Thr Asp Ser
 65                  70                  75

<210> SEQ ID NO 32
<211> LENGTH: 79
<212> TYPE: PRT
<213> ORGANISM: Arabidopsis thaliana

<400> SEQUENCE: 32

Met Ala Ser Ser Met Leu Ser Ser Ala Thr Met Val Ala Ser Pro Ala
  1               5                  10                  15

Gln Ala Thr Met Val Ala Pro Phe Asn Gly Leu Lys Ser Ser Ala Ala
                 20                  25                  30

Phe Pro Ala Thr Arg Lys Ala Asn Asn Asp Ile Thr Ser Ile Thr Ser
             35                  40                  45

Asn Gly Gly Arg Val Asn Cys Met Gln Val Trp Pro Pro Ile Gly Lys
         50                  55                  60

Lys Lys Phe Glu Thr Leu Ser Tyr Leu Pro Asp Leu Thr Asp Ser
 65                  70                  75

<210> SEQ ID NO 33
<211> LENGTH: 105
<212> TYPE: DNA
<213> ORGANISM: Arabidopsis thaliana
<220> FEATURE:
<221> NAME/KEY: CDS
<222> LOCATION: (1)..(105)
<223> OTHER INFORMATION: Partial Chlorophyll a/b binding protein
      comprising a chloroplast (stroma) targeting sequence
<300> PUBLICATION INFORMATION:
<308> DATABASE ACCESSION NUMBER: GenBank/X56062
<309> DATABASE ENTRY DATE: 1992-10-12

<400> SEQUENCE: 33
```

```
atg gcg tcg aac tcg ctt atg agc tgt ggc ata gcc gcc gtg tac cct      48
Met Ala Ser Asn Ser Leu Met Ser Cys Gly Ile Ala Ala Val Tyr Pro
1               5                   10                  15 tcg ctt ctc tct tct tcc aag tct aaa ttc gta tcc gcc gga gtt cca      96
Ser Leu Leu Ser Ser Ser Lys Ser Lys Phe Val Ser Ala Gly Val Pro
            20                  25                  30 ctc cca aac                                                         105
Leu Pro Asn
        35

<210> SEQ ID NO 34
<211> LENGTH: 35
<212> TYPE: PRT
<213> ORGANISM: Arabidopsis thaliana

<400> SEQUENCE: 34

Met Ala Ser Asn Ser Leu Met Ser Cys Gly Ile Ala Ala Val Tyr Pro
1               5                   10                  15

Ser Leu Leu Ser Ser Ser Lys Ser Lys Phe Val Ser Ala Gly Val Pro
            20                  25                  30

Leu Pro Asn
        35

<210> SEQ ID NO 35
<211> LENGTH: 204
<212> TYPE: DNA
<213> ORGANISM: Arabidopsis thaliana
<220> FEATURE:
<221> NAME/KEY: CDS
<222> LOCATION: (1)..(204)
<223> OTHER INFORMATION: Partial rubisco activase comprising a
      chloroplast (stroma) targeting sequence
<300> PUBLICATION INFORMATION:
<308> DATABASE ACCESSION NUMBER: GenBank/X14212
<309> DATABASE ENTRY DATE: 1993-09-12

<400> SEQUENCE: 35 atg gcc gcc gca gtt tcc acc gtc ggt gcc atc aac aga gct ccg ttg      48
Met Ala Ala Ala Val Ser Thr Val Gly Ala Ile Asn Arg Ala Pro Leu
1               5                   10                  15 agc ttg aac ggg tca gga tca gga gct gta tca gcc cca gct tca acc      96
Ser Leu Asn Gly Ser Gly Ser Gly Ala Val Ser Ala Pro Ala Ser Thr
            20                  25                  30 ttc ttg gga aag aaa gtt gta act gtg tcg aga ttc gca cag agc aac     144
Phe Leu Gly Lys Lys Val Val Thr Val Ser Arg Phe Ala Gln Ser Asn
            35                  40                  45 aag aag agc aac gga tca ttc aag gtg ttg gct gtg aaa gaa gac aaa     192
Lys Lys Ser Asn Gly Ser Phe Lys Val Leu Ala Val Lys Glu Asp Lys
        50                  55                  60 caa acc gat gga                                                     204
Gln Thr Asp Gly
65

<210> SEQ ID NO 36
<211> LENGTH: 68
<212> TYPE: PRT
<213> ORGANISM: Arabidopsis thaliana

<400> SEQUENCE: 36

Met Ala Ala Ala Val Ser Thr Val Gly Ala Ile Asn Arg Ala Pro Leu
1               5                   10                  15

Ser Leu Asn Gly Ser Gly Ser Gly Ala Val Ser Ala Pro Ala Ser Thr
            20                  25                  30
```

Phe Leu Gly Lys Lys Val Val Thr Val Ser Arg Phe Ala Gln Ser Asn
            35                  40                  45

Lys Lys Ser Asn Gly Ser Phe Lys Val Leu Ala Val Lys Glu Asp Lys
    50                  55                  60

Gln Thr Asp Gly
65

<210> SEQ ID NO 37
<211> LENGTH: 234
<212> TYPE: DNA
<213> ORGANISM: Arabidopsis thaliana
<220> FEATURE:
<221> NAME/KEY: CDS
<222> LOCATION: (1)..(234)
<223> OTHER INFORMATION: Partial gamma subunit of mitochindrial
      F1-ATPase comprising a mitochondria targeting sequence
<300> PUBLICATION INFORMATION:
<308> DATABASE ACCESSION NUMBER: GenBank/D88374
<309> DATABASE ENTRY DATE: 1999-02-07

<400> SEQUENCE: 37 atg gca atg gct gtt ttc cgt cgc gaa ggg agg cgt ctc ctc cct tca      48
Met Ala Met Ala Val Phe Arg Arg Glu Gly Arg Arg Leu Leu Pro Ser
1               5                   10                  15 atc gcc gct cgc cca atc gct gct atc cga tct cct ctc tct tct gac     96
Ile Ala Ala Arg Pro Ile Ala Ala Ile Arg Ser Pro Leu Ser Ser Asp
            20                  25                  30 cag gag gaa gga ctt ctt gga gtt cga tct atc tca act caa gtg gtg    144
Gln Glu Glu Gly Leu Leu Gly Val Arg Ser Ile Ser Thr Gln Val Val
        35                  40                  45 cgt aac cgc atg aag agt gtt aag aac atc caa aag atc aca aag gca    192
Arg Asn Arg Met Lys Ser Val Lys Asn Ile Gln Lys Ile Thr Lys Ala
    50                  55                  60 atg aag atg gtt gct gct tcc aag ctt aga gca gtt cag gcc            234
Met Lys Met Val Ala Ala Ser Lys Leu Arg Ala Val Gln Ala
65                  70                  75

<210> SEQ ID NO 38
<211> LENGTH: 78
<212> TYPE: PRT
<213> ORGANISM: Arabidopsis thaliana

<400> SEQUENCE: 38

Met Ala Met Ala Val Phe Arg Arg Glu Gly Arg Arg Leu Leu Pro Ser
1               5                   10                  15

Ile Ala Ala Arg Pro Ile Ala Ala Ile Arg Ser Pro Leu Ser Ser Asp
            20                  25                  30

Gln Glu Glu Gly Leu Leu Gly Val Arg Ser Ile Ser Thr Gln Val Val
        35                  40                  45

Arg Asn Arg Met Lys Ser Val Lys Asn Ile Gln Lys Ile Thr Lys Ala
    50                  55                  60

Met Lys Met Val Ala Ala Ser Lys Leu Arg Ala Val Gln Ala
65                  70                  75

<210> SEQ ID NO 39
<211> LENGTH: 2847
<212> TYPE: DNA
<213> ORGANISM: Arabidopsis thaliana
<220> FEATURE:
<221> NAME/KEY: gene
<222> LOCATION: (1)..(2847)
<223> OTHER INFORMATION: Gene for H+-ATPase comprising a plasma membrane
      targeting sequence

```
<220> FEATURE:
<221> NAME/KEY: CDS
<222> LOCATION: (1)..(2844)
<223> OTHER INFORMATION: H+-ATPase comprising a plasma membrane
      targeting sequence
<300> PUBLICATION INFORMATION:
<308> DATABASE ACCESSION NUMBER: GenBank/J05570
<309> DATABASE ENTRY DATE: 1993-04-27

<400> SEQUENCE: 39
```

| | | | | | | | | | | | | | | | | |
|---|---|---|---|---|---|---|---|---|---|---|---|---|---|---|---|---|
| atg | tcg | agt | ctc | gaa | gat | atc | aag | aac | gag | act | gtt | gat | ctg | gaa | aaa | 48 |
| Met | Ser | Ser | Leu | Glu | Asp | Ile | Lys | Asn | Glu | Thr | Val | Asp | Leu | Glu | Lys | |
| 1 | | | | 5 | | | | | 10 | | | | | 15 | | |
| att | ccg | att | gag | gaa | gtt | ttc | cag | cag | cta | aaa | tgt | tca | agg | gaa | gga | 96 |
| Ile | Pro | Ile | Glu | Glu | Val | Phe | Gln | Gln | Leu | Lys | Cys | Ser | Arg | Glu | Gly | |
| | | | 20 | | | | | 25 | | | | | 30 | | | |
| ttg | aca | acg | cag | gaa | ggg | gag | gac | agg | att | cag | atc | ttt | ggc | ccc | aac | 144 |
| Leu | Thr | Thr | Gln | Glu | Gly | Glu | Asp | Arg | Ile | Gln | Ile | Phe | Gly | Pro | Asn | |
| | | 35 | | | | | 40 | | | | | 45 | | | | |
| aag | ctc | gaa | gag | aaa | aag | gaa | agc | aaa | ctt | ctg | aag | ttt | ttg | ggg | ttt | 192 |
| Lys | Leu | Glu | Glu | Lys | Lys | Glu | Ser | Lys | Leu | Leu | Lys | Phe | Leu | Gly | Phe | |
| | 50 | | | | | 55 | | | | | 60 | | | | | |
| atg | tgg | aat | cca | ctt | tca | tgg | gtc | atg | gaa | atg | gct | gca | atc | atg | gcc | 240 |
| Met | Trp | Asn | Pro | Leu | Ser | Trp | Val | Met | Glu | Met | Ala | Ala | Ile | Met | Ala | |
| 65 | | | | | 70 | | | | | 75 | | | | | 80 | |
| att | gct | ttg | gcc | aac | ggt | gat | ggt | agg | cct | ccg | gat | tgg | cag | gat | ttt | 288 |
| Ile | Ala | Leu | Ala | Asn | Gly | Asp | Gly | Arg | Pro | Pro | Asp | Trp | Gln | Asp | Phe | |
| | | | 85 | | | | | 90 | | | | | 95 | | | |
| gtt | ggt | att | atc | tgt | ctg | ttg | gtt | atc | aac | tct | acc | atc | agt | ttt | atc | 336 |
| Val | Gly | Ile | Ile | Cys | Leu | Leu | Val | Ile | Asn | Ser | Thr | Ile | Ser | Phe | Ile | |
| | | | | 100 | | | | | 105 | | | | | 110 | | |
| gaa | gaa | aac | aat | gct | ggt | aat | gct | gct | gct | gct | ctt | atg | gct | ggt | ctt | 384 |
| Glu | Glu | Asn | Asn | Ala | Gly | Asn | Ala | Ala | Ala | Ala | Leu | Met | Ala | Gly | Leu | |
| | | | 115 | | | | | 120 | | | | | 125 | | | |
| gct | cct | aaa | acc | aag | gtt | ctt | agg | gat | gga | aag | tgg | agt | gaa | caa | gaa | 432 |
| Ala | Pro | Lys | Thr | Lys | Val | Leu | Arg | Asp | Gly | Lys | Trp | Ser | Glu | Gln | Glu | |
| | | 130 | | | | | 135 | | | | | 140 | | | | |
| gct | gct | att | ctt | gtc | cca | gga | gat | att | gtt | agc | att | aaa | tta | gga | gac | 480 |
| Ala | Ala | Ile | Leu | Val | Pro | Gly | Asp | Ile | Val | Ser | Ile | Lys | Leu | Gly | Asp | |
| 145 | | | | | 150 | | | | | 155 | | | | | 160 | |
| att | atc | cca | gct | gat | gcc | cgt | cta | ctt | gaa | ggt | gat | cct | tta | aag | gtt | 528 |
| Ile | Ile | Pro | Ala | Asp | Ala | Arg | Leu | Leu | Glu | Gly | Asp | Pro | Leu | Lys | Val | |
| | | | | 165 | | | | | 170 | | | | | 175 | | |
| gac | caa | tct | gct | cta | act | gga | gag | tcc | ctt | cct | gta | acc | aag | cac | ccg | 576 |
| Asp | Gln | Ser | Ala | Leu | Thr | Gly | Glu | Ser | Leu | Pro | Val | Thr | Lys | His | Pro | |
| | | | 180 | | | | | 185 | | | | | 190 | | | |
| ggt | caa | gaa | gtt | ttc | tct | ggt | tca | acc | tgc | aaa | caa | gga | gaa | atc | gag | 624 |
| Gly | Gln | Glu | Val | Phe | Ser | Gly | Ser | Thr | Cys | Lys | Gln | Gly | Glu | Ile | Glu | |
| | | 195 | | | | | 200 | | | | | 205 | | | | |
| gcg | gtt | gtt | att | gcc | act | ggg | gtt | cat | acc | ttc | ttc | ggt | aaa | gct | gct | 672 |
| Ala | Val | Val | Ile | Ala | Thr | Gly | Val | His | Thr | Phe | Phe | Gly | Lys | Ala | Ala | |
| | | | 210 | | | | | 215 | | | | | 220 | | | |
| cac | ctt | gtg | gac | agc | act | aac | caa | gtt | gga | cat | ttc | cag | aag | gtt | ctt | 720 |
| His | Leu | Val | Asp | Ser | Thr | Asn | Gln | Val | Gly | His | Phe | Gln | Lys | Val | Leu | |
| 225 | | | | | 230 | | | | | 235 | | | | | 240 | |
| aca | gcc | att | ggg | aac | ttc | tgt | atc | tgt | tcc | att | gct | atc | ggt | atg | gtg | 768 |
| Thr | Ala | Ile | Gly | Asn | Phe | Cys | Ile | Cys | Ser | Ile | Ala | Ile | Gly | Met | Val | |
| | | | | 245 | | | | | 250 | | | | | 255 | | |
| att | gag | atc | atc | gtc | atg | tat | ccg | atc | caa | cgc | cga | aag | tac | aga | gat | 816 |
| Ile | Glu | Ile | Ile | Val | Met | Tyr | Pro | Ile | Gln | Arg | Arg | Lys | Tyr | Arg | Asp | |
| | | | | | 260 | | | | | 265 | | | | | 270 | |

-continued

| | | |
|---|---|---|
| gga att gac aac ctt ttg gtc ctc ttg atc ggt ggt atc ccc att gct<br>Gly Ile Asp Asn Leu Leu Val Leu Leu Ile Gly Gly Ile Pro Ile Ala<br>275                             280                           285 | 864 |
| atg cct aca gtc ttg tcc gtg acc atg gct att ggg tct cac agg ttg<br>Met Pro Thr Val Leu Ser Val Thr Met Ala Ile Gly Ser His Arg Leu<br>    290                           295                         300 | 912 |
| tct cag caa ggt gcc atc acc aag cgt atg act gcc att gaa gag atg<br>Ser Gln Gln Gly Ala Ile Thr Lys Arg Met Thr Ala Ile Glu Glu Met<br>305                             310                           315                 320 | 960 |
| gca gga atg gat gtc ctg tgc agt gac aaa acc ggg aca cta acc ctc<br>Ala Gly Met Asp Val Leu Cys Ser Asp Lys Thr Gly Thr Leu Thr Leu<br>                       325                         330                         335 | 1008 |
| aac aaa ttg agt gtg gac aaa aac ttg gtc gag gtt ttc tgc aag ggt<br>Asn Lys Leu Ser Val Asp Lys Asn Leu Val Glu Val Phe Cys Lys Gly<br>             340                         345                         350 | 1056 |
| gtg gag aaa gat caa gtc cta tta ttt gca gct atg gct tcc agg gtt<br>Val Glu Lys Asp Gln Val Leu Leu Phe Ala Ala Met Ala Ser Arg Val<br>                       355                         360                         365 | 1104 |
| gag aac cag gat gcc att gat gca gcc atg gtt ggg atg ctt gct gat<br>Glu Asn Gln Asp Ala Ile Asp Ala Ala Met Val Gly Met Leu Ala Asp<br>370                             375                           380 | 1152 |
| cca aag gag gct aga gct gga atc agg gaa gtt cac ttc ctt cca ttc<br>Pro Lys Glu Ala Arg Ala Gly Ile Arg Glu Val His Phe Leu Pro Phe<br>385                             390                           395                 400 | 1200 |
| aac cct gtg gat aag aga act gct ttg act tac att gac ggc agt ggt<br>Asn Pro Val Asp Lys Arg Thr Ala Leu Thr Tyr Ile Asp Gly Ser Gly<br>                       405                         410                         415 | 1248 |
| aac tgg cac aga gtc agt aaa ggt gct cct gag cag atc ctc gaa ctt<br>Asn Trp His Arg Val Ser Lys Gly Ala Pro Glu Gln Ile Leu Glu Leu<br>                     420                         425                         430 | 1296 |
| gcc aaa gcc agc aat gat ctt agc aag aag gtg ctc tcc att att gac<br>Ala Lys Ala Ser Asn Asp Leu Ser Lys Lys Val Leu Ser Ile Ile Asp<br>             435                         440                         445 | 1344 |
| aag tat gct gag cgt ggt ctt agg tcg ttg gct gtt gct cgc cag gtg<br>Lys Tyr Ala Glu Arg Gly Leu Arg Ser Leu Ala Val Ala Arg Gln Val<br>                       450                         455                         460 | 1392 |
| gtg cca gag aaa aca aag gaa agc cca ggt gcg cca tgg gaa ttt gtt<br>Val Pro Glu Lys Thr Lys Glu Ser Pro Gly Ala Pro Trp Glu Phe Val<br>465                             470                           475                 480 | 1440 |
| ggc ttg ttg cca ctt ttt gat ccc cca aga cat gac agt gct gaa aca<br>Gly Leu Leu Pro Leu Phe Asp Pro Pro Arg His Asp Ser Ala Glu Thr<br>                       485                         490                         495 | 1488 |
| att cga cgg gct ttg aat ctt ggt gtt aac gtc aag atg atc act ggt<br>Ile Arg Arg Ala Leu Asn Leu Gly Val Asn Val Lys Met Ile Thr Gly<br>                     500                         505                         510 | 1536 |
| gac caa ctt gct att ggt aag gaa act ggt cgc aga ctt gga atg gga<br>Asp Gln Leu Ala Ile Gly Lys Glu Thr Gly Arg Arg Leu Gly Met Gly<br>             515                         520                         525 | 1584 |
| aca aac atg tat cca tct tcg gct ctt ctt ggt aca cac aaa gac gca<br>Thr Asn Met Tyr Pro Ser Ser Ala Leu Leu Gly Thr His Lys Asp Ala<br>                       530                         535                         540 | 1632 |
| aac ctc gca tcc att cct gtt gag gag ttg att gaa aag gct gat gga<br>Asn Leu Ala Ser Ile Pro Val Glu Glu Leu Ile Glu Lys Ala Asp Gly<br>545                             550                           555                 560 | 1680 |
| ttt gcc gga gtc ttc cca gag cac aaa tac gaa att gtg aaa aag ttg<br>Phe Ala Gly Val Phe Pro Glu His Lys Tyr Glu Ile Val Lys Lys Leu<br>                       565                         570                         575 | 1728 |
| cag gag agg aag cat att gtt gga atg act ggt gat ggt gtc aat gat<br>Gln Glu Arg Lys His Ile Val Gly Met Thr Gly Asp Gly Val Asn Asp<br>                     580                         585                         590 | 1776 |

-continued

| | | |
|---|---|---|
| gcc cct gct cta aag aaa gct gat atc ggt att gct gtt gct gat gct<br>Ala Pro Ala Leu Lys Lys Ala Asp Ile Gly Ile Ala Val Ala Asp Ala<br>595                                  600                            605 | 1824 |
| aca gat gct gct cgt ggt gct tca gat atc gtg ctc act gag cct gga<br>Thr Asp Ala Ala Arg Gly Ala Ser Asp Ile Val Leu Thr Glu Pro Gly<br>610                                615                           620 | 1872 |
| ctc agc gtt att atc agt gct gtt ctc acc agc aga gct att ttc cag<br>Leu Ser Val Ile Ile Ser Ala Val Leu Thr Ser Arg Ala Ile Phe Gln<br>625                              630                           635                640 | 1920 |
| aga atg aag aac tat act atc tat gca gtc tca atc acc atc cgt att<br>Arg Met Lys Asn Tyr Thr Ile Tyr Ala Val Ser Ile Thr Ile Arg Ile<br>                              645                           650                         655 | 1968 |
| gtg ttt ggt ttc atg ctt att gct ttg ata tgg gaa ttt gac ttc tca<br>Val Phe Gly Phe Met Leu Ile Ala Leu Ile Trp Glu Phe Asp Phe Ser<br>660                              665                           670 | 2016 |
| gcc ttc atg gtt ctg atc att gcc att ctt aac gac ggt acc atc atg<br>Ala Phe Met Val Leu Ile Ile Ala Ile Leu Asn Asp Gly Thr Ile Met<br>               675                           680                           685 | 2064 |
| aca atc tca aag gac aga gtt aag cca tct ccc aca cct gat agc tgg<br>Thr Ile Ser Lys Asp Arg Val Lys Pro Ser Pro Thr Pro Asp Ser Trp<br>690                              695                           700 | 2112 |
| aaa ctt aaa gaa att ttt gct act gga gtc gtt cta gga ggc tac cag<br>Lys Leu Lys Glu Ile Phe Ala Thr Gly Val Val Leu Gly Gly Tyr Gln<br>705                              710                           715                720 | 2160 |
| gcc atc atg act gtt att ttc ttc tgg gcg gcg cac aag act gac ttt<br>Ala Ile Met Thr Val Ile Phe Phe Trp Ala Ala His Lys Thr Asp Phe<br>                              725                           730                         735 | 2208 |
| ttc tcg gac aca ttc ggt gtg agg tcc att agg gac aat aac cac gag<br>Phe Ser Asp Thr Phe Gly Val Arg Ser Ile Arg Asp Asn Asn His Glu<br>               740                           745                           750 | 2256 |
| cta atg ggt gcg gtg tac tta caa gtt agt atc att agt caa gct ctg<br>Leu Met Gly Ala Val Tyr Leu Gln Val Ser Ile Ile Ser Gln Ala Leu<br>755                              760                           765 | 2304 |
| atc ttc gtc aca aga tca agg agt tgg tct ttt gtt gaa cgt cct gga<br>Ile Phe Val Thr Arg Ser Arg Ser Trp Ser Phe Val Glu Arg Pro Gly<br>770                              775                           780 | 2352 |
| gca ttg ctg atg att gct ttc ctc att gca caa ctg att gct act ttg<br>Ala Leu Leu Met Ile Ala Phe Leu Ile Ala Gln Leu Ile Ala Thr Leu<br>785                              790                           795                800 | 2400 |
| att gcg gtt tac gcc aac tgg gaa ttt gca aag att agg ggt att gga<br>Ile Ala Val Tyr Ala Asn Trp Glu Phe Ala Lys Ile Arg Gly Ile Gly<br>                              805                           810                         815 | 2448 |
| tgg gga tgg gct ggt gtg atc tgg cta tac agt att gtc aca tac ttc<br>Trp Gly Trp Ala Gly Val Ile Trp Leu Tyr Ser Ile Val Thr Tyr Phe<br>                              820                           825                         830 | 2496 |
| cca ttg gac gtt ttc aag ttt gcc att cga tac atc ttg agc gga aag<br>Pro Leu Asp Val Phe Lys Phe Ala Ile Arg Tyr Ile Leu Ser Gly Lys<br>835                              840                           845 | 2544 |
| gcg tgg ctc aac ttg ttt gag aac aag acg gct ttc acg atg aag aaa<br>Ala Trp Leu Asn Leu Phe Glu Asn Lys Thr Ala Phe Thr Met Lys Lys<br>850                              855                           860 | 2592 |
| gat tac gga aaa gaa gag aga gag gct caa tgg gca ctt gct caa agg<br>Asp Tyr Gly Lys Glu Glu Arg Glu Ala Gln Trp Ala Leu Ala Gln Arg<br>865                              870                           875                880 | 2640 |
| aca ctt cac ggt tta cag cca aaa gaa gct gtt aac atc ttc cct gag<br>Thr Leu His Gly Leu Gln Pro Lys Glu Ala Val Asn Ile Phe Pro Glu<br>               885                           890                         895 | 2688 |
| aaa gga agt tac aga gaa ttg tct gag atc gct gag caa gct aag aga<br>Lys Gly Ser Tyr Arg Glu Leu Ser Glu Ile Ala Glu Gln Ala Lys Arg | 2736 |

```
                        900                 905                 910
aga gct gag atc gct agg ctt agg gag ctg cac aca ctc aag gga cat      2784
Arg Ala Glu Ile Ala Arg Leu Arg Glu Leu His Thr Leu Lys Gly His
            915                 920                 925 gtg gaa tca gtc gtg aag cta aag ggc ttg gac att gaa act ccc agt      2832
Val Glu Ser Val Val Lys Leu Lys Gly Leu Asp Ile Glu Thr Pro Ser
930                 935                 940 cac tac act gtg tag                                                  2847
His Tyr Thr Val
945

<210> SEQ ID NO 40
<211> LENGTH: 948
<212> TYPE: PRT
<213> ORGANISM: Arabidopsis thaliana

<400> SEQUENCE: 40

Met Ser Ser Leu Glu Asp Ile Lys Asn Glu Thr Val Asp Leu Glu Lys
1               5                   10                  15

Ile Pro Ile Glu Glu Val Phe Gln Gln Leu Lys Cys Ser Arg Glu Gly
            20                  25                  30

Leu Thr Thr Gln Glu Gly Glu Asp Arg Ile Gln Ile Phe Gly Pro Asn
        35                  40                  45

Lys Leu Glu Glu Lys Lys Glu Ser Lys Leu Leu Lys Phe Leu Gly Phe
    50                  55                  60

Met Trp Asn Pro Leu Ser Trp Val Met Glu Met Ala Ala Ile Met Ala
65                  70                  75                  80

Ile Ala Leu Ala Asn Gly Asp Gly Arg Pro Pro Asp Trp Gln Asp Phe
                85                  90                  95

Val Gly Ile Ile Cys Leu Leu Val Ile Asn Ser Thr Ile Ser Phe Ile
            100                 105                 110

Glu Glu Asn Asn Ala Gly Asn Ala Ala Ala Leu Met Ala Gly Leu
        115                 120                 125

Ala Pro Lys Thr Lys Val Leu Arg Asp Gly Lys Trp Ser Glu Gln Glu
    130                 135                 140

Ala Ala Ile Leu Val Pro Gly Asp Ile Val Ser Ile Lys Leu Gly Asp
145                 150                 155                 160

Ile Ile Pro Ala Asp Ala Arg Leu Leu Glu Gly Asp Pro Leu Lys Val
                165                 170                 175

Asp Gln Ser Ala Leu Thr Gly Glu Ser Leu Pro Val Thr Lys His Pro
            180                 185                 190

Gly Gln Glu Val Phe Ser Gly Ser Thr Cys Lys Gln Gly Glu Ile Glu
        195                 200                 205

Ala Val Val Ile Ala Thr Gly Val His Thr Phe Phe Gly Lys Ala Ala
    210                 215                 220

His Leu Val Asp Ser Thr Asn Gln Val Gly His Phe Gln Lys Val Leu
225                 230                 235                 240

Thr Ala Ile Gly Asn Phe Cys Ile Cys Ser Ile Ala Ile Gly Met Val
                245                 250                 255

Ile Glu Ile Ile Val Met Tyr Pro Ile Gln Arg Arg Lys Tyr Arg Asp
            260                 265                 270

Gly Ile Asp Asn Leu Leu Val Leu Leu Ile Gly Gly Ile Pro Ile Ala
        275                 280                 285

Met Pro Thr Val Leu Ser Val Thr Met Ala Ile Gly Ser His Arg Leu
    290                 295                 300
```

-continued

```
Ser Gln Gln Gly Ala Ile Thr Lys Arg Met Thr Ala Ile Glu Glu Met
305                 310                 315                 320

Ala Gly Met Asp Val Leu Cys Ser Asp Lys Thr Gly Thr Leu Thr Leu
                325                 330                 335

Asn Lys Leu Ser Val Asp Lys Asn Leu Val Glu Val Phe Cys Lys Gly
            340                 345                 350

Val Glu Lys Asp Gln Val Leu Leu Phe Ala Ala Met Ala Ser Arg Val
        355                 360                 365

Glu Asn Gln Asp Ala Ile Asp Ala Ala Met Val Gly Met Leu Ala Asp
    370                 375                 380

Pro Lys Glu Ala Arg Ala Gly Ile Arg Glu Val His Phe Leu Pro Phe
385                 390                 395                 400

Asn Pro Val Asp Lys Arg Thr Ala Leu Thr Tyr Ile Asp Gly Ser Gly
                405                 410                 415

Asn Trp His Arg Val Ser Lys Gly Ala Pro Glu Gln Ile Leu Glu Leu
            420                 425                 430

Ala Lys Ala Ser Asn Asp Leu Ser Lys Lys Val Leu Ser Ile Ile Asp
        435                 440                 445

Lys Tyr Ala Glu Arg Gly Leu Arg Ser Leu Ala Val Ala Arg Gln Val
    450                 455                 460

Val Pro Glu Lys Thr Lys Glu Ser Pro Gly Ala Pro Trp Glu Phe Val
465                 470                 475                 480

Gly Leu Leu Pro Leu Phe Asp Pro Pro Arg His Asp Ser Ala Glu Thr
                485                 490                 495

Ile Arg Arg Ala Leu Asn Leu Gly Val Asn Val Lys Met Ile Thr Gly
            500                 505                 510

Asp Gln Leu Ala Ile Gly Lys Glu Thr Gly Arg Arg Leu Gly Met Gly
        515                 520                 525

Thr Asn Met Tyr Pro Ser Ser Ala Leu Leu Gly Thr His Lys Asp Ala
    530                 535                 540

Asn Leu Ala Ser Ile Pro Val Glu Glu Leu Ile Glu Lys Ala Asp Gly
545                 550                 555                 560

Phe Ala Gly Val Phe Pro Glu His Lys Tyr Glu Ile Val Lys Lys Leu
                565                 570                 575

Gln Glu Arg Lys His Ile Val Gly Met Thr Gly Asp Gly Val Asn Asp
            580                 585                 590

Ala Pro Ala Leu Lys Lys Ala Asp Ile Gly Ile Ala Val Ala Asp Ala
        595                 600                 605

Thr Asp Ala Ala Arg Gly Ala Ser Asp Ile Val Leu Thr Glu Pro Gly
    610                 615                 620

Leu Ser Val Ile Ile Ser Ala Val Leu Thr Ser Arg Ala Ile Phe Gln
625                 630                 635                 640

Arg Met Lys Asn Tyr Thr Ile Tyr Ala Val Ser Ile Thr Ile Arg Ile
                645                 650                 655

Val Phe Gly Phe Met Leu Ile Ala Leu Ile Trp Glu Phe Asp Phe Ser
            660                 665                 670

Ala Phe Met Val Leu Ile Ile Ala Ile Leu Asn Asp Gly Thr Ile Met
        675                 680                 685

Thr Ile Ser Lys Asp Arg Val Lys Pro Ser Pro Thr Pro Asp Ser Trp
    690                 695                 700

Lys Leu Lys Glu Ile Phe Ala Thr Gly Val Val Leu Gly Gly Tyr Gln
705                 710                 715                 720

Ala Ile Met Thr Val Ile Phe Phe Trp Ala Ala His Lys Thr Asp Phe
```

-continued

```
                725                 730                 735
    Phe Ser Asp Thr Phe Gly Val Arg Ser Ile Arg Asp Asn Asn His Glu
                    740                 745                 750

Leu Met Gly Ala Val Tyr Leu Gln Val Ser Ile Ile Ser Gln Ala Leu
                    755                 760                 765

Ile Phe Val Thr Arg Ser Arg Ser Trp Ser Phe Val Glu Arg Pro Gly
                    770                 775                 780

Ala Leu Leu Met Ile Ala Phe Leu Ile Ala Gln Leu Ile Ala Thr Leu
    785                 790                 795                 800

Ile Ala Val Tyr Ala Asn Trp Glu Phe Ala Lys Ile Arg Gly Ile Gly
                    805                 810                 815

Trp Gly Trp Ala Gly Val Ile Trp Leu Tyr Ser Ile Val Thr Tyr Phe
                    820                 825                 830

Pro Leu Asp Val Phe Lys Phe Ala Ile Arg Tyr Ile Leu Ser Gly Lys
                    835                 840                 845

Ala Trp Leu Asn Leu Phe Glu Asn Lys Thr Ala Phe Thr Met Lys Lys
                    850                 855                 860

Asp Tyr Gly Lys Glu Glu Arg Glu Ala Gln Trp Ala Leu Ala Gln Arg
    865                 870                 875                 880

Thr Leu His Gly Leu Gln Pro Lys Glu Ala Val Asn Ile Phe Pro Glu
                    885                 890                 895

Lys Gly Ser Tyr Arg Glu Leu Ser Glu Ile Ala Glu Gln Ala Lys Arg
                    900                 905                 910

Arg Ala Glu Ile Ala Arg Leu Arg Glu Leu His Thr Leu Lys Gly His
                    915                 920                 925

Val Glu Ser Val Val Lys Leu Lys Gly Leu Asp Ile Glu Thr Pro Ser
    930                 935                 940

His Tyr Thr Val
    945

<210> SEQ ID NO 41
<211> LENGTH: 525
<212> TYPE: DNA
<213> ORGANISM: Rattus norvegicus
<220> FEATURE:
<221> NAME/KEY: gene
<222> LOCATION: (1)..(525)
<223> OTHER INFORMATION: Gene for partial pleckstrin homology domain of
      phospholipase C-delta 1 comprising phosphatidylinositol 4,5-
      diphosphate targeting sequence
<220> FEATURE:
<221> NAME/KEY: CDS
<222> LOCATION: (1)..(522)
<223> OTHER INFORMATION: Partial pleckstrin homology domain of
      phospholipase C-delta 1 comprising phosphatidylinositol 4,5-
      diphosphate targeting sequence
<300> PUBLICATION INFORMATION:
<308> DATABASE ACCESSION NUMBER: GenBank/NM_017035
<309> DATABASE ENTRY DATE: 2000-11-01

<400> SEQUENCE: 41 gac tcg ggt agg gac ttc ctg acc ctg cac ggg ctc cag gat gac ccg        48
Asp Ser Gly Arg Asp Phe Leu Thr Leu His Gly Leu Gln Asp Asp Pro
1               5                   10                  15 gac ctt cag gcc ctt ctg aag ggc agc cag ctt ctg aag gtg aag tcc        96
Asp Leu Gln Ala Leu Leu Lys Gly Ser Gln Leu Leu Lys Val Lys Ser
                20                  25                  30 agc tcg tgg cgt agg gaa cgc ttc tac aag cta cag gag gac tgc aag       144
Ser Ser Trp Arg Arg Glu Arg Phe Tyr Lys Leu Gln Glu Asp Cys Lys
            35                  40                  45
```

-continued

| | |
|---|---|
| acc atc tgg cag gaa tct cga aag gtc atg agg tcc ccg gag tcg cag<br>Thr Ile Trp Gln Glu Ser Arg Lys Val Met Arg Ser Pro Glu Ser Gln<br>    50                        55                    60 | 192 |
| ctg ttc tcc atc gag gac att cag gag gta cgg atg gga cac cgc aca<br>Leu Phe Ser Ile Glu Asp Ile Gln Glu Val Arg Met Gly His Arg Thr<br>65                      70                    75                    80 | 240 |
| gaa ggc ctg gag aag ttt gcc cga gac atc ccc gag gat cga tgc ttc<br>Glu Gly Leu Glu Lys Phe Ala Arg Asp Ile Pro Glu Asp Arg Cys Phe<br>                      85                    90                    95 | 288 |
| tcc att gtc ttc aag gac cag cgc aac acc cta gac ctc att gcc cca<br>Ser Ile Val Phe Lys Asp Gln Arg Asn Thr Leu Asp Leu Ile Ala Pro<br>               100                   105                   110 | 336 |
| tca cca gct gac gct cag cac tgg gtg cag ggc ctg cgc aag atc atc<br>Ser Pro Ala Asp Ala Gln His Trp Val Gln Gly Leu Arg Lys Ile Ile<br>           115                   120                   125 | 384 |
| cac cac tcc ggc tcc atg gac cag cgg cag aag ctg cag cac tgg att<br>His His Ser Gly Ser Met Asp Gln Arg Gln Lys Leu Gln His Trp Ile<br>   130                   135                   140 | 432 |
| cac tcc tgc ttg cga aag gct gat aaa aac aag gac aac aag atg aac<br>His Ser Cys Leu Arg Lys Ala Asp Lys Asn Lys Asp Asn Lys Met Asn<br>145                 150                   155                   160 | 480 |
| ttc aag gag ctg aag gac ttc ctg aag gag ctc aac atc cag tga<br>Phe Lys Glu Leu Lys Asp Phe Leu Lys Glu Leu Asn Ile Gln<br>                 165                   170 | 525 |

<210> SEQ ID NO 42
<211> LENGTH: 174
<212> TYPE: PRT
<213> ORGANISM: Rattus norvegicus

<400> SEQUENCE: 42

Asp Ser Gly Arg Asp Phe Leu Thr Leu His Gly Leu Gln Asp Asp Pro
1               5                   10                  15

Asp Leu Gln Ala Leu Leu Lys Gly Ser Gln Leu Leu Lys Val Lys Ser
            20                  25                  30

Ser Ser Trp Arg Arg Glu Arg Phe Tyr Lys Leu Gln Glu Asp Cys Lys
        35                  40                  45

Thr Ile Trp Gln Glu Ser Arg Lys Val Met Arg Ser Pro Glu Ser Gln
    50                  55                  60

Leu Phe Ser Ile Glu Asp Ile Gln Glu Val Arg Met Gly His Arg Thr
65                  70                  75                  80

Glu Gly Leu Glu Lys Phe Ala Arg Asp Ile Pro Glu Asp Arg Cys Phe
                85                  90                  95

Ser Ile Val Phe Lys Asp Gln Arg Asn Thr Leu Asp Leu Ile Ala Pro
            100                 105                 110

Ser Pro Ala Asp Ala Gln His Trp Val Gln Gly Leu Arg Lys Ile Ile
        115                 120                 125

His His Ser Gly Ser Met Asp Gln Arg Gln Lys Leu Gln His Trp Ile
    130                 135                 140

His Ser Cys Leu Arg Lys Ala Asp Lys Asn Lys Asp Asn Lys Met Asn
145                 150                 155                 160

Phe Lys Glu Leu Lys Asp Phe Leu Lys Glu Leu Asn Ile Gln
                165                 170

<210> SEQ ID NO 43
<211> LENGTH: 282
<212> TYPE: DNA
<213> ORGANISM: Mus musculus
<220> FEATURE:

-continued

```
<221> NAME/KEY: CDS
<222> LOCATION: (1)..(282)
<223> OTHER INFORMATION: Partial pleckstrin homology domain of FAPP
      (family A (phosphoinositide binding specific) member 3),
      comprising a phosphatidylinositol 4-phosphate targeting sequence
<300> PUBLICATION INFORMATION:
<308> DATABASE ACCESSION NUMBER: GenBank/BC031110
<309> DATABASE ENTRY DATE: 2002-06-13

<400> SEQUENCE: 43 atg gag ggg gtt ctg tac aag tgg acc aac tat ctc aca ggt tgg cag       48
Met Glu Gly Val Leu Tyr Lys Trp Thr Asn Tyr Leu Thr Gly Trp Gln
1               5                   10                  15 cct cga tgg ttt gtt ctg gat aat gga atc ctg tcc tac tat gac tca       96
Pro Arg Trp Phe Val Leu Asp Asn Gly Ile Leu Ser Tyr Tyr Asp Ser
            20                  25                  30 cag gat gat gtc tgc aaa ggg agc aaa ggg agt ata aag atg gcg gtc      144
Gln Asp Asp Val Cys Lys Gly Ser Lys Gly Ser Ile Lys Met Ala Val
        35                  40                  45 tgt gag att aaa gtc cat ccc gca gac aac aca aga atg gag tta atc      192
Cys Glu Ile Lys Val His Pro Ala Asp Asn Thr Arg Met Glu Leu Ile
    50                  55                  60 att cca gga gag cag cat ttc tac atg aag gca gta aat gcc gcc gag      240
Ile Pro Gly Glu Gln His Phe Tyr Met Lys Ala Val Asn Ala Ala Glu
65                  70                  75                  80 aga cag agg tgg ctg gtt gcc ctt ggg agc tcc aaa gcg tgc              282
Arg Gln Arg Trp Leu Val Ala Leu Gly Ser Ser Lys Ala Cys
                85                  90

<210> SEQ ID NO 44
<211> LENGTH: 94
<212> TYPE: PRT
<213> ORGANISM: Mus musculus

<400> SEQUENCE: 44

Met Glu Gly Val Leu Tyr Lys Trp Thr Asn Tyr Leu Thr Gly Trp Gln
1               5                   10                  15

Pro Arg Trp Phe Val Leu Asp Asn Gly Ile Leu Ser Tyr Tyr Asp Ser
            20                  25                  30

Gln Asp Asp Val Cys Lys Gly Ser Lys Gly Ser Ile Lys Met Ala Val
        35                  40                  45

Cys Glu Ile Lys Val His Pro Ala Asp Asn Thr Arg Met Glu Leu Ile
    50                  55                  60

Ile Pro Gly Glu Gln His Phe Tyr Met Lys Ala Val Asn Ala Ala Glu
65                  70                  75                  80

Arg Gln Arg Trp Leu Val Ala Leu Gly Ser Ser Lys Ala Cys
                85                  90

<210> SEQ ID NO 45
<211> LENGTH: 741
<212> TYPE: DNA
<213> ORGANISM: Tobacco vein mottling virus
<220> FEATURE:
<221> NAME/KEY: gene
<222> LOCATION: (1)..(741)
<223> OTHER INFORMATION: Gene for NIa protease
<220> FEATURE:
<221> NAME/KEY: CDS
<222> LOCATION: (1)..(738)
<223> OTHER INFORMATION: NIa protease
<300> PUBLICATION INFORMATION:
<308> DATABASE ACCESSION NUMBER: GenBank/AF222050
<309> DATABASE ENTRY DATE: 2000-02-07

<400> SEQUENCE: 45
```

```
atg tca aag gcg cta ctt aag gga gtg cga gat ttt aat cca atc tct      48
Met Ser Lys Ala Leu Leu Lys Gly Val Arg Asp Phe Asn Pro Ile Ser
1               5                   10                  15 gct tgc gta tgc ctc ctt gag aac tcc tcg gat ggg cat agt gag aga      96
Ala Cys Val Cys Leu Leu Glu Asn Ser Ser Asp Gly His Ser Glu Arg
            20                  25                  30 ctg ttt ggc att ggt ttt ggc cca tat atc att gcc aac caa cat ctt     144
Leu Phe Gly Ile Gly Phe Gly Pro Tyr Ile Ile Ala Asn Gln His Leu
        35                  40                  45 ttt aga agg aac aat gga gag ttg act atc aaa acc atg cat ggt gag     192
Phe Arg Arg Asn Asn Gly Glu Leu Thr Ile Lys Thr Met His Gly Glu
    50                  55                  60 ttc aaa gtc aag aac tca aca caa ttg cag atg aaa cca gtt gag ggc     240
Phe Lys Val Lys Asn Ser Thr Gln Leu Gln Met Lys Pro Val Glu Gly
65                  70                  75                  80 aga gac ata ata gtt atc aaa atg gct aag gac ttc cca cca ttc cct     288
Arg Asp Ile Ile Val Ile Lys Met Ala Lys Asp Phe Pro Pro Phe Pro
                85                  90                  95 caa aaa cta aaa ttc aga cag cct acc atc aaa gat aga gtg tgc atg     336
Gln Lys Leu Lys Phe Arg Gln Pro Thr Ile Lys Asp Arg Val Cys Met
            100                 105                 110 gta tcc aca aat ttt cag cag aaa agt gtc tct agt cta gtg tct gag     384
Val Ser Thr Asn Phe Gln Gln Lys Ser Val Ser Ser Leu Val Ser Glu
        115                 120                 125 tca tca cac att gtg cat aaa gag gac act tca ttc tgg caa cac tgg     432
Ser Ser His Ile Val His Lys Glu Asp Thr Ser Phe Trp Gln His Trp
    130                 135                 140 ata aca aca aag gat gga caa tgt gga agt ccg ctg gtt tca atc att     480
Ile Thr Thr Lys Asp Gly Gln Cys Gly Ser Pro Leu Val Ser Ile Ile
145                 150                 155                 160 gat gga aat att ttg ggg atc cac agc ctg acg cat acg acc aat ggt     528
Asp Gly Asn Ile Leu Gly Ile His Ser Leu Thr His Thr Thr Asn Gly
                165                 170                 175 agc aat tac ttc gtg gaa ttt cct gag aag ttc gta gct aca tat ctt     576
Ser Asn Tyr Phe Val Glu Phe Pro Glu Lys Phe Val Ala Thr Tyr Leu
            180                 185                 190 gat gcc gct gat ggt tgg tgc aag aat tgg aag ttc aat gct gat aag     624
Asp Ala Ala Asp Gly Trp Cys Lys Asn Trp Lys Phe Asn Ala Asp Lys
        195                 200                 205 atc agt tgg ggt tcc ttt aca tta gtt gag gat gcg ccc gaa gat gac     672
Ile Ser Trp Gly Ser Phe Thr Leu Val Glu Asp Ala Pro Glu Asp Asp
    210                 215                 220 ttc atg gcc aag aaa act gtt gcc gcc atc atg gac gat ttg gtc cgc     720
Phe Met Ala Lys Lys Thr Val Ala Ala Ile Met Asp Asp Leu Val Arg
225                 230                 235                 240 act caa ggg gga gaa gct tga                                         741
Thr Gln Gly Gly Glu Ala
                245
```

<210> SEQ ID NO 46
<211> LENGTH: 246
<212> TYPE: PRT
<213> ORGANISM: Tobacco vein mottling virus

<400> SEQUENCE: 46

```
Met Ser Lys Ala Leu Leu Lys Gly Val Arg Asp Phe Asn Pro Ile Ser
1               5                   10                  15

Ala Cys Val Cys Leu Leu Glu Asn Ser Ser Asp Gly His Ser Glu Arg
            20                  25                  30
```

```
Leu Phe Gly Ile Gly Phe Gly Pro Tyr Ile Ile Ala Asn Gln His Leu
         35                  40                  45

Phe Arg Arg Asn Asn Gly Glu Leu Thr Ile Lys Thr Met His Gly Glu
 50                  55                  60

Phe Lys Val Lys Asn Ser Thr Gln Leu Gln Met Lys Pro Val Glu Gly
 65                  70                  75                  80

Arg Asp Ile Ile Val Ile Lys Met Ala Lys Asp Phe Pro Pro Phe Pro
                 85                  90                  95

Gln Lys Leu Lys Phe Arg Gln Pro Thr Ile Lys Asp Arg Val Cys Met
             100                 105                 110

Val Ser Thr Asn Phe Gln Gln Lys Ser Val Ser Ser Leu Val Ser Glu
             115                 120                 125

Ser Ser His Ile Val His Lys Glu Asp Thr Ser Phe Trp Gln His Trp
130                 135                 140

Ile Thr Thr Lys Asp Gly Gln Cys Gly Ser Pro Leu Val Ser Ile Ile
145                 150                 155                 160

Asp Gly Asn Ile Leu Gly Ile His Ser Leu Thr His Thr Thr Asn Gly
                165                 170                 175

Ser Asn Tyr Phe Val Glu Phe Pro Glu Lys Phe Val Ala Thr Tyr Leu
            180                 185                 190

Asp Ala Ala Asp Gly Trp Cys Lys Asn Trp Lys Phe Asn Ala Asp Lys
            195                 200                 205

Ile Ser Trp Gly Ser Phe Thr Leu Val Glu Asp Ala Pro Glu Asp Asp
210                 215                 220

Phe Met Ala Lys Lys Thr Val Ala Ala Ile Met Asp Asp Leu Val Arg
225                 230                 235                 240

Thr Gln Gly Gly Glu Ala
                245

<210> SEQ ID NO 47
<211> LENGTH: 12
<212> TYPE: DNA
<213> ORGANISM: Artificial
<220> FEATURE:
<223> OTHER INFORMATION: Synthetic Sequence
<220> FEATURE:
<221> NAME/KEY: CDS
<222> LOCATION: (1)..(12)
<223> OTHER INFORMATION: NIa protease cleavage sequence

<400> SEQUENCE: 47 gtg cgc ttc cag                                                      12
Val Arg Phe Gln
 1

<210> SEQ ID NO 48
<211> LENGTH: 4
<212> TYPE: PRT
<213> ORGANISM: Artificial
<220> FEATURE:
<223> OTHER INFORMATION: Synthetic Sequence

<400> SEQUENCE: 48

Val Arg Phe Gln
 1

<210> SEQ ID NO 49
<211> LENGTH: 21
<212> TYPE: DNA
<213> ORGANISM: Artificial
<220> FEATURE:
```

```
<223> OTHER INFORMATION: Synthetic Sequence
<220> FEATURE:
<221> NAME/KEY: CDS
<222> LOCATION: (1)..(21)
<223> OTHER INFORMATION: NIa protease cleavage sequence
<300> PUBLICATION INFORMATION:
<308> DATABASE ACCESSION NUMBER: GenBank/AX427722
<309> DATABASE ENTRY DATE: 2002-06-20

<400> SEQUENCE: 49 gaa cca gtc tat ttc caa ggg                                          21
Glu Pro Val Tyr Phe Gln Gly
1               5

<210> SEQ ID NO 50
<211> LENGTH: 7
<212> TYPE: PRT
<213> ORGANISM: Artificial
<220> FEATURE:
<223> OTHER INFORMATION: Synthetic Sequence

<400> SEQUENCE: 50

Glu Pro Val Tyr Phe Gln Gly
1               5

<210> SEQ ID NO 51
<211> LENGTH: 1638
<212> TYPE: DNA
<213> ORGANISM: Artificial
<220> FEATURE:
<223> OTHER INFORMATION: Synthetic Sequence
<220> FEATURE:
<221> NAME/KEY: gene
<222> LOCATION: (1)..(1638)
<223> OTHER INFORMATION: Gene for RFP:PS(NIa protease):AtOEP7:GFP
<220> FEATURE:
<221> NAME/KEY: CDS
<222> LOCATION: (1)..(1635)
<223> OTHER INFORMATION: RFP:PS(NIa protease):AtOEP7:GFP hybrid protein
<220> FEATURE:
<221> NAME/KEY: misc_feature
<223> OTHER INFORMATION: CDS: RFP(1..678); CDS: NIa protease proteolytic
      site(700..711); CDS: AtOEP7(712..900); CDS: GFP(922..1635)

<400> SEQUENCE: 51 atg gtg cgc tcc tcc aag aac gtc atc aag gag ttc atg cgc ttc aag     48
Met Val Arg Ser Ser Lys Asn Val Ile Lys Glu Phe Met Arg Phe Lys
1               5                   10                  15 gtg cgc atg gag ggc acc gtg aac ggc cac gag ttc gag atc gag ggc     96
Val Arg Met Glu Gly Thr Val Asn Gly His Glu Phe Glu Ile Glu Gly
                20                  25                  30 gag ggc gag ggc cgc ccc tac gag ggc cac aac acc gtg aag ctg aag    144
Glu Gly Glu Gly Arg Pro Tyr Glu Gly His Asn Thr Val Lys Leu Lys
            35                  40                  45 gtg acc aag ggc ggc ccc ctg ccc ttc gcc tgg gac atc ctg tcc ccc    192
Val Thr Lys Gly Gly Pro Leu Pro Phe Ala Trp Asp Ile Leu Ser Pro
        50                  55                  60 cag ttc cag tac ggc tcc aag gtg tac gtg aag cac ccc gcc gac atc    240
Gln Phe Gln Tyr Gly Ser Lys Val Tyr Val Lys His Pro Ala Asp Ile
65                  70                  75                  80 ccc gac tac aag aag ctg tcc ttc ccc gag ggc ttc aag tgg gag cgc    288
Pro Asp Tyr Lys Lys Leu Ser Phe Pro Glu Gly Phe Lys Trp Glu Arg
                85                  90                  95 gtg atg aac ttc gag gac ggc ggc gtg gtg acc gtg acc cag gac tcc    336
Val Met Asn Phe Glu Asp Gly Gly Val Val Thr Val Thr Gln Asp Ser
                100                 105                 110 tcc ctg cag gac ggc tgc ttc atc tac aag gtg aag ttc atc ggc gtg    384
```

```
                Ser Leu Gln Asp Gly Cys Phe Ile Tyr Lys Val Lys Phe Ile Gly Val
                        115                 120                 125 aac ttc ccc tcc gac ggc ccc gta atg cag aag aag acc atg ggc tgg       432
Asn Phe Pro Ser Asp Gly Pro Val Met Gln Lys Lys Thr Met Gly Trp
        130                 135                 140 gag gcc tcc acc gag cgc ctg tac ccc cgc gac ggc gtg ctg aag ggc       480
Glu Ala Ser Thr Glu Arg Leu Tyr Pro Arg Asp Gly Val Leu Lys Gly
145                 150                 155                 160 gag atc cac aag gcc ctg aag ctg aag gac ggc ggc cac tac ctg gtg       528
Glu Ile His Lys Ala Leu Lys Leu Lys Asp Gly Gly His Tyr Leu Val
                165                 170                 175 gag ttc aag tcc atc tac atg gcc aag aag ccc gtg cag ctg ccc ggc       576
Glu Phe Lys Ser Ile Tyr Met Ala Lys Lys Pro Val Gln Leu Pro Gly
        180                 185                 190 tac tac tac gtg gac tcc aag ctg gac atc acc tcc cac aac gag gac       624
Tyr Tyr Tyr Val Asp Ser Lys Leu Asp Ile Thr Ser His Asn Glu Asp
            195                 200                 205 tac acc atc gtg gag cag tac gag cgc acc gag ggc cgc cac cac ctg       672
Tyr Thr Ile Val Glu Gln Tyr Glu Arg Thr Glu Gly Arg His His Leu
    210                 215                 220 ttc ctg ccc cgg gca atc aag ctg ggt gtg cgc ttc cag gga aaa act       720
Phe Leu Pro Arg Ala Ile Lys Leu Gly Val Arg Phe Gln Gly Lys Thr
225                 230                 235                 240 tcg gga gcg aaa cag gcg act gtg gtg gtc gca gcg atg gcg tta gga       768
Ser Gly Ala Lys Gln Ala Thr Val Val Val Ala Ala Met Ala Leu Gly
                245                 250                 255 tgg tta gcc ata gag atc gct ttc aag cct ttc ctc gat aaa ttc cgc       816
Trp Leu Ala Ile Glu Ile Ala Phe Lys Pro Phe Leu Asp Lys Phe Arg
        260                 265                 270 tcc tca atc gac aaa tct gac cca acc aaa gac ccc gat gac ttc gac       864
Ser Ser Ile Asp Lys Ser Asp Pro Thr Lys Asp Pro Asp Asp Phe Asp
            275                 280                 285 acc gcc gct act gca acc aca tcc aaa gag ggt ttg ggg atc caa gga       912
Thr Ala Ala Thr Ala Thr Thr Ser Lys Glu Gly Leu Gly Ile Gln Gly
    290                 295                 300 gat ata aca atg agt aaa gga gaa gaa ctt ttc act gga gtt gtc cca       960
Asp Ile Thr Met Ser Lys Gly Glu Glu Leu Phe Thr Gly Val Val Pro
305                 310                 315                 320 att ctt gtt gaa tta gat ggt gat gtt aat ggg cac aaa ttt tct gtc      1008
Ile Leu Val Glu Leu Asp Gly Asp Val Asn Gly His Lys Phe Ser Val
                325                 330                 335 agt gga gag ggt gaa ggt gat gca aca tac gga aaa ctt acc ctt aaa      1056
Ser Gly Glu Gly Glu Gly Asp Ala Thr Tyr Gly Lys Leu Thr Leu Lys
        340                 345                 350 ttt att tgc act act gga aaa cta cct gtt cca tgg cca aca ctt gtc      1104
Phe Ile Cys Thr Thr Gly Lys Leu Pro Val Pro Trp Pro Thr Leu Val
            355                 360                 365 act act ttc tct tat ggt gtt caa tgc ttt tca aga tac cca gat cat      1152
Thr Thr Phe Ser Tyr Gly Val Gln Cys Phe Ser Arg Tyr Pro Asp His
    370                 375                 380 atg aag cgg cac gac ttc ttc aag agc gcc atg cct gag gga tac gtg      1200
Met Lys Arg His Asp Phe Phe Lys Ser Ala Met Pro Glu Gly Tyr Val
385                 390                 395                 400 cag gag agg acc atc tct ttc aag gac gac ggg aac tac aag aca cgt      1248
Gln Glu Arg Thr Ile Ser Phe Lys Asp Asp Gly Asn Tyr Lys Thr Arg
                405                 410                 415 gct gaa gtc aag ttt gag gga gac acc ctc gtc aac agg atc gag ctt      1296
Ala Glu Val Lys Phe Glu Gly Asp Thr Leu Val Asn Arg Ile Glu Leu
        420                 425                 430
```

-continued

```
aag gga atc gat ttc aag gag gac gga aac atc ctc ggc cac aag ttg    1344
Lys Gly Ile Asp Phe Lys Glu Asp Gly Asn Ile Leu Gly His Lys Leu
        435                 440                 445 gaa tac aac tac aac tcc cac aac gta tac atc acg gca gac aaa caa    1392
Glu Tyr Asn Tyr Asn Ser His Asn Val Tyr Ile Thr Ala Asp Lys Gln
450                 455                 460 aag aat gga atc aaa gct aac ttc aaa att aga cac aac att gaa gat    1440
Lys Asn Gly Ile Lys Ala Asn Phe Lys Ile Arg His Asn Ile Glu Asp
465                 470                 475                 480 gga agc gtt caa cta gca gac cat tat caa caa aat act cca att ggc    1488
Gly Ser Val Gln Leu Ala Asp His Tyr Gln Gln Asn Thr Pro Ile Gly
                485                 490                 495 gat ggc cct gtc ctt tta cca gac aac cat tac ctg tcc aca caa tct    1536
Asp Gly Pro Val Leu Leu Pro Asp Asn His Tyr Leu Ser Thr Gln Ser
            500                 505                 510 gcc ctt tcg aaa gat ccc aac gaa aag aga gac cac atg gtc ctt ctt    1584
Ala Leu Ser Lys Asp Pro Asn Glu Lys Arg Asp His Met Val Leu Leu
        515                 520                 525 gag ttt gta aca gct gct ggg att aca cat ggc atg gat gaa cta tac    1632
Glu Phe Val Thr Ala Ala Gly Ile Thr His Gly Met Asp Glu Leu Tyr
530                 535                 540 aaa taa                                                            1638
Lys
545
```

<210> SEQ ID NO 52
<211> LENGTH: 545
<212> TYPE: PRT
<213> ORGANISM: Artificial
<220> FEATURE:
<223> OTHER INFORMATION: Synthetic Sequence

<400> SEQUENCE: 52

```
Met Val Arg Ser Ser Lys Asn Val Ile Lys Glu Phe Met Arg Phe Lys
1               5                   10                  15

Val Arg Met Glu Gly Thr Val Asn Gly His Glu Phe Glu Ile Glu Gly
            20                  25                  30

Glu Gly Glu Gly Arg Pro Tyr Glu Gly His Asn Thr Val Lys Leu Lys
        35                  40                  45

Val Thr Lys Gly Gly Pro Leu Pro Phe Ala Trp Asp Ile Leu Ser Pro
    50                  55                  60

Gln Phe Gln Tyr Gly Ser Lys Val Tyr Val Lys His Pro Ala Asp Ile
65                  70                  75                  80

Pro Asp Tyr Lys Lys Leu Ser Phe Pro Glu Gly Phe Lys Trp Glu Arg
                85                  90                  95

Val Met Asn Phe Glu Asp Gly Gly Val Val Thr Val Thr Gln Asp Ser
            100                 105                 110

Ser Leu Gln Asp Gly Cys Phe Ile Tyr Lys Val Lys Phe Ile Gly Val
        115                 120                 125

Asn Phe Pro Ser Asp Gly Pro Val Met Gln Lys Lys Thr Met Gly Trp
    130                 135                 140

Glu Ala Ser Thr Glu Arg Leu Tyr Pro Arg Asp Gly Val Leu Lys Gly
145                 150                 155                 160

Glu Ile His Lys Ala Leu Lys Leu Lys Asp Gly Gly His Tyr Leu Val
                165                 170                 175

Glu Phe Lys Ser Ile Tyr Met Ala Lys Lys Pro Val Gln Leu Pro Gly
            180                 185                 190

Tyr Tyr Tyr Val Asp Ser Lys Leu Asp Ile Thr Ser His Asn Glu Asp
```

```
              195                 200                 205
Tyr Thr Ile Val Glu Gln Tyr Glu Arg Thr Glu Gly Arg His His Leu
    210                 215                 220

Phe Leu Pro Arg Ala Ile Lys Leu Gly Val Arg Phe Gln Gly Lys Thr
225                 230                 235                 240

Ser Gly Ala Lys Gln Ala Thr Val Val Ala Ala Met Ala Leu Gly
                245                 250                 255

Trp Leu Ala Ile Glu Ile Ala Phe Lys Pro Phe Leu Asp Lys Phe Arg
                260                 265                 270

Ser Ser Ile Asp Lys Ser Asp Pro Thr Lys Asp Pro Asp Phe Asp
            275                 280                 285

Thr Ala Ala Thr Ala Thr Thr Ser Lys Glu Gly Leu Gly Ile Gln Gly
    290                 295                 300

Asp Ile Thr Met Ser Lys Gly Glu Glu Leu Phe Thr Gly Val Val Pro
305                 310                 315                 320

Ile Leu Val Glu Leu Asp Gly Asp Val Asn Gly His Lys Phe Ser Val
                325                 330                 335

Ser Gly Glu Gly Glu Gly Asp Ala Thr Tyr Gly Lys Leu Thr Leu Lys
                340                 345                 350

Phe Ile Cys Thr Thr Gly Lys Leu Pro Val Pro Trp Pro Thr Leu Val
                355                 360                 365

Thr Thr Phe Ser Tyr Gly Val Gln Cys Phe Ser Arg Tyr Pro Asp His
    370                 375                 380

Met Lys Arg His Asp Phe Phe Lys Ser Ala Met Pro Glu Gly Tyr Val
385                 390                 395                 400

Gln Glu Arg Thr Ile Ser Phe Lys Asp Asp Gly Asn Tyr Lys Thr Arg
                405                 410                 415

Ala Glu Val Lys Phe Glu Gly Asp Thr Leu Val Asn Arg Ile Glu Leu
                420                 425                 430

Lys Gly Ile Asp Phe Lys Glu Asp Gly Asn Ile Leu Gly His Lys Leu
            435                 440                 445

Glu Tyr Asn Tyr Asn Ser His Asn Val Tyr Ile Thr Ala Asp Lys Gln
450                 455                 460

Lys Asn Gly Ile Lys Ala Asn Phe Lys Ile Arg His Asn Ile Glu Asp
465                 470                 475                 480

Gly Ser Val Gln Leu Ala Asp His Tyr Gln Gln Asn Thr Pro Ile Gly
                485                 490                 495

Asp Gly Pro Val Leu Leu Pro Asp Asn His Tyr Leu Ser Thr Gln Ser
                500                 505                 510

Ala Leu Ser Lys Asp Pro Asn Glu Lys Arg Asp His Met Val Leu Leu
            515                 520                 525

Glu Phe Val Thr Ala Ala Gly Ile Thr His Gly Met Asp Glu Leu Tyr
    530                 535                 540

Lys
545

<210> SEQ ID NO 53
<211> LENGTH: 3579
<212> TYPE: DNA
<213> ORGANISM: Artificial
<220> FEATURE:
<223> OTHER INFORMATION: Synthetic Sequence
<220> FEATURE:
<221> NAME/KEY: gene
<222> LOCATION: (1)..(3579)
<223> OTHER INFORMATION: Gene for H+-ATPase:PS(NIa protease):GFP hybrid
```

```
        protein
<220> FEATURE:
<221> NAME/KEY: CDS
<222> LOCATION: (1)..(3576)
<223> OTHER INFORMATION: H+-ATPase:PS(NIa protease):GFP hybrid protein
<220> FEATURE:
<221> NAME/KEY: misc_feature
<223> OTHER INFORMATION: CDS:H+-ATPase(1..2844); CDS:NIa protease
      cleavage sequence(2851..2862); CDS:GFP(2863..3576)

<400> SEQUENCE: 53 atg tcg agt ctc gaa gat atc aag aac gag act gtt gat ctg gaa aaa         48
Met Ser Ser Leu Glu Asp Ile Lys Asn Glu Thr Val Asp Leu Glu Lys
1               5                  10                  15 att ccg att gag gaa gtt ttc cag cag cta aaa tgt tca agg gaa gga         96
Ile Pro Ile Glu Glu Val Phe Gln Gln Leu Lys Cys Ser Arg Glu Gly
            20                  25                  30 ttg aca acg cag gaa ggg gag gac agg att cag atc ttt ggc ccc aac        144
Leu Thr Thr Gln Glu Gly Glu Asp Arg Ile Gln Ile Phe Gly Pro Asn
        35                  40                  45 aag ctc gaa gag aaa aag gaa agc aaa ctt ctg aag ttt ttg ggg ttt        192
Lys Leu Glu Glu Lys Lys Glu Ser Lys Leu Leu Lys Phe Leu Gly Phe
    50                  55                  60 atg tgg aat cca ctt tca tgg gtc atg gaa atg gct gca atc atg gcc        240
Met Trp Asn Pro Leu Ser Trp Val Met Glu Met Ala Ala Ile Met Ala
65                  70                  75                  80 att gct ttg gcc aac ggt gat ggt agg cct ccg gat tgg cag gat ttt        288
Ile Ala Leu Ala Asn Gly Asp Gly Arg Pro Pro Asp Trp Gln Asp Phe
                85                  90                  95 gtt ggt att atc tgt ctg ttg gtt atc aac tct acc atc agt ttt atc        336
Val Gly Ile Ile Cys Leu Leu Val Ile Asn Ser Thr Ile Ser Phe Ile
            100                 105                 110 gaa gaa aac aat gct ggt aat gct gct gct gct ctt atg gct ggt ctt        384
Glu Glu Asn Asn Ala Gly Asn Ala Ala Ala Ala Leu Met Ala Gly Leu
        115                 120                 125 gct cct aaa acc aag gtt ctt agg gat gga aag tgg agt gaa caa gaa        432
Ala Pro Lys Thr Lys Val Leu Arg Asp Gly Lys Trp Ser Glu Gln Glu
    130                 135                 140 gct gct att ctt gtc cca gga gat att gtt agc att aaa tta gga gac        480
Ala Ala Ile Leu Val Pro Gly Asp Ile Val Ser Ile Lys Leu Gly Asp
145                 150                 155                 160 att atc cca gct gat gcc cgt cta ctt gaa ggt gat cct tta aag gtt        528
Ile Ile Pro Ala Asp Ala Arg Leu Leu Glu Gly Asp Pro Leu Lys Val
                165                 170                 175 gac caa tct gct cta act gga gag tcc ctt cct gta acc aag cac ccg        576
Asp Gln Ser Ala Leu Thr Gly Glu Ser Leu Pro Val Thr Lys His Pro
            180                 185                 190 ggt caa gaa gtt ttc tct ggt tca acc tgc aaa caa gga gaa atc gag        624
Gly Gln Glu Val Phe Ser Gly Ser Thr Cys Lys Gln Gly Glu Ile Glu
        195                 200                 205 gcg gtt gtt att gcc act ggg gtt cat acc ttc ttc ggt aaa gct gct        672
Ala Val Val Ile Ala Thr Gly Val His Thr Phe Phe Gly Lys Ala Ala
    210                 215                 220 cac ctt gtg gac agc act aac caa gtt gga cat ttc cag aag gtt ctt        720
His Leu Val Asp Ser Thr Asn Gln Val Gly His Phe Gln Lys Val Leu
225                 230                 235                 240 aca gcc att ggg aac ttc tgt atc tgt tcc att gct atc ggt atg gtg        768
Thr Ala Ile Gly Asn Phe Cys Ile Cys Ser Ile Ala Ile Gly Met Val
                245                 250                 255 att gag atc atc gtc atg tat ccg atc caa cgc cga aag tac aga gat        816
Ile Glu Ile Ile Val Met Tyr Pro Ile Gln Arg Arg Lys Tyr Arg Asp
            260                 265                 270
```

-continued

```
gga att gac aac ctt ttg gtc ctc ttg atc ggt ggt atc ccc att gct      864
Gly Ile Asp Asn Leu Leu Val Leu Leu Ile Gly Gly Ile Pro Ile Ala
        275                 280                 285 atg cct aca gtc ttg tcc gtg acc atg gct att ggg tct cac agg ttg      912
Met Pro Thr Val Leu Ser Val Thr Met Ala Ile Gly Ser His Arg Leu
    290                 295                 300 tct cag caa ggt gcc atc acc aag cgt atg act gcc att gaa gag atg      960
Ser Gln Gln Gly Ala Ile Thr Lys Arg Met Thr Ala Ile Glu Glu Met
305                 310                 315                 320 gca gga atg gat gtc ctg tgc agt gac aaa acc ggg aca cta acc ctc     1008
Ala Gly Met Asp Val Leu Cys Ser Asp Lys Thr Gly Thr Leu Thr Leu
                325                 330                 335 aac aaa ttg agt gtg gac aaa aac ttg gtc gag gtt ttc tgc aag ggt     1056
Asn Lys Leu Ser Val Asp Lys Asn Leu Val Glu Val Phe Cys Lys Gly
            340                 345                 350 gtg gag aaa gat caa gtc cta tta ttt gca gct atg gct tcc agg gtt     1104
Val Glu Lys Asp Gln Val Leu Leu Phe Ala Ala Met Ala Ser Arg Val
        355                 360                 365 gag aac cag gat gcc att gat gca gcc atg gtt ggg atg ctt gct gat     1152
Glu Asn Gln Asp Ala Ile Asp Ala Ala Met Val Gly Met Leu Ala Asp
370                 375                 380 cca aag gag gct aga gct gga atc agg gaa gtt cac ttc ctt cca ttc     1200
Pro Lys Glu Ala Arg Ala Gly Ile Arg Glu Val His Phe Leu Pro Phe
385                 390                 395                 400 aac cct gtg gat aag aga act gct ttg act tac att gac ggc agt ggt     1248
Asn Pro Val Asp Lys Arg Thr Ala Leu Thr Tyr Ile Asp Gly Ser Gly
                405                 410                 415 aac tgg cac aga gtc agt aaa ggt gct cct gag cag atc ctc gaa ctt     1296
Asn Trp His Arg Val Ser Lys Gly Ala Pro Glu Gln Ile Leu Glu Leu
            420                 425                 430 gcc aaa gcc agc aat gat ctt agc aag aag gtg ctc tcc att att gac     1344
Ala Lys Ala Ser Asn Asp Leu Ser Lys Lys Val Leu Ser Ile Ile Asp
        435                 440                 445 aag tat gct gag cgt ggt ctt agg tcg ttg gct gtt gct cgc cag gtg     1392
Lys Tyr Ala Glu Arg Gly Leu Arg Ser Leu Ala Val Ala Arg Gln Val
    450                 455                 460 gtg cca gag aaa aca aag gaa agc cca ggt gcg cca tgg gaa ttt gtt     1440
Val Pro Glu Lys Thr Lys Glu Ser Pro Gly Ala Pro Trp Glu Phe Val
465                 470                 475                 480 ggc ttg ttg cca ctt ttt gat ccc cca aga cat gac agt gct gaa aca     1488
Gly Leu Leu Pro Leu Phe Asp Pro Pro Arg His Asp Ser Ala Glu Thr
                485                 490                 495 att cga cgg gct ttg aat ctt ggt gtt aac gtc aag atg atc act ggt     1536
Ile Arg Arg Ala Leu Asn Leu Gly Val Asn Val Lys Met Ile Thr Gly
            500                 505                 510 gac caa ctt gct att ggt aag gaa act ggt cgc aga ctt gga atg gga     1584
Asp Gln Leu Ala Ile Gly Lys Glu Thr Gly Arg Arg Leu Gly Met Gly
        515                 520                 525 aca aac atg tat cca tct tcg gct ctt ctt ggt aca cac aaa gac gca     1632
Thr Asn Met Tyr Pro Ser Ser Ala Leu Leu Gly Thr His Lys Asp Ala
    530                 535                 540 aac ctc gca tcc att cct gtt gag gag ttg att gaa aag gct gat gga     1680
Asn Leu Ala Ser Ile Pro Val Glu Glu Leu Ile Glu Lys Ala Asp Gly
545                 550                 555                 560 ttt gcc gga gtc ttc cca gag cac aaa tac gaa att gtg aaa aag ttg     1728
Phe Ala Gly Val Phe Pro Glu His Lys Tyr Glu Ile Val Lys Lys Leu
                565                 570                 575 cag gag agg aag cat att gtt gga atg act ggt gat ggt gtc aat gat     1776
Gln Glu Arg Lys His Ile Val Gly Met Thr Gly Asp Gly Val Asn Asp
```

```
                580                 585                 590
gcc cct gct cta aag aaa gct gat atc ggt att gct gtt gct gat gct      1824
Ala Pro Ala Leu Lys Lys Ala Asp Ile Gly Ile Ala Val Ala Asp Ala
        595                 600                 605 aca gat gct gct cgt ggt gct tca gat atc gtg ctc act gag cct gga      1872
Thr Asp Ala Ala Arg Gly Ala Ser Asp Ile Val Leu Thr Glu Pro Gly
610                 615                 620 ctc agc gtt att atc agt gct gtt ctc acc agc aga gct att ttc cag      1920
Leu Ser Val Ile Ile Ser Ala Val Leu Thr Ser Arg Ala Ile Phe Gln
625                 630                 635                 640 aga atg aag aac tat act atc tat gca gtc tca atc acc atc cgt att      1968
Arg Met Lys Asn Tyr Thr Ile Tyr Ala Val Ser Ile Thr Ile Arg Ile
                645                 650                 655 gtg ttt ggt ttc atg ctt att gct ttg ata tgg gaa ttt gac ttc tca      2016
Val Phe Gly Phe Met Leu Ile Ala Leu Ile Trp Glu Phe Asp Phe Ser
            660                 665                 670 gcc ttc atg gtt ctg atc att gcc att ctt aac gac ggt acc atc atg      2064
Ala Phe Met Val Leu Ile Ile Ala Ile Leu Asn Asp Gly Thr Ile Met
        675                 680                 685 aca atc tca aag gac aga gtt aag cca tct ccc aca cct gat agc tgg      2112
Thr Ile Ser Lys Asp Arg Val Lys Pro Ser Pro Thr Pro Asp Ser Trp
690                 695                 700 aaa ctt aaa gaa att ttt gct act gga gtc gtt cta gga ggc tac cag      2160
Lys Leu Lys Glu Ile Phe Ala Thr Gly Val Val Leu Gly Gly Tyr Gln
705                 710                 715                 720 gcc atc atg act gtt att ttc ttc tgg gcg gcg cac aag act gac ttt      2208
Ala Ile Met Thr Val Ile Phe Phe Trp Ala Ala His Lys Thr Asp Phe
                725                 730                 735 ttc tcg gac aca ttc ggt gtg agg tcc att agg gac aat aac cac gag      2256
Phe Ser Asp Thr Phe Gly Val Arg Ser Ile Arg Asp Asn Asn His Glu
            740                 745                 750 cta atg ggt gcg gtg tac tta caa gtt agt atc att agt caa gct ctg      2304
Leu Met Gly Ala Val Tyr Leu Gln Val Ser Ile Ile Ser Gln Ala Leu
        755                 760                 765 atc ttc gtc aca aga tca agg agt tgg tct ttt gtt gaa cgt cct gga      2352
Ile Phe Val Thr Arg Ser Arg Ser Trp Ser Phe Val Glu Arg Pro Gly
770                 775                 780 gca ttg ctg atg att gct ttc ctc att gca caa ctg att gct act ttg      2400
Ala Leu Leu Met Ile Ala Phe Leu Ile Ala Gln Leu Ile Ala Thr Leu
785                 790                 795                 800 att gcg gtt tac gcc aac tgg gaa ttt gca aag att agg ggt att gga      2448
Ile Ala Val Tyr Ala Asn Trp Glu Phe Ala Lys Ile Arg Gly Ile Gly
                805                 810                 815 tgg gga tgg gct ggt gtg atc tgg cta tac agt att gtc aca tac ttc      2496
Trp Gly Trp Ala Gly Val Ile Trp Leu Tyr Ser Ile Val Thr Tyr Phe
            820                 825                 830 cca ttg gac gtt ttc aag ttt gcc att cga tac atc ttg agc gga aag      2544
Pro Leu Asp Val Phe Lys Phe Ala Ile Arg Tyr Ile Leu Ser Gly Lys
        835                 840                 845 gcg tgg ctc aac ttg ttt gag aac aag acg gct ttc acg atg aag aaa      2592
Ala Trp Leu Asn Leu Phe Glu Asn Lys Thr Ala Phe Thr Met Lys Lys
850                 855                 860 gat tac gga aaa gaa gag aga gag gct caa tgg gca ctt gct caa agg      2640
Asp Tyr Gly Lys Glu Glu Arg Glu Ala Gln Trp Ala Leu Ala Gln Arg
865                 870                 875                 880 aca ctt cac ggt tta cag cca aaa gaa gct gtt aac atc ttc cct gag      2688
Thr Leu His Gly Leu Gln Pro Lys Glu Ala Val Asn Ile Phe Pro Glu
                885                 890                 895 aaa gga agt tac aga gaa ttg tct gag atc gct gag caa gct aag aga      2736
```

```
                                                          -continued

Lys Gly Ser Tyr Arg Glu Leu Ser Glu Ile Ala Glu Gln Ala Lys Arg
        900                 905                 910 aga gct gag atc gct agg ctt agg gag ctg cac aca ctc aag gga cat        2784
Arg Ala Glu Ile Ala Arg Leu Arg Glu Leu His Thr Leu Lys Gly His
            915                 920                 925 gtg gaa tca gtc gtg aag cta aag ggc ttg gac att gaa act ccc agt        2832
Val Glu Ser Val Val Lys Leu Lys Gly Leu Asp Ile Glu Thr Pro Ser
930                 935                 940 cac tac act gtg ctc gag gtg cgc ttc cag atg agt aaa gga gaa gaa        2880
His Tyr Thr Val Leu Glu Val Arg Phe Gln Met Ser Lys Gly Glu Glu
945                 950                 955                 960 ctt ttc act gga gtt gtc cca att ctt gtt gaa tta gat ggt gat gtt        2928
Leu Phe Thr Gly Val Val Pro Ile Leu Val Glu Leu Asp Gly Asp Val
                965                 970                 975 aat ggg cac aaa ttt tct gtc agt gga gag ggt gaa ggt gat gca aca        2976
Asn Gly His Lys Phe Ser Val Ser Gly Glu Gly Glu Gly Asp Ala Thr
            980                 985                 990 tac gga aaa ctt acc ctt aaa ttt att tgc act act gga aaa cta cct        3024
Tyr Gly Lys Leu Thr Leu Lys Phe Ile Cys Thr Thr Gly Lys Leu Pro
        995                 1000                1005 gtt cca tgg cca aca ctt gtc act act ttc tct tat ggt gtt caa        3069
Val Pro Trp Pro Thr Leu Val Thr Thr Phe Ser Tyr Gly Val Gln
    1010                1015                1020 tgc ttt tca aga tac cca gat cat atg aag cgg cac gac ttc ttc        3114
Cys Phe Ser Arg Tyr Pro Asp His Met Lys Arg His Asp Phe Phe
    1025                1030                1035 aag agc gcc atg cct gag gga tac gtg cag gag agg acc atc tct        3159
Lys Ser Ala Met Pro Glu Gly Tyr Val Gln Glu Arg Thr Ile Ser
    1040                1045                1050 ttc aag gac gac ggg aac tac aag aca cgt gct gaa gtc aag ttt        3204
Phe Lys Asp Asp Gly Asn Tyr Lys Thr Arg Ala Glu Val Lys Phe
    1055                1060                1065 gag gga gac acc ctc gtc aac agg atc gag ctt aag gga atc gat        3249
Glu Gly Asp Thr Leu Val Asn Arg Ile Glu Leu Lys Gly Ile Asp
    1070                1075                1080 ttc aag gag gac gga aac atc ctc ggc cac aag ttg gaa tac aac        3294
Phe Lys Glu Asp Gly Asn Ile Leu Gly His Lys Leu Glu Tyr Asn
    1085                1090                1095 tac aac tcc cac aac gta tac atc acg gca gac aaa caa aag aat        3339
Tyr Asn Ser His Asn Val Tyr Ile Thr Ala Asp Lys Gln Lys Asn
    1100                1105                1110 gga atc aaa gct aac ttc aaa att aga cac aac att gaa gat gga        3384
Gly Ile Lys Ala Asn Phe Lys Ile Arg His Asn Ile Glu Asp Gly
    1115                1120                1125 agc gtt caa cta gca gac cat tat caa caa aat act cca att ggc        3429
Ser Val Gln Leu Ala Asp His Tyr Gln Gln Asn Thr Pro Ile Gly
    1130                1135                1140 gat ggc cct gtc ctt tta cca gac aac cat tac ctg tcc aca caa        3474
Asp Gly Pro Val Leu Leu Pro Asp Asn His Tyr Leu Ser Thr Gln
    1145                1150                1155 tct gcc ctt tcg aaa gat ccc aac gaa aag aga gac cac atg gtc        3519
Ser Ala Leu Ser Lys Asp Pro Asn Glu Lys Arg Asp His Met Val
    1160                1165                1170 ctt ctt gag ttt gta aca gct gct ggg att aca cat ggc atg gat        3564
Leu Leu Glu Phe Val Thr Ala Ala Gly Ile Thr His Gly Met Asp
    1175                1180                1185 gaa cta tac aaa taa                                                3579
Glu Leu Tyr Lys
    1190
```

<210> SEQ ID NO 54
<211> LENGTH: 1192
<212> TYPE: PRT
<213> ORGANISM: Artificial
<220> FEATURE:
<223> OTHER INFORMATION: Synthetic Sequence

<400> SEQUENCE: 54

```
Met Ser Ser Leu Glu Asp Ile Lys Asn Glu Thr Val Asp Leu Glu Lys
1               5                   10                  15

Ile Pro Ile Glu Glu Val Phe Gln Gln Leu Lys Cys Ser Arg Glu Gly
            20                  25                  30

Leu Thr Thr Gln Glu Gly Glu Asp Arg Ile Gln Ile Phe Gly Pro Asn
        35                  40                  45

Lys Leu Glu Glu Lys Lys Glu Ser Lys Leu Leu Lys Phe Leu Gly Phe
    50                  55                  60

Met Trp Asn Pro Leu Ser Trp Val Met Glu Met Ala Ala Ile Met Ala
65                  70                  75                  80

Ile Ala Leu Ala Asn Gly Asp Gly Arg Pro Pro Asp Trp Gln Asp Phe
                85                  90                  95

Val Gly Ile Ile Cys Leu Leu Val Ile Asn Ser Thr Ile Ser Phe Ile
            100                 105                 110

Glu Glu Asn Asn Ala Gly Asn Ala Ala Ala Leu Met Ala Gly Leu
            115                 120                 125

Ala Pro Lys Thr Lys Val Leu Arg Asp Gly Lys Trp Ser Glu Gln Glu
    130                 135                 140

Ala Ala Ile Leu Val Pro Gly Asp Ile Val Ser Ile Lys Leu Gly Asp
145                 150                 155                 160

Ile Ile Pro Ala Asp Ala Arg Leu Leu Glu Gly Asp Pro Leu Lys Val
                165                 170                 175

Asp Gln Ser Ala Leu Thr Gly Glu Ser Leu Pro Val Thr Lys His Pro
            180                 185                 190

Gly Gln Glu Val Phe Ser Gly Ser Thr Cys Lys Gln Gly Glu Ile Glu
        195                 200                 205

Ala Val Val Ile Ala Thr Gly Val His Thr Phe Phe Gly Lys Ala Ala
    210                 215                 220

His Leu Val Asp Ser Thr Asn Gln Val Gly His Phe Gln Lys Val Leu
225                 230                 235                 240

Thr Ala Ile Gly Asn Phe Cys Ile Cys Ser Ile Ala Ile Gly Met Val
                245                 250                 255

Ile Glu Ile Ile Val Met Tyr Pro Ile Gln Arg Arg Lys Tyr Arg Asp
            260                 265                 270

Gly Ile Asp Asn Leu Leu Val Leu Leu Ile Gly Gly Ile Pro Ile Ala
        275                 280                 285

Met Pro Thr Val Leu Ser Val Thr Met Ala Ile Gly Ser His Arg Leu
    290                 295                 300

Ser Gln Gln Gly Ala Ile Thr Lys Arg Met Thr Ala Ile Glu Glu Met
305                 310                 315                 320

Ala Gly Met Asp Val Leu Cys Ser Asp Lys Thr Gly Thr Leu Thr Leu
                325                 330                 335

Asn Lys Leu Ser Val Asp Lys Asn Leu Val Glu Val Phe Cys Lys Gly
            340                 345                 350

Val Glu Lys Asp Gln Val Leu Leu Phe Ala Ala Met Ala Ser Arg Val
        355                 360                 365
```

-continued

```
Glu Asn Gln Asp Ala Ile Asp Ala Ala Met Val Gly Met Leu Ala Asp
    370                 375                 380
Pro Lys Glu Ala Arg Ala Gly Ile Arg Glu Val His Phe Leu Pro Phe
385                 390                 395                 400
Asn Pro Val Asp Lys Arg Thr Ala Leu Thr Tyr Ile Asp Gly Ser Gly
                405                 410                 415
Asn Trp His Arg Val Ser Lys Gly Ala Pro Glu Gln Ile Leu Glu Leu
                420                 425                 430
Ala Lys Ala Ser Asn Asp Leu Ser Lys Lys Val Leu Ser Ile Ile Asp
            435                 440                 445
Lys Tyr Ala Glu Arg Gly Leu Arg Ser Leu Ala Val Ala Arg Gln Val
    450                 455                 460
Val Pro Glu Lys Thr Lys Glu Ser Pro Gly Ala Pro Trp Glu Phe Val
465                 470                 475                 480
Gly Leu Leu Pro Leu Phe Asp Pro Pro Arg His Asp Ser Ala Glu Thr
                485                 490                 495
Ile Arg Arg Ala Leu Asn Leu Gly Val Asn Val Lys Met Ile Thr Gly
                500                 505                 510
Asp Gln Leu Ala Ile Gly Lys Glu Thr Gly Arg Arg Leu Gly Met Gly
            515                 520                 525
Thr Asn Met Tyr Pro Ser Ser Ala Leu Leu Gly Thr His Lys Asp Ala
    530                 535                 540
Asn Leu Ala Ser Ile Pro Val Glu Glu Leu Ile Glu Lys Ala Asp Gly
545                 550                 555                 560
Phe Ala Gly Val Phe Pro Glu His Lys Tyr Glu Ile Val Lys Lys Leu
                565                 570                 575
Gln Glu Arg Lys His Ile Val Gly Met Thr Gly Asp Gly Val Asn Asp
            580                 585                 590
Ala Pro Ala Leu Lys Lys Ala Asp Ile Gly Ile Ala Val Ala Asp Ala
    595                 600                 605
Thr Asp Ala Ala Arg Gly Ala Ser Asp Ile Val Leu Thr Glu Pro Gly
    610                 615                 620
Leu Ser Val Ile Ile Ser Ala Val Leu Thr Ser Arg Ala Ile Phe Gln
625                 630                 635                 640
Arg Met Lys Asn Tyr Thr Ile Tyr Ala Val Ser Ile Thr Ile Arg Ile
                645                 650                 655
Val Phe Gly Phe Met Leu Ile Ala Leu Ile Trp Glu Phe Asp Phe Ser
                660                 665                 670
Ala Phe Met Val Leu Ile Ile Ala Ile Leu Asn Asp Gly Thr Ile Met
            675                 680                 685
Thr Ile Ser Lys Asp Arg Val Lys Pro Ser Pro Thr Pro Asp Ser Trp
    690                 695                 700
Lys Leu Lys Glu Ile Phe Ala Thr Gly Val Val Leu Gly Gly Tyr Gln
705                 710                 715                 720
Ala Ile Met Thr Val Ile Phe Phe Trp Ala Ala His Lys Thr Asp Phe
                725                 730                 735
Phe Ser Asp Thr Phe Gly Val Arg Ser Ile Arg Asp Asn Asn His Glu
                740                 745                 750
Leu Met Gly Ala Val Tyr Leu Gln Val Ser Ile Ser Gln Ala Leu
            755                 760                 765
Ile Phe Val Thr Arg Ser Arg Ser Trp Ser Phe Val Glu Arg Pro Gly
    770                 775                 780
Ala Leu Leu Met Ile Ala Phe Leu Ile Ala Gln Leu Ile Ala Thr Leu
```

-continued

```
            785                 790                 795                 800
Ile Ala Val Tyr Ala Asn Trp Glu Phe Ala Lys Ile Arg Gly Ile Gly
                805                 810                 815

Trp Gly Trp Ala Gly Val Ile Trp Leu Tyr Ser Ile Val Thr Tyr Phe
                820                 825                 830

Pro Leu Asp Val Phe Lys Phe Ala Ile Arg Tyr Ile Leu Ser Gly Lys
                835                 840                 845

Ala Trp Leu Asn Leu Phe Glu Asn Lys Thr Ala Phe Thr Met Lys Lys
    850                 855                 860

Asp Tyr Gly Lys Glu Glu Arg Glu Ala Gln Trp Ala Leu Ala Gln Arg
865                 870                 875                 880

Thr Leu His Gly Leu Gln Pro Lys Ala Val Asn Ile Phe Pro Glu
                885                 890                 895

Lys Gly Ser Tyr Arg Glu Leu Ser Glu Ile Ala Glu Gln Ala Lys Arg
                900                 905                 910

Arg Ala Glu Ile Ala Arg Leu Arg Glu Leu His Thr Leu Lys Gly His
                915                 920                 925

Val Glu Ser Val Val Lys Leu Lys Gly Leu Asp Ile Glu Thr Pro Ser
            930                 935                 940

His Tyr Thr Val Leu Glu Val Arg Phe Gln Met Ser Lys Gly Glu Glu
945                 950                 955                 960

Leu Phe Thr Gly Val Val Pro Ile Leu Val Glu Leu Asp Gly Asp Val
                965                 970                 975

Asn Gly His Lys Phe Ser Val Ser Gly Glu Gly Glu Gly Asp Ala Thr
                980                 985                 990

Tyr Gly Lys Leu Thr Leu Lys Phe  Ile Cys Thr Thr Gly  Lys Leu Pro
                995                 1000                1005

Val Pro  Trp Pro Thr Leu Val  Thr Thr Phe Ser Tyr  Gly Val Gln
    1010                1015                1020

Cys Phe  Ser Arg Tyr Pro Asp  His Met Lys Arg His  Asp Phe Phe
    1025                1030                1035

Lys Ser  Ala Met Pro Glu Gly  Tyr Val Gln Glu Arg  Thr Ile Ser
    1040                1045                1050

Phe Lys  Asp Asp Gly Asn Tyr  Lys Thr Arg Ala Glu  Val Lys Phe
    1055                1060                1065

Glu Gly  Asp Thr Leu Val Asn  Arg Ile Glu Leu Lys  Gly Ile Asp
    1070                1075                1080

Phe Lys  Glu Asp Gly Asn Ile  Leu Gly His Lys Leu  Glu Tyr Asn
    1085                1090                1095

Tyr Asn  Ser His Asn Val Tyr  Ile Thr Ala Asp Lys  Gln Lys Asn
    1100                1105                1110

Gly Ile  Lys Ala Asn Phe Lys  Ile Arg His Asn Ile  Glu Asp Gly
    1115                1120                1125

Ser Val  Gln Leu Ala Asp His  Tyr Gln Gln Asn Thr  Pro Ile Gly
    1130                1135                1140

Asp Gly  Pro Val Leu Leu Pro  Asp Asn His Tyr Leu  Ser Thr Gln
    1145                1150                1155

Ser Ala  Leu Ser Lys Asp Pro  Asn Glu Lys Arg Asp  His Met Val
    1160                1165                1170

Leu Leu  Glu Phe Val Thr Ala  Ala Gly Ile Thr His  Gly Met Asp
    1175                1180                1185

Glu Leu  Tyr Lys
    1190
```

```
<210> SEQ ID NO 55
<211> LENGTH: 303
<212> TYPE: DNA
<213> ORGANISM: Human immunodeficiency virus type 1
<220> FEATURE:
<221> NAME/KEY: gene
<222> LOCATION: (1)..(303)
<223> OTHER INFORMATION: Gene for HIV-1 protease
<220> FEATURE:
<221> NAME/KEY: CDS
<222> LOCATION: (1)..(300)
<223> OTHER INFORMATION: HIV-1 protease
<300> PUBLICATION INFORMATION:
<308> DATABASE ACCESSION NUMBER: GenBank/U31398
<309> DATABASE ENTRY DATE: 1996-03-07

<400> SEQUENCE: 55 atg cct cag gtc act ctt tgg caa cga ccc ctc gtc aca ata aag ata      48
Met Pro Gln Val Thr Leu Trp Gln Arg Pro Leu Val Thr Ile Lys Ile
1               5                   10                  15 ggg gga caa cta aag gaa gct cta tta gat aca gga gca gat gat aca      96
Gly Gly Gln Leu Lys Glu Ala Leu Leu Asp Thr Gly Ala Asp Asp Thr
                20                  25                  30 gta tta gaa gaa atg agt ttg cca gga aga tgg aaa cca aaa atg ata     144
Val Leu Glu Glu Met Ser Leu Pro Gly Arg Trp Lys Pro Lys Met Ile
        35                  40                  45 ggg gga att gga ggt ttt atc aaa gta aga cag tat gat cag ata ctc     192
Gly Gly Ile Gly Gly Phe Ile Lys Val Arg Gln Tyr Asp Gln Ile Leu
    50                  55                  60 ata gaa atc tgt gga cat aaa gct ata ggt aca gta tta gta gga cct     240
Ile Glu Ile Cys Gly His Lys Ala Ile Gly Thr Val Leu Val Gly Pro
65                  70                  75                  80 aca cct gtc aac ata att gga aga aat ctg ttg act cag att ggt tgc     288
Thr Pro Val Asn Ile Ile Gly Arg Asn Leu Leu Thr Gln Ile Gly Cys
                85                  90                  95 act tta aat ttt tga                                                  303
Thr Leu Asn Phe
            100

<210> SEQ ID NO 56
<211> LENGTH: 100
<212> TYPE: PRT
<213> ORGANISM: Human immunodeficiency virus type 1

<400> SEQUENCE: 56

Met Pro Gln Val Thr Leu Trp Gln Arg Pro Leu Val Thr Ile Lys Ile
1               5                   10                  15

Gly Gly Gln Leu Lys Glu Ala Leu Leu Asp Thr Gly Ala Asp Asp Thr
                20                  25                  30

Val Leu Glu Glu Met Ser Leu Pro Gly Arg Trp Lys Pro Lys Met Ile
        35                  40                  45

Gly Gly Ile Gly Gly Phe Ile Lys Val Arg Gln Tyr Asp Gln Ile Leu
    50                  55                  60

Ile Glu Ile Cys Gly His Lys Ala Ile Gly Thr Val Leu Val Gly Pro
65                  70                  75                  80

Thr Pro Val Asn Ile Ile Gly Arg Asn Leu Leu Thr Gln Ile Gly Cys
                85                  90                  95

Thr Leu Asn Phe
            100

<210> SEQ ID NO 57
```

```
<211> LENGTH: 21
<212> TYPE: DNA
<213> ORGANISM: Artificial
<220> FEATURE:
<223> OTHER INFORMATION: Synthetic Sequence
<220> FEATURE:
<221> NAME/KEY: CDS
<222> LOCATION: (1)..(21)
<223> OTHER INFORMATION: HIV-1 protease cleavage sequence

<400> SEQUENCE: 57 agc caa aat tac cct ata gtg                                          21
Ser Gln Asn Tyr Pro Ile Val
1               5

<210> SEQ ID NO 58
<211> LENGTH: 7
<212> TYPE: PRT
<213> ORGANISM: Artificial
<220> FEATURE:
<223> OTHER INFORMATION: Synthetic Sequence

<400> SEQUENCE: 58

Ser Gln Asn Tyr Pro Ile Val
1               5

<210> SEQ ID NO 59
<211> LENGTH: 21
<212> TYPE: DNA
<213> ORGANISM: Artificial
<220> FEATURE:
<223> OTHER INFORMATION: Synthetic Sequence
<220> FEATURE:
<221> NAME/KEY: CDS
<222> LOCATION: (1)..(21)
<223> OTHER INFORMATION: HIV-1 protease cleavage sequence

<400> SEQUENCE: 59 gca aga gtt ttg gct gaa gca                                          21
Ala Arg Val Leu Ala Glu Ala
1               5

<210> SEQ ID NO 60
<211> LENGTH: 7
<212> TYPE: PRT
<213> ORGANISM: Artificial
<220> FEATURE:
<223> OTHER INFORMATION: Synthetic Sequence

<400> SEQUENCE: 60

Ala Arg Val Leu Ala Glu Ala
1               5

<210> SEQ ID NO 61
<211> LENGTH: 21
<212> TYPE: DNA
<213> ORGANISM: Artificial
<220> FEATURE:
<223> OTHER INFORMATION: Synthetic Sequence
<220> FEATURE:
<221> NAME/KEY: CDS
<222> LOCATION: (1)..(21)
<223> OTHER INFORMATION: HIV-1 protease cleavage sequence

<400> SEQUENCE: 61 gct acc ata atg atg cag aga                                          21
Ala Thr Ile Met Met Gln Arg
1               5
```

```
<210> SEQ ID NO 62
<211> LENGTH: 7
<212> TYPE: PRT
<213> ORGANISM: Artificial
<220> FEATURE:
<223> OTHER INFORMATION: Synthetic Sequence

<400> SEQUENCE: 62

Ala Thr Ile Met Met Gln Arg
1               5

<210> SEQ ID NO 63
<211> LENGTH: 21
<212> TYPE: DNA
<213> ORGANISM: Artificial
<220> FEATURE:
<223> OTHER INFORMATION: Synthetic Sequence
<220> FEATURE:
<221> NAME/KEY: CDS
<222> LOCATION: (1)..(21)
<223> OTHER INFORMATION: HIV-1 protease cleavage sequence

<400> SEQUENCE: 63 aga cag gct aat ttt tta ggg                                          21
Arg Gln Ala Asn Phe Leu Gly
1               5

<210> SEQ ID NO 64
<211> LENGTH: 7
<212> TYPE: PRT
<213> ORGANISM: Artificial
<220> FEATURE:
<223> OTHER INFORMATION: Synthetic Sequence

<400> SEQUENCE: 64

Arg Gln Ala Asn Phe Leu Gly
1               5

<210> SEQ ID NO 65
<211> LENGTH: 21
<212> TYPE: DNA
<213> ORGANISM: Artificial
<220> FEATURE:
<223> OTHER INFORMATION: Synthetic Sequence
<220> FEATURE:
<221> NAME/KEY: CDS
<222> LOCATION: (1)..(21)
<223> OTHER INFORMATION: HIV-1 protease cleavage sequence

<400> SEQUENCE: 65 cca ggg aat ttt ctt cag agc                                          21
Pro Gly Asn Phe Leu Gln Ser
1               5

<210> SEQ ID NO 66
<211> LENGTH: 7
<212> TYPE: PRT
<213> ORGANISM: Artificial
<220> FEATURE:
<223> OTHER INFORMATION: Synthetic Sequence

<400> SEQUENCE: 66

Pro Gly Asn Phe Leu Gln Ser
1               5

<210> SEQ ID NO 67
<211> LENGTH: 15
<212> TYPE: DNA
<213> ORGANISM: Artificial
```

```
<220> FEATURE:
<223> OTHER INFORMATION: Synthetic Sequence
<220> FEATURE:
<221> NAME/KEY: CDS
<222> LOCATION: (1)..(15)
<223> OTHER INFORMATION: HIV-1 protease cleavage sequence

<400> SEQUENCE: 67 agc gtg cct caa ata                                              15
Ser Val Pro Gln Ile
1               5

<210> SEQ ID NO 68
<211> LENGTH: 5
<212> TYPE: PRT
<213> ORGANISM: Artificial
<220> FEATURE:
<223> OTHER INFORMATION: Synthetic Sequence

<400> SEQUENCE: 68

Ser Val Pro Gln Ile
1               5

<210> SEQ ID NO 69
<211> LENGTH: 21
<212> TYPE: DNA
<213> ORGANISM: Artificial
<220> FEATURE:
<223> OTHER INFORMATION: Synthetic Sequence
<220> FEATURE:
<221> NAME/KEY: CDS
<222> LOCATION: (1)..(21)
<223> OTHER INFORMATION: HIV-1 protease cleavage sequence

<400> SEQUENCE: 69 act tta aat ttt ccc att agc                                      21
Thr Leu Asn Phe Pro Ile Ser
1               5

<210> SEQ ID NO 70
<211> LENGTH: 7
<212> TYPE: PRT
<213> ORGANISM: Artificial
<220> FEATURE:
<223> OTHER INFORMATION: Synthetic Sequence

<400> SEQUENCE: 70

Thr Leu Asn Phe Pro Ile Ser
1               5

<210> SEQ ID NO 71
<211> LENGTH: 21
<212> TYPE: DNA
<213> ORGANISM: Artificial
<220> FEATURE:
<223> OTHER INFORMATION: Synthetic Sequence
<220> FEATURE:
<221> NAME/KEY: CDS
<222> LOCATION: (1)..(21)
<223> OTHER INFORMATION: HIV-1 protease cleavage sequence

<400> SEQUENCE: 71 gca gaa acc ttc tat gta gat                                      21
Ala Glu Thr Phe Tyr Val Asp
1               5

<210> SEQ ID NO 72
<211> LENGTH: 7
<212> TYPE: PRT
```

```
<213> ORGANISM: Artificial
<220> FEATURE:
<223> OTHER INFORMATION: Synthetic Sequence

<400> SEQUENCE: 72

Ala Glu Thr Phe Tyr Val Asp
1               5

<210> SEQ ID NO 73
<211> LENGTH: 21
<212> TYPE: DNA
<213> ORGANISM: Artificial
<220> FEATURE:
<223> OTHER INFORMATION: Synthetic Sequence
<220> FEATURE:
<221> NAME/KEY: CDS
<222> LOCATION: (1)..(21)
<223> OTHER INFORMATION: HIV-1 protease cleavage sequence

<400> SEQUENCE: 73 agg aaa gta cta ttt tta gat                              21
Arg Lys Val Leu Phe Leu Asp
1               5

<210> SEQ ID NO 74
<211> LENGTH: 7
<212> TYPE: PRT
<213> ORGANISM: Artificial
<220> FEATURE:
<223> OTHER INFORMATION: Synthetic Sequence

<400> SEQUENCE: 74

Arg Lys Val Leu Phe Leu Asp
1               5

<210> SEQ ID NO 75
<211> LENGTH: 1647
<212> TYPE: DNA
<213> ORGANISM: Artificial
<220> FEATURE:
<223> OTHER INFORMATION: Synthetic Sequence
<220> FEATURE:
<221> NAME/KEY: gene
<222> LOCATION: (1)..(1647)
<223> OTHER INFORMATION: Gene for RFP:PS(HIV-1 protease):AtOEP7:GFP
      hybrid protein
<220> FEATURE:
<221> NAME/KEY: CDS
<222> LOCATION: (1)..(1644)
<223> OTHER INFORMATION: RFP:PS(HIV-1 protease):AtOEP7:GFP hybrid
      protein
<220> FEATURE:
<221> NAME/KEY: misc_feature
<223> OTHER INFORMATION: CDS: RFP(1..678); CDS: HIV-1 protease
      proteolytic site(700..720); CDS: AtOEP7(721..909); CDS:
      GFP(931..1644)

<400> SEQUENCE: 75 atg gtg cgc tcc tcc aag aac gtc atc aag gag ttc atg cgc ttc aag    48
Met Val Arg Ser Ser Lys Asn Val Ile Lys Glu Phe Met Arg Phe Lys
1               5                   10                  15 gtg cgc atg gag ggc acc gtg aac ggc cac gag ttc gag atc gag ggc    96
Val Arg Met Glu Gly Thr Val Asn Gly His Glu Phe Glu Ile Glu Gly
            20                  25                  30 gag ggc gag ggc cgc ccc tac gag ggc cac aac acc gtg aag ctg aag   144
Glu Gly Glu Gly Arg Pro Tyr Glu Gly His Asn Thr Val Lys Leu Lys
        35                  40                  45 gtg acc aag ggc ggc ccc ctg ccc ttc gcc tgg gac atc ctg tcc ccc   192
Val Thr Lys Gly Gly Pro Leu Pro Phe Ala Trp Asp Ile Leu Ser Pro
```

```
              50                   55                    60
cag ttc cag tac ggc tcc aag gtg tac gtg aag cac ccc gcc gac atc        240
Gln Phe Gln Tyr Gly Ser Lys Val Tyr Val Lys His Pro Ala Asp Ile
 65                  70                   75                  80 ccc gac tac aag aag ctg tcc ttc ccc gag ggc ttc aag tgg gag cgc        288
Pro Asp Tyr Lys Lys Leu Ser Phe Pro Glu Gly Phe Lys Trp Glu Arg
                 85                   90                  95 gtg atg aac ttc gag gac ggc ggc gtg gtg acc gtg acc cag gac tcc        336
Val Met Asn Phe Glu Asp Gly Gly Val Val Thr Val Thr Gln Asp Ser
            100                  105                 110 tcc ctg cag gac ggc tgc ttc atc tac aag gtg aag ttc atc ggc gtg        384
Ser Leu Gln Asp Gly Cys Phe Ile Tyr Lys Val Lys Phe Ile Gly Val
        115                  120                  125 aac ttc ccc tcc gac ggc ccc gta atg cag aag aag acc atg ggc tgg        432
Asn Phe Pro Ser Asp Gly Pro Val Met Gln Lys Lys Thr Met Gly Trp
    130                  135                  140 gag gcc tcc acc gag cgc ctg tac ccc cgc gac ggc gtg ctg aag ggc        480
Glu Ala Ser Thr Glu Arg Leu Tyr Pro Arg Asp Gly Val Leu Lys Gly
145                  150                  155                 160 gag atc cac aag gcc ctg aag ctg aag gac ggc ggc cac tac ctg gtg        528
Glu Ile His Lys Ala Leu Lys Leu Lys Asp Gly Gly His Tyr Leu Val
                 165                  170                 175 gag ttc aag tcc atc tac atg gcc aag aag ccc gtg cag ctg ccc ggc        576
Glu Phe Lys Ser Ile Tyr Met Ala Lys Lys Pro Val Gln Leu Pro Gly
            180                  185                 190 tac tac tac gtg gac tcc aag ctg gac atc acc tcc cac aac gag gac        624
Tyr Tyr Tyr Val Asp Ser Lys Leu Asp Ile Thr Ser His Asn Glu Asp
        195                  200                  205 tac acc atc gtg gag cag tac gag cgc acc gag ggc cgc cac cac ctg        672
Tyr Thr Ile Val Glu Gln Tyr Glu Arg Thr Glu Gly Arg His His Leu
    210                  215                  220 ttc ctg ccc cgg gca atc aag ctg ggt aga cag gct aat ttt tta ggg        720
Phe Leu Pro Arg Ala Ile Lys Leu Gly Arg Gln Ala Asn Phe Leu Gly
225                  230                  235                 240 gga aaa act tcg gga gcg aaa cag gcg act gtg gtg gtc gca gcg atg        768
Gly Lys Thr Ser Gly Ala Lys Gln Ala Thr Val Val Val Ala Ala Met
                 245                  250                 255 gcg tta gga tgg tta gcc ata gag atc gct ttc aag cct ttc ctc gat        816
Ala Leu Gly Trp Leu Ala Ile Glu Ile Ala Phe Lys Pro Phe Leu Asp
            260                  265                 270 aaa ttc cgc tcc tca atc gac aaa tct gac cca acc aaa gac ccc gat        864
Lys Phe Arg Ser Ser Ile Asp Lys Ser Asp Pro Thr Lys Asp Pro Asp
        275                  280                  285 gac ttc gac acc gcc gct act gca acc aca tcc aaa gag ggt ttg ggg        912
Asp Phe Asp Thr Ala Ala Thr Ala Thr Thr Ser Lys Glu Gly Leu Gly
    290                  295                  300 atc caa gga gat ata aca atg agt aaa gga gaa gaa ctt ttc act gga        960
Ile Gln Gly Asp Ile Thr Met Ser Lys Gly Glu Glu Leu Phe Thr Gly
305                  310                  315                 320 gtt gtc cca att ctt gtt gaa tta gat ggt gat gtt aat ggg cac aaa       1008
Val Val Pro Ile Leu Val Glu Leu Asp Gly Asp Val Asn Gly His Lys
                 325                  330                 335 ttt tct gtc agt gga gag ggt gaa ggt gat gca aca tac gga aaa ctt       1056
Phe Ser Val Ser Gly Glu Gly Glu Gly Asp Ala Thr Tyr Gly Lys Leu
            340                  345                 350 acc ctt aaa ttt att tgc act act gga aaa cta cct gtt cca tgg cca       1104
Thr Leu Lys Phe Ile Cys Thr Thr Gly Lys Leu Pro Val Pro Trp Pro
        355                  360                  365 aca ctt gtc act act ttc tct tat ggt gtt caa tgc ttt tca aga tac       1152
```

```
      Thr Leu Val Thr Thr Phe Ser Tyr Gly Val Gln Cys Phe Ser Arg Tyr
          370                 375                 380 cca gat cat atg aag cgg cac gac ttc ttc aag agc gcc atg cct gag         1200
Pro Asp His Met Lys Arg His Asp Phe Phe Lys Ser Ala Met Pro Glu
385                 390                 395                 400 gga tac gtg cag gag agg acc atc tct ttc aag gac gac ggg aac tac         1248
Gly Tyr Val Gln Glu Arg Thr Ile Ser Phe Lys Asp Asp Gly Asn Tyr
                405                 410                 415 aag aca cgt gct gaa gtc aag ttt gag gga gac acc ctc gtc aac agg         1296
Lys Thr Arg Ala Glu Val Lys Phe Glu Gly Asp Thr Leu Val Asn Arg
            420                 425                 430 atc gag ctt aag gga atc gat ttc aag gag gac gga aac atc ctc ggc         1344
Ile Glu Leu Lys Gly Ile Asp Phe Lys Glu Asp Gly Asn Ile Leu Gly
        435                 440                 445 cac aag ttg gaa tac aac tac aac tcc cac aac gta tac atc acg gca         1392
His Lys Leu Glu Tyr Asn Tyr Asn Ser His Asn Val Tyr Ile Thr Ala
    450                 455                 460 gac aaa caa aag aat gga atc aaa gct aac ttc aaa att aga cac aac         1440
Asp Lys Gln Lys Asn Gly Ile Lys Ala Asn Phe Lys Ile Arg His Asn
465                 470                 475                 480 att gaa gat gga agc gtt caa cta gca gac cat tat caa caa aat act         1488
Ile Glu Asp Gly Ser Val Gln Leu Ala Asp His Tyr Gln Gln Asn Thr
                485                 490                 495 cca att ggc gat ggc cct gtc ctt tta cca gac aac cat tac ctg tcc         1536
Pro Ile Gly Asp Gly Pro Val Leu Leu Pro Asp Asn His Tyr Leu Ser
            500                 505                 510 aca caa tct gcc ctt tcg aaa gat ccc aac gaa aag aga gac cac atg         1584
Thr Gln Ser Ala Leu Ser Lys Asp Pro Asn Glu Lys Arg Asp His Met
        515                 520                 525 gtc ctt ctt gag ttt gta aca gct gct ggg att aca cat ggc atg gat         1632
Val Leu Leu Glu Phe Val Thr Ala Ala Gly Ile Thr His Gly Met Asp
    530                 535                 540 gaa cta tac aaa taa                                                     1647
Glu Leu Tyr Lys
545

<210> SEQ ID NO 76
<211> LENGTH: 548
<212> TYPE: PRT
<213> ORGANISM: Artificial
<220> FEATURE:
<223> OTHER INFORMATION: Synthetic Sequence

<400> SEQUENCE: 76

Met Val Arg Ser Ser Lys Asn Val Ile Lys Glu Phe Met Arg Phe Lys
1               5                   10                  15

Val Arg Met Glu Gly Thr Val Asn Gly His Glu Phe Glu Ile Glu Gly
                20                  25                  30

Glu Gly Glu Gly Arg Pro Tyr Glu Gly His Asn Thr Val Lys Leu Lys
            35                  40                  45

Val Thr Lys Gly Gly Pro Leu Pro Phe Ala Trp Asp Ile Leu Ser Pro
        50                  55                  60

Gln Phe Gln Tyr Gly Ser Lys Val Tyr Val Lys His Pro Ala Asp Ile
65                  70                  75                  80

Pro Asp Tyr Lys Lys Leu Ser Phe Pro Glu Gly Phe Lys Trp Glu Arg
                85                  90                  95

Val Met Asn Phe Glu Asp Gly Gly Val Val Thr Val Thr Gln Asp Ser
            100                 105                 110

Ser Leu Gln Asp Gly Cys Phe Ile Tyr Lys Val Lys Phe Ile Gly Val
```

-continued

```
              115                 120                 125
Asn Phe Pro Ser Asp Gly Pro Val Met Gln Lys Lys Thr Met Gly Trp
        130                 135                 140
Glu Ala Ser Thr Glu Arg Leu Tyr Pro Arg Asp Gly Val Leu Lys Gly
145                 150                 155                 160
Glu Ile His Lys Ala Leu Lys Leu Lys Asp Gly His Tyr Leu Val
                165                 170                 175
Glu Phe Lys Ser Ile Tyr Met Ala Lys Lys Pro Val Gln Leu Pro Gly
                180                 185                 190
Tyr Tyr Tyr Val Asp Ser Lys Leu Asp Ile Thr Ser His Asn Glu Asp
                195                 200                 205
Tyr Thr Ile Val Glu Gln Tyr Glu Arg Thr Glu Gly Arg His His Leu
        210                 215                 220
Phe Leu Pro Arg Ala Ile Lys Leu Gly Arg Gln Ala Asn Phe Leu Gly
225                 230                 235                 240
Gly Lys Thr Ser Gly Ala Lys Gln Ala Thr Val Val Ala Ala Met
                245                 250                 255
Ala Leu Gly Trp Leu Ala Ile Glu Ile Ala Phe Lys Pro Phe Leu Asp
                260                 265                 270
Lys Phe Arg Ser Ser Ile Asp Lys Ser Asp Pro Thr Lys Asp Pro Asp
                275                 280                 285
Asp Phe Asp Thr Ala Ala Thr Ala Thr Thr Ser Lys Glu Gly Leu Gly
        290                 295                 300
Ile Gln Gly Asp Ile Thr Met Ser Lys Gly Glu Leu Phe Thr Gly
305                 310                 315                 320
Val Val Pro Ile Leu Val Glu Leu Asp Gly Asp Val Asn Gly His Lys
                325                 330                 335
Phe Ser Val Ser Gly Glu Gly Glu Gly Asp Ala Thr Tyr Gly Lys Leu
                340                 345                 350
Thr Leu Lys Phe Ile Cys Thr Thr Gly Lys Leu Pro Val Pro Trp Pro
                355                 360                 365
Thr Leu Val Thr Thr Phe Ser Tyr Gly Val Gln Cys Phe Ser Arg Tyr
        370                 375                 380
Pro Asp His Met Lys Arg His Asp Phe Phe Lys Ser Ala Met Pro Glu
385                 390                 395                 400
Gly Tyr Val Gln Glu Arg Thr Ile Ser Phe Lys Asp Asp Gly Asn Tyr
                405                 410                 415
Lys Thr Arg Ala Glu Val Lys Phe Glu Gly Asp Thr Leu Val Asn Arg
                420                 425                 430
Ile Glu Leu Lys Gly Ile Asp Phe Lys Glu Asp Gly Asn Ile Leu Gly
                435                 440                 445
His Lys Leu Glu Tyr Asn Tyr Asn Ser His Asn Val Tyr Ile Thr Ala
        450                 455                 460
Asp Lys Gln Lys Asn Gly Ile Lys Ala Asn Phe Lys Ile Arg His Asn
465                 470                 475                 480
Ile Glu Asp Gly Ser Val Gln Leu Ala Asp His Tyr Gln Gln Asn Thr
                485                 490                 495
Pro Ile Gly Asp Gly Pro Val Leu Leu Pro Asp Asn His Tyr Leu Ser
                500                 505                 510
Thr Gln Ser Ala Leu Ser Lys Asp Pro Asn Glu Lys Arg Asp His Met
                515                 520                 525
Val Leu Leu Glu Phe Val Thr Ala Ala Gly Ile Thr His Gly Met Asp
        530                 535                 540
```

Glu Leu Tyr Lys
545

<210> SEQ ID NO 77
<211> LENGTH: 1893
<212> TYPE: DNA
<213> ORGANISM: Hepatitis C virus
<220> FEATURE:
<221> NAME/KEY: CDS
<222> LOCATION: (1)..(1893)
<223> OTHER INFORMATION: HCV NS3 protease
<300> PUBLICATION INFORMATION:
<308> DATABASE ACCESSION NUMBER: GenBank/D16435
<309> DATABASE ENTRY DATE: 2000-02-01

<400> SEQUENCE: 77

| | | | | | | | | | | | | | | | | |
|---|---|---|---|---|---|---|---|---|---|---|---|---|---|---|---|---|
| gcg | cct | atc | acg | gcc | tat | tcc | caa | caa | acg | cgg | ggc | ctg | ctt | ggc | tgt | 48 |
| Ala | Pro | Ile | Thr | Ala | Tyr | Ser | Gln | Gln | Thr | Arg | Gly | Leu | Leu | Gly | Cys | |
| 1 | | | | 5 | | | | | 10 | | | | | 15 | | |
| atc | atc | act | agc | ctc | aca | ggt | cgg | gac | aag | aac | cag | gtc | gat | ggg | gag | 96 |
| Ile | Ile | Thr | Ser | Leu | Thr | Gly | Arg | Asp | Lys | Asn | Gln | Val | Asp | Gly | Glu | |
| | | | 20 | | | | | 25 | | | | | 30 | | | |
| gtt | cag | gtg | ctc | tcc | acc | gca | acg | caa | tct | ttc | ctg | gcg | acc | tgc | gtc | 144 |
| Val | Gln | Val | Leu | Ser | Thr | Ala | Thr | Gln | Ser | Phe | Leu | Ala | Thr | Cys | Val | |
| | | 35 | | | | | 40 | | | | | 45 | | | | |
| aat | ggc | gtg | tgt | tgg | acc | gtc | tac | cat | ggt | gcc | ggc | tcg | aag | acc | ctg | 192 |
| Asn | Gly | Val | Cys | Trp | Thr | Val | Tyr | His | Gly | Ala | Gly | Ser | Lys | Thr | Leu | |
| 50 | | | | | 55 | | | | | 60 | | | | | | |
| gcc | ggc | ccg | aag | ggt | cca | atc | acc | caa | atg | tac | acc | aat | gta | gac | cag | 240 |
| Ala | Gly | Pro | Lys | Gly | Pro | Ile | Thr | Gln | Met | Tyr | Thr | Asn | Val | Asp | Gln | |
| 65 | | | | 70 | | | | | 75 | | | | | 80 | | |
| gac | ctc | gtc | ggc | tgg | ccg | gcg | ccc | ccc | ggg | gcg | cgc | tcc | atg | aca | ccg | 288 |
| Asp | Leu | Val | Gly | Trp | Pro | Ala | Pro | Pro | Gly | Ala | Arg | Ser | Met | Thr | Pro | |
| | | | | 85 | | | | | 90 | | | | | 95 | | |
| tgc | acc | tgc | ggc | agc | tcg | gac | ctt | tac | ttg | gtc | acg | agg | cat | gcc | gat | 336 |
| Cys | Thr | Cys | Gly | Ser | Ser | Asp | Leu | Tyr | Leu | Val | Thr | Arg | His | Ala | Asp | |
| | | | | 100 | | | | | 105 | | | | | 110 | | |
| gtc | att | ccg | gtg | cgc | cgg | cga | ggc | gac | agc | agg | ggg | agt | cta | ctc | tcc | 384 |
| Val | Ile | Pro | Val | Arg | Arg | Arg | Gly | Asp | Ser | Arg | Gly | Ser | Leu | Leu | Ser | |
| | | | 115 | | | | | 120 | | | | | 125 | | | |
| cct | agg | ccc | gtc | tcc | tac | ctg | aag | ggc | tcc | tcg | ggt | gga | cca | ctg | ctt | 432 |
| Pro | Arg | Pro | Val | Ser | Tyr | Leu | Lys | Gly | Ser | Ser | Gly | Gly | Pro | Leu | Leu | |
| | | 130 | | | | | 135 | | | | | 140 | | | | |
| tgc | cct | tcg | ggg | cac | gtt | gta | ggc | atc | ttc | cgg | gct | gct | gtg | tgc | acc | 480 |
| Cys | Pro | Ser | Gly | His | Val | Val | Gly | Ile | Phe | Arg | Ala | Ala | Val | Cys | Thr | |
| 145 | | | | | 150 | | | | | 155 | | | | | 160 | |
| cgg | ggg | gtt | gcg | aag | gcg | gtg | gac | ttc | ata | ccc | gtt | gag | tct | atg | gaa | 528 |
| Arg | Gly | Val | Ala | Lys | Ala | Val | Asp | Phe | Ile | Pro | Val | Glu | Ser | Met | Glu | |
| | | | | 165 | | | | | 170 | | | | | 175 | | |
| act | acc | atg | cgg | tct | ccg | gtc | ttc | aca | gac | aac | tca | tcc | cct | ccg | gcc | 576 |
| Thr | Thr | Met | Arg | Ser | Pro | Val | Phe | Thr | Asp | Asn | Ser | Ser | Pro | Pro | Ala | |
| | | | 180 | | | | | 185 | | | | | 190 | | | |
| gta | ccg | caa | aca | ttc | caa | gtg | gca | cat | tta | cac | gct | ccc | act | ggc | agc | 624 |
| Val | Pro | Gln | Thr | Phe | Gln | Val | Ala | His | Leu | His | Ala | Pro | Thr | Gly | Ser | |
| | | 195 | | | | | 200 | | | | | 205 | | | | |
| ggc | aag | agc | acc | aaa | gtg | ccg | gct | gca | tat | gca | gcc | caa | ggg | tac | aag | 672 |
| Gly | Lys | Ser | Thr | Lys | Val | Pro | Ala | Ala | Tyr | Ala | Ala | Gln | Gly | Tyr | Lys | |
| | 210 | | | | | 215 | | | | | 220 | | | | | |
| gtg | ctc | gtc | cta | aac | ccg | tcc | gtt | gct | gcc | aca | ttg | ggc | ttt | gga | gcg | 720 |
| Val | Leu | Val | Leu | Asn | Pro | Ser | Val | Ala | Ala | Thr | Leu | Gly | Phe | Gly | Ala | |
| 225 | | | | | 230 | | | | | 235 | | | | | 240 | |

-continued

| | | |
|---|---|---|
| tat atg tcc aag gca cat ggc atc gag cct aac atc aga act ggg gta<br>Tyr Met Ser Lys Ala His Gly Ile Glu Pro Asn Ile Arg Thr Gly Val<br>245 250 255 | | 768 |
| agg acc atc acc acg ggc ggc ccc atc acg tac tcc acc tat ggc aag<br>Arg Thr Ile Thr Thr Gly Gly Pro Ile Thr Tyr Ser Thr Tyr Gly Lys<br>260 265 270 | | 816 |
| ttc ctt gcc gac ggt gga tgc tcc ggg ggc gcc tat gac atc ata ata<br>Phe Leu Ala Asp Gly Gly Cys Ser Gly Gly Ala Tyr Asp Ile Ile Ile<br>275 280 285 | | 864 |
| tgt gac gaa tgc cac tca act gac tgg aca acc atc ttg ggc atc ggc<br>Cys Asp Glu Cys His Ser Thr Asp Trp Thr Thr Ile Leu Gly Ile Gly<br>290 295 300 | | 912 |
| aca gtc ctg gat cag gca gag acg gct gga gcg cgg ctc gtc gtg ctc<br>Thr Val Leu Asp Gln Ala Glu Thr Ala Gly Ala Arg Leu Val Val Leu<br>305 310 315 320 | | 960 |
| gcc acc gcc acg cct ccg gga tcg atc acc gtg cca cac ccc aac atc<br>Ala Thr Ala Thr Pro Pro Gly Ser Ile Thr Val Pro His Pro Asn Ile<br>325 330 335 | | 1008 |
| gag gaa gtg gcc ctg tcc aac act ggg gag att ccc ttc tat ggc aaa<br>Glu Glu Val Ala Leu Ser Asn Thr Gly Glu Ile Pro Phe Tyr Gly Lys<br>340 345 350 | | 1056 |
| gcc atc ccc att gag gcc atc aag ggg gga agg cat ctc atc ttc tgc<br>Ala Ile Pro Ile Glu Ala Ile Lys Gly Gly Arg His Leu Ile Phe Cys<br>355 360 365 | | 1104 |
| cat tcc aag aag aag tgt gac gag ctc gcc gca aag ctg aca ggc ctc<br>His Ser Lys Lys Lys Cys Asp Glu Leu Ala Ala Lys Leu Thr Gly Leu<br>370 375 380 | | 1152 |
| gga ctc aat gct gta gcg tat tac cgg ggt ctc gat gtg tcc gtc ata<br>Gly Leu Asn Ala Val Ala Tyr Tyr Arg Gly Leu Asp Val Ser Val Ile<br>385 390 395 400 | | 1200 |
| ccg act agc gga gac gtc gtt gtc gtg gca aca gac gct cta atg acg<br>Pro Thr Ser Gly Asp Val Val Val Val Ala Thr Asp Ala Leu Met Thr<br>405 410 415 | | 1248 |
| ggc ttt acc ggc gac ttt gac tca gtg atc gac tgc aac aca tgt gtc<br>Gly Phe Thr Gly Asp Phe Asp Ser Val Ile Asp Cys Asn Thr Cys Val<br>420 425 430 | | 1296 |
| acc cag aca gtc gat ttc agc ttg gat ccc acc ttc acc att gag acg<br>Thr Gln Thr Val Asp Phe Ser Leu Asp Pro Thr Phe Thr Ile Glu Thr<br>435 440 445 | | 1344 |
| aca acc gtg ccc caa gac gcg gtg tcg cgc tcg cag cgg cga ggt agg<br>Thr Thr Val Pro Gln Asp Ala Val Ser Arg Ser Gln Arg Arg Gly Arg<br>450 455 460 | | 1392 |
| act ggc agg ggc agg agt ggc atc tac agg ttt gtg act cca gga gaa<br>Thr Gly Arg Gly Arg Ser Gly Ile Tyr Arg Phe Val Thr Pro Gly Glu<br>465 470 475 480 | | 1440 |
| cgg ccc tca ggc atg ttc gac tcc tcg gtc ctg tgt gag tgc tat gac<br>Arg Pro Ser Gly Met Phe Asp Ser Ser Val Leu Cys Glu Cys Tyr Asp<br>485 490 495 | | 1488 |
| gca ggc tgc gct tgg tat gag ctc acg ccc gct gag act aca gtc agg<br>Ala Gly Cys Ala Trp Tyr Glu Leu Thr Pro Ala Glu Thr Thr Val Arg<br>500 505 510 | | 1536 |
| ttg cgg gct tac ctg aat aca cca ggg ttg ccc gtc tgc cag gac cat<br>Leu Arg Ala Tyr Leu Asn Thr Pro Gly Leu Pro Val Cys Gln Asp His<br>515 520 525 | | 1584 |
| ctg gag ttc tgg gaa agc gtc ttc aca ggc ctc acc cac ata gat gcc<br>Leu Glu Phe Trp Glu Ser Val Phe Thr Gly Leu Thr His Ile Asp Ala<br>530 535 540 | | 1632 |
| cac ttc ctg tcc caa acc aag cag gca gga gac aac ttc ccc tac ctg<br>His Phe Leu Ser Gln Thr Lys Gln Ala Gly Asp Asn Phe Pro Tyr Leu<br>545 550 555 560 | | 1680 |

```
gtg gca tac caa gcc acg gtg tgc gcc agg gct cag gct cca cct cca    1728
Val Ala Tyr Gln Ala Thr Val Cys Ala Arg Ala Gln Ala Pro Pro Pro
            565                 570                 575 tcg tgg gat caa atg tgg aag tgt ctc ata cgg ctt aaa cct acg ctg    1776
Ser Trp Asp Gln Met Trp Lys Cys Leu Ile Arg Leu Lys Pro Thr Leu
        580                 585                 590 cac ggg cca aca ccc ctg ctg tat agg cta gga gcc gtt caa aat gag    1824
His Gly Pro Thr Pro Leu Leu Tyr Arg Leu Gly Ala Val Gln Asn Glu
            595                 600                 605 atc acc ctc aca cat ccc ata acc aaa ttc gtc atg gca tgc atg tcg    1872
Ile Thr Leu Thr His Pro Ile Thr Lys Phe Val Met Ala Cys Met Ser
    610                 615                 620 gcc gac ctg gag gtc gtc act                                        1893
Ala Asp Leu Glu Val Val Thr
625             630

<210> SEQ ID NO 78
<211> LENGTH: 631
<212> TYPE: PRT
<213> ORGANISM: Hepatitis C virus

<400> SEQUENCE: 78

Ala Pro Ile Thr Ala Tyr Ser Gln Gln Thr Arg Gly Leu Leu Gly Cys
1               5                   10                  15

Ile Ile Thr Ser Leu Thr Gly Arg Asp Lys Asn Gln Val Asp Gly Glu
            20                  25                  30

Val Gln Val Leu Ser Thr Ala Thr Gln Ser Phe Leu Ala Thr Cys Val
        35                  40                  45

Asn Gly Val Cys Trp Thr Val Tyr His Gly Ala Gly Ser Lys Thr Leu
    50                  55                  60

Ala Gly Pro Lys Gly Pro Ile Thr Gln Met Tyr Thr Asn Val Asp Gln
65              70                  75                  80

Asp Leu Val Gly Trp Pro Ala Pro Gly Ala Arg Ser Met Thr Pro
                85                  90                  95

Cys Thr Cys Gly Ser Ser Asp Leu Tyr Leu Val Thr Arg His Ala Asp
            100                 105                 110

Val Ile Pro Val Arg Arg Gly Asp Ser Arg Gly Ser Leu Leu Ser
        115                 120                 125

Pro Arg Pro Val Ser Tyr Leu Lys Gly Ser Ser Gly Pro Leu Leu
    130                 135                 140

Cys Pro Ser Gly His Val Val Gly Ile Phe Arg Ala Ala Val Cys Thr
145             150                 155                 160

Arg Gly Val Ala Lys Ala Val Asp Phe Ile Pro Val Glu Ser Met Glu
                165                 170                 175

Thr Thr Met Arg Ser Pro Val Phe Thr Asp Asn Ser Ser Pro Pro Ala
            180                 185                 190

Val Pro Gln Thr Phe Gln Val Ala His Leu His Ala Pro Thr Gly Ser
        195                 200                 205

Gly Lys Ser Thr Lys Val Pro Ala Ala Tyr Ala Ala Gln Gly Tyr Lys
    210                 215                 220

Val Leu Val Leu Asn Pro Ser Val Ala Ala Thr Leu Gly Phe Gly Ala
225             230                 235                 240

Tyr Met Ser Lys Ala His Gly Ile Glu Pro Asn Ile Arg Thr Gly Val
                245                 250                 255

Arg Thr Ile Thr Thr Gly Gly Pro Ile Thr Tyr Ser Thr Tyr Gly Lys
            260                 265                 270
```

```
Phe Leu Ala Asp Gly Gly Cys Ser Gly Gly Ala Tyr Asp Ile Ile Ile
            275                 280                 285

Cys Asp Glu Cys His Ser Thr Asp Trp Thr Thr Ile Leu Gly Ile Gly
        290                 295                 300

Thr Val Leu Asp Gln Ala Glu Thr Ala Gly Ala Arg Leu Val Val Leu
305                 310                 315                 320

Ala Thr Ala Thr Pro Pro Gly Ser Ile Thr Val Pro His Pro Asn Ile
            325                 330                 335

Glu Glu Val Ala Leu Ser Asn Thr Gly Glu Ile Pro Phe Tyr Gly Lys
        340                 345                 350

Ala Ile Pro Ile Glu Ala Ile Lys Gly Gly Arg His Leu Ile Phe Cys
        355                 360                 365

His Ser Lys Lys Lys Cys Asp Glu Leu Ala Ala Lys Leu Thr Gly Leu
        370                 375                 380

Gly Leu Asn Ala Val Ala Tyr Tyr Arg Gly Leu Asp Val Ser Val Ile
385                 390                 395                 400

Pro Thr Ser Gly Asp Val Val Val Ala Thr Asp Ala Leu Met Thr
            405                 410                 415

Gly Phe Thr Gly Asp Phe Asp Ser Val Ile Asp Cys Asn Thr Cys Val
            420                 425                 430

Thr Gln Thr Val Asp Phe Ser Leu Asp Pro Thr Phe Thr Ile Glu Thr
        435                 440                 445

Thr Thr Val Pro Gln Asp Ala Val Ser Arg Ser Gln Arg Arg Gly Arg
        450                 455                 460

Thr Gly Arg Gly Arg Ser Gly Ile Tyr Arg Phe Val Thr Pro Gly Glu
465                 470                 475                 480

Arg Pro Ser Gly Met Phe Asp Ser Ser Val Leu Cys Glu Cys Tyr Asp
            485                 490                 495

Ala Gly Cys Ala Trp Tyr Glu Leu Thr Pro Ala Glu Thr Thr Val Arg
        500                 505                 510

Leu Arg Ala Tyr Leu Asn Thr Pro Gly Leu Pro Val Cys Gln Asp His
        515                 520                 525

Leu Glu Phe Trp Glu Ser Val Phe Thr Gly Leu Thr His Ile Asp Ala
        530                 535                 540

His Phe Leu Ser Gln Thr Lys Gln Ala Gly Asp Asn Phe Pro Tyr Leu
545                 550                 555                 560

Val Ala Tyr Gln Ala Thr Val Cys Ala Arg Ala Gln Ala Pro Pro Pro
            565                 570                 575

Ser Trp Asp Gln Met Trp Lys Cys Leu Ile Arg Leu Lys Pro Thr Leu
        580                 585                 590

His Gly Pro Thr Pro Leu Leu Tyr Arg Leu Gly Ala Val Gln Asn Glu
        595                 600                 605

Ile Thr Leu Thr His Pro Ile Thr Lys Phe Val Met Ala Cys Met Ser
        610                 615                 620

Ala Asp Leu Glu Val Val Thr
625                 630

<210> SEQ ID NO 79
<211> LENGTH: 30
<212> TYPE: DNA
<213> ORGANISM: Artificial
<220> FEATURE:
<223> OTHER INFORMATION: Synthetic Sequence
<220> FEATURE:
<221> NAME/KEY: CDS
```

<222> LOCATION: (1)..(30)
<223> OTHER INFORMATION: HCV NS3 protease cleavage sequence

<400> SEQUENCE: 79

```
gat gaa atg gaa gag tgc gcc tca cac ctc                          30
Asp Glu Met Glu Glu Cys Ala Ser His Leu
1               5                   10
```

<210> SEQ ID NO 80
<211> LENGTH: 10
<212> TYPE: PRT
<213> ORGANISM: Artificial
<220> FEATURE:
<223> OTHER INFORMATION: Synthetic Sequence

<400> SEQUENCE: 80

```
Asp Glu Met Glu Glu Cys Ala Ser His Leu
1               5                   10
```

<210> SEQ ID NO 81
<211> LENGTH: 30
<212> TYPE: DNA
<213> ORGANISM: Artificial
<220> FEATURE:
<223> OTHER INFORMATION: Synthetic Sequence
<220> FEATURE:
<221> NAME/KEY: CDS
<222> LOCATION: (1)..(30)
<223> OTHER INFORMATION: HCV NS3 protease cleavage sequence

<400> SEQUENCE: 81

```
gac tgc tcc acg cca tgc tcc ggc tcg tgg                          30
Asp Cys Ser Thr Pro Cys Ser Gly Ser Trp
1               5                   10
```

<210> SEQ ID NO 82
<211> LENGTH: 10
<212> TYPE: PRT
<213> ORGANISM: Artificial
<220> FEATURE:
<223> OTHER INFORMATION: Synthetic Sequence

<400> SEQUENCE: 82

```
Asp Cys Ser Thr Pro Cys Ser Gly Ser Trp
1               5                   10
```

<210> SEQ ID NO 83
<211> LENGTH: 30
<212> TYPE: DNA
<213> ORGANISM: Artificial
<220> FEATURE:
<223> OTHER INFORMATION: Synthetic Sequence
<220> FEATURE:
<221> NAME/KEY: CDS
<222> LOCATION: (1)..(30)
<223> OTHER INFORMATION: HCV NS3 protease cleavage sequence

<400> SEQUENCE: 83

```
gac gac atc gtc tgc tgc tca atg tcc tac                          30
Asp Asp Ile Val Cys Cys Ser Met Ser Tyr
1               5                   10
```

<210> SEQ ID NO 84
<211> LENGTH: 10
<212> TYPE: PRT
<213> ORGANISM: Artificial
<220> FEATURE:
<223> OTHER INFORMATION: Synthetic Sequence -continued

```
<400> SEQUENCE: 84

Asp Asp Ile Val Cys Cys Ser Met Ser Tyr
1               5                   10

<210> SEQ ID NO 85
<211> LENGTH: 1908
<212> TYPE: DNA
<213> ORGANISM: Human herpesvirus 1
<220> FEATURE:
<221> NAME/KEY: gene
<222> LOCATION: (1)..(1908)
<223> OTHER INFORMATION: Gene for HSV-1 protease
<220> FEATURE:
<221> NAME/KEY: CDS
<222> LOCATION: (1)..(1905)
<223> OTHER INFORMATION: HSV-1 protease
<300> PUBLICATION INFORMATION:
<308> DATABASE ACCESSION NUMBER: GenBank/X14112
<309> DATABASE ENTRY DATE: 1997-04-17

<400> SEQUENCE: 85 atg gca gcc gat gcc ccg gga gac cgg atg gag gag ccc ctg ccc gac        48
Met Ala Ala Asp Ala Pro Gly Asp Arg Met Glu Glu Pro Leu Pro Asp
1               5                   10                  15 agg gcc gtg ccc att tac gtg gct ggg ttt ttg gcc ctg tat gac agc        96
Arg Ala Val Pro Ile Tyr Val Ala Gly Phe Leu Ala Leu Tyr Asp Ser
                20                  25                  30 ggg gac tcg ggc gag ttg gca ttg gat ccg gat acg gtg cgg gcg gcc       144
Gly Asp Ser Gly Glu Leu Ala Leu Asp Pro Asp Thr Val Arg Ala Ala
            35                  40                  45 ctg cct ccg gat aac cca ctc ccg att aac gtg gac cac cgc gct ggc       192
Leu Pro Pro Asp Asn Pro Leu Pro Ile Asn Val Asp His Arg Ala Gly
        50                  55                  60 tgc gag gtg ggg cgg gtg ctg gcc gtg gtc gac gac ccc cgc ggg ccg       240
Cys Glu Val Gly Arg Val Leu Ala Val Val Asp Asp Pro Arg Gly Pro
65                  70                  75                  80 ttt ttt gtg ggg ctg atc gcc tgc gtg cag ctg gag cgc gtc ctc gag       288
Phe Phe Val Gly Leu Ile Ala Cys Val Gln Leu Glu Arg Val Leu Glu
                85                  90                  95 acg gcc gcc agc gct gcg att ttc gag cgc cgc ggg ccg ccg ctc tcc       336
Thr Ala Ala Ser Ala Ala Ile Phe Glu Arg Arg Gly Pro Pro Leu Ser
                100                 105                 110 cgg gag gag cgc ctg ttg tac ctg atc acc aac tac ctg ccc tcg gtc       384
Arg Glu Glu Arg Leu Leu Tyr Leu Ile Thr Asn Tyr Leu Pro Ser Val
            115                 120                 125 tcc ctg gcc aca aaa cgc ctg ggg ggc gag gcg cac ccc gat cgc acg       432
Ser Leu Ala Thr Lys Arg Leu Gly Gly Glu Ala His Pro Asp Arg Thr
        130                 135                 140 ctg ttc gcg cac gtc gcg ctg tgc gcg atc ggg cgg cgc ctc ggc act       480
Leu Phe Ala His Val Ala Leu Cys Ala Ile Gly Arg Arg Leu Gly Thr
145                 150                 155                 160 atc gtc acc tac gac acc ggt ctc gac gcc gcc atc gcg ccc ttt cgc       528
Ile Val Thr Tyr Asp Thr Gly Leu Asp Ala Ala Ile Ala Pro Phe Arg
                165                 170                 175 cac ctg tcg ccg gcg tct cgc gag ggg gcg cgg cga ctg gcc gcc gag       576
His Leu Ser Pro Ala Ser Arg Glu Gly Ala Arg Arg Leu Ala Ala Glu
                180                 185                 190 gcc gag ctc gcg ctg tcc ggg cgc acc tgg gcg ccc ggc gtg gag gcg       624
Ala Glu Leu Ala Leu Ser Gly Arg Thr Trp Ala Pro Gly Val Glu Ala
            195                 200                 205 ctg acc cac acg ctg ctt tcc acc gcc gtt aac aac atg atg ctg cgg       672
Leu Thr His Thr Leu Leu Ser Thr Ala Val Asn Asn Met Met Leu Arg
        210                 215                 220
```

```
gac cgc tgg agc ctg gtg gcc gag cgg cgg cgg cag gcc ggg atc gcc       720
Asp Arg Trp Ser Leu Val Ala Glu Arg Arg Arg Gln Ala Gly Ile Ala
225                 230                 235                 240 gga cac acc tac ctc cag gcg agc gaa aaa ttc aaa atg tgg ggg gcg       768
Gly His Thr Tyr Leu Gln Ala Ser Glu Lys Phe Lys Met Trp Gly Ala
            245                 250                 255 gag cct gtt tcc gcg ccg gcg cgc ggg tat aag aac ggg gcc ccg gag       816
Glu Pro Val Ser Ala Pro Ala Arg Gly Tyr Lys Asn Gly Ala Pro Glu
        260                 265                 270 tcc acg gac ata ccg ccc ggc tcg atc gct gcc gcg ccg cag ggt gac       864
Ser Thr Asp Ile Pro Pro Gly Ser Ile Ala Ala Ala Pro Gln Gly Asp
    275                 280                 285 cgg tgc cca atc gtc cgt cag cgc ggg gtc gcc ttg tcc ccg gta ctg       912
Arg Cys Pro Ile Val Arg Gln Arg Gly Val Ala Leu Ser Pro Val Leu
290                 295                 300 ccc ccc atg aac ccc gtt ccg aca tcg ggc acc ccg gcc ccc gcg ccg       960
Pro Pro Met Asn Pro Val Pro Thr Ser Gly Thr Pro Ala Pro Ala Pro
305                 310                 315                 320 ccc ggc gac ggg agc tac ctg tgg atc ccg gcc tcc cat tac aac cag      1008
Pro Gly Asp Gly Ser Tyr Leu Trp Ile Pro Ala Ser His Tyr Asn Gln
            325                 330                 335 ctc gtc gcc ggc cat gcc gcg ccc caa ccc cag ccg cat tcc gcg ttt      1056
Leu Val Ala Gly His Ala Ala Pro Gln Pro Gln Pro His Ser Ala Phe
        340                 345                 350 ggt ttc ccg gct gcg gcg ggg tcc gtg gcc tat ggg cct cac ggt gcg      1104
Gly Phe Pro Ala Ala Ala Gly Ser Val Ala Tyr Gly Pro His Gly Ala
    355                 360                 365 ggt ctt tcc cag cat tac cct ccc cac gtc gcc cat cag tat ccc ggg      1152
Gly Leu Ser Gln His Tyr Pro Pro His Val Ala His Gln Tyr Pro Gly
370                 375                 380 gtg ctg ttc tcg gga ccc agc cca ctc gag gcg cag ata gcc gcg ttg      1200
Val Leu Phe Ser Gly Pro Ser Pro Leu Glu Ala Gln Ile Ala Ala Leu
385                 390                 395                 400 gtg ggg gcc ata gcc gcg gac cgc cag gcg ggc ggt cag ccg gcc gcg      1248
Val Gly Ala Ile Ala Ala Asp Arg Gln Ala Gly Gly Gln Pro Ala Ala
            405                 410                 415 gga gac cct ggg gtc cgg ggg tcg gga aag cgt cgc cgg tac gag gcg      1296
Gly Asp Pro Gly Val Arg Gly Ser Gly Lys Arg Arg Arg Tyr Glu Ala
        420                 425                 430 ggg ccg tcg gag tcc tac tgc gac cag gac gaa ccg gac gcg gac tac      1344
Gly Pro Ser Glu Ser Tyr Cys Asp Gln Asp Glu Pro Asp Ala Asp Tyr
    435                 440                 445 ccg tac tac ccc ggg gag gct cga ggc gcg ccg cgc ggg gtc gac tcc      1392
Pro Tyr Tyr Pro Gly Glu Ala Arg Gly Ala Pro Arg Gly Val Asp Ser
450                 455                 460 cgg cgc gcg gcc cgc cat tct ccc ggg acc aac gag acc atc acg gcg      1440
Arg Arg Ala Ala Arg His Ser Pro Gly Thr Asn Glu Thr Ile Thr Ala
465                 470                 475                 480 ctg atg ggg gcg gtg acg tct ctg cag cag gaa ctg gcg cac atg cgg      1488
Leu Met Gly Ala Val Thr Ser Leu Gln Gln Glu Leu Ala His Met Arg
            485                 490                 495 gct cgg acc agc gcc ccc tat gga atg tac acg ccg gtg gcg cac tat      1536
Ala Arg Thr Ser Ala Pro Tyr Gly Met Tyr Thr Pro Val Ala His Tyr
        500                 505                 510 cgc cct cag gtg ggg gag ccg gaa cca aca acg acc cac ccg gcc ctt      1584
Arg Pro Gln Val Gly Glu Pro Glu Pro Thr Thr Thr His Pro Ala Leu
    515                 520                 525 tgt ccc ccg gag gcc gtg tat cgc ccc cca cac agc gcc ccc tac         1632
Cys Pro Pro Glu Ala Val Tyr Arg Pro Pro His Ser Ala Pro Tyr
```

-continued

```
         530                 535                 540
ggt cct ccc cag ggt ccg gcg tcc cat gcc ccc act ccc ccg tat gcc      1680
Gly Pro Pro Gln Gly Pro Ala Ser His Ala Pro Thr Pro Pro Tyr Ala
545                 550                 555                 560 cca gct gcc tgc ccg cca ggc ccg cca ccg ccc cca tgt cct tcc acc      1728
Pro Ala Ala Cys Pro Pro Gly Pro Pro Pro Pro Pro Cys Pro Ser Thr
                565                 570                 575 cag acg cgc gcc cct cta ccg acg gag ccc gcg ttc ccc ccc gcc gcc      1776
Gln Thr Arg Ala Pro Leu Pro Thr Glu Pro Ala Phe Pro Pro Ala Ala
            580                 585                 590 acc gga tcc caa ccg gag gca tcc aac gcg gag gcc ggg gcc ctt gtc      1824
Thr Gly Ser Gln Pro Glu Ala Ser Asn Ala Glu Ala Gly Ala Leu Val
        595                 600                 605 aac gcc agc agc gca gca cac gtg gac gtt gac acg gcc cgc gcc gcc      1872
Asn Ala Ser Ser Ala Ala His Val Asp Val Asp Thr Ala Arg Ala Ala
    610                 615                 620 gat ttg ttc gtc tct cag atg atg ggg gcc cgc tga                       1908
Asp Leu Phe Val Ser Gln Met Met Gly Ala Arg
625                 630                 635

<210> SEQ ID NO 86
<211> LENGTH: 635
<212> TYPE: PRT
<213> ORGANISM: Human herpesvirus 1

<400> SEQUENCE: 86

Met Ala Ala Asp Ala Pro Gly Asp Arg Met Glu Glu Pro Leu Pro Asp
1               5                   10                  15

Arg Ala Val Pro Ile Tyr Val Ala Gly Phe Leu Ala Leu Tyr Asp Ser
                20                  25                  30

Gly Asp Ser Gly Glu Leu Ala Leu Asp Pro Asp Thr Val Arg Ala Ala
            35                  40                  45

Leu Pro Pro Asp Asn Pro Leu Pro Ile Asn Val Asp His Arg Ala Gly
        50                  55                  60

Cys Glu Val Gly Arg Val Leu Ala Val Val Asp Asp Pro Arg Gly Pro
65                  70                  75                  80

Phe Phe Val Gly Leu Ile Ala Cys Val Gln Leu Glu Arg Val Leu Glu
                85                  90                  95

Thr Ala Ala Ser Ala Ala Ile Phe Glu Arg Arg Gly Pro Pro Leu Ser
            100                 105                 110

Arg Glu Glu Arg Leu Leu Tyr Leu Ile Thr Asn Tyr Leu Pro Ser Val
        115                 120                 125

Ser Leu Ala Thr Lys Arg Leu Gly Gly Glu Ala His Pro Asp Arg Thr
130                 135                 140

Leu Phe Ala His Val Ala Leu Cys Ala Ile Gly Arg Arg Leu Gly Thr
145                 150                 155                 160

Ile Val Thr Tyr Asp Thr Gly Leu Asp Ala Ala Ile Ala Pro Phe Arg
                165                 170                 175

His Leu Ser Pro Ala Ser Arg Glu Gly Ala Arg Arg Leu Ala Ala Glu
            180                 185                 190

Ala Glu Leu Ala Leu Ser Gly Arg Thr Trp Ala Pro Gly Val Glu Ala
        195                 200                 205

Leu Thr His Thr Leu Leu Ser Thr Ala Val Asn Asn Met Met Leu Arg
    210                 215                 220

Asp Arg Trp Ser Leu Val Ala Glu Arg Arg Gln Ala Gly Ile Ala
225                 230                 235                 240
```

```
Gly His Thr Tyr Leu Gln Ala Ser Glu Lys Phe Lys Met Trp Gly Ala
            245                 250                 255

Glu Pro Val Ser Ala Pro Ala Arg Gly Tyr Lys Asn Gly Ala Pro Glu
        260                 265                 270

Ser Thr Asp Ile Pro Pro Gly Ser Ile Ala Ala Pro Gln Gly Asp
        275                 280                 285

Arg Cys Pro Ile Val Arg Gln Arg Gly Val Ala Leu Ser Pro Val Leu
    290                 295                 300

Pro Pro Met Asn Pro Val Pro Thr Ser Gly Thr Pro Ala Pro Ala Pro
305                 310                 315                 320

Pro Gly Asp Gly Ser Tyr Leu Trp Ile Pro Ala Ser His Tyr Asn Gln
                325                 330                 335

Leu Val Ala Gly His Ala Ala Pro Gln Pro Gln Pro His Ser Ala Phe
            340                 345                 350

Gly Phe Pro Ala Ala Ala Gly Ser Val Ala Tyr Gly Pro His Gly Ala
        355                 360                 365

Gly Leu Ser Gln His Tyr Pro Pro His Val Ala His Gln Tyr Pro Gly
    370                 375                 380

Val Leu Phe Ser Gly Pro Ser Pro Leu Glu Ala Gln Ile Ala Ala Leu
385                 390                 395                 400

Val Gly Ala Ile Ala Ala Asp Arg Gln Ala Gly Gln Pro Ala Ala
                405                 410                 415

Gly Asp Pro Gly Val Arg Gly Ser Gly Lys Arg Arg Tyr Glu Ala
            420                 425                 430

Gly Pro Ser Glu Ser Tyr Cys Asp Gln Asp Glu Pro Asp Ala Asp Tyr
        435                 440                 445

Pro Tyr Tyr Pro Gly Glu Ala Arg Gly Ala Pro Arg Gly Val Asp Ser
    450                 455                 460

Arg Arg Ala Ala Arg His Ser Pro Gly Thr Asn Glu Thr Ile Thr Ala
465                 470                 475                 480

Leu Met Gly Ala Val Thr Ser Leu Gln Gln Glu Leu Ala His Met Arg
                485                 490                 495

Ala Arg Thr Ser Ala Pro Tyr Gly Met Tyr Thr Pro Val Ala His Tyr
            500                 505                 510

Arg Pro Gln Val Gly Glu Pro Glu Thr Thr Thr His Pro Ala Leu
        515                 520                 525

Cys Pro Pro Glu Ala Val Tyr Arg Pro Pro His Ser Ala Pro Tyr
530                 535                 540

Gly Pro Pro Gln Gly Pro Ala Ser His Ala Pro Thr Pro Tyr Ala
545                 550                 555                 560

Pro Ala Ala Cys Pro Pro Gly Pro Pro Pro Pro Cys Pro Ser Thr
                565                 570                 575

Gln Thr Arg Ala Pro Leu Pro Thr Glu Pro Ala Phe Pro Pro Ala Ala
            580                 585                 590

Thr Gly Ser Gln Pro Glu Ala Ser Asn Ala Glu Ala Gly Ala Leu Val
        595                 600                 605

Asn Ala Ser Ser Ala Ala His Val Asp Val Asp Thr Ala Arg Ala Ala
    610                 615                 620

Asp Leu Phe Val Ser Gln Met Met Gly Ala Arg
625                 630                 635

<210> SEQ ID NO 87
<211> LENGTH: 15
<212> TYPE: DNA
```

```
<213> ORGANISM: Artificial
<220> FEATURE:
<223> OTHER INFORMATION: Synthetic Sequence
<220> FEATURE:
<221> NAME/KEY: CDS
<222> LOCATION: (1)..(15)
<223> OTHER INFORMATION: HSV-1 protease cleavage sequence
<220> FEATURE:
<221> NAME/KEY: misc_feature
<222> LOCATION: (1)..(15)
<223> OTHER INFORMATION: n= a, g, c, or t; r= a or g; y= c or t

<400> SEQUENCE: 87 ctn gtn ctn gcn agy                                              15
Xaa Val Xaa Ala Xaa
1

<221> NAME/KEY: misc_feature
<222> LOCATION: (5)..(5)
<223> OTHER INFORMATION: The 'Xaa' at location 5 stands for Ser.
<220> FEATURE:
<221> NAME/KEY: misc_feature
<222> LOCATION: (6)..(6)
<223> OTHER INFORMATION: The 'Xaa' at location 6 stands for Ser.
<220> FEATURE:
<223> OTHER INFORMATION: Synthetic Sequence

<400> SEQUENCE: 90

Xaa Val Xaa Ala Xaa Xaa
1               5

<210> SEQ ID NO 91
<211> LENGTH: 501
<212> TYPE: DNA
<213> ORGANISM: Human T-lymphotropic virus 1
<220> FEATURE:
<221> NAME/KEY: gene
<222> LOCATION: (1)..(501)
<223> OTHER INFORMATION: Gene for HTLV-1 protease
<220> FEATURE:
<221> NAME/KEY: CDS
<222> LOCATION: (1)..(498)
<223> OTHER INFORMATION: HTLV-1 protease
<300> PUBLICATION INFORMATION:
<308> DATABASE ACCESSION NUMBER: GenBank/L36905
<309> DATABASE ENTRY DATE: 1996-01-18

<400> SEQUENCE: 91

| | | |
|---|---|---|
| atg aca gtc ctt ccg ata gcc ttg ttc tca agt aat act ccc ctc aga<br>Met Thr Val Leu Pro Ile Ala Leu Phe Ser Ser Asn Thr Pro Leu Arg<br>1               5                   10                  15 | | 48 |
| aat aca tcc gta tta ggg gca ggg ggc caa acc caa gat cac ttt aag<br>Asn Thr Ser Val Leu Gly Ala Gly Gly Gln Thr Gln Asp His Phe Lys<br>            20                  25                  30 | | 96 |
| ctc acc tcc ctt cct gta cta ata cgc ctc cct ttc cgg aca acg cct<br>Leu Thr Ser Leu Pro Val Leu Ile Arg Leu Pro Phe Arg Thr Thr Pro<br>        35                  40                  45 | | 144 |
| att gtt tta aca tct tgc cta gtt gat acc aaa aac aac tgg gcc atc<br>Ile Val Leu Thr Ser Cys Leu Val Asp Thr Lys Asn Asn Trp Ala Ile<br>    50                  55                  60 | | 192 |
| ata ggt cgt gat gcc tta caa caa tgc caa ggc gcc ctg tac ctc cct<br>Ile Gly Arg Asp Ala Leu Gln Gln Cys Gln Gly Ala Leu Tyr Leu Pro<br>65                  70                  75                  80 | | 240 |
| gag gca aaa ggg ccg cct gta atc ttg cca ata cag gcg cca gcc gtc<br>Glu Ala Lys Gly Pro Pro Val Ile Leu Pro Ile Gln Ala Pro Ala Val<br>                85                  90                  95 | | 288 |
| ctt ggg cta gaa cac ctc cca agg ccc ccc gaa atc agc cag ttc cct<br>Leu Gly Leu Glu His Leu Pro Arg Pro Pro Glu Ile Ser Gln Phe Pro<br>            100                 105                 110 | | 336 |
| tta aac cag aac ggc tcc agg cct tgc aac act tgg tcc gga agg ccc<br>Leu Asn Gln Asn Gly Ser Arg Pro Cys Asn Thr Trp Ser Gly Arg Pro<br>        115                 120                 125 | | 384 |
| tgg agg cag gcc ata tcg aac cct aca ccg ggc cag gaa ata acc cag<br>Trp Arg Gln Ala Ile Ser Asn Pro Thr Pro Gly Gln Glu Ile Thr Gln<br>    130                 135                 140 | | 432 |
| tat tcc cag tta aaa agg cca atg gaa cct ggc gat tca tcc acg acc<br>Tyr Ser Gln Leu Lys Arg Pro Met Glu Pro Gly Asp Ser Ser Thr Thr<br>145                 150                 155                 160 | | 480 |
| tgc ggg cca cta act ctc taa<br>Cys Gly Pro Leu Thr Leu<br>                165 | | 501 |

```
<210> SEQ ID NO 92
<211> LENGTH: 166
<212> TYPE: PRT
<213> ORGANISM: Human T-lymphotropic virus 1

<400> SEQUENCE: 92

Met Thr Val Leu Pro Ile Ala Leu Phe Ser Ser Asn Thr Pro Leu Arg
1               5                   10                  15

Asn Thr Ser Val Leu Gly Ala Gly Gln Thr Gln Asp His Phe Lys
            20                  25                  30

Leu Thr Ser Leu Pro Val Leu Ile Arg Leu Pro Phe Arg Thr Thr Pro
        35                  40                  45

Ile Val Leu Thr Ser Cys Leu Val Asp Thr Lys Asn Asn Trp Ala Ile
    50                  55                  60

Ile Gly Arg Asp Ala Leu Gln Gln Cys Gln Gly Ala Leu Tyr Leu Pro
65                  70                  75                  80

Glu Ala Lys Gly Pro Pro Val Ile Leu Pro Ile Gln Ala Pro Ala Val
                85                  90                  95

Leu Gly Leu Glu His Leu Pro Arg Pro Glu Ile Ser Gln Phe Pro
            100                 105                 110

Leu Asn Gln Asn Gly Ser Arg Pro Cys Asn Thr Trp Ser Gly Arg Pro
        115                 120                 125

Trp Arg Gln Ala Ile Ser Asn Pro Thr Pro Gly Gln Glu Ile Thr Gln
    130                 135                 140

Tyr Ser Gln Leu Lys Arg Pro Met Glu Pro Gly Asp Ser Ser Thr Thr
145                 150                 155                 160

Cys Gly Pro Leu Thr Leu
                165

<210> SEQ ID NO 93
<211> LENGTH: 36
<212> TYPE: DNA
<213> ORGANISM: Artificial
<220> FEATURE:
<223> OTHER INFORMATION: Synthetic Sequence
<220> FEATURE:
<221> NAME/KEY: CDS
<222> LOCATION: (1)..(36)
<223> OTHER INFORMATION: HTLV-1 protease cleavage sequence
<220> FEATURE:
<221> NAME/KEY: misc_feature
<222> LOCATION: (1)..(36)
<223> OTHER INFORMATION: n= a, g, c, or t; r= a or g; y= c or t

<400> SEQUENCE: 93 tcn cgn ccn car g

```
Xaa Arg Pro Gln Val Xaa Pro Val Met His Pro Asn
1               5                   10
```

<210> SEQ ID NO 95
<211> LENGTH: 36
<212> TYPE: DNA
<213> ORGANISM: Artificial
<220> FEATURE:
<223> OTHER INFORMATION: Synthetic Sequence
<220> FEATURE:
<221> NAME/KEY: CDS
<222> LOCATION: (1)..(36)
<223> OTHER INFORMATION: HTLV-1 protease cleavage sequence
<220> FEATURE:
<221> NAME/KEY: misc_feature
<222> LOCATION: (1)..(36)
<223> OTHER INFORMATION: n= a, g, c, or t; r= a or g; y= c or t

<400> SEQUENCE: 95

```
tcn aar acn aar gtn ctn gtn gtn car ccn aar aay           36
Xaa Lys Xaa Lys Val Xaa Val Val Gln Pro Lys Asn
1               5                   10
```

<210> SEQ ID NO 96
<211> LENGTH: 12
<212> TYPE: PRT
<213> ORGANISM: Artificial
<220> FEATURE:
<221> NAME/KEY: misc_feature
<222> LOCATION: (1)..(1)
<223> OTHER INFORMATION: The 'Xaa' at location 1 stands for Ser.
<220> FEATURE:
<221> NAME/KEY: misc_feature
<222> LOCATION: (3)..(3)
<223> OTHER INFORMATION: The 'Xaa' at location 3 stands for Thr.
<220> FEATURE:
<221> NAME/KEY: misc_feature
<222> LOCATION: (6)..(6)
<223> OTHER INFORMATION: The 'Xaa' at location 6 stands for Leu.
<220> FEATURE:
<223> OTHER INFORMATION: Synthetic Sequence

<400> SEQUENCE: 96

```
Xaa Lys Xaa Lys Val Xaa Val Val Gln Pro Lys Asn
1               5                   10
```

<210> SEQ ID NO 97
<211> LENGTH: 768
<212> TYPE: DNA
<213> ORGANISM: Human cytomegalovirus
<220> FEATURE:
<221> NAME/KEY: CDS
<222> LOCATION: (1)..(768)
<223> OTHER INFORMATION: HCMV assemblin(protease) contained in "UL80"
<300> PUBLICATION INFORMATION:
<308> DATABASE ACCESSION NUMBER: GenBank/X17403, P16753
<309> DATABASE ENTRY DATE: 1999-02-10

<400> SEQUENCE: 97

```
atg acg atg gac gag cag cag tcg cag gct gtg gcg ccg gtc tac gtg     48
Met Thr Met Asp Glu Gln Gln Ser Gln Ala Val Ala Pro Val Tyr Val
1               5                   10                  15 ggc ggc ttt ctc gcc cgc tac gac cag tct ccg gac gag gcc gaa ttg     96
Gly Gly Phe Leu Ala Arg Tyr Asp Gln Ser Pro Asp Glu Ala Glu Leu
            20                  25                  30 ctg ttg ccg cgg gac gta gtg gag cac tgg ttg cac gcg cag ggc cag    144
Leu Leu Pro Arg Asp Val Val Glu His Trp Leu His Ala Gln Gly Gln
        35                  40                  45 gga cag cct tcg ttg tcg gtc gcg ctc ccg ctc aac atc aac cac gac    192
```

| | | | | | | | | | | | | | | | | |
|---|---|---|---|---|---|---|---|---|---|---|---|---|---|---|---|---|
|Gly|Gln|Pro|Ser|Leu|Ser|Val|Ala|Leu|Pro|Leu|Asn|Ile|Asn|His|Asp| |
| |50| | | |55| | | |60| | | | | | | |

```
gac acg gcc gtt gta gga cac gtt gcg gcg atg cag agc gtc cgc gac      240
Asp Thr Ala Val Val Gly His Val Ala Ala Met Gln Ser Val Arg Asp
65              70                  75                  80 ggt ctt ttt tgc ctg ggc tgc gtc act tcg ccc agg ttt ctg gag att      288
Gly Leu Phe Cys Leu Gly Cys Val Thr Ser Pro Arg Phe Leu Glu Ile
                85                  90                  95 gta cgc cgc gct tcg gaa aag tcc gag ctg gtt tcg cgc ggg ccc gtc      336
Val Arg Arg Ala Ser Glu Lys Ser Glu Leu Val Ser Arg Gly Pro Val
            100                 105                 110 agt ccg ctg cag cca gac aag gtg gtg gag ttt ctc agc ggc agc tac      384
Ser Pro Leu Gln Pro Asp Lys Val Val Glu Phe Leu Ser Gly Ser Tyr
        115                 120                 125 gcc ggc ctc tcg ctc tcc agc cgg cgc tgc gac gac gtg gag gcc gcg      432
Ala Gly Leu Ser Leu Ser Ser Arg Arg Cys Asp Asp Val Glu Ala Ala
    130                 135                 140 acg tcg ctt tcg ggc tcg gaa acc acg ccg ttc aaa cac gtg gct ttg      480
Thr Ser Leu Ser Gly Ser Glu Thr Thr Pro Phe Lys His Val Ala Leu
145                 150                 155                 160 tgc agc gtg ggt cgg cgt cgc ggt acg ttg gcc gtg tac ggg cgc gat      528
Cys Ser Val Gly Arg Arg Arg Gly Thr Leu Ala Val Tyr Gly Arg Asp
                165                 170                 175 ccc gag tgg gtc aca cag cgg ttt cca gac ctc acg gcg gcc gac cgt      576
Pro Glu Trp Val Thr Gln Arg Phe Pro Asp Leu Thr Ala Ala Asp Arg
            180                 185                 190 gac ggg cta cgt gca cag tgg cag cgc tgc ggc agc act gct gtc gac      624
Asp Gly Leu Arg Ala Gln Trp Gln Arg Cys Gly Ser Thr Ala Val Asp
        195                 200                 205 gcg tcg ggc gat ccc ttt cgc tca gac agc tac ggc ctg ttg ggc aac      672
Ala Ser Gly Asp Pro Phe Arg Ser Asp Ser Tyr Gly Leu Leu Gly Asn
    210                 215                 220 agc gtg gac gcg ctc tac atc cgt gag cga ctg ccc aag ctg cgc tac      720
Ser Val Asp Ala Leu Tyr Ile Arg Glu Arg Leu Pro Lys Leu Arg Tyr
225                 230                 235                 240 gac aag caa cta gtc ggc gtg acg gag cgc gag tca tac gtc aag gcg      768
Asp Lys Gln Leu Val Gly Val Thr Glu Arg Glu Ser Tyr Val Lys Ala
                245                 250                 255

<210> SEQ ID NO 98
<211> LENGTH: 256
<212> TYPE: PRT
<213> ORGANISM: Human cytomegalovirus

<400> SEQUENCE: 98

Met Thr Met Asp Glu Gln Gln Ser Gln Ala Val Ala Pro Val Tyr Val
1               5                   10                  15

Gly Gly Phe Leu Ala Arg Tyr Asp Gln Ser Pro Asp Glu Ala Glu Leu
                20                  25                  30

Leu Leu Pro Arg Asp Val Val Glu His Trp Leu His Ala Gln Gly Gln
            35                  40                  45

Gly Gln Pro Ser Leu Ser Val Ala Leu Pro Leu Asn Ile Asn His Asp
        50                  55                  60

Asp Thr Ala Val Val Gly His Val Ala Ala Met Gln Ser Val Arg Asp
65              70                  75                  80

Gly Leu Phe Cys Leu Gly Cys Val Thr Ser Pro Arg Phe Leu Glu Ile
                85                  90                  95

Val Arg Arg Ala Ser Glu Lys Ser Glu Leu Val Ser Arg Gly Pro Val
            100                 105                 110
```

```
Ser Pro Leu Gln Pro Asp Lys Val Val Glu Phe Leu Ser Gly Ser Tyr
        115                 120                 125
Ala Gly Leu Ser Leu Ser Ser Arg Arg Cys Asp Asp Val Glu Ala Ala
    130                 135                 140
Thr Ser Leu Ser Gly Ser Glu Thr Thr Pro Phe Lys His Val Ala Leu
145                 150                 155                 160
Cys Ser Val Gly Arg Arg Gly Thr Leu Ala Val Tyr Gly Arg Asp
                165                 170                 175
Pro Glu Trp Val Thr Gln Arg Phe Pro Asp Leu Thr Ala Ala Asp Arg
            180                 185                 190
Asp Gly Leu Arg Ala Gln Trp Gln Arg Cys Gly Ser Thr Ala Val Asp
        195                 200                 205
Ala Ser Gly Asp Pro Phe Arg Ser Asp Ser Tyr Gly Leu Leu Gly Asn
    210                 215                 220
Ser Val Asp Ala Leu Tyr Ile Arg Glu Arg Leu Pro Lys Leu Arg Tyr
225                 230                 235                 240
Asp Lys Gln Leu Val Gly Val Thr Glu Arg Glu Ser Tyr Val Lys Ala
                245                 250                 255

<210> SEQ ID NO 99
<211> LENGTH: 15
<212> TYPE: DNA
<213> ORGANISM: Artificial
<220> FEATURE:
<223> OTHER INFORMATION: Synthetic Sequence
<220> FEATURE:
<221> NAME/KEY: CDS
<222> LOCATION: (1)..(15)
<223> OTHER INFORMATION: HCMV protease cleavage sequence

<400> SEQUENCE: 99 gtg gtg aac gcc agt                                              15
Val Val Asn Ala Ser
1               5

<210> SEQ ID NO 100
<211> LENGTH: 5
<212> TYPE: PRT
<213> ORGANISM: Artificial
<220> FEATURE:
<223> OTHER INFORMATION: Synthetic Sequence

<400> SEQUENCE: 100

Val Val Asn Ala Ser
1               5

<210> SEQ ID NO 101
<211> LENGTH: 15
<212> TYPE: DNA
<213> ORGANISM: Artificial
<220> FEATURE:
<223> OTHER INFORMATION: Synthetic Sequence
<220> FEATURE:
<221> NAME/KEY: CDS
<222> LOCATION: (1)..(15)
<223> OTHER INFORMATION: HCMV protease cleavage sequence

<400> SEQUENCE: 101 tac gtc aag gcg agc                                              15
Tyr Val Lys Ala Ser
1               5

<210> SEQ ID NO 102
```

```
<211> LENGTH: 5
<212> TYPE: PRT
<213> ORGANISM: Artificial
<220> FEATURE:
<223> OTHER INFORMATION: Synthetic Sequence

<400> SEQUENCE: 102

Tyr Val Lys Ala Ser
1               5

<210> SEQ ID NO 103
<211> LENGTH: 1506
<212> TYPE: DNA
<213> ORGANISM: Homo sapiens
<220> FEATURE:
<221> NAME/KEY: gene
<222> LOCATION: (1)..(1506)
<223> OTHER INFORMATION: Gene for APP beta-secretase
<220> FEATURE:
<221> NAME/KEY: CDS
<222> LOCATION: (1)..(1503)
<223> OTHER INFORMATION: APP beta-secretase
<300> PUBLICATION INFORMATION:
<308> DATABASE ACCESSION NUMBER: GenBank/AF201468
<309> DATABASE ENTRY DATE: 1999-12-19

<400> SEQUENCE: 103
```

| | | | | | | | | | | | | | | | | |
|---|---|---|---|---|---|---|---|---|---|---|---|---|---|---|---|---|
| atg | gcc | caa | gcc | ctg | ccc | tgg | ctc | ctg | ctg | tgg | atg | ggc | gcg | gga | gtg | 48 |
| Met | Ala | Gln | Ala | Leu | Pro | Trp | Leu | Leu | Leu | Trp | Met | Gly | Ala | Gly | Val | |
| 1 | | | | 5 | | | | | 10 | | | | | 15 | | |
| ctg | cct | gcc | cac | ggc | acc | cag | cac | ggc | atc | cgg | ctg | ccc | ctg | cgc | agc | 96 |
| Leu | Pro | Ala | His | Gly | Thr | Gln | His | Gly | Ile | Arg | Leu | Pro | Leu | Arg | Ser | |
| | | | 20 | | | | | 25 | | | | | 30 | | | |
| ggc | ctg | ggg | ggc | gcc | ccc | ctg | ggg | ctg | cgg | ctg | ccc | cgg | gag | acc | gac | 144 |
| Gly | Leu | Gly | Gly | Ala | Pro | Leu | Gly | Leu | Arg | Leu | Pro | Arg | Glu | Thr | Asp | |
| | | 35 | | | | | 40 | | | | | 45 | | | | |
| gaa | gag | ccc | gag | gag | ccc | ggc | cgg | agg | ggc | agc | ttt | gtg | gag | atg | gtg | 192 |
| Glu | Glu | Pro | Glu | Glu | Pro | Gly | Arg | Arg | Gly | Ser | Phe | Val | Glu | Met | Val | |
| | 50 | | | | | 55 | | | | | 60 | | | | | |
| gac | aac | ctg | agg | ggc | aag | tcg | ggg | cag | ggc | tac | tac | gtg | gag | atg | acc | 240 |
| Asp | Asn | Leu | Arg | Gly | Lys | Ser | Gly | Gln | Gly | Tyr | Tyr | Val | Glu | Met | Thr | |
| 65 | | | | | 70 | | | | | 75 | | | | | 80 | |
| gtg | ggc | agc | ccc | ccg | cag | acg | ctc | aac | atc | ctg | gtg | gat | aca | ggc | agc | 288 |
| Val | Gly | Ser | Pro | Pro | Gln | Thr | Leu | Asn | Ile | Leu | Val | Asp | Thr | Gly | Ser | |
| | | | | 85 | | | | | 90 | | | | | 95 | | |
| agt | aac | ttt | gca | gtg | ggt | gct | gcc | ccc | cac | ccc | ttc | ctg | cat | cgc | tac | 336 |
| Ser | Asn | Phe | Ala | Val | Gly | Ala | Ala | Pro | His | Pro | Phe | Leu | His | Arg | Tyr | |
| | | | 100 | | | | | 105 | | | | | 110 | | | |
| tac | cag | agg | cag | ctg | tcc | agc | aca | tac | cgg | gac | ctc | cgg | aag | ggt | gtg | 384 |
| Tyr | Gln | Arg | Gln | Leu | Ser | Ser | Thr | Tyr | Arg | Asp | Leu | Arg | Lys | Gly | Val | |
| | | 115 | | | | | 120 | | | | | 125 | | | | |
| tat | gtg | ccc | tac | acc | cag | ggc | aag | tgg | gaa | ggg | gag | ctg | ggc | acc | gac | 432 |
| Tyr | Val | Pro | Tyr | Thr | Gln | Gly | Lys | Trp | Glu | Gly | Glu | Leu | Gly | Thr | Asp | |
| | 130 | | | | | 135 | | | | | 140 | | | | | |
| ctg | gta | agc | atc | ccc | cat | ggc | ccc | aac | gtc | act | gtg | cgt | gcc | aac | att | 480 |
| Leu | Val | Ser | Ile | Pro | His | Gly | Pro | Asn | Val | Thr | Val | Arg | Ala | Asn | Ile | |
| 145 | | | | | 150 | | | | | 155 | | | | | 160 | |
| gct | gcc | atc | act | gaa | tca | gac | aag | ttc | ttc | atc | aac | ggc | tcc | aac | tgg | 528 |
| Ala | Ala | Ile | Thr | Glu | Ser | Asp | Lys | Phe | Phe | Ile | Asn | Gly | Ser | Asn | Trp | |
| | | | | 165 | | | | | 170 | | | | | 175 | | |
| gaa | ggc | atc | ctg | ggg | ctg | gcc | tat | gct | gag | att | gcc | agg | cct | gac | gac | 576 |
| Glu | Gly | Ile | Leu | Gly | Leu | Ala | Tyr | Ala | Glu | Ile | Ala | Arg | Pro | Asp | Asp | |
| | | | 180 | | | | | 185 | | | | | 190 | | | |
| tcc | ctg | gag | cct | ttc | ttt | gac | tct | ctg | gta | aag | cag | acc | cac | gtt | ccc | 624 |

-continued

| | | |
|---|---|---|
| Ser Leu Glu Pro Phe Phe Asp Ser Leu Val Lys Gln Thr His Val Pro<br>195                            200                     205 | | |
| aac ctc ttc tcc ctg cag ctt tgt ggt gct ggc ttc ccc ctc aac cag<br>Asn Leu Phe Ser Leu Gln Leu Cys Gly Ala Gly Phe Pro Leu Asn Gln<br>210                         215                     220 | | 672 |
| tct gaa gtg ctg gcc tct gtc gga ggg agc atg atc att gga ggt atc<br>Ser Glu Val Leu Ala Ser Val Gly Gly Ser Met Ile Ile Gly Gly Ile<br>225                       230                     235                   240 | | 720 |
| gac cac tcg ctg tac aca ggc agt ctc tgg tat aca ccc atc cgg cgg<br>Asp His Ser Leu Tyr Thr Gly Ser Leu Trp Tyr Thr Pro Ile Arg Arg<br>                     245                     250                   255 | | 768 |
| gag tgg tat tat gag gtc atc att gtg cgg gtg gag atc aat gga cag<br>Glu Trp Tyr Tyr Glu Val Ile Ile Val Arg Val Glu Ile Asn Gly Gln<br>                   260                     265                   270 | | 816 |
| gat ctg aaa atg gac tgc aag gag tac aac tat gac aag agc att gtg<br>Asp Leu Lys Met Asp Cys Lys Glu Tyr Asn Tyr Asp Lys Ser Ile Val<br>         275                     280                     285 | | 864 |
| gac agt ggc acc acc aac ctt cgt ttg ccc aag aaa gtg ttt gaa gct<br>Asp Ser Gly Thr Thr Asn Leu Arg Leu Pro Lys Lys Val Phe Glu Ala<br>290                         295                     300 | | 912 |
| gca gtc aaa tcc atc aag gca gcc tcc tcc acg gag aag ttc cct gat<br>Ala Val Lys Ser Ile Lys Ala Ala Ser Ser Thr Glu Lys Phe Pro Asp<br>305                   310                     315                   320 | | 960 |
| ggt ttc tgg cta gga gag cag ctg gtg tgc tgg caa gca ggc acc acc<br>Gly Phe Trp Leu Gly Glu Gln Leu Val Cys Trp Gln Ala Gly Thr Thr<br>                   325                     330                   335 | | 1008 |
| cct tgg aac att ttc cca gtc atc tca ctc tac cta atg ggt gag gtt<br>Pro Trp Asn Ile Phe Pro Val Ile Ser Leu Tyr Leu Met Gly Glu Val<br>                   340                     345                   350 | | 1056 |
| acc aac cag tcc ttc cgc atc acc atc ctt ccg cag caa tac ctg cgg<br>Thr Asn Gln Ser Phe Arg Ile Thr Ile Leu Pro Gln Gln Tyr Leu Arg<br>         355                     360                     365 | | 1104 |
| cca gtg gaa gat gtg gcc acg tcc caa gac gac tgt tac aag ttt gcc<br>Pro Val Glu Asp Val Ala Thr Ser Gln Asp Asp Cys Tyr Lys Phe Ala<br>370                         375                     380 | | 1152 |
| atc tca cag tca tcc acg ggc act gtt atg gga gct gtt atc atg gag<br>Ile Ser Gln Ser Ser Thr Gly Thr Val Met Gly Ala Val Ile Met Glu<br>385                         390                     395                   400 | | 1200 |
| ggc ttc tac gtt gtc ttt gat cgg gcc cga aaa cga att ggc ttt gct<br>Gly Phe Tyr Val Val Phe Asp Arg Ala Arg Lys Arg Ile Gly Phe Ala<br>                   405                     410                   415 | | 1248 |
| gtc agc gct tgc cat gtg cac gat gag ttc agg acg gca gcg gtg gaa<br>Val Ser Ala Cys His Val His Asp Glu Phe Arg Thr Ala Ala Val Glu<br>                 420                     425                   430 | | 1296 |
| ggc cct ttt gtc acc ttg gac atg gaa gac tgt ggc tac aac att cca<br>Gly Pro Phe Val Thr Leu Asp Met Glu Asp Cys Gly Tyr Asn Ile Pro<br>         435                     440                     445 | | 1344 |
| cag aca gat gag tca acc ctc atg acc ata gcc tat gtc atg gct gcc<br>Gln Thr Asp Glu Ser Thr Leu Met Thr Ile Ala Tyr Val Met Ala Ala<br>450                         455                     460 | | 1392 |
| atc tgc gcc ctc ttc atg ctg cca ctc tgc ctc atg gtg tgt cag tgg<br>Ile Cys Ala Leu Phe Met Leu Pro Leu Cys Leu Met Val Cys Gln Trp<br>465                         470                     475                   480 | | 1440 |
| cgc tgc ctc cgc tgc ctg cgc cag cag cat gat gac ttt gct gat gac<br>Arg Cys Leu Arg Cys Leu Arg Gln Gln His Asp Asp Phe Ala Asp Asp<br>                   485                     490                   495 | | 1488 |
| atc tcc ctg ctg aag tga<br>Ile Ser Leu Leu Lys<br>                 500 | | 1506 |

-continued

```
<210> SEQ ID NO 104
<211> LENGTH: 501
<212> TYPE: PRT
<213> ORGANISM: Homo sapiens

<400> SEQUENCE: 104
```

Met Ala Gln Ala Leu Pro Trp Leu Leu Leu Trp Met Gly Ala Gly Val
1               5                   10                  15

Leu Pro Ala His Gly Thr Gln His Gly Ile Arg Leu Pro Leu Arg Ser
            20                  25                  30

Gly Leu Gly Gly Ala Pro Leu Gly Leu Arg Leu Pro Arg Glu Thr Asp
        35                  40                  45

Glu Glu Pro Glu Glu Pro Gly Arg Arg Gly Ser Phe Val Glu Met Val
    50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu Leu Gly Thr Asp
    130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Pro Asp Asp
            180                 185                 190

Ser Leu Glu Pro Phe Phe Asp Ser Leu Val Lys Gln Thr His Val Pro
        195                 200                 205

Asn Leu Phe Ser Leu Gln Leu Cys Gly Ala Gly Phe Pro Leu Asn Gln
    210                 215                 220

Ser Glu Val Leu Ala Ser Val Gly Gly Ser Met Ile Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
            260                 265                 270

Asp Leu Lys Met Asp Cys Lys Glu Tyr Asn Tyr Asp Lys Ser Ile Val
        275                 280                 285

Asp Ser Gly Thr Thr Asn Leu Arg Leu Pro Lys Lys Val Phe Glu Ala
    290                 295                 300

Ala Val Lys Ser Ile Lys Ala Ala Ser Ser Thr Glu Lys Phe Pro Asp
305                 310                 315                 320

Gly Phe Trp Leu Gly Glu Gln Leu Val Cys Trp Gln Ala Gly Thr Thr
                325                 330                 335

Pro Trp Asn Ile Phe Pro Val Ile Ser Leu Tyr Leu Met Gly Glu Val
            340                 345                 350

Thr Asn Gln Ser Phe Arg Ile Thr Ile Leu Pro Gln Gln Tyr Leu Arg
        355                 360                 365

Pro Val Glu Asp Val Ala Thr Ser Gln Asp Asp Cys Tyr Lys Phe Ala
    370                 375                 380

```
Ile Ser Gln Ser Ser Thr Gly Thr Val Met Gly Ala Val Ile Met Glu
385                 390                 395                 400

Gly Phe Tyr Val Val Phe Asp Arg Ala Arg Lys Arg Ile Gly Phe Ala
                405                 410                 415

Val Ser Ala Cys His Val His Asp Glu Phe Arg Thr Ala Ala Val Glu
                420                 425                 430

Gly Pro Phe Val Thr Leu Asp Met Glu Asp Cys Gly Tyr Asn Ile Pro
                435                 440                 445

Gln Thr Asp Glu Ser Thr Leu Met Thr Ile Ala Tyr Val Met Ala Ala
                450                 455                 460

Ile Cys Ala Leu Phe Met Leu Pro Leu Cys Leu Met Val Cys Gln Trp
465                 470                 475                 480

Arg Cys Leu Arg Cys Leu Arg Gln Gln His Asp Asp Phe Ala Asp Asp
                485                 490                 495

Ile Ser Leu Leu Lys
                500

<210> SEQ ID NO 105
<211> LENGTH: 18
<212> TYPE: DNA
<213> ORGANISM: Artificial
<220> FEATURE:
<223> OTHER INFORMATION: Synthetic Sequence
<220> FEATURE:
<221> NAME/KEY: CDS
<222> LOCATION: (1)..(18)
<223> OTHER INFORMATION: APP beta secretase cleavage sequence

<400> SEQUENCE: 105 gaa gta aag atg gat gca                                           18
Glu Val Lys Met Asp Ala
1               5

<210> SEQ ID NO 106
<211> LENGTH: 6
<212> TYPE: PRT
<213> ORGANISM: Artificial
<220> FEATURE:
<223> OTHER INFORMATION: Synthetic Sequence

<400> SEQUENCE: 106

Glu Val Lys Met Asp Ala
1               5

<210> SEQ ID NO 107
<211> LENGTH: 834
<212> TYPE: DNA
<213> ORGANISM: Homo sapiens
<220> FEATURE:
<221> NAME/KEY: gene
<222> LOCATION: (1)..(834)
<223> OTHER INFORMATION: Gene for Caspase 3
<220> FEATURE:
<221> NAME/KEY: CDS
<222> LOCATION: (1)..(831)
<223> OTHER INFORMATION: Caspase 3 preproprotein
<220> FEATURE:
<221> NAME/KEY: misc_feature
<223> OTHER INFORMATION: CDS: Caspase 3, signal peptide(1..84); CDS:
      Caspase 3, large subunit(85..525); CDS: Caspase 3, small
      subunit(526..831)
<300> PUBLICATION INFORMATION:
<308> DATABASE ACCESSION NUMBER: GenBank/NM_004346
<309> DATABASE ENTRY DATE: 2001-07-13

<400> SEQUENCE: 107
```

```
atg gag aac act gaa aac tca gtg gat tca aaa tcc att aaa aat ttg      48
Met Glu Asn Thr Glu Asn Ser Val Asp Ser Lys Ser Ile Lys Asn Leu
 1               5                  10                  15 gaa cca aag atc ata cat gga agc gaa tca atg gac tct gga ata tcc      96
Glu Pro Lys Ile Ile His Gly Ser Glu Ser Met Asp Ser Gly Ile Ser
             20                  25                  30 ctg gac aac agt tat aaa atg gat tat cct gag atg ggt tta tgt ata     144
Leu Asp Asn Ser Tyr Lys Met Asp Tyr Pro Glu Met Gly Leu Cys Ile
         35                  40                  45 ata att aat aat aag aat ttt cat aaa agc act gga atg aca tct cgg     192
Ile Ile Asn Asn Lys Asn Phe His Lys Ser Thr Gly Met Thr Ser Arg
     50                  55                  60 tct ggt aca gat gtc gat gca gca aac ctc agg gaa aca ttc aga aac     240
Ser Gly Thr Asp Val Asp Ala Ala Asn Leu Arg Glu Thr Phe Arg Asn
 65                  70                  75                  80 ttg aaa tat gaa gtc agg aat aaa aat gat ctt aca cgt gaa gaa att     288
Leu Lys Tyr Glu Val Arg Asn Lys Asn Asp Leu Thr Arg Glu Glu Ile
                 85                  90                  95 gtg gaa ttg atg cgt gat gtt tct aaa gaa gat cac agc aaa agg agc     336
Val Glu Leu Met Arg Asp Val Ser Lys Glu Asp His Ser Lys Arg Ser
            100                 105                 110 agt ttt gtt tgt gtg ctt ctg agc cat ggt gaa gaa gga ata att ttt     384
Ser Phe Val Cys Val Leu Leu Ser His Gly Glu Glu Gly Ile Ile Phe
        115                 120                 125 gga aca aat gga cct gtt gac ctg aaa aaa ata aca aac ttt ttc aga     432
Gly Thr Asn Gly Pro Val Asp Leu Lys Lys Ile Thr Asn Phe Phe Arg
    130                 135                 140 ggg gat cgt tgt aga agt cta act gga aaa ccc aaa ctt ttc att att     480
Gly Asp Arg Cys Arg Ser Leu Thr Gly Lys Pro Lys Leu Phe Ile Ile
145                 150                 155                 160 cag gcc tgc cgt ggt aca gaa ctg gac tgt ggc att gag aca gac agt     528
Gln Ala Cys Arg Gly Thr Glu Leu Asp Cys Gly Ile Glu Thr Asp Ser
                165                 170                 175 ggt gtt gat gat gac atg gcg tgt cat aaa ata cca gtg gag gcc gac     576
Gly Val Asp Asp Asp Met Ala Cys His Lys Ile Pro Val Glu Ala Asp
            180                 185                 190 ttc ttg tat gca tac tcc aca gca cct ggt tat tat tct tgg cga aat     624
Phe Leu Tyr Ala Tyr Ser Thr Ala Pro Gly Tyr Tyr Ser Trp Arg Asn
        195                 200                 205 tca aag gat ggc tcc tgg ttc atc cag tcg ctt tgt gcc atg ctg aaa     672
Ser Lys Asp Gly Ser Trp Phe Ile Gln Ser Leu Cys Ala Met Leu Lys
    210                 215                 220 cag tat gcc gac aag ctt gaa ttt atg cac att ctt acc cgg gtt aac     720
Gln Tyr Ala Asp Lys Leu Glu Phe Met His Ile Leu Thr Arg Val Asn
225                 230                 235                 240 cga aag gtg gca aca gaa ttt gag tcc ttt tcc ttt gac gct act ttt     768
Arg Lys Val Ala Thr Glu Phe Glu Ser Phe Ser Phe Asp Ala Thr Phe
                245                 250                 255 cat gca aag aaa cag att cca tgt att gtt tcc atg ctc aca aaa gaa     816
His Ala Lys Lys Gln Ile Pro Cys Ile Val Ser Met Leu Thr Lys Glu
            260                 265                 270 ctc tat ttt tat cac taa                                             834
Leu Tyr Phe Tyr His
        275
```

<210> SEQ ID NO 108
<211> LENGTH: 277
<212> TYPE: PRT
<213> ORGANISM: Homo sapiens

<400> SEQUENCE: 108

```
Met Glu Asn Thr Glu Asn Ser Val Asp Ser Lys Ser Ile Lys Asn Leu
1               5                   10                  15

Glu Pro Lys Ile Ile His Gly Ser Glu Ser Met Asp Ser Gly Ile Ser
                20                  25                  30

Leu Asp Asn Ser Tyr Lys Met Asp Tyr Pro Glu Met Gly Leu Cys Ile
            35                  40                  45

Ile Ile Asn Asn Lys Asn Phe His Lys Ser Thr Gly Met Thr Ser Arg
    50                  55                  60

Ser Gly Thr Asp Val Asp Ala Ala Asn Leu Arg Glu Thr Phe Arg Asn
65                  70                  75                  80

Leu Lys Tyr Glu Val Arg Asn Lys Asn Asp Leu Thr Arg Glu Glu Ile
                85                  90                  95

Val Glu Leu Met Arg Asp Val Ser Lys Glu Asp His Ser Lys Arg Ser
                100                 105                 110

Ser Phe Val Cys Val Leu Leu Ser His Gly Glu Glu Gly Ile Ile Phe
            115                 120                 125

Gly Thr Asn Gly Pro Val Asp Leu Lys Lys Ile Thr Asn Phe Phe Arg
130                 135                 140

Gly Asp Arg Cys Arg Ser Leu Thr Gly Lys Pro Lys Leu Phe Ile Ile
145                 150                 155                 160

Gln Ala Cys Arg Gly Thr Glu Leu Asp Cys Gly Ile Glu Thr Asp Ser
                165                 170                 175

Gly Val Asp Asp Asp Met Ala Cys His Lys Ile Pro Val Glu Ala Asp
            180                 185                 190

Phe Leu Tyr Ala Tyr Ser Thr Ala Pro Gly Tyr Tyr Ser Trp Arg Asn
    195                 200                 205

Ser Lys Asp Gly Ser Trp Phe Ile Gln Ser Leu Cys Ala Met Leu Lys
210                 215                 220

Gln Tyr Ala Asp Lys Leu Glu Phe Met His Ile Leu Thr Arg Val Asn
225                 230                 235                 240

Arg Lys Val Ala Thr Glu Phe Glu Ser Phe Ser Phe Asp Ala Thr Phe
                245                 250                 255

His Ala Lys Lys Gln Ile Pro Cys Ile Val Ser Met Leu Thr Lys Glu
            260                 265                 270

Leu Tyr Phe Tyr His
        275
```

<210> SEQ ID NO 109
<211> LENGTH: 441
<212> TYPE: DNA
<213> ORGANISM: Homo sapiens
<220> FEATURE:
<221> NAME/KEY: CDS
<222> LOCATION: (1)..(441)
<223> OTHER INFORMATION: Caspase 3, large subunit
<300> PUBLICATION INFORMATION:
<308> DATABASE ACCESSION NUMBER: GenBank/XM_054686
<309> DATABASE ENTRY DATE: 2002-05-13

<400> SEQUENCE: 109

```
tct gga ata tcc ctg gac aac agt tat aaa atg gat tat cct gag atg    48
Ser Gly Ile Ser Leu Asp Asn Ser Tyr Lys Met Asp Tyr Pro Glu Met
1               5                   10                  15 ggt tta tgt ata ata att aat aat aag aat ttt cat aaa agc act gga    96
Gly Leu Cys Ile Ile Ile Asn Asn Lys Asn Phe His Lys Ser Thr Gly
                20                  25                  30
```

```
atg aca tct cgg tct ggt aca gat gtc gat gca gca aac ctc agg gaa    144
Met Thr Ser Arg Ser Gly Thr Asp Val Asp Ala Ala Asn Leu Arg Glu
         35                  40                  45 aca ttc aga aac ttg aaa tat gaa gtc agg aat aaa aat gat ctt aca    192
Thr Phe Arg Asn Leu Lys Tyr Glu Val Arg Asn Lys Asn Asp Leu Thr
 50                  55                  60 cgt gaa gaa att gtg gaa ttg atg cgt gat gtt tct aaa gaa gat cac    240
Arg Glu Glu Ile Val Glu Leu Met Arg Asp Val Ser Lys Glu Asp His
 65                  70                  75                  80 agc aaa agg agc agt ttt gtt tgt gtg ctt ctg agc cat ggt gaa gaa    288
Ser Lys Arg Ser Ser Phe Val Cys Val Leu Leu Ser His Gly Glu Glu
                 85                  90                  95 gga ata att ttt gga aca aat gga cct gtt gac ctg aaa aaa ata aca    336
Gly Ile Ile Phe Gly Thr Asn Gly Pro Val Asp Leu Lys Lys Ile Thr
            100                 105                 110 aac ttt tca aga ggg gat cgt tgt aga agt cta act gga aaa ccc aaa    384
Asn Phe Phe Arg Gly Asp Arg Cys Arg Ser Leu Thr Gly Lys Pro Lys
        115                 120                 125 ctt ttc att att cag gcc tgc cgt ggt aca gaa ctg gac tgt ggc att    432
Leu Phe Ile Ile Gln Ala Cys Arg Gly Thr Glu Leu Asp Cys Gly Ile
130                 135                 140 gag aca gac                                                        441
Glu Thr Asp
145

<210> SEQ ID NO 110
<211> LENGTH: 147
<212> TYPE: PRT
<213> ORGANISM: Homo sapiens

<400> SEQUENCE: 110

Ser Gly Ile Ser Leu Asp Asn Ser Tyr Lys Met Asp Tyr Pro Glu Met
1               5                   10                  15

Gly Leu Cys Ile Ile Ile Asn Asn Lys Asn Phe His Lys Ser Thr Gly
            20                  25                  30

Met Thr Ser Arg Ser Gly Thr Asp Val Asp Ala Ala Asn Leu Arg Glu
         35                  40                  45

Thr Phe Arg Asn Leu Lys Tyr Glu Val Arg Asn Lys Asn Asp Leu Thr
 50                  55                  60

Arg Glu Glu Ile Val Glu Leu Met Arg Asp Val Ser Lys Glu Asp His
 65                  70                  75                  80

Ser Lys Arg Ser Ser Phe Val Cys Val Leu Leu Ser His Gly Glu Glu
                 85                  90                  95

Gly Ile Ile Phe Gly Thr Asn Gly Pro Val Asp Leu Lys Lys Ile Thr
            100                 105                 110

Asn Phe Phe Arg Gly Asp Arg Cys Arg Ser Leu Thr Gly Lys Pro Lys
        115                 120                 125

Leu Phe Ile Ile Gln Ala Cys Arg Gly Thr Glu Leu Asp Cys Gly Ile
    130                 135                 140

Glu Thr Asp
145

<210> SEQ ID NO 111
<211> LENGTH: 306
<212> TYPE: DNA
<213> ORGANISM: Homo sapiens
<220> FEATURE:
<221> NAME/KEY: CDS
<222> LOCATION: (1)..(306)
<223> OTHER INFORMATION: Caspase 3, small subunit
```

<300> PUBLICATION INFORMATION:
<308> DATABASE ACCESSION NUMBER: GenBank/XM_054686
<309> DATABASE ENTRY DATE: 2002-05-13

<400> SEQUENCE: 111

| agt | ggt | gtt | gat | gat | gac | atg | gcg | tgt | cat | aaa | ata | cca | gtg | gag | gcc | 48 |
| Ser | Gly | Val | Asp | Asp | Asp | Met | Ala | Cys | His | Lys | Ile | Pro | Val | Glu | Ala | |
| 1 | | | | 5 | | | | | 10 | | | | | 15 | | |

| gac | ttc | ttg | tat | gca | tac | tcc | aca | gca | cct | ggt | tat | tat | tct | tgg | cga | 96 |
| Asp | Phe | Leu | Tyr | Ala | Tyr | Ser | Thr | Ala | Pro | Gly | Tyr | Tyr | Ser | Trp | Arg | |
| | | | 20 | | | | | 25 | | | | | 30 | | | |

| aat | tca | aag | gat | ggc | tcc | tgg | ttc | atc | cag | tcg | ctt | tgt | gcc | atg | ctg | 144 |
| Asn | Ser | Lys | Asp | Gly | Ser | Trp | Phe | Ile | Gln | Ser | Leu | Cys | Ala | Met | Leu | |
| | | 35 | | | | | 40 | | | | | 45 | | | | |

| aaa | cag | tat | gcc | gac | aag | ctt | gaa | ttt | atg | cac | att | ctt | acc | cgg | gtt | 192 |
| Lys | Gln | Tyr | Ala | Asp | Lys | Leu | Glu | Phe | Met | His | Ile | Leu | Thr | Arg | Val | |
| 50 | | | | | 55 | | | | | 60 | | | | | | |

| aac | cga | aag | gtg | gca | aca | gaa | ttt | gag | tcc | ttt | tcc | ttt | gac | gct | act | 240 |
| Asn | Arg | Lys | Val | Ala | Thr | Glu | Phe | Glu | Ser | Phe | Ser | Phe | Asp | Ala | Thr | |
| 65 | | | | 70 | | | | | 75 | | | | | 80 | | |

| ttt | cat | gca | aag | aaa | cag | att | cca | tgt | att | gtt | tcc | atg | ctc | aca | aaa | 288 |
| Phe | His | Ala | Lys | Lys | Gln | Ile | Pro | Cys | Ile | Val | Ser | Met | Leu | Thr | Lys | |
| | | | | 85 | | | | | 90 | | | | | 95 | | |

| gaa | ctc | tat | ttt | tat | cac | | | | | | | | | | | 306 |
| Glu | Leu | Tyr | Phe | Tyr | His | | | | | | | | | | | |
| | | | | 100 | | | | | | | | | | | | |

<210> SEQ ID NO 112
<211> LENGTH: 102
<212> TYPE: PRT
<213> ORGANISM: Homo sapiens

<400> SEQUENCE: 112

| Ser | Gly | Val | Asp | Asp | Asp | Met | Ala | Cys | His | Lys | Ile | Pro | Val | Glu | Ala |
| 1 | | | | 5 | | | | | 10 | | | | | 15 | |

| Asp | Phe | Leu | Tyr | Ala | Tyr | Ser | Thr | Ala | Pro | Gly | Tyr | Tyr | Ser | Trp | Arg |
| | | | 20 | | | | | 25 | | | | | 30 | | |

| Asn | Ser | Lys | Asp | Gly | Ser | Trp | Phe | Ile | Gln | Ser | Leu | Cys | Ala | Met | Leu |
| | | 35 | | | | | 40 | | | | | 45 | | | |

| Lys | Gln | Tyr | Ala | Asp | Lys | Leu | Glu | Phe | Met | His | Ile | Leu | Thr | Arg | Val |
| 50 | | | | | 55 | | | | | 60 | | | | | |

| Asn | Arg | Lys | Val | Ala | Thr | Glu | Phe | Glu | Ser | Phe | Ser | Phe | Asp | Ala | Thr |
| 65 | | | | 70 | | | | | 75 | | | | | 80 | |

| Phe | His | Ala | Lys | Lys | Gln | Ile | Pro | Cys | Ile | Val | Ser | Met | Leu | Thr | Lys |
| | | | | 85 | | | | | 90 | | | | | 95 | |

| Glu | Leu | Tyr | Phe | Tyr | His |
| | | | | 100 | |

<210> SEQ ID NO 113
<211> LENGTH: 12
<212> TYPE: DNA
<213> ORGANISM: Artificial
<220> FEATURE:
<223> OTHER INFORMATION: Synthetic Sequence
<220> FEATURE:
<221> NAME/KEY: CDS
<222> LOCATION: (1)..(12)
<223> OTHER INFORMATION: Caspase 3 protease cleavage sequence
<220> FEATURE:
<221> NAME/KEY: misc_feature
<222> LOCATION: (1)..(12)
<223> OTHER INFORMATION: r= a or g; y= c or t

```
<400> SEQUENCE: 113 gar agy atg gay                                                          12
Glu Xaa Met Asp
1

<210> SEQ ID NO 114
<211> LENGTH: 4
<212> TYPE: PRT
<213> ORGANISM: Artificial
<220> FEATURE:
<221> NAME/KEY: misc_feature
<222> LOCATION: (2)..(2)
<223> OTHER INFORMATION: The 'Xaa' at location 2 stands for Ser.
<220> FEATURE:
<223> OTHER INFORMATION: Synthetic Sequence

<400> SEQUENCE: 114

Glu Xaa Met Asp
1

<210> SEQ ID NO 115
<211> LENGTH: 1869
<212> TYPE: DNA
<213> ORGANISM: Homo sapiens
<220> FEATURE:
<221> NAME/KEY: gene
<222> LOCATION: (1)..(1869)
<223> OTHER INFORMATION: Gene for Homo sapiens coagulation factor II
      (thrombin)
<220> FEATURE:
<221> NAME/KEY: CDS
<222> LOCATION: (1)..(1866)
<223> OTHER INFORMATION: Coagulation factor II precursor
<220> FEATURE:
<221> NAME/KEY: misc_feature
<223> OTHER INFORMATION: CDS: Coagulation factor II signal
      peptide(1..129); CDS: Coagulation factor II (130..1866)
<300> PUBLICATION INFORMATION:
<308> DATABASE ACCESSION NUMBER: GenBank/NM_000506
<309> DATABASE ENTRY DATE: 2000-10-31

<400> SEQUENCE: 115 atg gcg cac gtc cga ggc ttg cag ctg cct ggc tgc ctg gcc ctg gct         48
Met Ala His Val Arg Gly Leu Gln Leu Pro Gly Cys Leu Ala Leu Ala
1               5                   10                  15 gcc ctg tgt agc ctt gtg cac agc cag cat gtg ttc ctg gct cct cag         96
Ala Leu Cys Ser Leu Val His Ser Gln His Val Phe Leu Ala Pro Gln
                20                  25                  30 caa gca cgg tcg ctg ctc cag cgg gtc cgg cga gcc aac acc ttc ttg        144
Gln Ala Arg Ser Leu Leu Gln Arg Val Arg Arg Ala Asn Thr Phe Leu
            35                  40                  45 gag gag gtg cgc aag ggc aac cta gag cga gag tgc gtg gag gag acg        192
Glu Glu Val Arg Lys Gly Asn Leu Glu Arg Glu Cys Val Glu Glu Thr
        50                  55                  60 tgc agc tac gag gag gcc ttc gag gct ctg gag tcc tcc acg gct acg        240
Cys Ser Tyr Glu Glu Ala Phe Glu Ala Leu Glu Ser Ser Thr Ala Thr
65                  70                  75                  80 gat gtg ttc tgg gcc aag tac aca gct tgt gag aca gcg agg acg cct        288
Asp Val Phe Trp Ala Lys Tyr Thr Ala Cys Glu Thr Ala Arg Thr Pro
                85                  90                  95 cga gat aag ctt gct gca tgt ctg gaa ggt aac tgt gct gag ggt ctg        336
Arg Asp Lys Leu Ala Ala Cys Leu Glu Gly Asn Cys Ala Glu Gly Leu
            100                 105                 110 ggt acg aac tac cga ggg cat gtg aac atc acc cgg tca ggc att gag        384
Gly Thr Asn Tyr Arg Gly His Val Asn Ile Thr Arg Ser Gly Ile Glu
        115                 120                 125
```

-continued

| | | |
|---|---|---|
| tgc cag cta tgg agg agt cgc tac cca cat aag cct gaa atc aac tcc<br>Cys Gln Leu Trp Arg Ser Arg Tyr Pro His Lys Pro Glu Ile Asn Ser<br>130                      135                      140 | | 432 |
| act acc cat cct ggg gcc gac cta cag gag aat ttc tgc cgc aac ccc<br>Thr Thr His Pro Gly Ala Asp Leu Gln Glu Asn Phe Cys Arg Asn Pro<br>145                      150                      155                      160 | | 480 |
| gac agc agc acc acg gga ccc tgg tgc tac act aca gac ccc acc gtg<br>Asp Ser Ser Thr Thr Gly Pro Trp Cys Tyr Thr Thr Asp Pro Thr Val<br>                  165                      170                      175 | | 528 |
| agg agg cag gaa tgc agc atc cct gtc tgt ggc cag gat caa gtc act<br>Arg Arg Gln Glu Cys Ser Ile Pro Val Cys Gly Gln Asp Gln Val Thr<br>                  180                      185                      190 | | 576 |
| gta gcg atg act cca cgc tcc gaa ggc tcc agt gtg aat ctg tca cct<br>Val Ala Met Thr Pro Arg Ser Glu Gly Ser Ser Val Asn Leu Ser Pro<br>            195                      200                      205 | | 624 |
| cca ttg gag cag tgt gtc cct gat cgg ggg cag cag tac cag ggg cgc<br>Pro Leu Glu Gln Cys Val Pro Asp Arg Gly Gln Gln Tyr Gln Gly Arg<br>210                      215                      220 | | 672 |
| ctg gcg gtg acc aca cat ggg ctc ccc tgc ctg gcc tgg gcc agc gca<br>Leu Ala Val Thr Thr His Gly Leu Pro Cys Leu Ala Trp Ala Ser Ala<br>225                      230                      235                      240 | | 720 |
| cag gcc aag gcc ctg agc aag cac cag gac ttc aac tca gct gtg cag<br>Gln Ala Lys Ala Leu Ser Lys His Gln Asp Phe Asn Ser Ala Val Gln<br>                  245                      250                      255 | | 768 |
| ctg gtg gag aac ttc tgc cgc aac cca gac ggg gat gag gag ggc gtg<br>Leu Val Glu Asn Phe Cys Arg Asn Pro Asp Gly Asp Glu Glu Gly Val<br>            260                      265                      270 | | 816 |
| tgg tgc tat gtg gcc ggg aag cct ggc gac ttt ggg tac tgc gac ctc<br>Trp Cys Tyr Val Ala Gly Lys Pro Gly Asp Phe Gly Tyr Cys Asp Leu<br>        275                      280                      285 | | 864 |
| aac tat tgt gag gag gcc gtg gag gag gag aca gga gat ggg ctg gat<br>Asn Tyr Cys Glu Glu Ala Val Glu Glu Glu Thr Gly Asp Gly Leu Asp<br>290                      295                      300 | | 912 |
| gag gac tca gac agg gcc atc gaa ggg cgt acc gcc acc agt gag tac<br>Glu Asp Ser Asp Arg Ala Ile Glu Gly Arg Thr Ala Thr Ser Glu Tyr<br>305                      310                      315                      320 | | 960 |
| cag act ttc ttc aat ccg agg acc ttt ggc tcg gga gag gca gac tgt<br>Gln Thr Phe Phe Asn Pro Arg Thr Phe Gly Ser Gly Glu Ala Asp Cys<br>                  325                      330                      335 | | 1008 |
| ggg ctg cga cct ctg ttc gag aag aag tcg ctg gag gac aaa acc gaa<br>Gly Leu Arg Pro Leu Phe Glu Lys Lys Ser Leu Glu Asp Lys Thr Glu<br>            340                      345                      350 | | 1056 |
| aga gag ctc ctg gaa tcc tac atc gac ggg cgc att gtg gag ggc tcg<br>Arg Glu Leu Leu Glu Ser Tyr Ile Asp Gly Arg Ile Val Glu Gly Ser<br>355                      360                      365 | | 1104 |
| gat gca gag atc ggc atg tca cct tgg cag gtg atg ctt ttc cgg aag<br>Asp Ala Glu Ile Gly Met Ser Pro Trp Gln Val Met Leu Phe Arg Lys<br>        370                      375                      380 | | 1152 |
| agt ccc cag gag ctg ctg tgt ggg gcc agc ctc atc agt gac cgc tgg<br>Ser Pro Gln Glu Leu Leu Cys Gly Ala Ser Leu Ile Ser Asp Arg Trp<br>385                      390                      395                      400 | | 1200 |
| gtc ctc acc gcc gcc cac tgc ctc ctg tac ccg ccc tgg gac aag aac<br>Val Leu Thr Ala Ala His Cys Leu Leu Tyr Pro Pro Trp Asp Lys Asn<br>                  405                      410                      415 | | 1248 |
| ttc acc gag aat gac ctt ctg gtg cgc att ggc aag cac tcc cgc aca<br>Phe Thr Glu Asn Asp Leu Leu Val Arg Ile Gly Lys His Ser Arg Thr<br>            420                      425                      430 | | 1296 |
| agg tac gag cga aac att gaa aag ata tcc atg ttg gaa aag atc tac<br>Arg Tyr Glu Arg Asn Ile Glu Lys Ile Ser Met Leu Glu Lys Ile Tyr<br>435                      440                      445 | | 1344 |

```
atc cac ccc agg tac aac tgg cgg gag aac ctg gac cgg gac att gcc    1392
Ile His Pro Arg Tyr Asn Trp Arg Glu Asn Leu Asp Arg Asp Ile Ala
    450                 455                 460 ctg atg aag ctg aag aag cct gtt gcc ttc agt gac tac att cac cct    1440
Leu Met Lys Leu Lys Lys Pro Val Ala Phe Ser Asp Tyr Ile His Pro
465                 470                 475                 480 gtg tgt ctg ccc gac agg gag acg gca gcc agc ttg ctc cag gct gga    1488
Val Cys Leu Pro Asp Arg Glu Thr Ala Ala Ser Leu Leu Gln Ala Gly
                485                 490                 495 tac aag ggg cgg gtg aca ggc tgg ggc aac ctg aag gag acg tgg aca    1536
Tyr Lys Gly Arg Val Thr Gly Trp Gly Asn Leu Lys Glu Thr Trp Thr
            500                 505                 510 gcc aac gtt ggt aag ggg cag ccc agt gtc ctg cag gtg gtg aac ctg    1584
Ala Asn Val Gly Lys Gly Gln Pro Ser Val Leu Gln Val Val Asn Leu
        515                 520                 525 ccc att gtg gag cgg ccg gtc tgc aag gac tcc acc cgg atc cgc atc    1632
Pro Ile Val Glu Arg Pro Val Cys Lys Asp Ser Thr Arg Ile Arg Ile
    530                 535                 540 act gac aac atg ttc tgt gct ggt tac aag cct gat gaa ggg aaa cga    1680
Thr Asp Asn Met Phe Cys Ala Gly Tyr Lys Pro Asp Glu Gly Lys Arg
545                 550                 555                 560 ggg gat gcc tgt gaa ggt gac agt ggg gga ccc ttt gtc atg aag agc    1728
Gly Asp Ala Cys Glu Gly Asp Ser Gly Gly Pro Phe Val Met Lys Ser
                565                 570                 575 ccc ttt aac aac cgc tgg tat caa atg ggc atc gtc tca tgg ggt gaa    1776
Pro Phe Asn Asn Arg Trp Tyr Gln Met Gly Ile Val Ser Trp Gly Glu
            580                 585                 590 ggc tgt gac cgg gat ggg aaa tat ggc ttc tac aca cat gtg ttc cgc    1824
Gly Cys Asp Arg Asp Gly Lys Tyr Gly Phe Tyr Thr His Val Phe Arg
        595                 600                 605 ctg aag aag tgg ata cag aag gtc att gat cag ttt gga gag tag        1869
Leu Lys Lys Trp Ile Gln Lys Val Ile Asp Gln Phe Gly Glu
    610                 615                 620

<210> SEQ ID NO 116
<211> LENGTH: 622
<212> TYPE: PRT
<213> ORGANISM: Homo sapiens

<400> SEQUENCE: 116

Met Ala His Val Arg Gly Leu Gln Leu Pro Gly Cys Leu Ala Leu Ala
1               5                   10                  15

Ala Leu Cys Ser Leu Val His Ser Gln His Val Phe Leu Ala Pro Gln
                20                  25                  30

Gln Ala Arg Ser Leu Leu Gln Arg Val Arg Arg Ala Asn Thr Phe Leu
            35                  40                  45

Glu Glu Val Arg Lys Gly Asn Leu Glu Arg Glu Cys Val Glu Glu Thr
        50                  55                  60

Cys Ser Tyr Glu Glu Ala Phe Glu Ala Leu Glu Ser Ser Thr Ala Thr
65                  70                  75                  80

Asp Val Phe Trp Ala Lys Tyr Thr Ala Cys Glu Thr Ala Arg Thr Pro
                85                  90                  95

Arg Asp Lys Leu Ala Ala Cys Leu Glu Gly Asn Cys Ala Glu Gly Leu
            100                 105                 110

Gly Thr Asn Tyr Arg Gly His Val Asn Ile Thr Arg Ser Gly Ile Glu
        115                 120                 125

Cys Gln Leu Trp Arg Ser Arg Tyr Pro His Lys Pro Glu Ile Asn Ser
    130                 135                 140
```

-continued

Thr Thr His Pro Gly Ala Asp Leu Gln Glu Asn Phe Cys Arg Asn Pro
145                 150                 155                 160

Asp Ser Ser Thr Thr Gly Pro Trp Cys Tyr Thr Thr Asp Pro Thr Val
            165                 170                 175

Arg Arg Gln Glu Cys Ser Ile Pro Val Cys Gly Gln Asp Gln Val Thr
        180                 185                 190

Val Ala Met Thr Pro Arg Ser Glu Gly Ser Ser Val Asn Leu Ser Pro
    195                 200                 205

Pro Leu Glu Gln Cys Val Pro Asp Arg Gly Gln Gln Tyr Gln Gly Arg
210                 215                 220

Leu Ala Val Thr Thr His Gly Leu Pro Cys Leu Ala Trp Ala Ser Ala
225                 230                 235                 240

Gln Ala Lys Ala Leu Ser Lys His Gln Asp Phe Asn Ser Ala Val Gln
                245                 250                 255

Leu Val Glu Asn Phe Cys Arg Asn Pro Asp Gly Asp Glu Glu Gly Val
            260                 265                 270

Trp Cys Tyr Val Ala Gly Lys Pro Gly Asp Phe Gly Tyr Cys Asp Leu
        275                 280                 285

Asn Tyr Cys Glu Glu Ala Val Glu Glu Thr Gly Asp Gly Leu Asp
290                 295                 300

Glu Asp Ser Asp Arg Ala Ile Glu Gly Arg Thr Ala Thr Ser Glu Tyr
305                 310                 315                 320

Gln Thr Phe Phe Asn Pro Arg Thr Phe Gly Ser Gly Glu Ala Asp Cys
                325                 330                 335

Gly Leu Arg Pro Leu Phe Glu Lys Lys Ser Leu Glu Asp Lys Thr Glu
            340                 345                 350

Arg Glu Leu Leu Glu Ser Tyr Ile Asp Gly Arg Ile Val Glu Gly Ser
        355                 360                 365

Asp Ala Glu Ile Gly Met Ser Pro Trp Gln Val Met Leu Phe Arg Lys
370                 375                 380

Ser Pro Gln Glu Leu Leu Cys Gly Ala Ser Leu Ile Ser Asp Arg Trp
385                 390                 395                 400

Val Leu Thr Ala Ala His Cys Leu Leu Tyr Pro Pro Trp Asp Lys Asn
                405                 410                 415

Phe Thr Glu Asn Asp Leu Leu Val Arg Ile Gly Lys His Ser Arg Thr
            420                 425                 430

Arg Tyr Glu Arg Asn Ile Glu Lys Ile Ser Met Leu Glu Lys Ile Tyr
        435                 440                 445

Ile His Pro Arg Tyr Asn Trp Arg Glu Asn Leu Asp Arg Asp Ile Ala
450                 455                 460

Leu Met Lys Leu Lys Lys Pro Val Ala Phe Ser Asp Tyr Ile His Pro
465                 470                 475                 480

Val Cys Leu Pro Asp Arg Glu Thr Ala Ala Ser Leu Leu Gln Ala Gly
                485                 490                 495

Tyr Lys Gly Arg Val Thr Gly Trp Gly Asn Leu Lys Glu Thr Trp Thr
            500                 505                 510

Ala Asn Val Gly Lys Gly Gln Pro Ser Val Leu Gln Val Val Asn Leu
        515                 520                 525

Pro Ile Val Glu Arg Pro Val Cys Lys Asp Ser Thr Arg Ile Arg Ile
530                 535                 540

Thr Asp Asn Met Phe Cys Ala Gly Tyr Lys Pro Asp Glu Gly Lys Arg
545                 550                 555                 560

```
Gly Asp Ala Cys Glu Gly Asp Ser Gly Pro Phe Val Met Lys Ser
            565                 570                 575

Pro Phe Asn Asn Arg Trp Tyr Gln Met Gly Ile Val Ser Trp Glu
            580                 585                 590

Gly Cys Asp Arg Asp Gly Lys Tyr Gly Phe Tyr Thr His Val Phe Arg
            595                 600                 605

Leu Lys Lys Trp Ile Gln Lys Val Ile Asp Gln Phe Gly Glu
    610                 615                 620

<210> SEQ ID NO 117
<211> LENGTH: 21
<212> TYPE: DNA
<213> ORGANISM: Artificial
<220> FEATURE:
<223> OTHER INFORMATION: Synthetic Sequence
<220> FEATURE:
<221> NAME/KEY: CDS
<222> LOCATION: (1)..(21)
<223> OTHER INFORMATION: Platelet glycoprotein V thrombin cleavage
      sequence

<400> SEQUENCE: 117 ccc ggg ccc cgg ggc ccg cct                                          21
Pro Gly Pro Arg Gly Pro Pro
1               5

<210> SEQ ID NO 118
<211> LENGTH: 7
<212> TYPE: PRT
<213> ORGANISM: Artificial
<220> FEATURE:
<223> OTHER INFORMATION: Synthetic Sequence

<400> SEQUENCE: 118

Pro Gly Pro Arg Gly Pro Pro
1               5

<210> SEQ ID NO 119
<211> LENGTH: 1878
<212> TYPE: DNA
<213> ORGANISM: Homo sapiens
<220> FEATURE:
<221> NAME/KEY: gene
<222> LOCATION: (1)..(1878)
<223> OTHER INFORMATION: Gene for Human factor XI (blood coagulation
      factor)
<220> FEATURE:
<221> NAME/KEY: CDS
<222> LOCATION: (1)..(1875)
<223> OTHER INFORMATION: Preprofactor XI
<220> FEATURE:
<221> NAME/KEY: misc_feature
<223> OTHER INFORMATION: CDS: Factor XI signal peptide(1..54); CDS:
      Factor XI heavy chain(55..1161); CDS: Factor XI light
      chain(1162....1875)
<300> PUBLICATION INFORMATION:
<308> DATABASE ACCESSION NUMBER: GenBank/M13142
<309> DATABASE ENTRY DATE: 1994-11-08

<400> SEQUENCE: 119 atg att ttc tta tat caa gtg gta cat ttc att tta ttt act tca gtt    48
Met Ile Phe Leu Tyr Gln Val Val His Phe Ile Leu Phe Thr Ser Val
1               5                   10                  15 tct ggt gaa tgt gtg act cag ttg ttg aag gac acc tgc ttt gaa gga    96
Ser Gly Glu Cys Val Thr Gln Leu Leu Lys Asp Thr Cys Phe Glu Gly
                20                  25                  30 ggg gac att act acg gtc ttc aca cca agc gcc aag tac tgc cag gta   144
Gly Asp Ile Thr Thr Val Phe Thr Pro Ser Ala Lys Tyr Cys Gln Val
```

```
                35                  40                  45
gtc tgc act tac cac cca aga tgt tta ctc ttc act ttc acg gcg gaa      192
Val Cys Thr Tyr His Pro Arg Cys Leu Leu Phe Thr Phe Thr Ala Glu
    50                  55                  60 tca cca tct gag gat ccc acc cga tgg ttt act tgt gtc ctg aaa gac      240
Ser Pro Ser Glu Asp Pro Thr Arg Trp Phe Thr Cys Val Leu Lys Asp
65                  70                  75                  80 agt gtt aca gaa aca ctg cca aga gtg aat agg aca gca gcg att tct      288
Ser Val Thr Glu Thr Leu Pro Arg Val Asn Arg Thr Ala Ala Ile Ser
                85                  90                  95 ggg tat tct ttc aag caa tgc tca cac caa ata agc gct tgc aac aaa      336
Gly Tyr Ser Phe Lys Gln Cys Ser His Gln Ile Ser Ala Cys Asn Lys
            100                 105                 110 gac att tat gtg gac cta gac atg aag ggc ata aac tat aac agc tca      384
Asp Ile Tyr Val Asp Leu Asp Met Lys Gly Ile Asn Tyr Asn Ser Ser
        115                 120                 125 gtt gcc aag agt gct caa gaa tgc caa gaa aga tgc acg gat gac gtc      432
Val Ala Lys Ser Ala Gln Glu Cys Gln Glu Arg Cys Thr Asp Asp Val
    130                 135                 140 cac tgc cac ttt ttc acg tac gcc aca agg cag ttt ccc agc ctg gag      480
His Cys His Phe Phe Thr Tyr Ala Thr Arg Gln Phe Pro Ser Leu Glu
145                 150                 155                 160 cat cgt aac att tgt cta ctg aag cac acc caa aca ggg aca cca acc      528
His Arg Asn Ile Cys Leu Leu Lys His Thr Gln Thr Gly Thr Pro Thr
                165                 170                 175 aga ata acg aag ctc gat aaa gtg gtg tct gga ttt tca ctg aaa tcc      576
Arg Ile Thr Lys Leu Asp Lys Val Val Ser Gly Phe Ser Leu Lys Ser
            180                 185                 190 tgt gca ctt tct aat ctg gct tgt att agg gac att ttc cct aat acg      624
Cys Ala Leu Ser Asn Leu Ala Cys Ile Arg Asp Ile Phe Pro Asn Thr
        195                 200                 205 gtg ttt gca gac agc aac atc gac agt gtc atg gct ccc gat gct ttt      672
Val Phe Ala Asp Ser Asn Ile Asp Ser Val Met Ala Pro Asp Ala Phe
    210                 215                 220 gtc tgt ggc cga atc tgc act cat cat ccc ggt tgc ttg ttt ttt acc      720
Val Cys Gly Arg Ile Cys Thr His His Pro Gly Cys Leu Phe Phe Thr
225                 230                 235                 240 ttc ttt tcc cag gaa tgg ccc aaa gaa tct caa aga aat ctt tgt ctc      768
Phe Phe Ser Gln Glu Trp Pro Lys Glu Ser Gln Arg Asn Leu Cys Leu
                245                 250                 255 ctt aaa aca tct gag agt gga ttg ccc agt aca cgc att aaa aag agc      816
Leu Lys Thr Ser Glu Ser Gly Leu Pro Ser Thr Arg Ile Lys Lys Ser
            260                 265                 270 aaa gct ctt tct ggt ttc agt cta caa agc tgc agg cac agc atc cca      864
Lys Ala Leu Ser Gly Phe Ser Leu Gln Ser Cys Arg His Ser Ile Pro
        275                 280                 285 gtg ttc tgc cat tct tca ttt tac cat gac act gat ttc ttg gga gaa      912
Val Phe Cys His Ser Ser Phe Tyr His Asp Thr Asp Phe Leu Gly Glu
    290                 295                 300 gaa ctg gat att gtt gct gca aaa agt cac gag gcc tgc cag aaa ctg      960
Glu Leu Asp Ile Val Ala Ala Lys Ser His Glu Ala Cys Gln Lys Leu
305                 310                 315                 320 tgc acc aat gcc gtc cgc tgc cag ttt ttt acc tat acc cca gcc caa     1008
Cys Thr Asn Ala Val Arg Cys Gln Phe Phe Thr Tyr Thr Pro Ala Gln
                325                 330                 335 gca tcc tgc aac gaa ggg aag ggc aag tgt tac tta aag ctt tct tca     1056
Ala Ser Cys Asn Glu Gly Lys Gly Lys Cys Tyr Leu Lys Leu Ser Ser
            340                 345                 350 aac gga tct cca act aaa ata ctt cac ggg aga gga ggc atc tct gga     1104
```

|                                                                                       |      |
|---------------------------------------------------------------------------------------|------|
| Asn Gly Ser Pro Thr Lys Ile Leu His Gly Arg Gly Ile Ser Gly<br>    355                   360                    365 | |
| tac aca tta agg ttg tgt aaa atg gat aat gag tgt acc acc aaa atc<br>Tyr Thr Leu Arg Leu Cys Lys Met Asp Asn Glu Cys Thr Thr Lys Ile<br>370                    375                        380 | 1152 |
| aag ccc agg atc gtt gga gga act gcg tct gtt cgt ggt gag tgg ccg<br>Lys Pro Arg Ile Val Gly Gly Thr Ala Ser Val Arg Gly Glu Trp Pro<br>385                    390                    395                    400 | 1200 |
| tgg cag gtg acc ctg cac aca acc tca ccc act cag aga cac ctg tgt<br>Trp Gln Val Thr Leu His Thr Thr Ser Pro Thr Gln Arg His Leu Cys<br>                405                    410                    415 | 1248 |
| gga ggc tcc atc att gga aac cag tgg ata tta aca gcc gct cac tgt<br>Gly Gly Ser Ile Ile Gly Asn Gln Trp Ile Leu Thr Ala Ala His Cys<br>                420                    425                    430 | 1296 |
| ttc tat ggg gta gag tca cct aag att ttg cgt gtc tac agt ggc att<br>Phe Tyr Gly Val Glu Ser Pro Lys Ile Leu Arg Val Tyr Ser Gly Ile<br>                435                    440                    445 | 1344 |
| tta aat caa tct gaa ata aaa gag gac aca tct ttc ttt ggg gtt caa<br>Leu Asn Gln Ser Glu Ile Lys Glu Asp Thr Ser Phe Phe Gly Val Gln<br>450                    455                    460 | 1392 |
| gaa ata ata atc cat gat cag tat aaa atg gca gaa agc ggg tat gat<br>Glu Ile Ile Ile His Asp Gln Tyr Lys Met Ala Glu Ser Gly Tyr Asp<br>465                    470                    475                    480 | 1440 |
| att gcc ttg ttg aaa ctg gaa acc aca gtg aat tac aca gat tct caa<br>Ile Ala Leu Leu Lys Leu Glu Thr Thr Val Asn Tyr Thr Asp Ser Gln<br>                485                    490                    495 | 1488 |
| cga ccc ata tgc ctg cct tcc aaa gga gat aga aat gta ata tac act<br>Arg Pro Ile Cys Leu Pro Ser Lys Gly Asp Arg Asn Val Ile Tyr Thr<br>                500                    505                    510 | 1536 |
| gat tgc tgg gtg act gga tgg ggg tac aga aaa cta aga gac aaa ata<br>Asp Cys Trp Val Thr Gly Trp Gly Tyr Arg Lys Leu Arg Asp Lys Ile<br>                515                    520                    525 | 1584 |
| caa aat act ctc cag aaa gcc aag ata ccc tta gtg acc aac gaa gag<br>Gln Asn Thr Leu Gln Lys Ala Lys Ile Pro Leu Val Thr Asn Glu Glu<br>530                    535                    540 | 1632 |
| tgc cag aag aga tac aga gga cat aaa ata acc cat aag atg atc tgt<br>Cys Gln Lys Arg Tyr Arg Gly His Lys Ile Thr His Lys Met Ile Cys<br>545                    550                    555                    560 | 1680 |
| gcc ggc tac agg gaa gga ggg aag gac gct tgc aag gga gat tcg gga<br>Ala Gly Tyr Arg Glu Gly Gly Lys Asp Ala Cys Lys Gly Asp Ser Gly<br>                565                    570                    575 | 1728 |
| ggc cct ctg tcc tgc aaa cac aat gag gtc tgg cat ctg gta ggc atc<br>Gly Pro Leu Ser Cys Lys His Asn Glu Val Trp His Leu Val Gly Ile<br>                580                    585                    590 | 1776 |
| acg agc tgg ggc gaa ggc tgt gct caa agg gag cgg cca ggt gtt tac<br>Thr Ser Trp Gly Glu Gly Cys Ala Gln Arg Glu Arg Pro Gly Val Tyr<br>                595                    600                    605 | 1824 |
| acc aac gtg gtc gag tac gtg gac tgg att ctg gag aaa act caa gca<br>Thr Asn Val Val Glu Tyr Val Asp Trp Ile Leu Glu Lys Thr Gln Ala<br>          610                    615                    620 | 1872 |
| gtg tga<br>Val<br>625 | 1878 |

<210> SEQ ID NO 120
<211> LENGTH: 625
<212> TYPE: PRT
<213> ORGANISM: Homo sapiens

<400> SEQUENCE: 120

-continued

```
Met Ile Phe Leu Tyr Gln Val Val His Phe Ile Leu Phe Thr Ser Val
1               5                   10                  15

Ser Gly Glu Cys Val Thr Gln Leu Leu Lys Asp Thr Cys Phe Glu Gly
            20                  25                  30

Gly Asp Ile Thr Thr Val Phe Thr Pro Ser Ala Lys Tyr Cys Gln Val
            35                  40                  45

Val Cys Thr Tyr His Pro Arg Cys Leu Leu Phe Thr Phe Thr Ala Glu
    50                  55                  60

Ser Pro Ser Glu Asp Pro Thr Arg Trp Phe Thr Cys Val Leu Lys Asp
65              70                  75                  80

Ser Val Thr Glu Thr Leu Pro Arg Val Asn Arg Thr Ala Ala Ile Ser
                85                  90                  95

Gly Tyr Ser Phe Lys Gln Cys Ser His Gln Ile Ser Ala Cys Asn Lys
                100                 105                 110

Asp Ile Tyr Val Asp Leu Asp Met Lys Gly Ile Asn Tyr Asn Ser Ser
            115                 120                 125

Val Ala Lys Ser Ala Gln Glu Cys Gln Glu Arg Cys Thr Asp Asp Val
    130                 135                 140

His Cys His Phe Phe Thr Tyr Ala Thr Arg Gln Phe Pro Ser Leu Glu
145                 150                 155                 160

His Arg Asn Ile Cys Leu Leu Lys His Thr Gln Thr Gly Thr Pro Thr
                165                 170                 175

Arg Ile Thr Lys Leu Asp Lys Val Val Ser Gly Phe Ser Leu Lys Ser
                180                 185                 190

Cys Ala Leu Ser Asn Leu Ala Cys Ile Arg Asp Ile Phe Pro Asn Thr
                195                 200                 205

Val Phe Ala Asp Ser Asn Ile Asp Ser Val Met Ala Pro Asp Ala Phe
    210                 215                 220

Val Cys Gly Arg Ile Cys Thr His His Pro Gly Cys Leu Phe Phe Thr
225                 230                 235                 240

Phe Phe Ser Gln Glu Trp Pro Lys Glu Ser Gln Arg Asn Leu Cys Leu
                245                 250                 255

Leu Lys Thr Ser Glu Ser Gly Leu Pro Ser Thr Arg Ile Lys Lys Ser
                260                 265                 270

Lys Ala Leu Ser Gly Phe Ser Leu Gln Ser Cys Arg His Ser Ile Pro
                275                 280                 285

Val Phe Cys His Ser Ser Phe Tyr His Asp Thr Asp Phe Leu Gly Glu
    290                 295                 300

Glu Leu Asp Ile Val Ala Ala Lys Ser His Glu Ala Cys Gln Lys Leu
305                 310                 315                 320

Cys Thr Asn Ala Val Arg Cys Gln Phe Phe Thr Tyr Thr Pro Ala Gln
                325                 330                 335

Ala Ser Cys Asn Glu Gly Lys Gly Lys Cys Tyr Leu Lys Leu Ser Ser
                340                 345                 350

Asn Gly Ser Pro Thr Lys Ile Leu His Gly Arg Gly Ile Ser Gly
                355                 360                 365

Tyr Thr Leu Arg Leu Cys Lys Met Asp Asn Glu Cys Thr Thr Lys Ile
    370                 375                 380

Lys Pro Arg Ile Val Gly Gly Thr Ala Ser Val Arg Gly Glu Trp Pro
385                 390                 395                 400

Trp Gln Val Thr Leu His Thr Thr Ser Pro Thr Gln Arg His Leu Cys
                405                 410                 415

Gly Gly Ser Ile Ile Gly Asn Gln Trp Ile Leu Thr Ala Ala His Cys
```

-continued

```
                    420                 425                 430
    Phe Tyr Gly Val Glu Ser Pro Lys Ile Leu Arg Val Tyr Ser Gly Ile
            435                 440                 445
Leu Asn Gln Ser Glu Ile Lys Glu Asp Thr Ser Phe Phe Gly Val Gln
    450                 455                 460
Glu Ile Ile Ile His Asp Gln Tyr Lys Met Ala Glu Ser Gly Tyr Asp
465                 470                 475                 480
Ile Ala Leu Leu Lys Leu Glu Thr Thr Val Asn Tyr Thr Asp Ser Gln
                485                 490                 495
Arg Pro Ile Cys Leu Pro Ser Lys Gly Asp Arg Asn Val Ile Tyr Thr
                500                 505                 510
Asp Cys Trp Val Thr Gly Trp Gly Tyr Arg Lys Leu Arg Asp Lys Ile
            515                 520                 525
Gln Asn Thr Leu Gln Lys Ala Lys Ile Pro Leu Val Thr Asn Glu Glu
        530                 535                 540
Cys Gln Lys Arg Tyr Arg Gly His Lys Ile Thr His Lys Met Ile Cys
545                 550                 555                 560
Ala Gly Tyr Arg Glu Gly Gly Lys Asp Ala Cys Lys Gly Asp Ser Gly
                565                 570                 575
Gly Pro Leu Ser Cys Lys His Asn Glu Val Trp His Leu Val Gly Ile
                580                 585                 590
Thr Ser Trp Gly Glu Gly Cys Ala Gln Arg Glu Arg Pro Gly Val Tyr
            595                 600                 605
Thr Asn Val Val Glu Tyr Val Asp Trp Ile Leu Glu Lys Thr Gln Ala
        610                 615                 620
Val
625

<210> SEQ ID NO 121
<211> LENGTH: 36
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 5' PCR primer for coding sequence of PS:GFP
      within H+-ATPase:PS(NIa protease):GFP hybrid protein

<400> SEQUENCE: 121
ctcgaggtgc gcttccagat gagtaaagga gaagaa                                   36

<210> SEQ ID NO 122
<211> LENGTH: 45
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 5' PCR primer for coding sequence of PS:GFP
      within H+-ATPase:PS(HIV-1 protease):GFP hybrid protein

<400> SEQUENCE: 122
ctcgagagac aggctaattt tttagggatg agtaaaggag aagaa                         45

<210> SEQ ID NO 123
<211> LENGTH: 24
<212> TYPE: DNA
<213> ORGANISM: Artificial
<220> FEATURE:
```

```
<223> OTHER INFORMATION: Synthetic Sequence
<220> FEATURE:
<221> NAME/KEY: misc_feature
<223> OTHER INFORMATION: 3' PCR primer for coding sequence of PS:GFP
      within H+-ATPase:PS(NIa or HIV-1 protease):GFP hybrid protein

<400> SEQUENCE: 123
gagctcttat ttgtatagtt catc                                          24

<210> SEQ ID NO 124
<211> LENGTH: 27
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 5' PCR primer for coding sequence of GFP
      within H+-ATPase:GFP:PS(NIa or HIV-1 protease):RFP hybrid protein

<400> SEQUENCE: 124
ctcgagatga gtaaaggaga agaactt                                       27

<210> SEQ ID NO 125
<211> LENGTH: 24
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 3' PCR primer for coding sequence of GFP within
      H+-ATPase:GFP:PS(NIa or HIV-1 protease):RFP hybrid protein

<400> SEQUENCE: 125
gagctctttg tatagttcat ccat                                          24

<210> SEQ ID NO 126
<211> LENGTH: 36
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 5' PCR primer for coding sequence of PS:RFP
      within H+-ATPase:GFP:PS(NIa protease):RFP hybrid protein

<400> SEQUENCE: 126
gagctcgtgc gcttccagat ggtgcgctcc tccaag                             36

<210> SEQ ID NO 127
<211> LENGTH: 45
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 5' PCR primer for coding sequence of PS:RFP
      within H+-ATPase:GFP:PS(HIV-1 protease):RFP hybrid protein

<400> SEQUENCE: 127
gagctcagac aggctaattt tttagggatg gtgcgctcct ccaag                   45

<210> SEQ ID NO 128
<211> LENGTH: 24
<212> TYPE: DNA
<213> ORGANISM: Artificial
```

```
<220> FEATURE:
<223> OTHER INFORMATION: Synthetic Sequence
<220> FEATURE:
<221> NAME/KEY: misc_feature
<223> OTHER INFORMATION: 3' PCR primer for coding sequence of PS:RFP
      within H+-ATPase:GFP:PS(NIa or HIV-1 protease):RFP hybrid protein

<400> SEQUENCE: 128
gagctcctac aggaacaggt ggtg                                             24

<210> SEQ ID NO 129
<211> LENGTH: 36
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 5' PCR primer for coding sequence of
      PS:AtOEP7:GFP within H+-ATPase:PS(NIa protease):AtOEP7:GFP hybrid
      protein

<400> SEQUENCE: 129
ctcgaggtgc gcttccaggg aaaaacttcg ggagcg                                36

<210> SEQ ID NO 130
<211> LENGTH: 45
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 5' PCR primer for coding sequence of
      PS:AtOEP7:GFP within H+-ATPase:PS(HIV-1 protease):AtOEP7:GFP
      hybrid protein

<400> SEQUENCE: 130
ctcgagagac aggctaattt tttaggggga aaaacttcgg gagcg                      45

<210> SEQ ID NO 131
<211> LENGTH: 24
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 3' PCR primer for coding sequence of
      PS:AtOEP7:GFP within H+-ATPase:PS(NIa or HIV-1
      protease):AtOEP7:GFP hybrid protein

<400> SEQUENCE: 131
gagctcttat ttgtatagtt catc                                             24

<210> SEQ ID NO 132
<211> LENGTH: 24
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 5' PCR primer for coding sequence of
      RFP:PS:AtOEP7:GFP within H+-ATPase:RFP:PS(NIa or HIV-1
      protease):AtOEP7:GFP hybrid protein

<400> SEQUENCE: 132
ctcgagatgg tgcgctcctc caag                                             24
```

```
<210> SEQ ID NO 133
<211> LENGTH: 24
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<223> OTHER INFORMATION: 3' PCR primer for coding sequence of
      RFP:PS:AtOEP7:GFP within H+-ATPase:RFP:PS(NIa or HIV-1
      protease):AtOEP7:GFP hybrid protein

<400> SEQUENCE: 133
gagctcttat ttgtatagtt catc                                              24
```

SYSTEM FOR DETECTING PROTEASE

CROSS-REFERENCE TO RELATED APPLICATION

The present application is a continuation of Korean patent application No.10-2001-0048123 as filed on Aug. 10, 2001 and entitled A System For In Vivo Screening Of Protease Inhibitors, the disclosure of which is hereby incorporated by reference.

FIELD OF THE INVENTION

The present invention generally relates to system for detecting protease inside a cell. A preferred system includes a chimeric substrate protein that includes as covalently linked components: 1) at least one optionally masked signal protein; 2) at least one protease-specific cleavage site; and 3) at least one detectable amino acid sequence. The invention has a broad spectrum of important applications including use in screens to detect compounds that block proteases produced by one or more human pathogens.

BACKGROUND

Protease is an enzyme that cleaves a specific peptide bond of proteins. In biological organisms, proteases having specific proteolytic activities, and their inhibitors are involved in regulation of various biological functions. In diverse biological processes, biologically necessary functions can be activated and regulated by proteolytic cleavage of a polyprotein precursor by a protease that results in formation of active proteins. Examples include blood coagulation, immuno-defensive processes, selective transports of proteins through intracellular membranes, viral proliferation in a host cell, etc. Therefore, protease is a major target in the development of specific protease inhibitors as new drugs.

Viral protease inhibitor is a representative example of a protease inhibitor developed as a new drug. Since the viral protease participates in the activation of polyprotein precursors via proteolytic cleavage, the protease is an essential element for the initiation of the viral proliferation and thus for the correct capsid assembly of replicated viruses in the host cell.

Protease inhibitors have been developed to block the proliferation of HIV that causes the acquired immune deficiency syndrome (AIDS). For example, amprenavir, nelfinavir, indinavir, ritonavir, and squinavir have been approved by FDA as drugs for inhibiting the HIV protease, and lopinavir and efavirenz are under clinical studies. Patients who were administered those medicines showed that the number of HIV particulates decreased to about 10% of that before the medicinal treatment. This shows that the protease inhibitor can be used as an efficient medicine. However, several side effects were reported during such treatments (Miller, T. L. et al., 2001), and mutants having mutated protease genes were reported in the cases of prolonged treatments (Jacobsen, H. et al., 1996; Cote, H. et al., 2001). Therefore, more diverse protease inhibitors that can specifically block the proliferation of various mutant HIV viruses need to be developed.

Protease inhibitors have been studied to inhibit other human and animal viruses such as HCV (Kasai, N. et al., 2001) and HERV (Kuhelj, R. et al., 2001). Researches for plant virus diseases have been also performed based on the same concept. For example, inhibition of the proteolytic cleavage of the polyproteins produced by TEV (tobacco etch virus) and PVY (potato virus Y) has been studied by expressing a recombinant protein as a protease inhibitor in a transgenic plant (Gutierres-Campos, R. et al., 1999). A study to identify proteolytic sites of a protease from a plant virus has been also performed (Yoon, H. Y. et al., 2000).

There have been attempts to develop protease inhibitors. For example, in many cases, screening of protease inhibitors has been performed by measuring cleavage of a substrate using electrophoresis, after a protease, its substrate peptide or protein, and a candidate chemical were mixed to react in vitro. As the importance of the proteolytic site has been recognized, peptides having amino acid sequences that are similar to the proteolytic site have been synthesized and used to find protease inhibitors (Kettner, C. A. and Korant, B. D., 1987). As it becomes easier to determine tertiary structures of proteins and also possible to design chemicals using computer simulation, many researches have been conducted to design and synthesize molecules that specifically bind to the active site of the enzyme (Wlodawer, A. and Erickson, J. W., 1993; Rodgers, J. D. et al., 1998; Mardis, K. L. et al., 2001). Also, attempts were made to use fluorescence-labeled substrates in order to increase the efficiency of the protease activity measurement (Ermolief, J. et al., 2000), and to use fragments of antibody expressed in the periplasm of *E. Coli* as protease inhibitors in order to enlarge the skeletal structure of the protease inhibitor (Kasai, N. et al., 2001).

Most of the protease activity screening methods used currently are performed in vitro. However, in the in vitro screening method, it is not possible to examine various complicated effects such as the transport efficiency of drug candidates into the cell, the stability and cytotoxicity of drug candidates in the cell, etc. Many additional time-consuming experiments are thus necessary before examining the drug candidates selected by the in vitro screening method in a living body. Therefore, a simpler and more generalized in vivo screening method needs to be developed to examine the cellular functions of the protease inhibitor candidates and also to screen more specific protease inhibitors.

There have been efforts to detect proteolytic cleavage and screening of protease inhibitors in more in vivo or in vivo-like conditions.

For example, there has been a report of a method using protease present in isolated vesicles (Hook, V. Y., 2001). Other disclosed methods include in situ zymography using a tissue section (Yi, C. -F. et al., 2001), and a method of treating cells with a polypeptide substrate of a protease (Kuhelj, R. et al., 2001).

However there is increasing recognition that these and related methods are associated with shortcomings.

For example, many of the methods are believed to only approximate in vivo environments. Accordingly, such methods do not always reflect intracellular environments that may substantially impact protease function.

Moreover, many of the prior methods are believed to be limited in terms of sensitivity, selectivity, and convenience. These and other drawbacks are believed to have lowered the efficiency and reliability of past screening attempts.

It would be desirable to have better in vivo methods for detecting protease inside cells that are more sensitive and easier to use. It would be especially desirable to have in vivo methods that can be readily adapted to detect inhibitors of mammalian and viral proteases.

SUMMARY OF THE INVENTION

The present invention relates to a system for detecting protease inside a cell or tissue. In one embodiment, the system includes at least one chimeric protein that includes as covalently linked components: 1) at least one optionally masked signal protein; 2) at least one protease-specific cleavage site; and 3) at least one detectable amino acid sequence. A preferred chimeric protein functions as a "molecular beacon" that changes position inside the cell in the presence of the protease. The invention has a wide range of applications including use in in vivo screens to detect compounds that inhibit or block proteases associated with a human pathogen.

Preferred use of the invention entails that the subject cells or tissue include at least one active protease therein. Suitable proteases include those that are endogenous to the cell, for instance, what are known as "housekeeping" enzymes. Additionally suitable proteases include those that are not naturally-occurring to the cell or tissue. For instance, such a protease can be a consequence of a pathogen infection. Alternatively, presence of the protease inside the cells or tissue can be a result of an experimental manipulation intended to introduce the protease therein. In these embodiments, a change in the subcellular position of the chimeric protein (or a detectable component thereof) is taken to indicative of the presence of the protease inside the cells or tissue. Thus the invention provides as a spatially sensitive "molecular beacon" whose location inside the cells or tissue is indicative of the presence (or absence) of the subject protease.

As will become apparent, the invention is one of general application. That is, it can be used to detect a wide spectrum of proteases inside the cells or tissue. Preferred proteases are capable of cleaving (hydrolyzing), preferably specifically, a cleavage site within the chimeric protein. Sometimes the chimeric proteins will be referred to herein as chimeric substrate proteins to denote cleavage potential by the protease of interest. Site specific cleavage is understood to break the chimeric molecule, generally at or near the specific cleavage site, and release at least one of components therefrom e.g., the optionally masked signal protein, cleavage site, or the detectable amino acid sequence. Preferred release involves at least one of the detectable amino acid sequences but it may involve other components of the chimeric molecule depending on use.

More preferred release of one or more of the components from the chimeric molecule is intended to provide the spatially sensitive molecular beacon. For example, and in one embodiment, the detectable amino acid sequence is released from the chimeric substrate protein and diffuses essentially freely throughout the host cells or tissue. That diffuse signal is readily detectable and can be taken as indicative of presence of the protease. However in another invention embodiment, release of one or more of the detectable amino acid sequences is associated with guidance of the molecule to another subcellular location by the optionally masked signal protein. In this example of the invention, a more focused and higher intensity signal serves as indication of the protease.

In some embodiments of the invention, it will be useful for the chimeric molecule to retain at least one of the detectable amino acid sequences, preferably as an in-frame fusion, even in the presence of the protease inside the cells or tissue. In this instance, localization of the chimeric molecule can be monitored by reference to the detectable amino acid sequence when the protease is present. In most cases, the release and subsequent subcellular localization of the detectable amino acid sequence (alone or in combination with another component of the detectable chimeric protein) is readily visualized in situ by one or a combination of conventional detection strategies.

It is thus an object of the invention to link presence and preferably activity of the protease of interest to a change in localization of the chimeric protein. That change is readily detectable as increase or decrease in signal location and, preferably, intensity. As an example, the subcellular distribution of a detectably labeled chimeric protein (or one or more of the components) can be initially confined to a relatively small location such as an cell organelle. That confinement produces a relatively high signal intensity. However in the presence of protease that specifically cleaves the chimeric protein, the distribution can be much less constrained and even diffuse. That lack of confinement produces a relatively low signal intensity. In this example, the specific cleavage by the protease can be associated with movement of the chimeric protein (or labeled component) from the organelle to a larger space such as the cytosol. Alternatively, signal intensity can increase sharply in embodiments where presence of active protease is linked by the invention to subcellular movement of labeled protein from the cytosol to a more confined space (e.g., organelle or vacuole). In yet another embodiment, the presence of active protease can be associated with little or no change in signal intensity. Instead, the change is monitored by labeled protein moving from one sub-cellular location to another as in, for instance, movement of the chimeric substrate protein from one organelle to another organelle or vacuole.

Practice of the present invention provides a number of important advantages.

For example, the invention provides chimeric proteins that are cleaved specifically by the subject protease to produce labeled (and unlabeled) component proteins. Preferred practice of the invention links the subcellular location and, preferably, the signal intensity of the labeled proteins to the presence (or absence) of the subject protease. This "two-factor" detection strategy provides for highly sensitive and reliable protease detection. That is, both the location of labeled protein and its signal intensity within the cells or tissues can be taken to be indicative of the presence of the active protease. The invention is also highly selective ie., it can readily discriminate between presence of different proteases or isozymes as well as presence of inactive and active versions of the same protease inside cells. Preferred chimeric proteins of the invention can be made with available reagents and standard recombinant manipulations making the invention easy to use.

Additionally, the invention is flexible and can be used to detect active protease in a wide range of cells, typically eukaryotes, including those derived from plants, yeast, fungi, animals, and insects. Preferred chimeric proteins have minimal impact on the gene expression in the cells or tissue, thereby avoiding potentially complicating genetic effects. The invention is also compatible with a variety of suitable protease cleavage sites and detectable amino acid sequences.

Accordingly, and in one aspect, the invention provides a system for detecting a protease inside a cell which system preferably includes at least one of the foregoing chimeric proteins. With respect to the chimeric protein, the order of linkage of each protein component (optionally masked signal protein, protease cleavage site, and detectable sequence) is not important so long as intended results are achieved.

Typically however, the linkage order starts from the N-terminus of one component and ends at the C-terminus of another component.

As mentioned, the chimeric protein includes as covalently linked components: 1) at least one optionally masked signal protein; 2) at least one protease-specific cleavage site; and 3) at least one detectable amino acid sequence. Preferably, the chimeric protein includes less than about 10 optionally masked signal proteins, more preferably less than about five of same, typically about 1, 2, or 3 of such signal proteins. By the phrase "optionally masked" is meant that an intended function (typically a trafficking signal) of the signal protein is masked or it is not masked. By the term "masked" is meant that an intended function of the signal protein is substantially reduced or preferably blocked completely, either reversibly or irreversibly, by covalently linking at least one masking sequence to the signal protein. Typically preferred signal proteins that are masked include about 1 to about 2 of such masking sequences. A generally preferred masking sequence consists of less than about 200 amino acid residues, preferably less than about 50 of same, with between from about 3 to about 20 residues being preferred for many applications. A specifically preferred masking sequence for many invention uses is at least one site specific protease cleavage site e.g., 1, 2, 3 or 4 of such sites.

Additionally preferred chimeric proteins in accord with the invention include, as covalently linked components, less than about 10 protease specific cleavage sites, preferably less than about 5 of same with about 1, 2, 3, or 4 of such sites being often preferred.

Still further preferred chimeric proteins include, as covalently linked components, less than about 10 of the detectable amino acid sequences, preferably less than about 5 of same with about 1, 2, 3, or 4 of such detectable amino sequences being preferred generally. In one embodiment, the sequences are fluorescent, phosphorescent or chemiluminescent proteins or functional fragments thereof. A functional fragment of the detectable amino acid sequence is capable of being detected with substantially the same sensitivity as the full-length sequence. In another embodiment, the amino acid sequence is an enzyme or catalytic fragment thereof that can be made fluorescent, phosphorescent or chemiluminscent upon contact with a suitable substrate. Methods for detecting and optionally quantifying signal from the detectable amino acid sequences are known in the field and explained in more detail below.

In another aspect, the invention provides a substantially pure chimeric protein that includes as covalently linked components: 1) at least one optionally masked signal protein; 2) at least one protease-specific cleavage site; and 3) at least one detectable amino acid sequence.

In yet another aspect, the invention features a nucleic acid that includes a sequence that encodes the chimeric protein. In one embodiment, the encoded chimeric protein includes as covalently linked components: 1) at least one optionally masked signal protein; 2) at least one protease-specific cleavage site; and 3) at least one detectable amino acid sequence.

Further provided by the present invention is a vector that includes a nucleic acid encoding the chimeric protein as disclosed herein. Also provided are cells such as plant, yeast, animal, fungi or insect cells, that include and preferably also express the chimeric protein.

Also provided by the present invention is a kit for detecting a protease inside a cell. In one embodiment, the kit includes the system described herein, which system preferably includes at least one of: a) a chimeric protein as described herein; and b) a vector comprising any of the nucleic acids encoding the chimeric proteins disclosed herein. Optionally, the kit may further include a vector comprising a nucleic acid encoding a protease specific to the chimeric protein and/or the cells that include and preferably also express the chimeric protein and the protease. The kit can also be used to screen inhibitors for the protease.

The invention provides additional uses and advantages. For instance, it is also an object of the present invention to provide an effective and generalized method for in vivo screening of inhibitors that are specific to a protease. Thus in one embodiment, the invention provides:

(1) a chimeric substrate protein comprising at least one signal protein directing transport to a subcellular organelle, at least one proteolytic cleavage site specific to a protease, and at least one fluorescent protein label, and generalized methods for constructing the chimeric substrate protein;

(2) a recombinant gene comprising a nucleic acid sequence encoding the chimeric substrate protein, which can be used to transform a cell to express the chimeric substrate protein;

(3) a system wherein the chimeric substrate protein and its specific protease co-exist in a living cell so that the proteolytic cleavage of the substrate by the protease can take place in a living cell;

(4) an efficient stepwise method for determining the protease activity in vivo by directly identifying the cleavage of the chimeric substrate protein by the protease in the living cell, via direct observation of the cell with the fluorescence signal emitted from the fluorescent protein label(s) conjugated to the substrate; and (5) an effective stepwise method for screening inhibitors specific to a protease by using the above system constructed for determination of the protease activity in the living cell.

By addressing the technical problems involved, the present invention provides more realistic in vivo methods for analyzing the activity of a specific protease and screening inhibitors for the protease, in which the protease and its specific substrate co-exist in a living cell so that the cleavage of the substrate by the protease can take place in a living cell and the result can be directly observed from the living cell.

In a related aspect, the invention provides a highly useful method for detecting a protease inside a cell or tissue. In an illustration of the invention, the method includes at least one and preferably all of the following steps:

a) introducing, into a subject cell or tissue, a first vector comprising nucleic acid encoding a chimeric protein comprising as covalently linked components: 1) at least one optionally masked signal protein; 2) at least one protease-specific cleavage site; and 3) at least one detectable amino acid sequence, b) incubating the cell or tissue under conditions conductive to expressing the chimeric protein encoded by the first vector; and c) detecting a change in at least one of the subcellular localization and signal intensity of the chimeric protein (or detectably labeled component thereof) as being indicative of the presence of the protease inside the cell.

As discussed, the method is flexible and can be readily adapted to suit an intended use. For example, if needed, the method can further include the step of introducing, into the subject cell or tissue, a second vector comprising nucleic acid sequence encoding the protease; and expressing the second vector in the cell or tissue to produce the protease inside the cell or tissue.

The invention also provides a method for detecting and optionally quantifying the in vivo activity of a protease inhibitor. Preferred inhibitors can be endogenous to the cell or tissue of interest. However, in many invention embodiments the inhibitor will be administered to same and include naturally-occurring, synthetic, and semi-synthetic molecules. Such molecules can be obtained from chemical libraries and may include those having known, suspected or completely unknown inhibitor activity. For example, in embodiments in which the activity of a particular protease inhibitor is established, the invention can be used to confirm the activity of the protease in a particular cell, tissue type, or culture conditions. In other embodiments, the invention can be used to screen candidate compounds from the chemical libraries. In one example of the invention, the detection method includes at least one and preferably all of the following steps:

a) introducing, into a subject cell or tissue, a first vector comprising nucleic acid encoding a chimeric protein comprising as covalently linked components: 1) at least one optionally masked signal protein; 2) at least one protease-specific cleavage site; and 3) at least one detectable amino acid sequence, b) introducing into the cell or tissue a second vector encoding at least one subject protease, preferably one of same, c) contacting the cell or tissue with candidate compound, d) incubating the cell or tissue under conditions conducive to expressing the chimeric protein encoded by the first vector and the protease encoded by the second vector; and e) detecting a change in at least one of the subcellular localization and signal intensity of the chimeric protein (or a detectably labeled component thereof) as being indicative of the presence of the protease inhibitor.

The foregoing detection method is flexible and can be readily adapted to screen candidate compounds in stand alone, low or high throughput modes. For example, and in one embodiment, the method further includes use of an automated or semi-automated device that is preferably intended to detect the change in subcellular localization and signal intensity of the detectably labeled chimeric protein or labeled component protein thereof. A more particular device includes an optical system adapted to detect the detectable sequence inside the cell or tissue which system can provide output to a user in real-time or as stored output.

If desired, the detectable change in the subcellular localization, signal intensity (or both) of the chimeric protein (or a detectably labeled component thereof) can be monitiored by reference to a suitable control. One suitable control is addition of water, saline or buffer instead of the compound to be tested in step c). Of course, use of a control may not be needed in embodiments in which the characteristics of the chimeric protein, the host cells or tissue, etc. are already established for a particular method.

As discussed, the invention is well-suited to detect protease inhibitors. Known protease inhibitors in accord with the invention are recognized viral disease inhibitors. Because the viral protease is essential for replication and reassembly of viral capsids, the protease inhibitor can be used for treatment of viral diseases by inhibiting the protease to suppress the viral proliferation. Animal viruses can cause diseases such as AIDS and hepatitis etc., and plant viruses reduce crop yield by causing wilting leaves and mottling.

In one aspect, the present invention provides a framework for effectively developing inhibitors specific to various proteases by supplying the substrates and the method for in vivo screening of inhibitors specific to various proteases. This method can be also used to determine the efficiency of the drug candidates screened by the conventional in vitro method.

BRIEF DESCRIPTION OF THE DRAWINGS

FIG. 1 shows schematic diagrams of signal proteins having trafficking signals to subcellular organelles and labeled with fluorescent proteins.

(a) shows that *Arabidopsis* outer envelope protein (AtOEP7) labeled with green fluorescent protein (GFP) is localized in chloroplast envelope;

(b), (c), and (d) show that Rubisco small subunit (RbcS), Chlorophyll a/b binding protein (Cab), and Rubisco activase (RA) labeled with GFP are localized in chloroplast stroma;

(e) shows that F1-ATPase labeled with GFP is localized in mitochondria;

(f) shows that peroxisome targeting motif (SKL) labeled with GFP is localized in peroxisome; and (g) and (h) show that $H^+$-ATPase and Pleckstrin homology domain (PH) labeled with GFP are localized in the plasma envelope.

Figure 3:
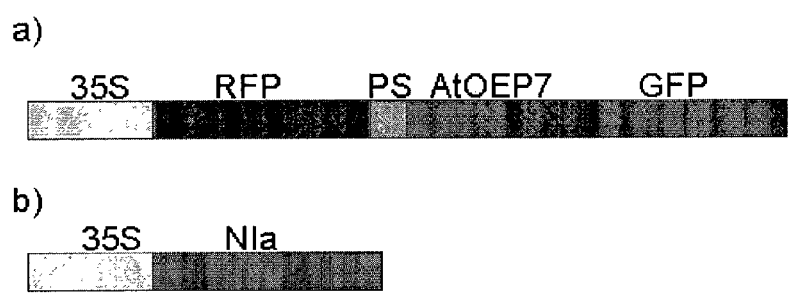

FIGS. 3(a)–(b) show schematic diagrams of recombinant genes for NIa protease and an in vivo substrate of NIa protease, RFP:PS(NIa):AtOEP7:GFP:

(a) shows the structure of the recombinant gene constructed to express the chimeric protein RFP:PS(NIa):AtOEP7:GFP used as an in vivo substrate of NIa protease in Example 2 of the present invention, wherein RFP, GFP, PS(NIa), AtOEP7, and 35S indicate red fluorescent protein, green fluorescent protein, the proteolytic cleavage site of the protease, *Arabidopsis* outer envelope protein, and CaMV35S promoter, respectively; and (b) shows the structure of the recombinant gene constructed to express NIa protease used in Example 2, wherein NIa represents the coding region of NIa protease from TVMV.

Figure 4:
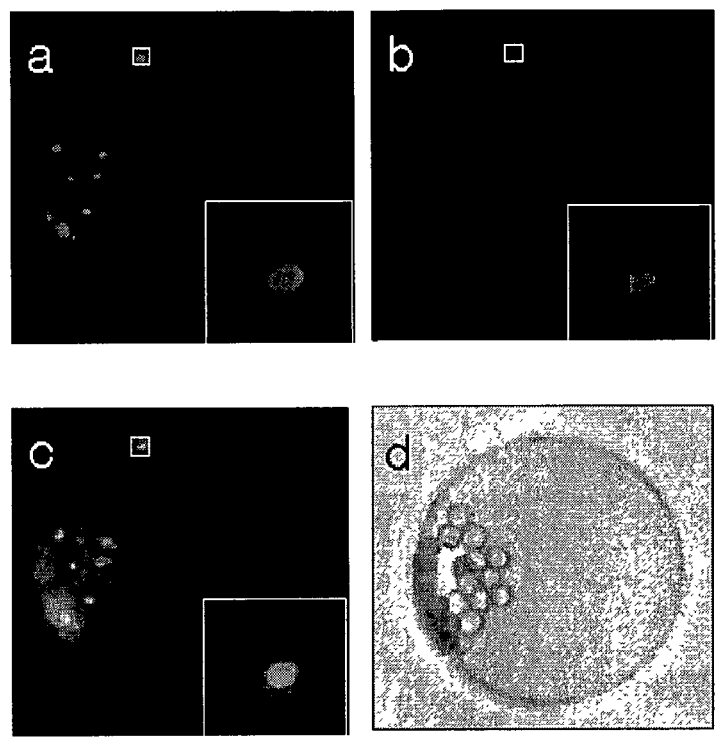

FIG. 4 shows fluorescence photographs observed after expressing the chimeric protein RFP:PS(NIa):AtOEP7:GFP in the *Arabidopsis* protoplast transformed with the recombinant gene shown in FIG. 3(a):

(a), (b), (c), and (d) are images of green fluorescence signal, red fluorescence signal, and overlap of green and red fluorescence signals, and an image captured under bright field, respectively. The red fluorescence signal observed in chloroplast is auto-fluorescence signal of chloroplast and the red fluorescence signal observed in cytosol originates from the red fluorescent protein.

Figure 5:
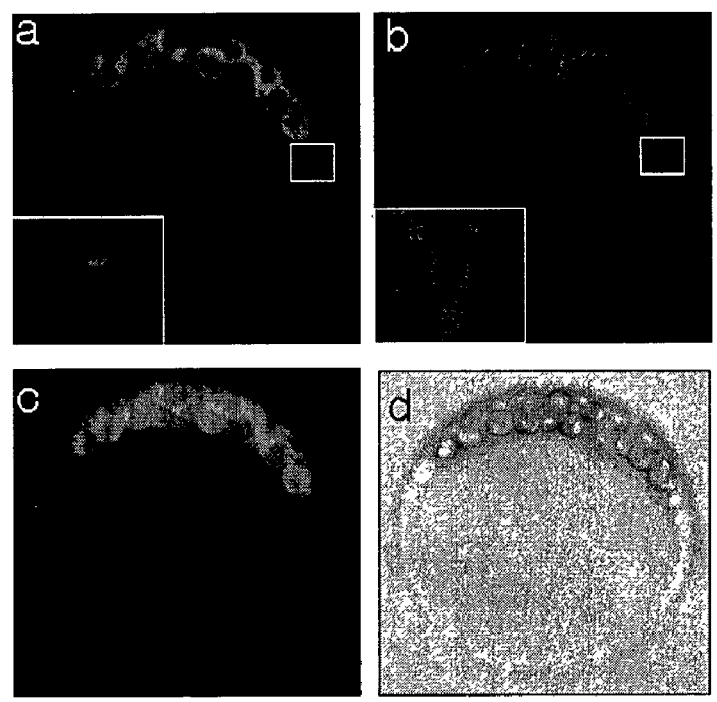

FIG. 5 shows fluorescence images observed after co-expressing the chimeric protein RFP:PS(NIa):AtOEP7:GFP and NIa protease in the *Arabidopsis* protoplast transformed with the recombinant genes shown in FIGS. 3(a) and 3(b), showing that the cleavage of RFP:PS(NIa):AtOEP7:GFP by NIa protease can be visualized:

(a), (b), (c), and (d) are images of green fluorescence signal, red fluorescence signal, and overlap of green and red fluorescence signals, and an image captured under bright field, respectively. The red fluorescence signal observed in chloroplast is auto-fluorescence signal of chloroplast and the red fluorescence signal observed in cytosol originates from the red fluorescent protein.

Figure 6:
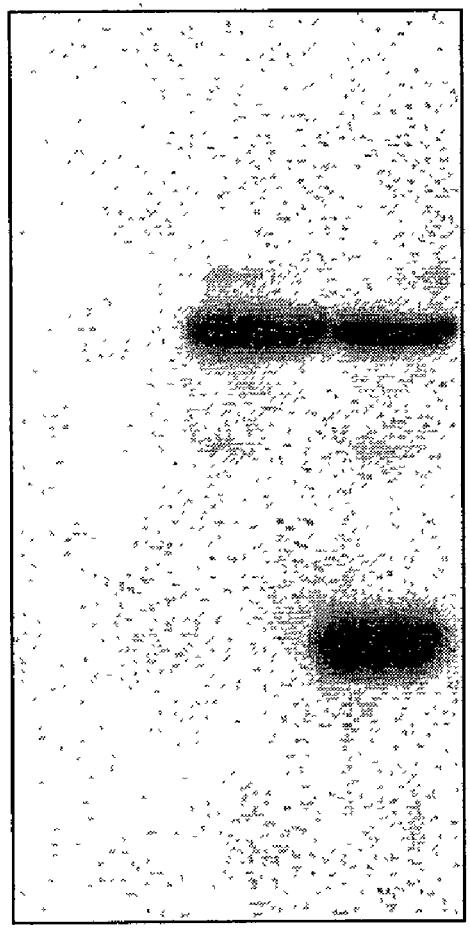
Figure 7A:
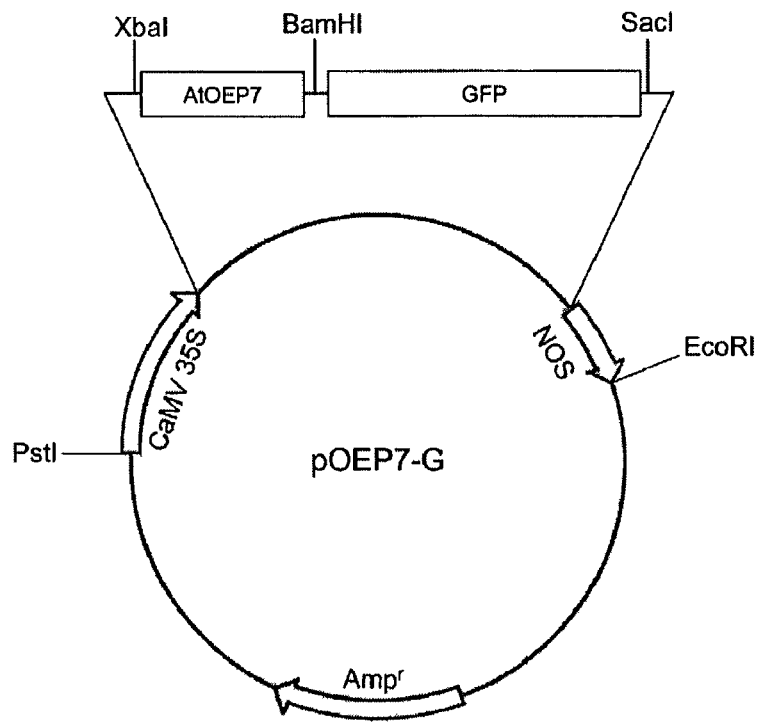
Figure 7B:
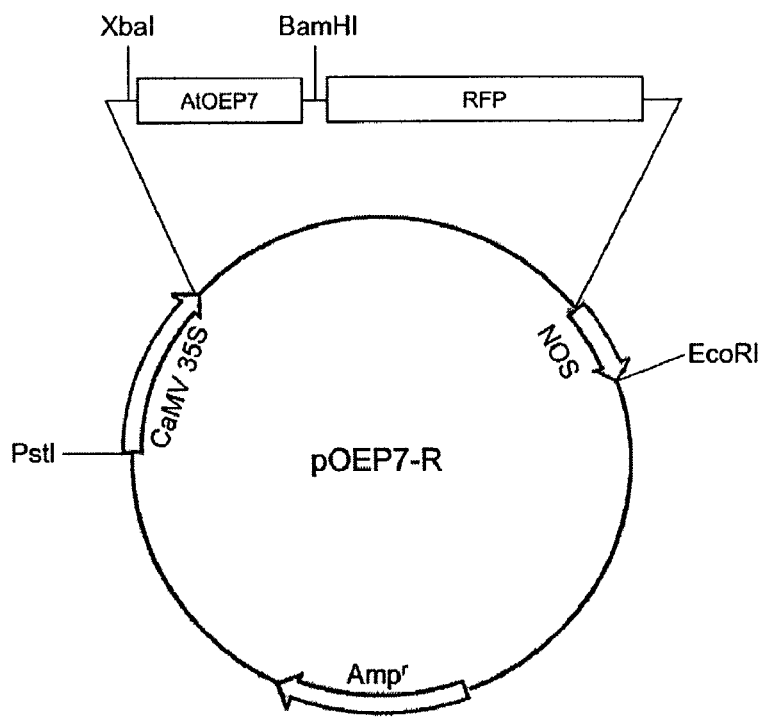
Figure 7C:
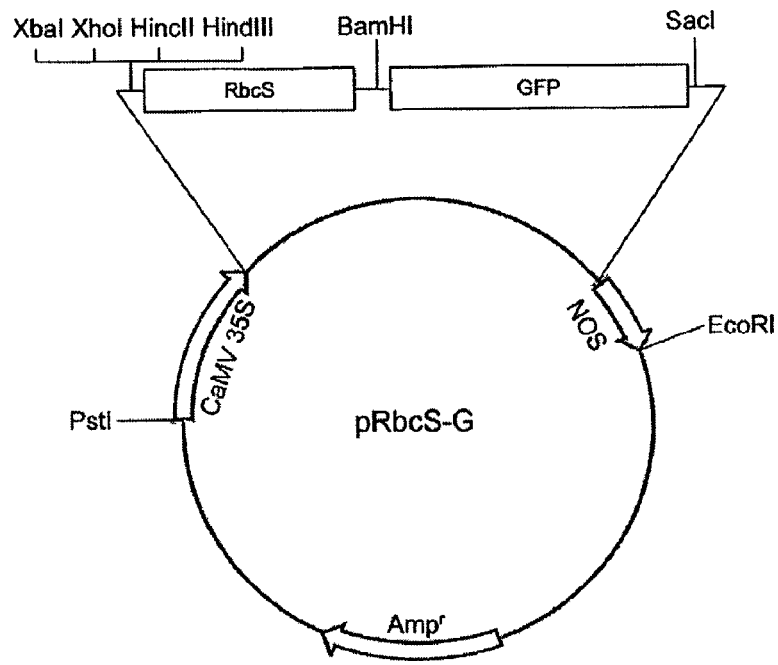
Figure 7D:
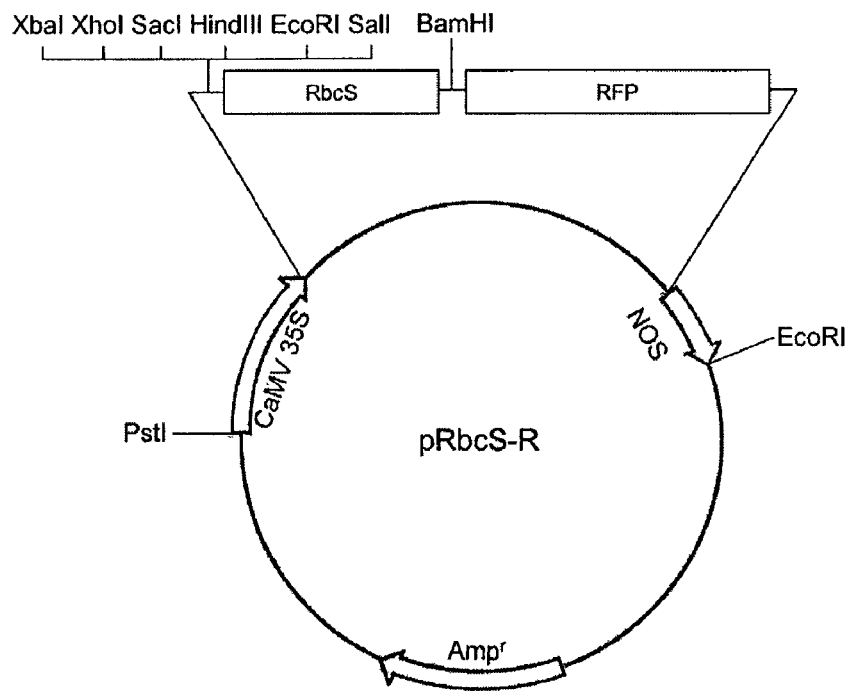
Figure 7E:
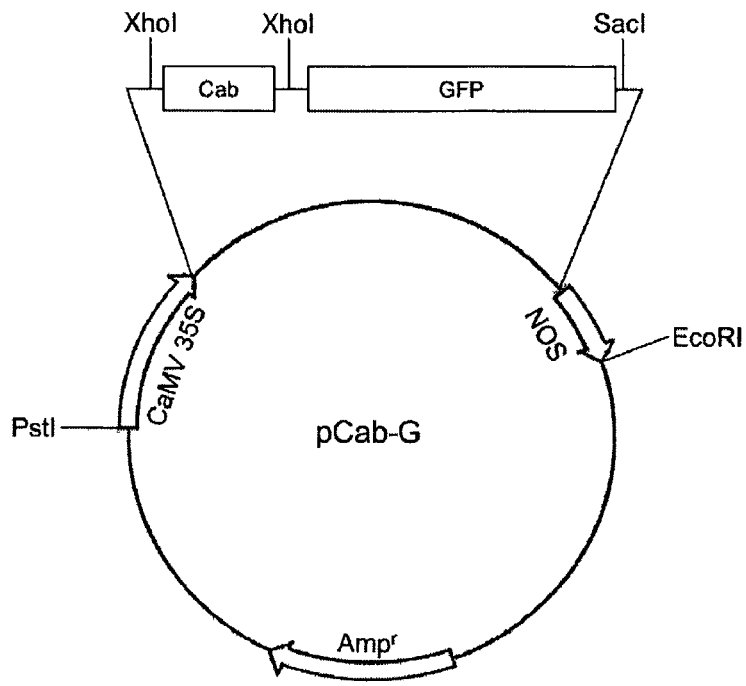
Figure 7F:
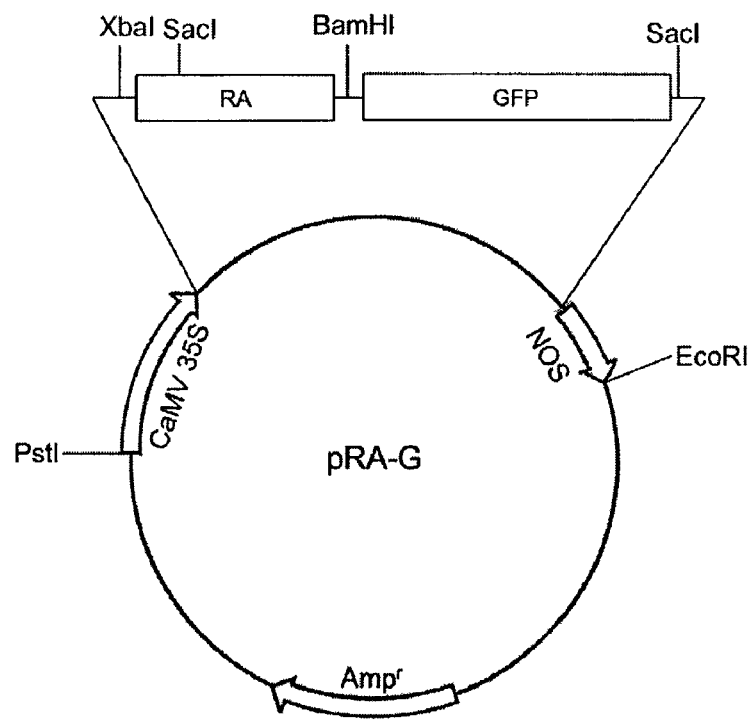
Figure 7G:
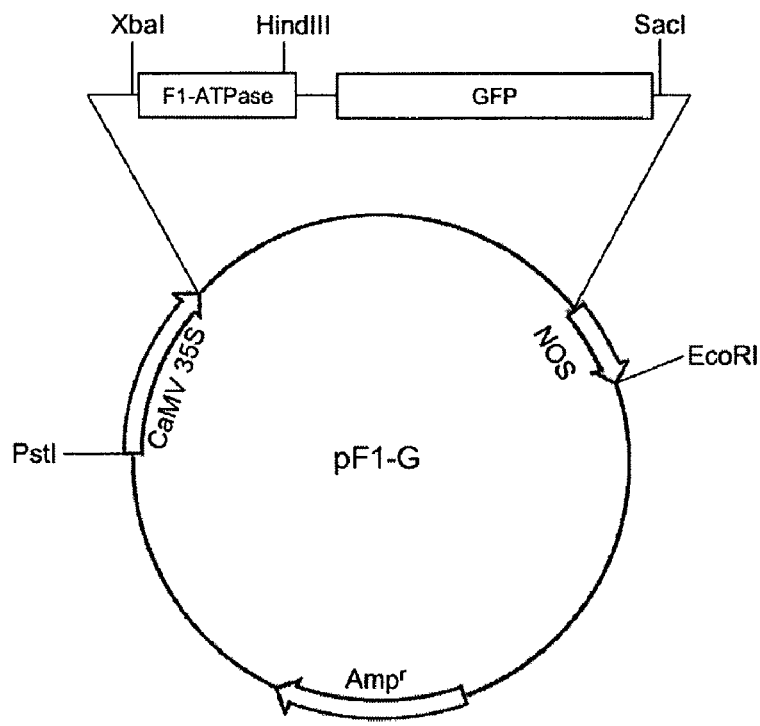
Figure 7H:
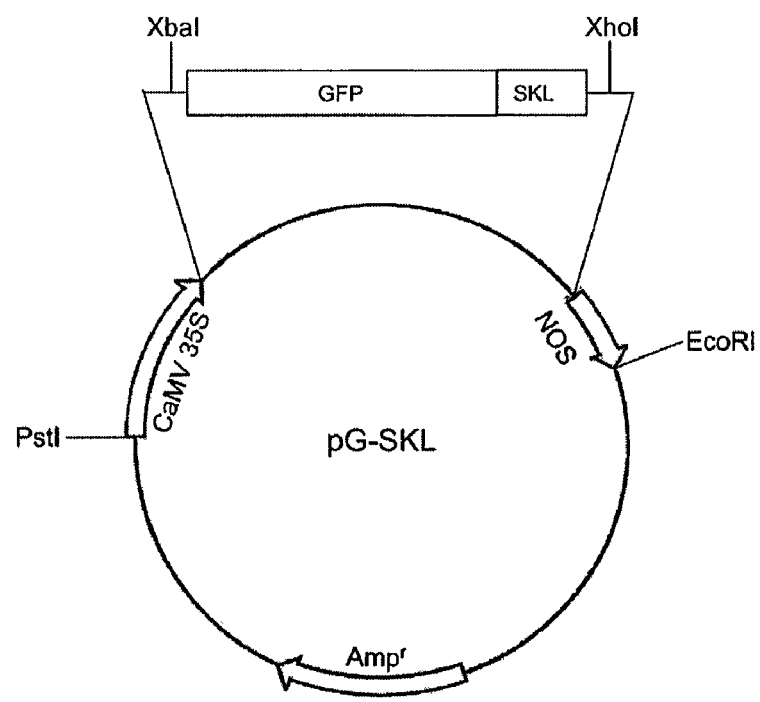
Figure 7I:
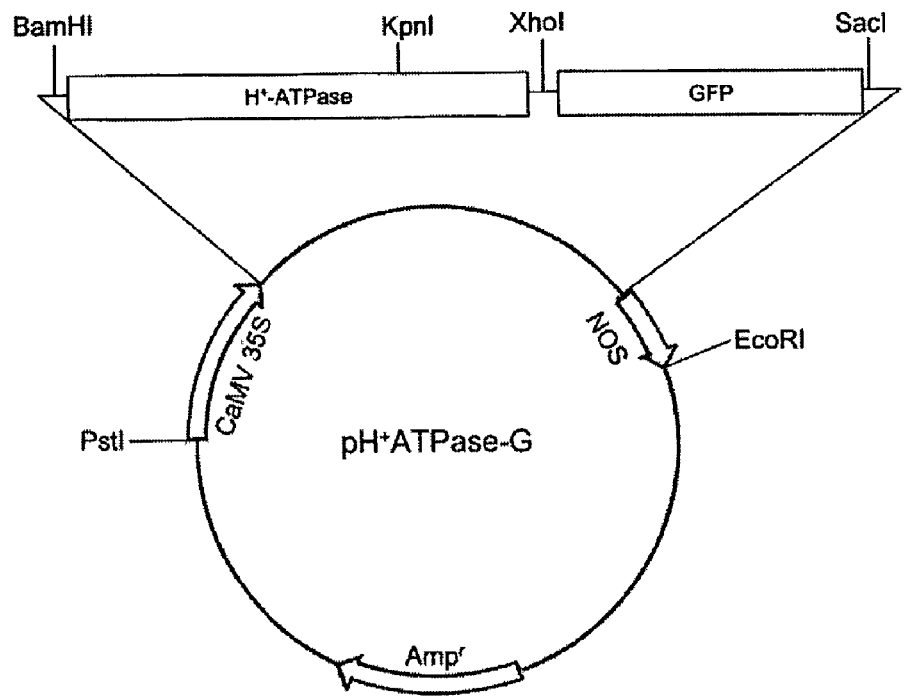
Figure 7J:
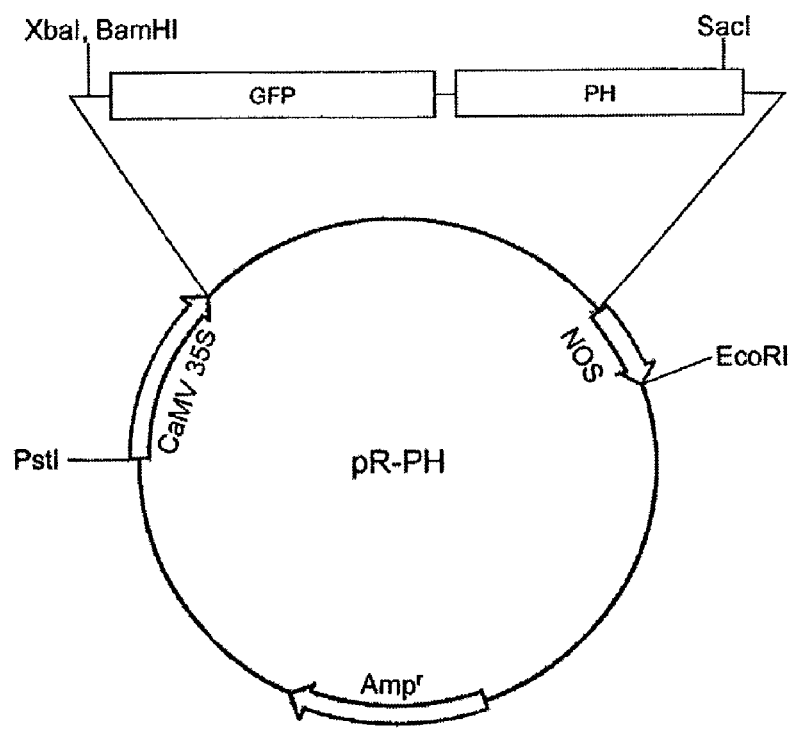

FIG. 6 is representation of a Western blot showing that the cleavage of the chimeric protein RFP:PS(NIa):AtOEP7:GFP by NIa protease takes place in the *Arabidopsis* protoplast. The case (+) of co-expressing RFP:PS(NIa):AtOEP7:GFP shown in FIG. 3(*a*) and NIa protease shown in FIG. 3(*b*) is compared with the case (−) of expressing RFP:PS(NIa): AtOEP7:GFP alone. The protein bands observed at 70 kD and 35 kD correspond to the intact chimeric protein RFP: PS(NIa):AtOEP7:GFP and the fragment protein AtOEP7: GFP produced by the proteolytic cleavage, respectively.

FIG. 7(*a*)-(*j*) are drawings showing plasmid maps of various constructs used to express the fusion proteins shown in FIGS. 1: (a) AtOEP7:GFP, (b) AtOEP7:RFP, (c) RbcS: GFP, (d) RbcS:RFP, (e) Cab:GFP, (f) RA:GFP, (g) F1-ATPase:GFP, (h) GFP:SKL, (i) $H^+$-ATPase:GFP, (j) GFP:PH.

FIGS. 8(*a*) and (*b*) show plasmid maps for NIa protease and its chimeric substrate protein RFP:PS(NIa):AtOEP7: GFP, respectively. An important part of the nucleic acid sequence for the chimeric substrate protein is noted.

FIGS. 9(*a*) and (*b*) show plasmid maps for HIV-1 protease and its chimeric substrate protein RFP:PS(HIV-1):AtOEP7: GFP, respectively. Nucleic acid and protein sequences for the proteolytic cleavage sites (SEQ ID NOs: 57–74) are noted.

Figure 10:
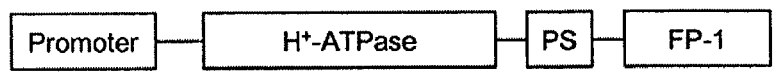
Figure 10:
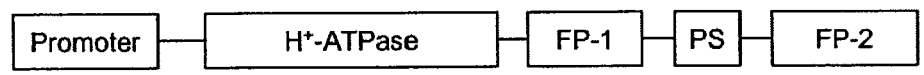
Figure 10:
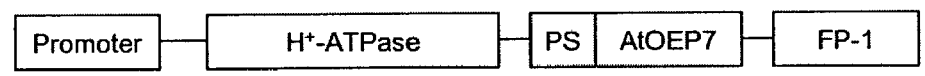
Figure 10:

FIGS. 10(*c*)–(*d*) show schematic diagrams of recombinant genes encoding examples of optionally masked chimeric substrate protein in which trafficking signal of one signal protein remains active. PS indicates the proteolytic cleavage site sequence. FP-1 and FP-2 indicate coding sequences for fluorescent proteins having different fluorescence wavelengths.

Figure 11:
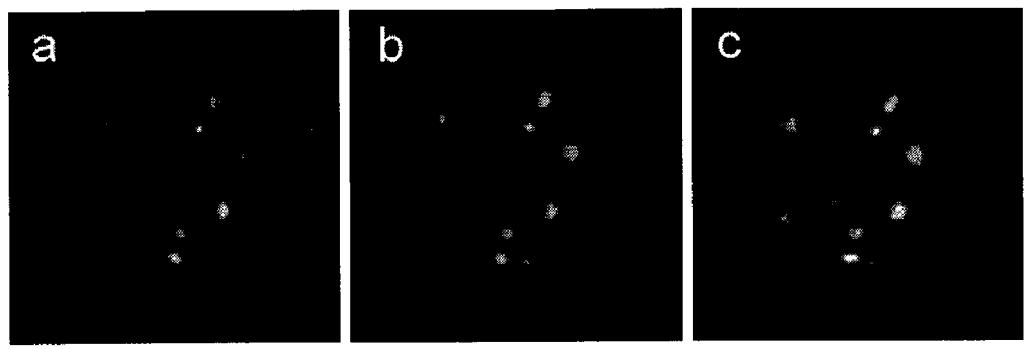

FIGS. 11(*a*)–(*c*) show fluorescence images observed after expressing a chimeric substrate protein RFP:PS(HIV-1): AtOEP7:GFP in the *Arabidopsis* protoplast transformed with one of the recombinant plasmids shown in FIG. 9(*b*). FIGS. 11(*a*), (*b*), and (*c*) are images of green fluorescence signal, red fluorescence signal, and overlap of green and red fluorescence signals, respectively. The weak red fluorescence signal observed in the green fluorescence image is auto-fluorescence of chloroplast.

Figure 12:
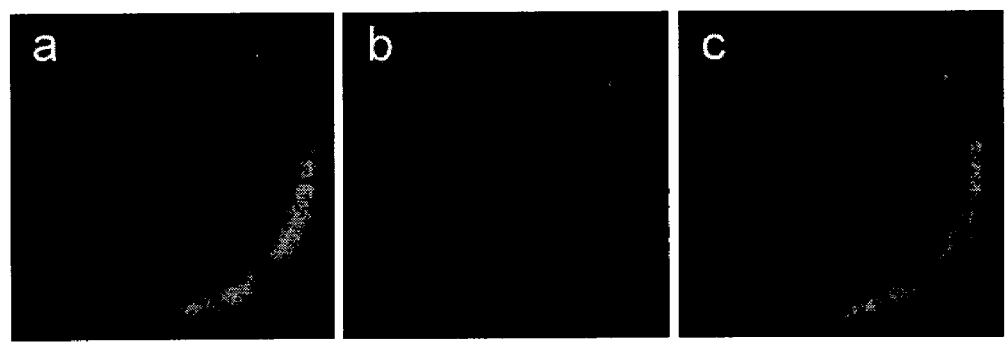

FIGS. 12(*a*)–(*c*) show fluorescence images observed after co-expressing HIV-1 protease and a chimeric substrate protein RFP:PS(HIV-1):AtOEP7:GFP in the *Arabidopsis* protoplast transformed with the recombinant genes shown in FIGS. 9(*a*) and (*b*). FIGS. 12(*a*), (*b*), and (*c*) are images of green fluorescence signal, red fluorescence signal, and overlap of green and red fluorescence signals, respectively. The weak red fluorescence signal observed in the green fluorescence image is auto-fluorescence of chloroplast.

Figure 13:
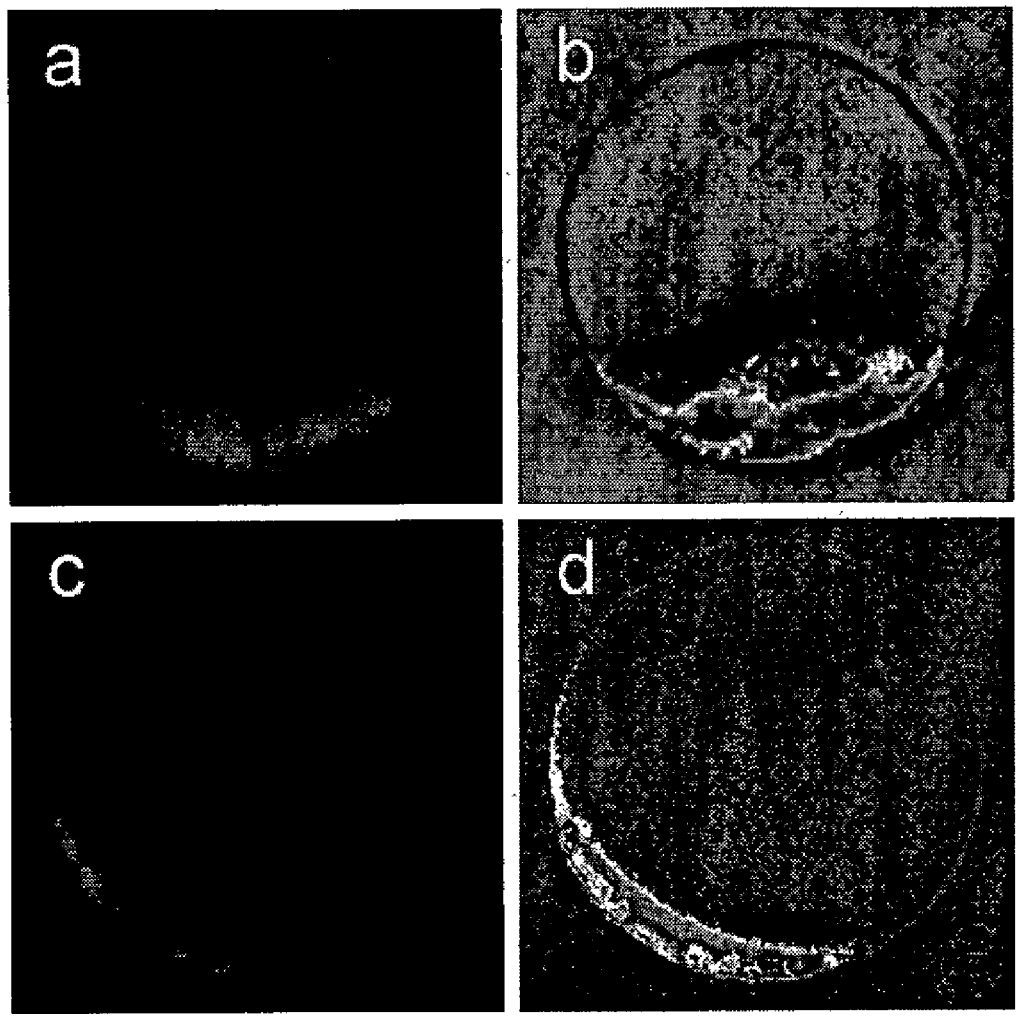

FIGS. 13(*a*) and (*b*) shows images observed after expressing a chimeric substrate protein $H^+$-ATPase:PS(NIa):GFP. FIGS. 13(*c*) and (*d*) show images observed after co-expressing NIa protease and a chimeric substrate protein $H^+$-ATPase:PS(NIa):GFP. FIGS. 13(*a*) and (*c*) are images of green fluorescence signal, and FIGS. 13(*b*) and (*d*) are images obtained under bright field. The red fluorescence observed in the green fluorescence images are auto-fluorescence of chloroplast.

DETAILED DESCRIPTION OF THE INVENTION

As discussed, the invention provides a highly useful system for detecting a protease inside a cell or tissue. If desired, the system is readily adapted to detect more than one protease, preferably less than about 3 of same, usually about 1 protease. Preferably, the system includes a chimeric protein that includes as covalently linked components: 1) at least one optionally masked signal protein; 2) at least one protease-specific cleavage site; and 3) at least one detectable amino acid sequence. Typically preferred chimeric proteins consist of less than about 20 components, more preferably less than about 10 of same, with between from about 3 to about 6 components being generally preferred for most of the proteins. The invention has a wide spectrum of important applications including use in screens to detect candidate compounds that reduce or completely block protease activity in vivo.

A "system" according to the invention includes one or more of the chimeric molecules described herein as well as any additional components which may be added thereto such as those which may facilitate solublization or stability of same. Examples include but are not limited to a serum protein such as bovine serum albumin, a buffer such as phosphate buffered saline, or an acceptable vehicle or stabilizer. See generally *Remington's Pharmaceutical Sciences*, Mack Pub. Co., Easton, Pa., 1980, for a discussion of acceptable vehicles, stabilizers, etc. Typical systems in accord with the invention will also include at least one of the nucleic acids, vectors, manipulated cells or tissue described herein. In such invention embodiments, the chimeric protein can serve as a useful experimental control. A preferred system includes from between about 1 to 10, preferably less than about 5 and more preferably about 1 of the chimeric proteins dissolved in an acceptable carrier such as water or buffered saline. Preferably, the system is provided sterile.

By the phrase "signal protein" is meant a polypeptide sequence that has either a specific trafficking signal targeting to a subcellular organelle or a specific property related to its localization in a cell such as aggregate formation. Preferred signal proteins can be found throughout this disclosure including the Examples section.

Preferred chimeric proteins according to the invention include an optionally masked signal protein, protease specific cleavage site, and detectable amino acid sequence that are covalently linked together (i.e. fused) by recombinant, chemical or other suitable method. In most embodiments, recombinant approaches will be preferred. Although not generally needed for most invention embodiments, one or more of the components can be fused at one or several sites through a peptide linker sequence. Particular peptide linker sequences will less than about 30 amino acids, more preferably less than about 15 amino acids, still more preferably from about 1 to about 5 amino acids. That peptide sequence can include one or more sites for cleavage by a pathogen induced or host cell induced protease. Alternatively, the peptide linker may be used to assist in construction of the chimeric protein. Specifically preferred chimeric proteins can be referred to as "in-frame" fusion molecules.

As noted, components of the chimeric proteins disclosed herein can be organized in nearly any fashion provided that the protein has the function for which it was intended. And as mentioned, each component of the chimeric protein can be spaced from another component by at least one suitable peptide linker sequence.

For instance, any one of the components of the chimeric protein can include the N-terminus of the protein. Additionally, any one of the components can include the C-terminus of the chimeric protein which terminus may include another component such as a purification tag sequence as discussed below. Unless specified otherwise, the phrase "covalently linked in sequence" means, with respect to an amino acid sequence, peptide bonds bound together in the N to C direction. With respect to a nucleotide sequence, the phrase is meant to denote joining of one nucleoside to another in a 5' to 3' direction.

As a more specific example of the system, the chimeric protein includes covalently linked in sequence: 1) the signal protein; 2) the protease-specific cleavage site; and 3) the detectable amino acid sequence. Alternatively, the chimeric protein can include covalently linked in sequence: 1) a masking sequence; 2) the protease cleavage site; 3) the signal protein; and 4) the detectable amino acid sequence. In another embodiment, the chimeric protein for use with the system features covalently linked in sequence: 1) the signal protein; 2) the protease cleavage site; 3) the masking sequence; and 4) the detectable amino acid sequence.

In invention embodiments in which more than one signal protein is needed in the chimeric protein, such a protein can include covalently linked in sequence: 1) a first signal protein; 2) the protease cleavage site; and 3) a second signal protein; and 4) the detectable amino acid sequence. More particularly, such a protein can include covalently linked in sequence: 1) the first signal protein; 2) a first protease cleavage site; 3) the masking sequence; 4) the second signal protein; and 5) the detectable amino acid sequence.

In some instances, it will be helpful to have a system in which the chimeric protein includes more than one protease cleavage site eg., 1, 2, 3 or 4. In such a case, the chimeric protein can include covalently linked in sequence: 1) the masking sequence; 2) a first protease cleavage site; 3) a first signal protein; 4) a second protease cleavage site; 5) a second signal protein; and 6) the detectable amino acid sequence. Alternatively, the chimeric protein can include covalently linked in sequence: 1) a first signal protein; 2) a first protease cleavage site; 3) a second signal protein; 4) a second protease cleavage site; 5) a masking sequence and 6) the detectable amino acid sequence.

In another invention embodiment, the chimeric protein include covalently linked in sequence: 1) the protease-specific cleavage site; 2) the signal protein; and 3) the detectable amino acid sequence. Alternatively, the chimeric protein can include covalently linked in sequence: 1) a first signal protein; 2) a first detectable sequence; 3) the protease cleavage site; and 4) a second detectable sequence. In this invention example, the protein can further include a second signal protein covalently linked between the C-terminus of the protease cleavage site and the N-terminus of the second detectable sequence.

The invention provides for still further chimeric proteins that include covalently linked in sequence: 1) a first signal protein; 2) the protease cleavage site; 3) a second signal protein; and 4) a second detectable sequence. Alternatively, the chimeric protein can include covalently linked in sequence: 1) a first detectable sequence; 2) the protease cleavage site; 3) the signal protein; and 4) a second detectable sequence.

More preferred chimeric proteins in accord with the invention will have a molecular size of less than about 250 kDa, preferably less than about 200 kDa, more preferably a molecular size of between about 25 to about 175 kDa as determined by standard SDS PAGE gel electrophoresis using appropriate molecular weight markers.

A "polypeptide" refers to any polymer preferably consisting essentially of any of the 20 natural amino acids regardless of its size. Although the term "protein" is often used in reference to relatively large proteins, and "peptide" is often used in reference to small polypeptides, use of these terms in the field often overlaps. The term "polypeptide" refers generally to proteins, polypeptides, and peptides unless otherwise noted.

As used herein, the term "cell" is intended to include any primary cell or immortalized cell line, any group of such cells as in, a tissue or an organ. Preferred cells include mammalian cells such of those of human origin, plant cells, yeast, fungi and insect cells. A "host cell" in accord with the invention can be an infected cell or it can be a cell such as E. coli that can be used to propagate a nucleic acid or vector as described herein.

It will be appreciated that particular uses of the invention will often require a specific chimeric protein configuration. Choice of a particular chimeric protein component or group of components will be guided by recognized parameters including the signal protein(s), protease specific cleavage site(s), and detectable amino acid sequences selected, the protease(s) to be monitored, and the level of sensitivity or selectivity required for an application.

By way of example, the invention encompasses embodiments in which the chimeric protein includes one signal protein, one detectable sequence and one protease specific cleavage site. In this example, it will often be helpful to include a masking sequence linked to the N- or C-terminus of the signal protein. That is, it is envisioned that linkage of the masking sequence to the detectable sequence will be less preferred for some of invention uses.

Other specific uses of the invention will typically require other specific chimeric protein configurations. For instance, where a particular protein has one signal protein, and one protease specific cleavage site positioned between two detectable amino acid sequences, it will often be desirable to remove one of the detectable amino acid sequences to optimize the system.

Still other uses of the invention will be facilitated by having multiple masking sequences which can be a signal sequence, detectable amino acid sequence or other suitable sequence such as a protease specific cleavage site. In these embodiments, having one or more additional masking sequences e.g., the protease cleavage site, may not be necessary to achieve maximal use of the system. However in embodiments that include two different signal proteins, one protease cleavage site and two detectable amino acid sequences, one or two masking sequences thereon can be helpful.

Additionally, particular chimeric proteins may include removable tagging sequences that, in some embodiments, may assist identification and/or purification of the chimeric protein. An example is 6×His and MYC tags. Other suitable tagging sequences are well known in the field and can be used with the invention if desired.

Practice of the invention is fully compatible with a wide variety of signal proteins and functional fragments thereof that are masked or unmasked. Preferred examples are generally sufficient to localize the chimeric protein (or detectable component of that protein such as the detectable sequence) to an organelle or other subcellular compartment. By the phrase "compartment" is meant an internally limited space such as a vacuole, peroxisome, mitochondrion, etc.

Preferred plant signal proteins localize the chimeric protein or at least one of its components to the nucleus, golgi body, lytic vacuole, storage vacuole, peroxisome, mitochondrion, endoplasmic reticulum, plasma membrane, or chloroplast of a plant cell. More preferred plant signal proteins include AtOEP7; RbcS; Cab; RA; SKL; F1-ATPase; PH; FAPP; $H^+$-ATPase; or a functional fragment thereof. Preferred animal signal proteins localize the chimeric protein or at least one of its components to the nucleus, golgi body, storage vacuole, lysosome, peroxisome, endoplasmic reticulum, plasma membrane, or mitochrondrion of an animal cell. Examples include human peptide methionine sulfoxide reductase (MSRA), cytochrome b2, 11-beta-hydroxysteroid dehydrogenase (11β-HSD), G9-AKL, peroxisomal integral membrane protein 47 (PMP47); or a functional fragment thereof. See the Examples below for sequences of preferred animal signal proteins.

As discussed, practice of the invention is compatible with use of signal proteins that are functional in animal cells. Typical examples include, but are not limited to, the animal signals shown in the following Table I.

TABLE I

| Protein | Organelle | Position of signal | Type[1] |
| --- | --- | --- | --- |
| MSRA | Mitochondria | N-terminal | A |
| Cytochrome b2 | Mitochondria | N-terminal | A |
| 11β-HSD | ER | N-terminal | A & B |
| G9-AKL | Peroxisome | C-terminal | A |
| PMP47 | Peroxisome | A domain in the middle of protein | B |

[1] A type: Signal protein can be used as a masked signal protein.
B type: Signal protein can be used as unmasked signal protein.

See Hansel A et al. *FASEB J* 2002 June; 16: 911–31 (human peptide methionine sulfoxide reductase; "MSRA"); Bomer U et al. (1997) *J Biol Chem* 272 30439–30446 (Cytochrome b2); Naray-Fejes-Toth A and Fejes-Toth G (1996) *J Biol Chem* 271 15436–1544 (11β-hydroxysteroid dehydrogenase (11β-HSD)); McNew J A and Goodman J M (1994) *J Cell Biol* 127 1245–1257 (G9-AKL); Dyer et al., (1996) *J. Cell Biol.* 133 269–280 (PMP47 (peroxisomal integral membrane protein 47)).

By the phrase "functional fragment", when used herein to describe a signal protein, is meant a fragment of a particular signal protein that is capable of providing at least about 70%, preferably higher than about 90% of the shuttling function of the full-length sequence. Methods for detecting and quantifying signal protein function are known and include localization and quantification of signal intensity using the fluorescence imaging techniques described in the Examples section.

As should be apparent, the invention is flexible and not limited to use of any particular protease specific cleavage site. For example, the cleavage site can be specifically cleaved by a mammalian or viral protease. By the phrase "specifically cleaved" is meant that peptide bonds in a specified protease cleavage site are specifically broken (i.e. hydrolyzed) by a subject protease. That is, the protease cleavage sites are not broken by proteases which naturally occur in the host cell including what is generally referred to as housekeeping proteases. Specific cleavage of those protease cleavage sites can be monitored by a variety of techniques including SDS-polyacrylamide gel electrophoretic methods.

Preferred protease cleavage sites are those that are specifically hydrolyzed by a protease associated with a human pathogen e.g., yeast, bacterium, fungus, nematode, virus or protozoan. More specific examples include cytomegalovirus (CMV); herpes simplex virus (HSV); hepatitis virus, preferably type A or C; a *plasmodium*, human immunodeficiency virus (HIV), Kaposi's sarcoma-associated herpes virus (KSHV), yellow fever virus, flavivirus, rhinovirus, or a *plasmodium* such as *P. falciparum, P. vivax, P. ovale*, or *P. malariae*. Typically, the plasmodia cause malaria or various medical complications relating to malaria. There is recognition that the proteases plasmepsin I and plasmepsin II are implicated. In embodiments in which HSV is of interest, the protease will be the maturational protease of HSV.

A variety of particular HIV-1 and HCV protease specific cleavage sites have been disclosed. See eg., Gluzman, I. Y. et al., *J. Clin. Invest.*, 94:1602 (1994); Grakoui, A. et al., *J. of Virol.*, 67:2832 (1993); Kolykholov, A.A. et al., *J. of Virol.*, 68:7525 (1994); and Barrie, K. A. et al., *Virology*, 219:407 (1996), the disclosures of which are incorporated by reference.

Additional pathogen-specific proteases and specified cleavage sites have been described and can be used in accord with the present invention. For example, an HSV-1 maturational protease and protease cleavage site has been described. See e.g. Hall, M. R. T. and W. Gibson, *Virology*, 227:160 (1997). Further, the plasmepsins I and II have been found in the digestive vacuole of *P. falciparum*. The corresponding proteinase cleavage sites have also been disclosed. See e.g., Moon, R. P., *Eur. J. Biochem.*, 244:552 (1997).

Additional protease specific cleavage sites for use with the invention are specifically cleaved by a mammalian protease associated with blood coagulation, apoptosis, or the extracellular matrix. See the Examples and discussion that follows.

Practice of the invention is compatible with use of one or a combination of detectable amino acid sequences e.g., those that are directly or indirectly fluorescent, phosphorescent, luminescent or chemiluminescent. In embodiments in which two or more of such detectable sequences are used, the emission wavelength of one of the detectable sequences will often be different from at least one other of the detectable sequences. For example, a preferred detectable sequence is derived from certain well-known jellyfish fluorescent protein including those that are recognized to emit green, red, and yellow light under appropriate excitation conditions.

As discussed, the invention further provides substantially pure chimeric proteins. Such chimeric proteins can be separated and purified by appropriate combination of known techniques. If desired, such proteins can include one or more purification tags as described herein. These methods include, for example, methods utilizing solubility such as salt precipitation and solvent precipitation, methods utilizing the difference in molecular weight such as dialysis, ultra-filtration, gel-filtration, and SDS-polyacrylamide gel electrophoresis, methods utilizing a difference in electrical charge such as ion-exchange column chromatography, methods utilizing specific affinity such as affinity chromatograph, methods utilizing a difference in hydrophobicity such as reverse-phase high performance liquid chromatograph and methods utilizing a difference in isoelectric point, such as isoelectric focusing electrophoresis, metal affinity columns such as Ni-NTA. See generally Sambrook et al., *Molecular Cloning: A Laboratory Manual*, 2nd ed. (1989); Ausubel et al., *Current Protocols in Molecular Biology*, John Wiley & Sons, New York (1989); and Ausubel et al., *Short Protocols in Molecular Biology*, John Wiley & Sons, New York (1999) for disclosure relating to these methods.

It is preferred that the chimeric proteins of the present invention be substantially pure. That is, the chimeric proteins have been isolated from cell substituents that naturally accompany it so that the chimeric proteins are present preferably in at least 80% or 90% to 95% homogeneity (w/w). Chimeric proteins having at least 98 to 99% homogeneity (w/w) are most preferred for many pharmaceutical, clinical and research applications. Once substantially purified the chimeric protein should be substantially free of contaminants for cell culture and related applications. Once purified partially or to substantial purity, the soluble chimeric proteins can be used therapeutically, or in performing in vitro or in vivo assays as disclosed herein. Substantial purity can be determined by a variety of standard techniques such as chromatography and gel electrophoresis.

A suitable host cell can be used for preparative purposes to propagate nucleic acid encoding a desired chimeric protein. Thus a host cell can include a prokaryotic, plant or eukaryotic cell in which production of the chimeric protein is specifically intended. Thus host cells specifically include yeast, fly, worm, plant, frog, mammalian cells, plant cells and organs that are capable of propagating nucleic acid encoding the chimeric protein. Non-limiting examples of mammalian cell lines which can be used include CHO dhfl-cells (Urlaub and Chasm, *Proc. Natl. Acad. Sci. USA*, 77:4216 (1980)), 293 cells (Graham et al., *J Gen. Virol.*, 36:59 (1977)), myeloma cells like SP2 or NSO (Galfre and Milstein, *Meth. Enzymol.*, 73(B):3 (1981)). Other suitable cells are disclosed in Sambrook et al., supra.

Host cells capable of propagating nucleic acid encoding a desired chimeric protein encompass non-mammalian eukaryotic cells as well, including insect (e.g., *Sp. frugiperda*), yeast (e.g., *S. cerevisiae, S. pombe, P. pastoris., K. lactis, H. polymorpha*; as generally reviewed by Fleer, R., *Current Opinion in Biotechnology*, 3(5):486496 (1992)), fungal and plant cells (eg., *Arabidopsis* and *Nicotinia*). Also contemplated are use of certain prokaryotes such as *E. coli* and *Bacillus*.

Nucleic acid encoding a desired chimeric protein can be introduced into a host cell by standard techniques for transfecting cells. The term "transfecting" or "transfection" is intended to encompass all conventional techniques for introducing nucleic acid into host cells, including calcium phosphate co-precipitation, DEAE-dextran-mediated transfection, lipofection, electroporation, microinjection, viral transduction and/or integration. Suitable methods for transfecting host cells can be found in Sambrook et al. supra, and other laboratory textbooks.

The present invention further provides a production process for isolating a chimeric protein of interest. In the process, a host cell (e.g., a yeast, fungus, insect, bacterial or animal cell), into which has been introduced a nucleic acid encoding the protein of the interest operatively linked to a regulatory sequence, is grown at production scale in a culture medium in the presence of the chimeric protein to stimulate transcription of the nucleotides sequence encoding the chimeric protein of interest. Subsequently, the chimeric protein of interest is isolated from harvested host cells or from the culture medium. Standard protein purification techniques can be used to isolate the protein of interest from the medium or from the harvested cells. In particular, the purification techniques can be used to express and purify a desired chimeric protein on a large-scale (i.e. in at least milligram quantities) from a variety of implementations including roller bottles, spinner flasks, tissue culture plates, bioreactor, or a fermentor.

Thus the invention further provides a nucleic acid sequence encoding the chimeric substrate protein. The nucleic acid encoding the chimeric substrate protein can be used to transform a cell to express the chimeric substrate protein in the cell. In order to transform the cell, the recombinant gene must include a promoter and other regulatory nucleic acid sequences operably linked to the coding region of the chimeric substrate protein. Choice of a promoter will be guided by recognized parameters, typically selection of the host cell.

As discussed, the invention also provides nucleic acid sequences and particularly DNA sequences that encode the present chimeric proteins. Preferably, the DNA sequence is carried by a vector suited for extrachromosomal replication such as a phage, virus, plasmid, phagemid, cosmid, YAC, or episome. In particular, a DNA vector that encodes a desired chimeric protein can be used to facilitate preparative methods described herein and to obtain significant quantities of the chimeric protein. The DNA sequence can be inserted into an appropriate expression vector, i.e., a vector which contains the necessary elements for the transcription and translation of the inserted protein-coding sequence. A variety of host-vector systems may be utilized to express the protein-coding sequence. These include mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA or cosmid DNA. Depending on the host-vector system utilized, any one of a number of suitable transcription and translation elements may be used. See generally Sambrook et al., supra and Ausubel et al. supra.

In general, a preferred DNA vector according to the invention comprises a nucleotide sequence linked by phosphodiester bonds comprising, in a 5' to 3' direction a first cloning site for introduction of a first nucleotide sequence encoding a chimeric protein as described herein. If desired, the protein can be linked to DNA encoding one or more suitable tag sequences. FIGS. 7(a)–(j); 8(a)–(b); and 9(a)–(c) provide examples of such vectors.

In some invention embodiments, it will be preferred that the chimeric protein encoded by the DNA vector be provided in a "cassette" format. By the term "cassette" is meant that the encoded protein (or a component thereof) can be readily substituted for another component by standard recombinant methods. In particular, a DNA vector configured in a cassette format is particularly desirable when it is useful to "swap" one site specific protease cleavage site or detectable amino acid sequence for another. See FIGS. 7(a)–(j); 8(a)–(b); and 9(a)–(c) in which a core vector is used to express a variety of chimeric proteins.

More specifically, it is envisioned that in some cases, certain pathogen serotypes, especially viral strains, may be associated with individual protease cleavage sites specific for that serotype or strain. In this regard, the emergence of drug resistant HIV serotypes has been particularly problematic. In this case, one or more existing protease cleavage sites in a DNA vector formatted as a cassette can be replaced with other pre-determined protease cleavage sites as needed. Particular protease cleavage sites can be selected in accord with presence of the pathogen in individual human patients.

Significantly, the present invention can serve as an effective "warning system" that can register changes in protease activity in a subject cell or tissue. For instance, in cases where a PCR or hybridization experiment has indicated presence of genomic DNA encoding a pathogen-associated protease, use of the present invention can detect presence of active protease in the cells or tissue. This feature of the invention is useful in a variety of settings including cell culture in which pathogen contamination is known or suspected.

As discussed, the invention can be used to detect the presence of one or more proteases in a host cell or tissue of interest. The methods and compositions described herein are especially useful for detecting and analyzing protease inhibitor molecules, which as discussed, may be naturally-occurring or be part of a pool of such molecules (ie., a chemical library).

A. Use of the Invention to Screen Candidate Protease Inhibitors

1. General Considerations

In addition to the plant protoplasts as used in the examples described in this invention, normal plant cells with cell wall or human, animal, or insect cells can also be used to screen protease inhibitors according to the present invention. Plant cells will often be preferred because transformation and cultivation are easier and also identification of the protein localization can be facilitated due to the regular spherical shape of the protoplast. However, other cells and tissue may be useful e.g., if the protease of interest cannot be expressed as an active form in plant cells. For instance, such a protease may be difficult to express due to inappropriate post-translational modification. Suitable animal or insect cells may be used to overcome this problem if it arises. In such case, signal proteins that can work in the selected cell must be used. For example, if human, animal, or insect cells are to be used for screening, the chloroplast targeting signal proteins such as AtOEP7, RbcS, Cab, and RA cannot be used because chloroplasts are not present in these cells. For human, animal, or insect cells, signal proteins targeting to other subcelluar organelles such as mitochondria, peroxisome, plasma membrane, etc can be used. In addition, the vector system including the promoter and other regulatory elements must be selected appropriately depending on the cells to be used.

For in vivo screening of protease inhibitors according to the present invention, transformed cells that can express both a protease of interest and a chimeric substrate protein specific to the protease are prepared. The most preferred method to prepare the transformed cell is to co-transform the cell with a recombinant plasmid encoding the protease and a recombinant plasmid encoding a chimeric substrate protein provided by the present invention. If the protease is a viral protease, viral infection could also be used to express the protease in the transformed cell.

Methods for transforming a wide variety of plant, animal, yeast, fungi and insect cells are established. For instance, methods for transforming cells by introducing recombinant plasmids include, but are not limited to, chemical-mediated methods using PEG (polyethylene glycol), potassium phosphate, or DEAE-dextran, cationic lipid-mediated lipofection, microinjection, electroporation, electrofusion, and DNA bombardment. Depending on the type of the cell to be used, an appropriate transformation method has to be selected and the conditions need to be optimized to achieve efficient transformation. If protoplasts of plant cells such as *Arabidopsis* or Tobacco protoplasts are to be used, the PEG-mediated transformation method described in Example 1(c) is a preferred method. The conditions given in Example 1(c) are optimized for *Arabidopsis* protoplasts. If normal plant cells with cell wall are to be used, DNA bombardment with a gene gun or the PEG-mediated transformation method could be used depending on the type of the plant cell. For human, animal, or insect cells, potassium phosphate-mediated or DEAD-dextran-mediated transfection method or cationic lipid-mediated lipofection method can be used to transform the cells.

To screen protease inhibitors, the transformed cells need to be contacted by a candidate compound during the expression of the protease and the chimeric substrate protein. Typically, a candidate compound is added to the solution containing the transformed cells and the resulting solution is incubated at appropriate temperature. The candidate inhibitor can be one selected from the group consisting of chemical compounds, peptides, mixtures of chemical compounds or peptides, and extracts of natural products. The incubation time to express the proteins can vary depending on the type of the cell and the incubation temperature. It could range about 1 hr to several days. For the *Arabidopsis* protoplast, the incubation time could be as short as 4 hrs and as long as about a week depending on the incubation conditions. When the *Arabidopsis* protoplasts are incubated in the W5 solution at 22° C., preferred incubation time ranges from 12 to 48 hrs. The concentration of the candidate inhibitor that can be examined is about 0.1 to 100 µg/ml. In typical screening, concentration of about 1 to a few µg/ml can be used. In the case that a large number of candidate compounds need to be screened, mixtures of about 5–30 candidate inhibitors can be used in the first round of the screening.

Nearly any compound or group of compounds can be screened for anti-protease activity in accord with this invention. Examples include, but are not limited to, cytokines, tumor suppressors, antibodies, receptors, muteins, fragments or portions of such proteins, and active RNA molecules, e.g., an antisense RNA molecule or ribozyme. A preferred compound for screening purposes is a synthetic or semi-synthetic drug (referred to sometimes as a "small molecule"). For example, a pool of derivatives of known inhibitors of human viral pathogens can be readily tested by the present methods. See e.g., U.S. Pat. Nos. 6,420,438; 6,329,525; 6,287,840; 6,147,188; and 6,046,190 (disclosing a variety of testable molecules and derivatives thereof).

It is possible to use the invention to screen additional compounds. See Pillay et al. (1995) *Rev. Med. Virol*. (disclosing a variety of potential viral protease inhibitor compounds); and Wei et al. (1995) *Nature,* 373: 117 (disclosing indinavir, ABT-538); Ho et al. (1992) Ann. Intern. Med. 113: 111 (disclosing an anti-herpes agent). Also, derivatives of the forgoing specific compounds can be screened in accord with the invention including, but not limited to, saquinavir and derivatives thereof.

In order to identify inhibition of the protease activity by the candidate compound, it is preferred to monitor the fluorescence images of the transformed cells as a function of time. The expression time could vary depending on the condition of the cells and therefore the proteolytic activity or inhibition could appear in different times. If the *Arabidopsis* protoplasts are the cells to be used, preferred time sequence to monitor the fluorescence images is 12, 18, 24, 36, and 48 hrs after the expression is started. If the chimeric substrate protein has two or more different fluorescence labels, it is preferred to monitor fluorescence images at two or more fluorescence wavelengths specific to the fluorescence labels. It is preferred to monitor the bright field image because it can facilitate identification of the subcellular organelles. In order to facilitate identification of the protease inhibitors, it is also preferred to monitor the fluorescence images of the transformed cells that are not contacted with the candidate inhibitor for comparison. A standard fluorescence microscope equipped with multicolor fluorescence filter sets such as Zeiss Axioplan fluorescence microscope or Nikon E800 fluorescence microscope can be used to monitor the fluorescence images with magnification of 200×, 400×, or 600×. The scanning confocal microscope can be used to obtain higher resolution images.

It will be apparent that the invention is compatible with the construction and use of a wide spectrum of chimeric substrate proteins. See Example 1, for instance.

2. Illustrative Use of the NIa Protease

To measure the protease activity using the chimeric substrate protein as described above, NIa protease of Tobacco Vein Mottling Virus (TVMV) was used as a model system in the Examples of the present invention. NIa protease is one of the best-characterized viral proteases, and it is known that it cleaves seven specific sites of the polyprotein produced by TVMV. In order to achieve the optimum protease activity, six amino acid residues (P6–P1) on N-terminus and four amino acid residues (P1'–P4') on C-terminus are needed and four conserved amino acid residues (V-R-F-Q) must be included at P4–P1 of the substrate protein. If any one of the four conserved amino acid residues is mutated to glycine (Gly), the proteolytic cleavage of the substrate protein cannot take place (Yoon, H. Y. et al., 2000).

When the recombinant gene for expressing the chimeric substrate protein, RFP:PS(NIa):AtOEP7:GFP including the proteolytic site (PS(NIa)) of NIa protease was introduced into a protoplast by a polyethyleneglycol-mediated transformation method, GFP and RFP were accumulated as large aggregates in cytosol (FIG. 4). This result corresponds to the case in which the protease does not function. In this case, accumulation of the aggregates in cytosol is suspected to result from hydrophobic interactions among the hydrophobic regions of the AtOEP7 proteins. In the case that the red fluorescence signal of the chimeric substrate protein is not readily distinguishable from auto-fluorescence of chloroplast (FIG. 4(b)), it is possible to clearly determine the reaction of the substrate by using two different fluorescence labels and observing whether or not the green fluorescence coincides with the red fluorescence in the overlapped fluorescence image (FIG. 4(c)). When the plasmid encoding NIa protease and the plasmid encoding RFP:PS(NIa):AtOEP7: GFP were introduced together in the transformation, green and red fluorescent signals were separated into chloroplast outer envelope membrane and cytosol, respectively (FIG. 5). This result suggests that NIa protease successfully cleaved the proteolytic site of the chimeric substrate protein to generate two proteins, RFP and AtOEP7:GFP. The protease reaction can be identified by observing the green fluorescence signal translocated to chloroplast outer envelope membrane by the action of the signal protein (FIG. 5(a)), the red fluorescent signal dispersed in cytosol (FIG. 5(b)), and the overlapped image of both fluorescence signals (FIG. 5(c)).

The efficiency of the present invention for identifying the result of the enzyme reaction can be more clearly observed by comparing with the control experiment. Comparing FIGS. 4(a) and 5(a), it can be observed that the proteolytic cleavage activates the masked trafficking signal of the signal protein, inducing the change in the distribution of the fluorescence. Comparing FIGS. 4(b) and 5(b), it can be observed that the red fluorescent protein used as the signal masking protein plays a role in altering the distribution of the fluorescence signal in addition to the masking of the trafficking signal.

Accordingly, it is proposed that the chimeric substrate protein comprising a chimeric protein including a signal protein and a fluorescent protein, and a signal masking protein including a proteolytic site can be used as a substrate to determine the activity of a protease and also to screen its inhibitors in vivo.

3. High Throughput Screening Assays: General Considerations

The in vivo protease inhibitor screening method provided by the present invention can be easily adapted to use in a high throughput assay. The high throughput screening method comprises contacting the cells transformed to express a protease and its chimeric substrate protein with a candidate compound, incubating the transformed cells, obtaining fluorescence images of the transformed cells, converting the fluorescence images into digital data, and analyzing the digital data to determine whether the candidate compound has inhibited the protease.

In the high throughput screening of the present invention, equal amounts of the transformed cell solution are loaded into arrays of wells in standard microtiter plates with 96 or 384 wells, and different candidate compounds are added to each well. The transformed cells in the microtiter plates are then incubated to express the protease and its chimeric substrate protein at a controlled environment (at appropriate temperature, humidity, and air composition). Fluorescence images of the transformed cells in each well are obtained using a fluorescenece microscope after a preselected incubation times.

The high throughput screening apparatus consists of (1) an incubator for transformed cell sample arrays in multiples of microtiter plates, (2) an automated sampler, (3) an automated fluorescence microscope equipped with a XY-translation sample stage and a high resolution digital camera. After a preselected incubation time, the automated sampler samples a small portion of the transformed cell solution from each well and loads it to an observation plate such as a slide glass. Sampling can be done in a parallel manner using multiple tips or pipets or in a sequential manner using a single tip or pipet. After each sampling, the tip(s) or pipet(s) is subject to be washed with appropriate washing solution. The transformed cell samples are loaded on the observation plate in a form of arrays at preselected positions. The XY translation stage holds and moves the observation plate in the XY direction to locate the each sample under the microscope objective. A Z-axis focus drive moves either the microscope objective or the observation plate in the Z direction for focusing. For each sample, fluorescence images at preselected fluorescence wavelengths are captured using the digital camera, fed into a PC, and stored as a digital data. An automation controller is provided to control the pipet sampler, the XY translation stage, and the Z focus drive. The PC provides a display and a data analysis software.

The hits for the protease inhibitors can be automatically determined by examining the subcellular fluorescence distribution. In general, the extent of the localization or dispersion of the fluorescence signal within the size of the observed cell could be calculated from the digital image data and used as criteria for decision. For some cases, pattern or shape of the fluorescence signal distribution could be used as criteria for decision.

An example of a high throughput screening protocol suitable for use with the invention has been disclosed in U.S. Pat. No. 5,989,835 and PCT Application WO 00/79241 A2.

The following Tables 2 and 3 provide sequence information for use with the invention:

TABLE 2

SEQ ID NOs of PCR Primers

|  | 5' primer | 3'-primer |
|---|---|---|
| Partial AtOEP7 | 1 | 2 |
| Partial RbcS | 3 | 4 |
| Partial Cab | 5 | 6 |
| Partial RA | 7 | 8 |
| Partial F1-ATPase | 9 | 10 |

TABLE 2-continued

SEQ ID NOs of PCR Primers

| | 5' primer | 3'-primer |
|---|---|---|
| SKL | 11 | 12 |
| H+-ATPase | 13 | 14 |
| Substrate protein for NIa protease | 15 | 16 |
| HIV-1 protease | 17 | 18 |
| Substrate proteins for HIV-1 protease | 19, 20, 21, 22, 23, 24, 25, 26, 27 | 28 |

TABLE 3

SEQ ID NOs of Signal Proteins

| | Nucleic acid sequence | Protein sequence |
|---|---|---|
| Partial AtOEP7 | 29 | 30 |
| Partial RbcS | 31 | 32 |
| Partial Cab | 33 | 34 |
| Partial RA | 35 | 36 |
| Partial F1-ATPase | 37 | 38 |
| H+-ATPase | 39 | 40 |
| Partial PH | 41 | 42 |
| Partial FAPP | 43 | 44 |

The following provides illustrative nucleic acid and protein sequence information for use with the invention. Examples of proteases and their cleavage sites are provided in SEQ ID NOs: 45–50, 55–74, and 77–120. Examples include NIa protease (SEQ ID NOs: 45 and 46) and its cleavage sites (SEQ ID NOs: 47–50), HIV-1 protease (SEQ ID NOs: 55 and 56) and its cleavage sites (SEQ ID NOs: 57–74), HCV NS3 protease (SEQ ID NOs: 77 and 78) and its cleavage sites (SEQ ID NOs: 79–84), HSV-1 protease (SEQ ID NOs: 85 and 86) and its cleavage sites (SEQ ID NOs: 87–90), HTLV-1 protease (SEQ ID NOs: 91 and 92) and its cleavage sites (SEQ ID NOs: 93–96), HCMV protease (SEQ ID NOs: 97 and 98) and its cleavage sites (SEQ ID NOs: 99–102), APP beta-secretase (SEQ ID NOs: 103 and 104) and its cleavage site (SEQ ID NOs: 105 and 106), caspase 3 (SEQ ID NOs: 107 and 108) and its cleavage site (SEQ ID NOs: 113 and 114), the large subunit of caspase 3 (SEQ ID NOs: 109 and 110), the small subunit of caspase 3 (SEQ ID NOs: 111 and 112), human blood coagulation factor II (SEQ ID NOs: 115 and 116) and its cleavage site (SEQ ID NOs: 117 and 118), and human blood coagulation factor XI (SEQ ID NOs: 119 and 120).

Nucleic acid and protein sequences of two NIa protease substrate proteins are provided in SEQ ID NOs: 51–54 and those for a HIV-1 protease substrate protein are provided in SEQ ID NOs: 55 and 56.

The following discussion relates to Korean application No.10-2001-0048123 in which additional uses and advantages of the present invention have been disclosed.

As provided therein, the invention provides important chimeric substrate proteins that can be used to screen protease inhibitors in vivo. As particularly disclosed therein, the invention relates to a system for screening protease inhibitors and it provides: (i) a chimeric substrate protein constructed to induce change in the subcellular localization and distribution of fluorescence by the specific function of a protease, (ii) a recombinant gene comprising a nucleic acid sequence encoding the chimeric substrate protein that can be used to express the chimeric substrate protein in a cell, (iii) a method to identify the activity of the protease by detecting the subcellular localization and distribution of fluorescence under the circumstance that the protease and the chimeric substrate protein are present together in a cell so that a proteolytic cleavage by the protease can take place in the cell, and (iv) a method to screen protease inhibitors in vivo using the chimeric substrate protein and the method described above.

More particularly, the Korean application No. 10-2001-0048123 discloses that such chimeric substrate proteins can be used in a cell in which the signal protein directs trafficking to a subcellular organelle when expressed in a cell. In further detail, the trafficking signal toward a specific subcellular organelle, included in the signal protein, can be inactivated by linking a signal masking protein to the N- or C-terminal of the signal protein. In the present invention, a signal protein is linked to a signal masking protein with a proteolytic cleavage site of a protease so that the trafficking of the signal protein can be activated or inactivated depending on the cleavage at the proteolytic site. In other words, the trafficking of the chimeric substrate protein, in which the signal protein and the signal masking protein are linked with the proteolytic site, does not occur until the signal masking protein is cleaved off by the protease. Such cleavage induces normal trafficking of the signal protein. In the present invention, the signal protein and/or the signal masking protein are labeled with fluorescent proteins so that the activity of the protease can be determined by measuring changes in the localization and distribution characteristics of the fluorescence signal. Therefore, the chimeric protein used as a substrate of the protease in the present invention has the following characteristics:

(1) The chimeric substrate protein includes at least one signal protein that has a trafficking signal directing transport to a specific subcellular organelle.

(2) The chimeric substrate protein includes at least one proteolytic cleavage site for a specific protease.

(3) The trafficking signal of the signal protein clarified in (1) is inactivated by linking the proteolytic cleavage site to the signal protein or by linking a signal masking protein to the signal protein through the proteolytic cleavage site.

(4) The inactivated trafficking signal of the signal protein can be activated when cleavage at the proteolytic site occurs by the protease.

(5) The chimeric substrate protein is labeled with at least one fluorescent protein and the fluorescence signal from the cell changes depending on the proteolytic cleavage by the protease.

As discussed in the Korean application No. 10-2001-0048123, the invention further provides for a method for measuring the protease activity in vivo using the chimeric substrate protein described herein. Also provided is method for screening protease inhibitors using the method for measuring the protease activity.

As further disclosed in the Korean application No. 10-2001-0048123, to measure the protease activity in vivo, a protease and a chimeric substrate protein specific to the protease must co-exist in a cell.

Also, the recombinant gene for the chimeric substrate protein according to one invention aspect is introduced into the cell to express the chimeric substrate protein in the cell. The target protease for screening protease inhibitors can be an endogeneous protease present in the cell or an exogeneous protease expressed by transforming with a recombinant gene or infecting with a virus. However, when an endogeneous protease is a target, the accuracy and efficiency of the screening may be low e.g., due to the difficulties in regulating the expression of the protease and also in detecting under a low level of the protease expression. Therefore, the present invention provides a system for more efficiently determining the protease activity in vivo, wherein a specific protease can be over-expressed or expressed in a regulated manner by transforming the cell with a recombinant gene or infecting the cell with a virus. Viral infection can be used in the case of a viral protease. However, regulation of viral protease expression is not completely understood, it is more preferable to use a protease expressed by transforming the cell with a recombinant gene encoding the protease. Since the expressed protease is located in cytosol, it is necessary to make the chimeric substrate protein located in cytosol as well. Therefore, a system for efficiently measuring the protease activity in vivo can be constructed by using the chimeric substrate protein according to the first aspect of the present invention, wherein the trafficking signal of the signal protein included in the chimeric substrate protein is masked.

Furthermore, inhibitors of the protease can be selected by detecting changes in the localization and distribution of the fluorescence signal, caused by treating the cell with a candidate chemical before, after, or at the same time as the protease and its chimeric substrate protein are expressed in the cell.

In many enzymatic reactions, reactants cannot be completely converted to products. In the case that the reaction is inhibited by an inhibitor, it could also be partially inhibited rather than completely inhibited. Moreover, when multiple cells are observed, the level of the protease activity in each cell could vary considerably. Therefore, there may be a considerable ambiguity in determining the inhibition activity of the protease inhibitor if the method used for determining the protease activity has low sensitivity or low contrast. In order to avoid such ambiguity, it is important in the construction of the chimeric substrate protein to select a signal protein that can induce a clearly distinguishable change in the cellular localization and distribution of the fluorescence signal depending on the proteolytic cleavage. In addition, the efficiency of determining the inhibition activity can be enhanced employing two or more fluorescent proteins having different fluorescence wavelengths. In Example 2 of the present invention, GFP and RFP were employed in the construction of the chimeric substrate protein so that they can be localized in different subcellular organelles upon proteolytic cleavage.

As discussed above, certain signal proteins according to the invention are optionally masked. In this embodiment, the signal protein included in the chimeric substrate protein provided by the present invention is inactivated due to the signal masking by the proteolytic site or the signal masking protein linked to the signal protein and thus the chimeric substrate protein is present in cytosol. The signal protein can be activated by the proteolytic cleavage to direct its trafficking to a subcellular organelle. Different characteristics of signal proteins need to be considered in selecting the signal protein whose trafficking signal is inactivated in the chimeric substrate protein. The endosomal trafficking proteins are translocated to the Golgi body, the lytic vacuole, the storage vacuole, or the plasma membrane as enclosed in the endoplasmic reticulum as soon as they are synthesized. The trafficking signals of the endosomal trafficking proteins are recognized during the translation process. Therefore, it may not be possible to inactivate and activate the trafficking signals of the endosomal trafficking proteins by simply linking and cleaving off the proteolytic site with or without the signal masking protein. Therefore, these endosomal trafficking proteins are less adequate for use in the present invention as the signal proteins whose trafficking signals are inactivated. Proteins expressed in the cytosol and transported directly to the subcellular organelles can be used as the signal protein because their trafficking signals can be masked according to the present invention. Among the latter signal proteins, signal proteins having the nuclear location signal (NLS) are not dependant on the N- or C-terminus and thus it is difficult to control the trafficking of these signal proteins by linking or cleaving off the proteolytic site with or without the signal masking protein. It is thus desirable to select a signal protein that has a trafficking signal targeting to mitochondria, chloroplast, or peroxisome. In the case of plant cells, it is more preferable to use a chloroplast targeting signal protein because chloroplast is relatively big and thus easier to detect its shape and distribution.

The signal masking protein included in the chimeric substrate protein of the present invention inactivates the trafficking signal of the signal protein by being linked to the signal protein through the proteolytic site. The signal masking protein can be an amino acid, a peptide, or a protein that is linked to the signal protein through the proteolytic site. For some cases, it may be possible to inactivate the trafficking signal of the signal protein by linking the proteolytic site alone to the signal protein. The signal masking protein and the proteolytic site must not interfere the binding of the substrate with the protease. In addition to the simple signal masking, the signal masking protein can also be used to change the overall characteristics of the chimeric substrate protein, or to attach an additional trafficking signal or a fluorescent label. For example, if another signal protein is selected as a signal masking protein, this signal protein will move to its target organelle when cleaved off by the protease. In such case, if this signal protein is also labeled with a fluorescent protein, it will be possible to more clearly identify the cleavage of the substrate protein by detecting two different fluorescence signals. In another example, a fluorescent protein can be used as a signal masking protein. In this case, the fluorescent protein formed by the proteolytic cleavage will stay in cytosol. It is thus possible to increase the efficiency of determining the protease activity or detecting the inhibition activity of a protease inhibitor by observing distinctively the fluorescence signal from cytosol and that from the subcellular organelle to which the signal protein formed by the proteolytic cleavage is translocated.

One or a combination of standard recombinant methods can be employed to make the chimeric substrate proteins disclosed herein. That is, the method for constructing the chimeric substrate protein can be characterized by its expandability. For example, if at least two proteolytic sites are included in the chimeric substrate protein of the protease, trafficking of two or more signal proteins can be observed. If proteolytic sites for two or more different proteases are introduced, the activities of two or more proteases can be examined simultaneously.

Detailed methods for selecting the signal protein and the signal masking protein and constructing the chimeric substrate protein are as follows. The mark—↓—indicates the proteolytic site of the protease and M represents the signal masking protein.

(1) In the case that the trafficking signal is present at the N-terminus of the signal protein (nS), the signal masking protein is placed at the N-terminal side of the signal protein: (M-↓-nS).

(2) In the case that the trafficking signal is present at the C-terminus of the signal protein (Sc), the signal masking protein is placed at the C-terminal side of the signal protein: (Sc-↓-M).

(3) In the case that another signal protein S' is used as the signal masking protein, S' can be selected to possess the trafficking signal in the opposite side compared to that of S. The trafficking signals of the two signal proteins can be simultaneously masked by constructing the chimeric substrate protein with the trafficking signal parts of the two signal proteins being linked: (Sc-↓-nS' or S'c-↓-nS).

(4) In the construction as in (3), if two proteolytic sites are to be introduced, the signal masking protein has to be placed between two signal proteins: (Sc-↓-M-↓-nS' or Sc'-↓-M-↓-nS).

(5) If the trafficking signals of a signal protein (S) and the other signal protein (S') that acts as a signal masking protein are on the same sides, another signal masking protein that masks the trafficking signal of S' needs to be linked: (M-↓-nS'-↓-nS or Sc-↓-Sc'-↓-M).

By extending the constructions of (1) to (5) described above, the chimeric substrate protein can be constructed with three or more proteolytic sites: ($Sc_m$-↓- . . . -↓-$Sc_2$-↓-$Sc_1$-↓-M-↓-$nS_1$-↓-$nS_2$-↓- . . . -↓-$nS_n$).

The construction methods described above are the representative examples of possible construction methods.

In addition to the cases described above, wherein the trafficking signals of all the signal proteins included in the chimeric substrate protein are masked, there are other construction methods that can provide the chimeric substrate protein with its proteolytic cleavage to occur in cytosol. If the trafficking signal of only one signal protein included in the chimeric substrate protein remains active and all the trafficking signals of the rest of the signal proteins are masked, the chimeric substrate protein will be translocated to a subcellular organelle that is the target of the active signal protein. Herein, in the case that the translocated chimeric substrate protein resides on the membrane of a subcellular organelle, the chimeric substrate protein can be constructed in which at least one proteolytic site and at least one inactivated signal protein is exposed to cytosol so as to achieve the same effect as in the case of using the chimeric substrate protein with all the trafficking signals of the signal proteins being masked. If this chimeric protein having only one signal protein remaining active is used as a substrate, the proteolytic reaction can occur by the protease present in cytosol because the proteolytic site is exposed to cytosol, although the chimeric substrate protein is not freely dispersed in cytosol. In this case, the inactivated signal protein exposed to cytosol becomes activated by the proteolytic cleavage. Therefore, the fragment protein that includes this activated signal protein will be translocated to a specific subcellular organelle that is different from the subcellular organelle where the chimeric substrate protein resided, resulting in alteration in the localization and distribution of the fluorescence signal attached to the activated signal protein.

Another possible method for constructing the chimeric substrate protein with the trafficking signal of only one signal protein remaining active is to link a fluorescent protein such as GFP or RFP, that has no trafficking signal, to the proteolytic site exposed to cytosol, instead of linking a signal protein. In this case, since the fluorescent protein produced by the proteolytic cleavage becomes dispersed in cytosol, the distribution of the fluorescent signal changes from a specific cellular organelle to cytosol. In this case, however, clearness for distinguishing whether the fluorescence signal is located in membrane or cytosol could be low due to incompleteness of the enzyme reaction. In addition, there may be considerable difficulties in constructing the chimeric substrate protein with only one signal protein remaining active, because detailed information is needed not only for the subcellular organelle to which the signal protein is translocated, but also for the orientation and position of the translocated signal protein.

Signal proteins targeting to outer membranes of mitochondria, chloroplast, and nucleus, peroxisome membrane, and plasma membrane can be used as the signal protein that remains active in the chimeric substrate protein. Signal proteins that can specifically bind to phospholipids can also be used. Examples includes Pleckstrin homology domain (PH) that binds to phosphatidylinositol 4,5-diphosphate (PI(4,5)P2) as shown in FIG. 2(*h*) and pleckstrin homology domain of FAPP (family A (phosphoinositide binding specific) member 3) that binds to phophatidylinositol 4-phosphate (PI(4)P).

In Example 2, Western blot analysis was performed for the cells transformed to express a protease and its chimeric substrate protein constructed according to the present invention, and it was confirmed that the protease reaction was taking place correctly. Comparing with the Western blot analysis in which the cells were lysed and the crude extract was electrophoresed and identified with antibody, the system provided by the present invention in which the identification can be carried out by simply observing the cell itself is more efficient in terms of both time and cost.

In Example 1 of the present invention, a system was constructed in which trafficking and distribution of a protein can be visually determined in a cell. Chimeric proteins were constructed to visualize the localization of the proteins after translocation by selecting signal proteins that have trafficking signals to subcellular organelles and labeling with a fluorescent protein. It is shown that localization of the chimeric protein can be identified by observing the fluorescent image of the cell transformed with a recombinant plasmid that includes a recombinant gene for the chimeric protein.

Among these chimeric proteins, AtOEP7:GFP was selected and a proteolytic site of a protease was linked to construct a chimeric substrate protein that can be used for screening protease inhibitors in vivo. AtOEP7 is a protein targeting to *Arabidopsis* chloroplast outer envelope membrane, and it was already mentioned that it is more desirable to select a chloroplast targeting protein for plant cells. A signal masking protein was linked to the N-terminal side of AtOEP7:GFP, because AtOEP7 has its trafficking signal at N-terminus. As a signal masking protein, red fluorescent protein (RFP) was selected. Therefore, the substrate chimeric protein was constructed such that the green fluorescence localizes to chloroplast envelope membrane and the red fluorescence distributes in cytosol after the proteolytic cleavage.

In general, preparation of the fusion molecules of the invention includes conventional recombinant steps involving, e.g., polymerase chain amplification reactions (PCR), preparation of plasmid DNA, cleavage of DNA with restriction enzymes, preparation of oligonucleotides, ligation of DNA, isolation of mRNA, introduction of the DNA into a suitable cell, and culturing of the cell. Additionally, the chimeric proteins described herein can be isolated and purified in accordance with well known techniques including methods that comprise standard electrophoretic, centrifugation and chromatographic manipulations. See generally, Sambrook et al., supra; and Ausubel et al., supra; for disclosure relating to these methods.

DNA and protein sequences described herein can be obtained from a variety of public sources including those specifically mentioned. A preferred source is the National Center for Biotechnology Information (NCBI)-Genetic Sequence Data Bank (Genbank) at the National Library of Medicine, 38A, 8N05, Rockville Pike, Bethesda, Md. 20894. Genbank is also available on the internet. See generally Benson, D. A. et al., *Nucl. Acids. Res.*, 25:1 (1997) for a description of Genbank.

Other reagents used in the examples such as antibodies, cells and viruses can be obtained from recognized commercial or public sources such as *Linscott's Directory* (40 Glen Drive, Mill Valley Calif. 94941), and the American Type Culture Collection (ATCC) 12301 Parklawn Drive, Rockville, Md. 20852.

All documents mentioned herein are incorporated herein by reference.

The present invention is further illustrated by the following Examples. These Examples are provided to aid in the understanding of the invention and are not construed as a limitation thereof.

EXAMPLE 1

Detection of Chimeric Proteins and Trafficking to the Subcellular Organelles (a) Construction of Recombinant Plasmids for Expression of the Chimeric Proteins The coding region of the outer envelope membrane protein of *Arabidopsis*, AtOEP7, that is a homolog of OEP14 of pea, was amplified by polymerase chain reaction (PCR) from *Arabidopsis* genomic DNA using two specific primers (5'-GACGACGACGCAGCGATG and 5'-GGATC-CCCAAACCCTCTTTGGATGT) designed to remove the natural termination codon. Then, it was ligated in frame to the 5' end of the coding region of the green or red fluorescent protein to construct recombinant plasmids for AtOEP7:GFP and AtOEP7:RFP, respectively. The ligated genes were regulated by the 35S promoter in the recombinant plasmids. The same method was used for construction of other recombinant plasmids described hereafter.

For expression of the chimeric protein of Rubisco (ribulose bisphosphate carboxylase) complex protein, the coding region for the transit peptide of the small subunit of the Rubisco complex was amplified by PCR from a λZAPII cDNA library using two specific primers (5'-CCTCAGTCA-CACAAAGAG and 5'-ACTCGAGGGAATCGGTAAGGT-CAG). The resulting PCR product was subcloned into pBluescript and subsequently ligated in-frame to the 5' end of the coding region of GFP or RFP to construct recombinant plasmids for RbcS:GFP or RbcS:RFP, respectively.

For expression of the chlorophyll a/b binding protein, the corresponding gene was amplified by PCR from a λZAPII cDNA library using two specific primers (5'-TAGAGAGAAACGATGGCG and 5'-GGATC-CCGTTTGGGAGTGGAACTCC) to construct a recombinant plasmid for Cab:GFP.

The coding region for the transit peptide of rubisco activase (RA) was amplified by PCR from a λZAPII cDNA library using two specific primers (5'-TCTAGAATGGC-CGCCGCAGTTTCC and 5'-GGATCCATCTGTCTC-CATCGGTTTG) and ligated to the 5' end of the coding region of GFP to construct a recombinant plasmid for RA:GFP.

The coding region for the transit peptide of F1-ATPase-(accession number: D88374) was amplified by PCR from λZAPII cDNA library using two specific primers (5'-CTT-TAATCAATGGCAATG and 5'-CCATGGCCTGAACT-GCTCTAAGCTT) and ligated to the 5' end of the coding region of GFP to construct F1-ATPase:GFP.

A recombinant plasmid for the peroxisome targeting protein, GFP:SKL, was constructed by PCR amplification with 326GFP (Davis, S. J. and Viestra, R. D., 1998) as a template using two specific primers (5'-CCGTATGTTA-CATCACC and 5'-TTATAGCTTTGATTTGTATAGT-TCATCCAT).

The full length H$^+$-ATPase (AHA2 of *Arabidopsis*) was amplified with two specific primers (5'-GAGATGTC-GAGTCTCGAA and 5'-CTCGAGCACAGTGTAGT-GACTGG) using the above method and ligated to the 5' end of the coding region of GFP to construct a recombinant plasmid for H$^+$-ATPase:GFP.

A recombinant plasmid for the chimeric protein of the PH domain (Pleckstrin homology domain), GFP:PH, was constructed according to the method described by Kost, B. et al. (1998).

Schematic structures of the chimeric proteins expressed from the recombinant plasmids constructed according to the above method are shown in FIG. 1.

(b) Preparation of Protoplasts

Leaf tissues (5 g) of 3–4 week-old *Arabidopsis* plants grown on soil in a green house were cut into small squares (5–10 mm$^2$) with a new razor blade and incubated with 50 ml of the enzyme solution (0.25% Macerozyme R-10, 1.0% Cellulase R-10, 400 mM mannitol, 8 mM CaCl$_2$, 5 mM Mes-KOH, pH 5.6) at 22° C. with gentle agitation (50–75 rpm). After incubation, the protoplast suspension was filtered through 100 μm mesh and protoplasts were collected by centrifugation at 46×g for 5 min. The pelleted protoplasts were resuspended in 5 to 10 ml of the W5 solution (154 mM NaCl, 125 mM CaCl$_2$, 5 mM KCl, 5 mM glucose, 1.5 mM Mes-KOH, pH 5.6), overlaid on top of 20 ml of 21% sucrose, and centrifuged at 78×g for 10 min. The intact protoplasts at the interface were transferred to 20 ml of the W5 solution. The protoplasts were pelleted again by centrifugation at 55×g for 5 min, resuspended in 20 ml of the W5 solution, and then incubated on ice for 30 min.

(c) Isolation of the Recombinant Plasmid DNAs and Transformation of the Protoplast Recombinant plasmids were purified using Qiagen columns (Valencia, Calif.) according to the manufacture's protocol. To transform the protoplasts with the DNA, the protoplasts were pelleted again at 46×g for 5 min and resuspended in the MaMg solution (400 mM Mannitol, 15 mM MgCl$_2$, 5 mM Mes-KOH, pH 5.6) at a density of 5×10$^6$ protoplasts/ml. The recombinant plasmid constructs were introduced into the *Arabidodsis* protoplasts by PEG (polyethylene glycol)-mediated transformation method (Jin et al., 2001). About 20–50 μg of the plasmid DNA at a concentration of 2 μg/μl was mixed with 300 μl of the protoplast suspension, and 325 μl of the PEG (polyethylene glycol) solution (400 mM Mannitol, 100 mM Ca(NO$_3$)$_2$, 40% PEG 4000) was added and gently mixed. The mixture was incubated for 30 min at room temperature. After incubation, the mixture was diluted with 10 ml of W5 solution. The protoplasts were recovered by centrifugation at 50×g for 5 min, resuspended in 3 ml of the W5 solution, and incubated at 22° C. in the dark.

(d) Expression of the Chimeric Proteins and Observation of Their Subcellular Localizations The recombinant plasmid DNAs constructed in Example 1(a) were used to transform the protoplasts according to the method described in Example 1(c). The expression of the chimeric proteins after the transformation was monitored as a function of time by capturing images using a fluorescence microscope (Axioplan fluorescence microscope, Zeiss, Germany) equipped with a cooled charge-coupled device camera. The filter sets used were XF116 (exciter: 474AF20, dichroic: 500DRLP, emitter: 510AF23), XF33/E (exciter: 535DF35, dichroic: 570DRLP, emitter: 605DF50), and XF137 (exciter: 540AF30, dichroic: 570DRLP, emitter: 585ALP) (Omega, Inc, Brattleboro, Vt.) for GFP, RFP, and auto-fluorescence of chlorophyll, respectively. Data were then processed using Adobe (Mountain View, Calif.) Photoshop software and presented in pseudo-color format.

Green fluorescence of the chimeric protein of AtOEP7: GFP was observed at the outer envelope membrane of the chloroplast (FIG. 2(a)). This result indicates that the chimeric protein comprising the chloroplast envelope targeting signal peptide and the fluorescent protein label was correctly targeted to the chloroplast envelope membrane.

Figure 2:
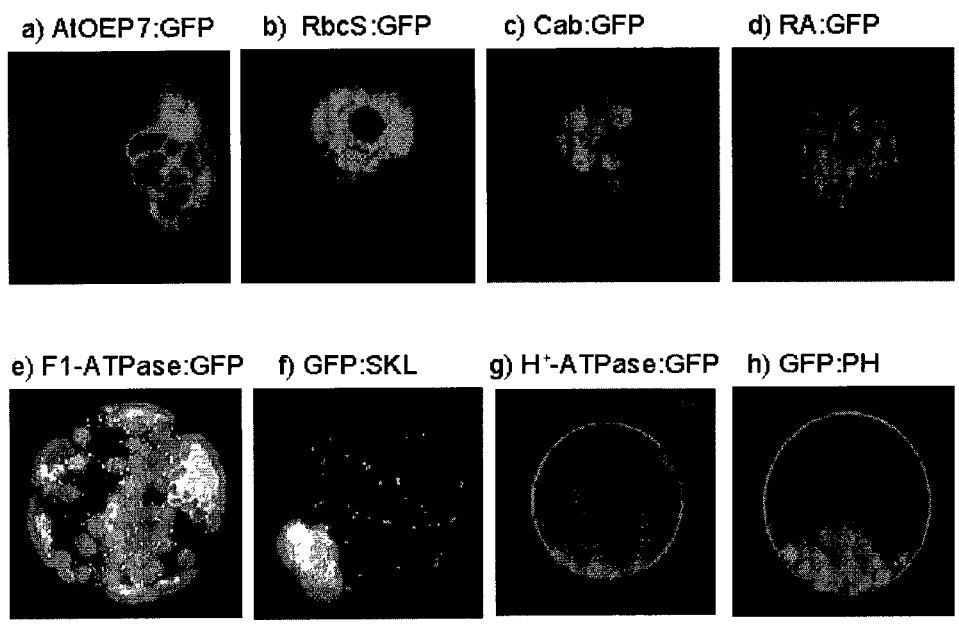
FIGS. 2(a)–(h) show fluorescence photographs visualizing the localized distributions of the signal proteins labeled with the fluorescent proteins when they are expressed correctly in a cell.

Localization of the green fluorescence from the chimeric proteins RbcS:GFP, Cab:GFP and RA:GFP are presented in (b), (c), and (d) of FIG. 2, respectively. As shown in the figures, RbcS:GFP was located in the stroma of chloroplast, and Cab:GFP and RA:GFP also emitted the fluorescence in chloroplast. These results indicate that the chimeric proteins comprising the signal peptide of RbcS, Cab, or RA, and the fluorescence protein label were targeted to chloroplast.

The green fluorescence signals of the chimeric proteins, F1-ATPase:GFP, GFP:SKL, and H+-ATPase:GFP were observed in mitochondria, peroxisome, and plasma membrane (FIGS. 2(e)–(g)), respectively. The red fluorescent signals in these results were auto-fluorescence of chloroplast.

The green fluorescence signal of GFP:PH, comprising the PH domain (Pleckstrin homology domain) that specifically binds to a phospholipid, was distributed on the plasma membrane where phosphatidylinositol 4, 5-diphosphate (PI (4, 5)P2) was present (FIG. 2(h)).

FIGS. 7(a)–(j) is explained in more detail as follows. The figure shows plasmid maps of the recombinant plasmids used to express the fusion proteins depicted in FIG. 1. The methods for constructing these recombinant plasmids are described in the present example. Nucleic acid and protein sequences of the signal proteins included in these fusion proteins are provided in SEQ ID NOs: 29–42. In addition, nucleic acid and protein sequences of partial pleckstrin homology domain of FAPP (family A (phosphoinositide binding specific) member 3) are provided in SEQ ID NOs: 43 and 44.

These signal proteins are examples of the signal proteins that can be used as either inactivated signal proteins or active signal proteins according to the present invention. AtOEP7, RbcS, Cab, RA, F1-ATPase, and SKL (peroxisome targeting sequence) are examples of signal proteins that are inactivated by masking in the chimeric substrate protein. AtOEP7, H+-ATPase, PH, and FAPP are examples of signal proteins that remain active in the chimeric substrate protein.

EXAMPLE 2

Detection of Cleavage of the Chimeric Substrate Protein by Protease (a) Construction of the Recombinant Plasmids The recombinant plasmid for NIa protease was constructed by placing the coding region of NIa protease under the control of the 35S promoter in a pUC vector.

The recombinant plasmid for *Arabidopsis* outer envelope membrane protein:green fluorescent protein (AtOEP7:GFP) was constructed by ligating the AtOEP7 coding region without the termination codon to the 5' end of the coding region of the green fluorescent protein in the 326GFP vector (obtained from *Arabidopsis* Biological Resource Center, Ohio University, USA). The cleavage site of the protease, VRFQ, was ligated to the N-terminus of AtOEP7:GFP by PCR amplification of this plasmid with two primers (5' primer, 5'-CCCGGGGTGTGCGCTTCCAGG-GAAAAACTTCGGGAGCG and 3' primer, 5'-GAGCTCT-TATTTGTATAGTTCATC). The PCR product (SmaI and XhoI fragment) was then ligated to HindIII (filled in) and XhoI sites of the 326RFP-nt vector to construct the recombinant plasmid for the chimeric substrate protein RFP: VRFQ:AtOEP7:GFP (FIG. 3(a)).

(b) Transformation with the Recombinant Plasmids

Transformation was performed as in (b) and (c) of Example 1.

(c) Detection of the Fluorescent Proteins Using a Fluorescence Microscope

Detection of the fluorescent protein was carried out as in (d) of Example 1. The final recombinant plasmid for expression of the chimeric substrate protein RFP:VRFQ:AtOEP7: GFP was introduced to the protoplast and the subcellular trafficking was examined for 24–36 hrs after transformation. As shown in FIG. 4, the chimeric substrate protein was localized as large speckles or aggregates in the protoplast but not targeted to the chloroplast. Both of the red and green fluorescent signals were observed in the same speckle.

In the next experiment, it was examined whether NIa protease can cleave the cleavage site in the chimeric substrate protein. When the protoplast was co-transformed with the recombinant plasmid for NIa protease, the green fluorescence signal was observed at the envelope membrane of the chloroplast whereas the red fluorescence signal was observed as uniformly dispersed in the cytosol, as shown in FIG. 5. Furthermore, the red and green fluorescence signals no longer overlapped each other, strongly suggesting that NIa protease cleaved the chimeric substrate protein in vivo.

(d) Western Blot Analysis

The transformed protoplasts were harvested and lysed in 50 μl of cell lysis buffer (50 mM Tris-HCl, pH 7.5, 1 mM DTT, 1 mM EDTA, 50 mM NaCl). Expression of the chimeric substrate protein RFP:VRFQ:AtOEP7:GFP and cleavage of the chimeric substrate protein into RFP and AtOEP7:GFP by NIa protease were identified by Western blot analysis using monoclonal anti-GFP antibody (Clontech, Inc) and the ECL kit (Amersham, Inc).

As shown in FIG. 6, when NIa protease was not co-transformed, the chimeric substrate protein RFP:VRFQ: AtOEP7:GFP was detected at the expected size of 70 kDa. In contrast, when NIa protease was co-transformed, the anti-GFP antibody detected a protein at 35 kDa, an expected size of AtOEP7:GFP. This result indicates that the chimeric substrate protein RFP:VRFQ:AtOEP7:GFP was cleaved into two proteins, RFP and AtOEP7:GFP. Therefore, this result clearly demonstrates that NIa protease can cleave the chimeric substrate protein in vivo and the cleavage reaction can be easily assayed by detecting the localization of the green fluorescence signal at the chloroplast envelope membrane and the dispersed distribution of the red fluorescence signal in the cytosol.

Figure 8A:
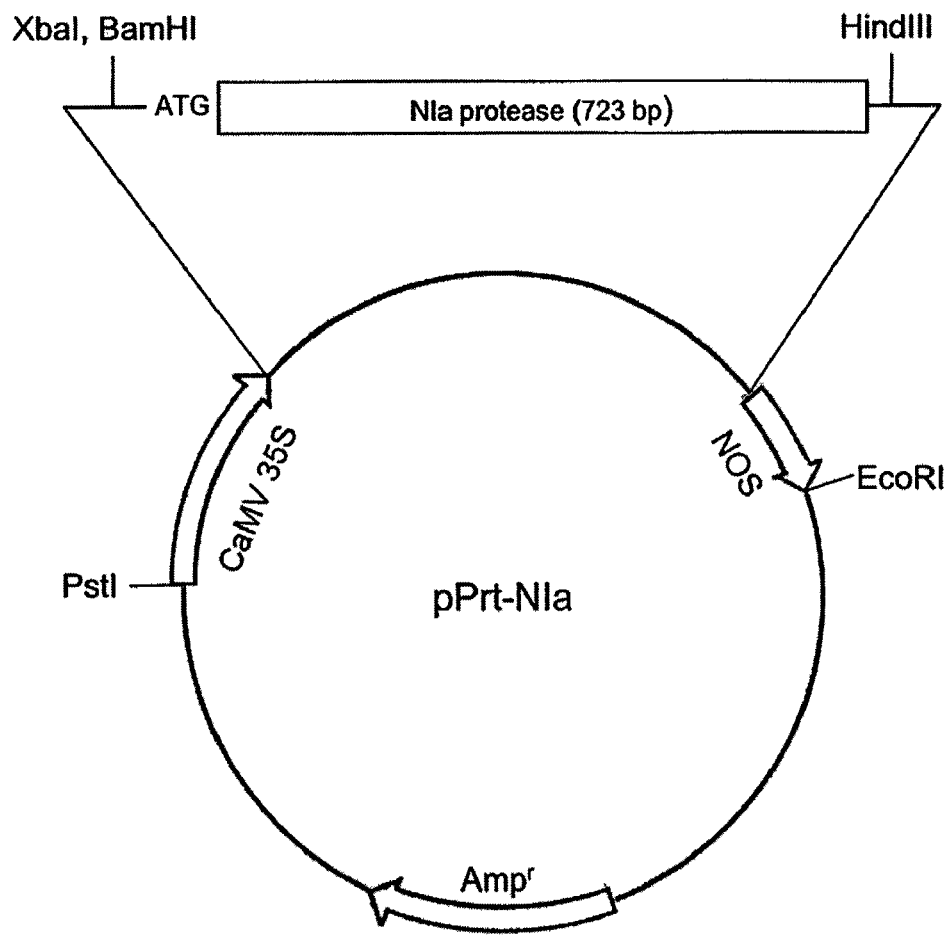
Figure 8B:
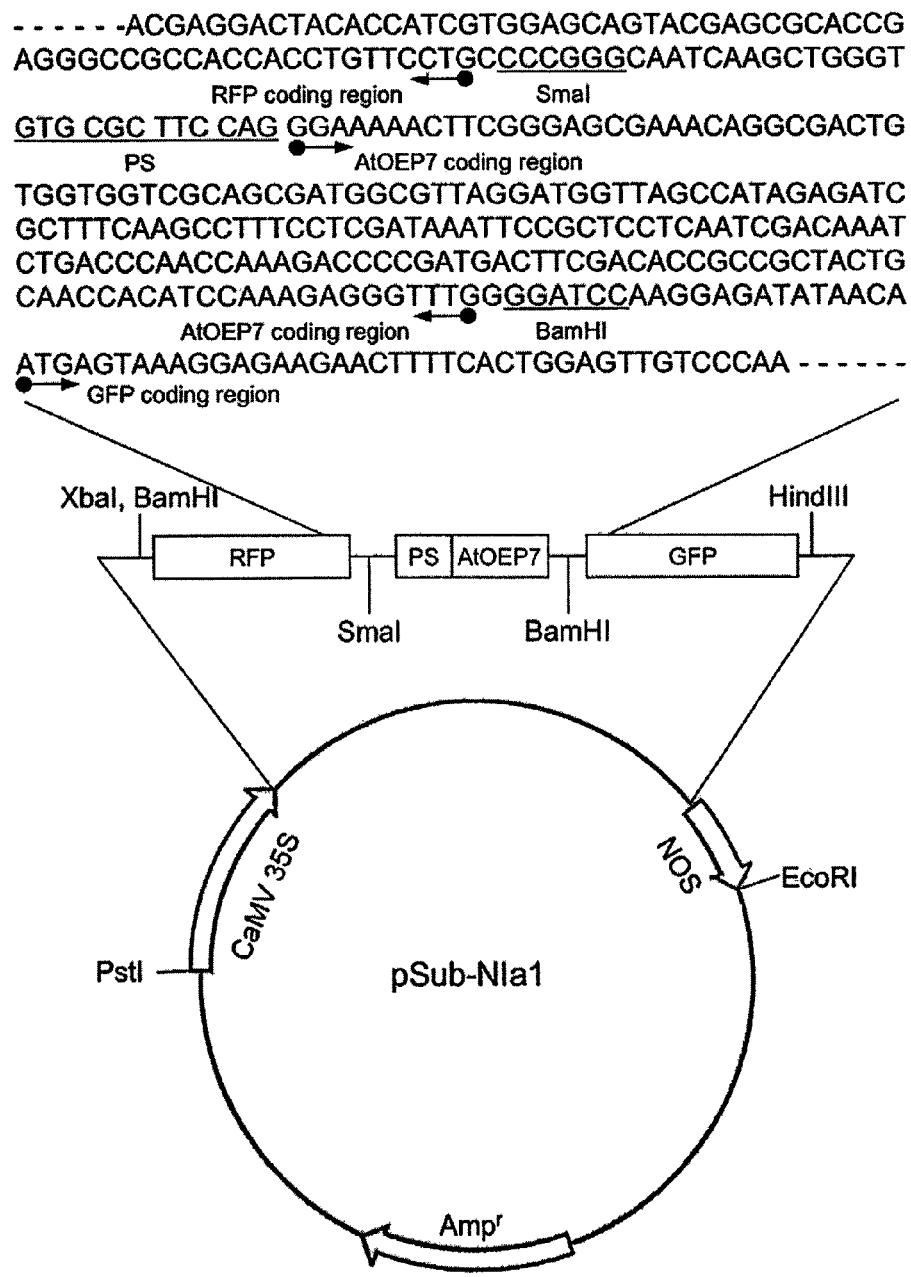

FIG. 8(a)-(b) are explained in more detail as follows. The figure shows plasmid maps of the recombinant plasmids used in the present example to express NIa protease and its chimeric substrate protein RFP:PS(NIa):AtOEP7:GFP, respectively. Nucleic acid and protein sequences of NIa protease and its cleavage sites are provided in SEQ ID NOs: 45–50. Full nucleic acid and protein sequences of this chimeric substrate protein are given in SEQ ID NOs: 51 and 52, respectively.

EXAMPLE 3

In vivo Screening System for HIV-1 Protease Inhibitors

A convenient in vivo screening system for detecting inhibitors of the human immunodeficiency virus (HIV-1) protease was performed as follows.

(a) Construction of Recombinant Plasmids for Expression of HIV-1 Protease

To construct a recombinant plasmid for HIV-1 protease, the coding region of HIV-1 protease was PCR amplified with two primers: (5'-TCTAGAATGCCTCAGGT-CACTCTTTGG-3' and 5'-CTCGAGTCAAAAATT-TAAAGTGCAACC-3') using pHX2BΔRT as a template. The pHX-2BΔRT is a plasmid clone containing HX2B (GenBank accession number K03455) without the reverse transcriptase coding region. The amplified product was subcloned into pBluescript-T vector and subsequently cloned into XbaI and XhoI sites of a pUC vector under the control of the 35S promotor.

Figure 9A:
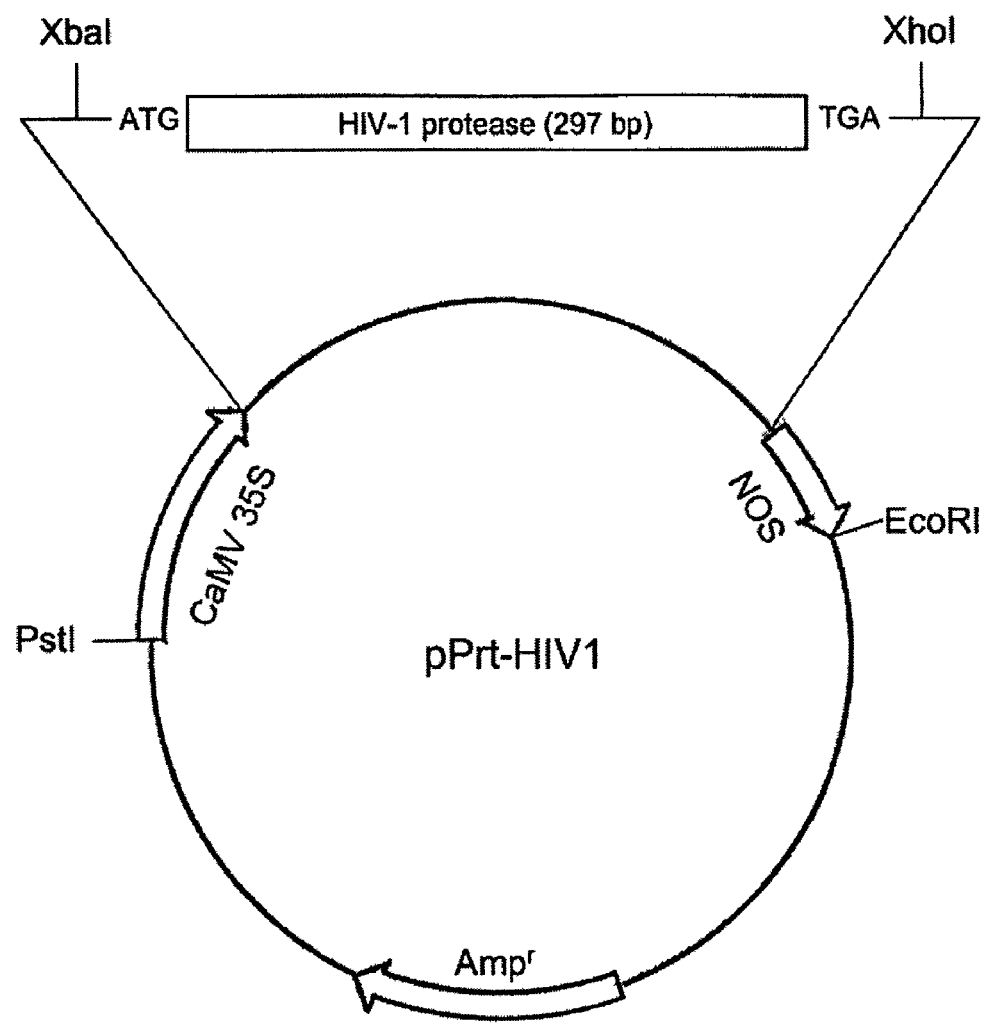

The plasmids maps for HIV-1 protease is shown in FIG. 9(a) and the nucleic acid and protein sequences are given in SEQ ID NOs: 55 and 56, respectively.

(b) Construction of Recombinant Plasmids for Expression of Chimeric Substrate Proteins for HIV-1 Protease Recombinant plasmids for total of 9 chimeric substrate proteins were constructed.

Primers used are as follows: Forward primers used were

5'-CCCGGGTAGCCAAAATTACCCTATAGTGGGAAAAACTTCGGGAGCG-3',

5'-CCCGGGTGCAAGAGTTTTGGCTGAAGCAGGAAAAACTTCGGGAGCG-3',

5'-CCCGGGTGCTACCATAATGATGCAGAGAGGAAAAACTTCGGGAGCG-3',

5'-CCCGGGTAGACAGGCTAATTTTTTAGGGGGAAAAACTTCGGGAGCG-3',

5'-CCCGGGTCCAGGGAATTTTCTTCAGAGCGGAAAAACTTCGGGA GCG-3',

5'-CCCGGGTAGCGTGCCTCAAATAGGAAAAACTTCGGGAGCG-3',

5'-CCCGGGTACTTTAAATTTTCCCATTAGCGGAAAAACTTCGGGA GCG-3',

5'-CCCGGGTGCAGAAACCTTCTATGTAGATGGAAAAACTTCGGGAGCG-3', and

5'-CCCGGGTAGGAAAGTACTATTTTTAGATGGAAAAACTTCGGGAGCG-3'.

Common reverse primer used was 5'-CTCGAGT-TATTTGTATAGTTCATC-3'. These primers were designed to contain the proteolytic sites of the HIV-1 protease. The underlined regions in the forward primers correspond to the proteolytic site sequences (SEQ ID NOs: 57, 59, 61, 63, 65, 67, 69, 71, and 73). PCR amplification was performed with one of the forward primers and the common primer described above using the plasmid for the NIa protease substrate protein (SEQ ID NO: 51) as a template. PCR product was restriction digested with SmaI and XhoI and subcloned into HindIII (filled-in) and XhoI digested 326RFP-nt vector. Therefore, each of the 9 resulting plasmids contains a DNA sequence encoding one of the chimeric substrate proteins of the composition RFP:PS(HIV-1):AtOEP7:GFP with PS(HIV-1) being one of the proteolytic site sequences of the HIV-1 protease. Nucleic acid and protein sequences of one of these chimeric substrate proteins are provided in SEQ ID NOs: 75 and 76.

(c) HIV-1 Protease Inhibitor Screening in vivo

Preparation and transformation of the protoplast of *Arabidopsis* leaf tissue were performed according to the procedures described in Example 1(b) and (c). Detection of the fluorescence images of the transformed protoplasts was carried out as described in Example 1(d) (but using a Nikon E800 fluorescence microscope using the same types of the filter sets).

As a working example for detecting inhibition of HIV-1 protease in vivo, the protoplasts were transformed with a recombinant plasmid for a HIV-1 protease substrate protein, RFP:PS(HIV-1):AtOEP7:GFP. The proteolytic site sequence included in the chimeric substrate protein was RQANFLG (SEQ ID NO: 64). The transformed protoplasts were incubated at 22° C. in the W5 solution for 18–48 hrs to express the chimeric substrate protein, and the subcellular localization of the fluorescence signals from the expressed chimeric substrate protein was monitored using a fluorescence microscope.

As shown in FIG. 11, both the green and red fluorescence signals were observed at the same positions in the cytosol as large speckles or aggregates, but not targeted to the chloroplast. This result indicates that the chimeric substrate proteins were not cleaved and thus they are present in the cytosol as an un-cleaved form. This data corresponds to results when complete inhibition of HIV-1 protease occurs.

Detection of HIV-1 proteolytic activity was performed as follows. Protoplasts were co-transformed with the recombinant plasmid for HIV-1 protease and the recombinant plasmid for a HIV-1 protease substrate protein RFP:PS(HIV-1):AtOEP7:GFP. The proteolytic site sequence included in the chimeric substrate protein was RQANFLG (SEQ ID NO: 64). The subcellular localization of the fluorescence signals from the expressed chimeric substrate protein was monitored 18–48 hrs after the transformation using a fluorescence microscope. As shown in FIG. 12, the red fluorescence signal was observed as uniformly dispersed in the cytosol, while most of the green fluorescence signal was observed around the chloroplasts. These results indicates that the chimeric substrate proteins were cleaved by HIV-1 protease.

This system can be used to detect molecules that decrease the dispersed red fluorescence signal and the chloroplast-trageted green fluorescence signal, and thus block or inhibit HIV-1 protease activity in the protoplasts.

FIGS. 9(a) and (b) are explained in more detail as follows. The figures show plasmid maps for the recombinant plasmids for HIV-1 protease and the chimeric substrate proteins RFP:PS(HIV-1):AtOEP7:GFP. These recombinant plasmids can be used to express HIV-1 protease and the chimeric substrate protein in plant cells such as *Arabidopsis thaliana*, Tobacco, etc. Nucleic acid and protein sequences of HIV-1 protease and its cleavage sites are provided in SEQ ID NOs: 55–74. Full nucleic acid and protein sequences of the chimeric substrate protein used in Example 3 are provided in SEQ ID NOs: 75 and 76, respectively.

EXAMPLE 4

Preparation and Use of Optionally Masked Chimeric Proteins with One Signal Protein Remaining Active As discussed above, it is an object of the present invention to provide recombinant chimeric proteins in which at least some of the signal proteins are masked by at least one suitable amino acid sequence. For instance, all the signal proteins of a particular chimeric protein in accord with the invention can be masked or they can be unmasked as needed. Alternatively, a portion of the signal component of the chimeric protein can be unmasked and the remaining signal(s) can be masked. Such "optionally masked" chimeric proteins provide significant flexibility to the invention and have a wide range of important applications.

For instance, such chimeric proteins can be used in screens to detect in vivo protease activity by virtue of a change in subcellular localization of one or more fluorescence signals of the chimeric protein. Such a screen is highly sensitive, namely because it can register slight changes in the spatial distribution of the chimeric protein. Choice of whether to mask or unmask one or more than one signal proteins included within a subject chimeric molecule will be guided by intended invention use.

FIG. 10 provides an illustrative collection of "optionally masked" chimeric proteins. More specifically, the figure shows schematic diagrams of recombinant genes encoding chimeric substrate protein in which the trafficking signal of one signal protein remains active. $H^+$-ATPase is used as an example of the active signal protein whose trafficking signal is not masked in the chimeric substrate protein. Other examples that can be used as the active signal protein include AtOEP7, PH, and FAPP. AtOEP7 is used as an example of the inactivated signal protein whose trafficking signal is masked by linking a proteolytic cleavage site or a signal masking protein through a proteolytic cleavage site. Other examples that can be used as the inactivated signal protein include RbcS, Cab, RA, F1-ATPase, and SKL. These chimeric substrate proteins are designed to induce a change in the subcellular fluorescence signal distribution upon proteolytic cleavage. Nearly any of the protease cleavage sequences disclosed herein can be used to provide the cleavage site (PS) of the chimeric proteins exemplified in FIG. 10. Accordingly, such optionally masked chimeric proteins can be used to detect a wide variety of protease inhibitor molecules. Of course, nearly any of the protease cleavage sequences disclosed herein can be used to provide the cleavage site (PS) of the chimeric proteins exemplified in FIG. 10.

FIG. 10 is explained in more detail as follows. FIG. 10(a) shows a construct where the fluorescence signal (FP-1) is translocated from the plasma membrane to the cytosol upon proteolytic cleavage. In the case of FIG. 10(b), one fluorescence signal (FP-2) is translocated in the same manner as in the case of FIG. 10(a), but the other fluorescence signal (FP-1) remains on the plasma membrane. In the case of FIG. 10(c), the fluorescence signal (FP-1) is translocated from the plasma membrane to the chlorophyll upon proteolytic cleavage. In the case of FIG. 10(d), one fluorescence signal (FP-2) is translocated in the same manner as in the case of FIG. 10(c), but the other fluorescence signal (FP-1) remains on the plasma membrane.

(a) Construction of Recombinant Plasmids for Expression of Chimeric Substrate Proteins with One Signal Protein Remaining Active Examples of the recombinant plasmids depicted FIG. 10 were constructed as follows.

Two recombinant plasmids encoding $H^+$-ATPase:PS:GFP (FIG. 10(a)) with the proteolytic cleavage site sequences being VRFQ (SEQ ID NO: 48) and RQANFLG (SEQ ID NO: 64) were constructed as follows.

Forward primers 5'-CTCGAG PS ATGAGTAAAG-GAGAAGAA-3' (here PS is GTGCGCTTCCAG for VRFQ NIa cleavage site or AGACAGGCTAATTTTTTAGGG for RQANFLG HIV-1 cleavage site) and a reverse primer 5'-GAGCTCTTATTTGTATAGTTCATC-3' were used for PCR amplification of 326GFP vector. These PCR products, containing a proteolytic cleavage site for NIa or HIV-1 protease, restriction sites (Xho I and Sac I) for subcloning, and stop codon at C-terminal of GFP, were subcloned into pBluscript-T vetor. Xho I/Sac I fragments of these subclones were ligated into Xho I and Sac I digested $pH^+$ATPase-G vector (FIG. 7(i)).

Two recombinant plasmids encoding $H^+$-ATPase:GFP:PS:RFP (FIG. 10(b)) with the proteolytic cleavage site sequences being VRFQ (SEQ ID NO: 48) and RQANFLG (SEQ ID NO: 64) were constructed as follows.

In order to prepare GFP without stop codon, PCR amplification was performed with primers 5'-CTCGAGAT-GAAAGGAGAAGAACTT-3' and 5'-GAGCTCTTTGTAT-AGTTCATCCAT-3'. The PCR product containing Xho I and Sac I sites was subcloned into pBluescript-T vector and subsequently restriction digested with Xho I and Sac I. This Xho I/Sac I fragment was subcloned into Xho I and Sac I digested $pH^+$ATPase-G vector (FIG. 7(i)).

In order to place proteolytic cleavage site upstream of RFP, forward primers 5'-GAGCTC PS ATGGTGCGCTC-CTCCAAG-3' (here PS is GTGCGCTTCCAG for VRFQ NIa cleavage site, or AGACAGGCTAATTTTTTAGGG for RQANFLG HIV-1 cleavage site) and a reverse primer 5'-GAGCTCCTACAGGAACAGGTGGTG-3' were used for PCR amplification of 326RFP vector. The constructs containing PS:RFP, which also contained Sac I sites, were restriction digested with Sac I and these Sac I fragments were subcloned into Sac I sites of the $H^+$-ATPase:GFP (without stop codon) subclone prepared as described above to generate recombinant plasmids for $H^+$ATPase:GFP:PS:RFP.

Two recombinant plasmids encoding $H^+$-ATPase:PS:AtOEP7:GFP (FIG. 10(c)) with the proteolytic cleavage site sequences being VRFQ (SEQ ID NO: 48) and RQANFLG (SEQ ID NO: 64) were constructed as follows.

The pSub-NIa1 vector (FIG. 8(b)) was PCR amplified with primers 5'-CTCGAG PS GGAAAAACTTCGG-GAGCG-3' (here PS is GTGCGCTTCCAG for VRFQ NIa cleavage site, or AGACAGGCTAATTTTTTAGGG for RQANFLG HIV-1 cleavage site) and 5'-GAGCTC TTATTTGTATAGTTCATC-3'. Thus, the PCR products contained Xho I and Sac I sites. Sho I/Sac I fragments of these subclones were ligated into Xho I and Sac I digested $pH^+$ATPase-G vector (FIG. 7(i)) to generate recombinant plasmids for $H^+$-ATPase:PS:AtOEP7:GFP.

Two recombinant plasmids encoding $H^+$-ATPase:RFP:PS:AtOEP7:GFP (FIG. 10(d)) with the proteolytic cleavage site sequences being VRFQ (SEQ ID NO: 48) and RQANFLG (SEQ ID NO: 64) were constructed as follows.

Figure 9B:
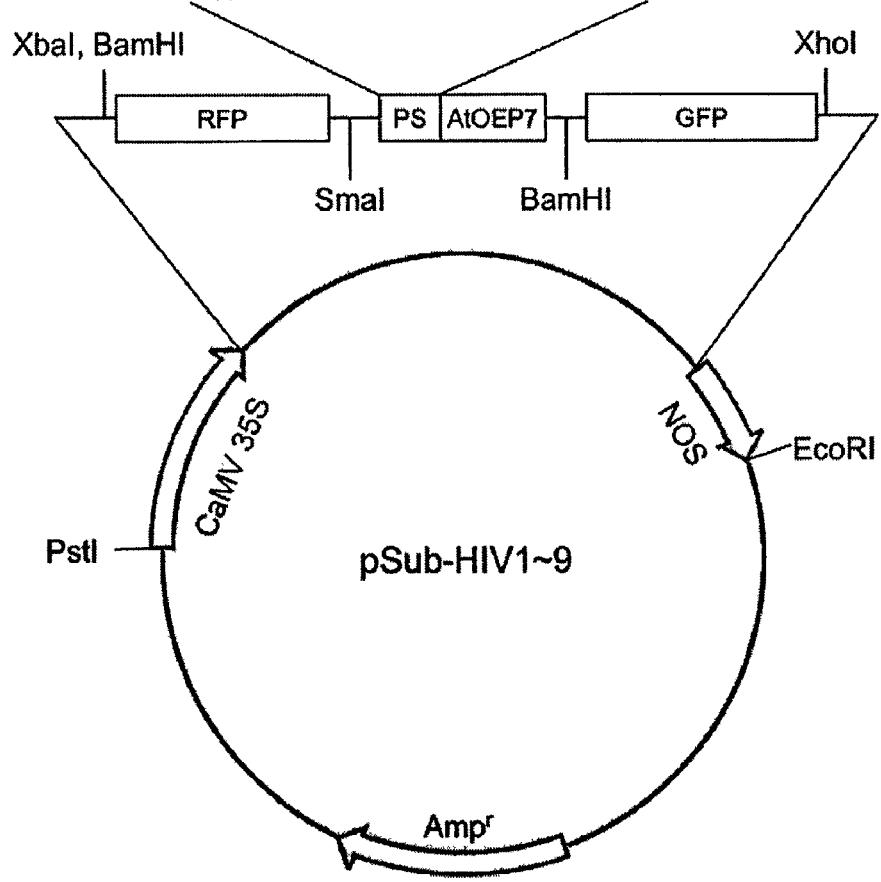

Primers 5'-CTCGAGATGGTGCGCTCCTCCAAG-3' and 5'-GAGCTCTTATTTGTATAGTTCATC-3' were used to PCR amplify the pSub-NIa1 vector (FIG. 8(b)) and the pSub-HIV4 vector (FIG. 9(b)). Thus, these PCR products contained Xho I and Sac I sites. Sho I/Sac I fragments of these subclones were ligated into Xho I and Sac I digested $pH^+$ATPase-G vector (FIG. 7(i)) to generate recombinant plasmids for $H^+$-ATPase:RFP:PS:AtOEP7:GFP.

(b) A Working Example Using a Recombinant Plasmid Depicted in FIG. 10(a)

Preparation and transformation of the protoplast of Arabidopsis leaf tissue were performed according to the procedures described in Example 1(b) and (c). Detection of the fluorescence images of the transformed protoplasts was carried out as described in Example 1(d) (but using a Nikon E800 fluorescence microscope using the same types of the filter sets).

As a working example for detecting inhibition of NIa protease, the protoplasts were transformed with a recombinant plasmid encoding a chimeric substrate protein $H^+$-ATPase:PS:GFP prepared as described in Example 4(a). The proteolytic site sequence included in the chimeric substrate protein was VRQF (SEQ ID NO: 48). The transformed protoplasts were incubated at 22° C. in the W5 solution for 18–48 hrs to express the chimeric substrate protein, and the subcellular localization of the fluorescence signal from the expressed chimeric substrate protein was monitored using a fluorescence microscope. As shown in FIG. 13(a), the green fluorescence signal was translocated to the plasma membrane. This result indicates that the chimeric substrate proteins were not cleaved as expected, and thus the attached green fluorescence proteins were targeted to the plasma membrane by the trafficking signal of $H^+$-ATPase. This data corresponds to results when complete inhibition of the protease occurs.

Detection of NIa proteolytic activity was performed as follows. Protoplasts were co-transformed with the recombinant plasmid for NIa protease (SEQ ID NO: 45) and the recombinant plasmid for a chimeric substrate protein $H^+$-ATPase:PS:GFP (SEQ ID NO: 53). The proteolytic site sequence included in the chimeric substrate protein was VRQF (SEQ ID NO: 48). The subcellular localization of the fluorescence signal from the expressed chimeric substrate protein was monitored 18–48 hrs after the transformation using a fluorescence microscope. As shown in FIG. 13(c), the green fluorescence signal was observed in the cytosol, but not targeted to the plasma membrane. This data indicates that GFP was cleaved off from the chimeric substrate protein by the protease.

All references disclosed herein are incorporated by reference. The following references are specifically incorporated by reference.

Hook, V. Y. H. U.S. Pat. No. 6,245,884 (2001).

Kettner, C. A. and Korant, B. D. U.S. Pat. No. 4,644,055 (1987).

Cote, H. C. F., Brumme, Z. L., and Harrigan, P. R. (2001). J. Virol. 75, 589–594.

Davis, S. J. and Vierstra, R. D. (1998). Plant Physiol. 112, 833–844.

Ermolieff, J., Loy, J. A., Koelsch, G., and Tang, J. (2000). Biochem. 39, 12450–12456.

Gillooly, D. J., Morrow, I. C., Lindsay, M., Gould, R., Bryant, N. J., Gaullier, J.-M., Parton, R. G., and Stenmark, H. (2000). EMBO J. 19, 4577–4588.

Gutierrez-Campos, R., Torress-Acosta, J. A., Saucedo-Arias, L. et al. (1999). Nat. Biotechnol. 17, 1223–1226.

Jacobsen, H., Hanggi, M., Ott, M., Duncan, I. B., and Owen, S. (1996). J. Infect. Dis. 173, 1379–1387.

Kasai, N., Tsumoto, K., Niwa, S., Misawa, S., Ueno, T., Hayashi, H., and Kumagai, I. (2001). Biochem. Biophys. Res. Comm. 281, 416–424.

Kuhelj, R., Rizzo, C. J., Chang, C.-H., Jadha, P. K., Towler, E. M., and Korant, B. D. (2001). J. Biol. Chem. 276, 16674–16682.

Kost, B., Spielhofer, P., and Chua, N. H. (1998). Plant J. 16, 383–401.

Mardis, K. L., Luo, R., and Gilson, M. K. (2001). J. Mol. Biol. 309, 507–517.

Miller, T. L., Mawn, B. E., Orav, E. J., Wilk, D., Weinberg, G. A., Nicchitta, J., Furuta, L., Cutroni, R., McIntosh, K., Burchett, S. K., and Gorbach, S. L. (2001). Pediat. 107–5, 1–6.

Morise, H., Shimomura, O., Johnson, F. H., and Winant, J. (1974). Biochem. 13, 2656–2662.

Pih, K. T., Yi, M. J., Liang, Y. S., Shin, B. J., Cho, M. J., Hwang, I., and Son, D. (2000). Plant Physiol. 123, 51–58.

Rogers, J. D., Lam, P. Y., Johnson, B. L., Wang, H. S., Ko, S. S., Seits, S. P., Trainor, G. L., Anderson, P. S., Klabe, R. M., Bachelor, L. T., Cordova, B., Garber, S., Reid, C., Wright, M. R., Chang, C. H., and Erickson-Biitanen, S. (1998). Chem. Biol. 5, 597–608.

Wlodawer, A. and Erickson, J. W. (1983). Annu. Rev. Biochem. 61, 543–585.

Yi, C.-F., Gosiewska, A., Burtis, D., and Geesin, J. (2001). Anal. Biochem. 291, 27–33.

Yoon, H. Y., Hwang, D. C., Choi, K. Y., and Song, B. D. (2000). Mol. Cell 10, 213–219.

The invention has been described in detail with reference to preferred embodiments thereof. However, it will be appreciated that those skilled in the art, upon consideration of this disclosure, may make modifications and improvements within the spirit and scope of the invention.

What is claimed is:

1. A chimeric protein comprising at least one signal protein that has a trafficking signal targeting to a subcellular organelle and at least one proteolytic cleavage site for a protease, which is constructed such that
   (a) the trafficking signals of all the signal proteins are inactivated by linking the proteolytic site or a signal masking protein through the proteolytic site to the N- or C-terminus of the signal proteins, and thus the chimeric protein is present in cytosol;
   (b) the trafficking signal of at least one signal protein is activated when the proteolytic cleavage site is cleaved by the protease, and as a result at least one fragment protein that includes the activated signal protein is transported to a subcellular organelle; and
   (c) the chimeric protein is labeled with at least one detectable amino acid sequence and the position and intensity distribution of the detectable amino acid sequence signal in the cell is altered depending on the cleavage by the protease.

2. A chimeric protein comprising at least two signal proteins that have trafficking signals targeting to subcellular organelles and at least one proteolytic cleavage site for a protease, which is constructed such that
   (a) the trafficking signal of one signal protein remains active, and those of the rest of the signal proteins are inactivated by linking the proteolytic site or a signal masking protein through the proteolytic site to the N- or C-terminus of the signal proteins, and thus the chimeric protein is transported to a specific subcellular organelle targeted by the trafficking signal of the active signal protein;
   (b) at least one proteolytic site and at least one inactivated signal protein are exposed to cytosol after the chimeric protein is transported to the subcellular organelle;
   (c) the trafficking signal of the at least one inactivated signal protein exposed to cytosol is activated when the proteolytic cleavage site is cleaved by the protease, and as a result the fragment protein that includes the activated signal protein is transported to a subcellular organelle that is different from the subcellular organelle to which the chimeric protein was transported; and
   (d) the chimeric protein is labeled with at least one detectable amino acid sequence and the position and intensity distribution of the detectable amino acid sequence in the cell is altered depending on the cleavage by the protease.

3. The chimeric protein according to claim 1 or 2, wherein among the fragment proteins produced by the proteolytic cleavage, at least two fragment proteins with different cellular localization characteristics includes different detectable amino acid sequences.

4. The chimeric protein according to claim 1 or 2, wherein among the fragment proteins including a signal protein whose inactivated trafficking signal is activated by the proteolytic cleavage, at least one fragment protein includes the detectable amino acid sequence.

5. The chimeric protein according to claim 1 or 2, wherein the trafficking signal of the inactivated signal protein is a signal targeting to a subcellular organelle selected from the group consisting of mitochondria, chloroplast, and peroxisome.

6. The chimeric protein according to claim 1 or 2, wherein the signal protein that is inactivated is a full length protein selected from the group consisting of *Arabidopsis* outer envelope membrane protein 7 (AtOEP7), Rubisco small subunit (RbcS), Chlorophyll a/b binding protein (Cab), Rubisco activase (RA), F1-ATPase, and Peroxisome-targeting motif (SKL), or a portion thereof that includes the trafficking signal.

7. The chimeric protein according to claim 2, wherein the trafficking signal of the signal protein remaining active is a signal targeting to one selected from the group consisting of outer membranes of mitochondria, chloroplast, and nucleus, peroxisome membrane, and plasma membrane.

8. The chimeric protein according to claim 2, wherein the signal protein remaining active is a protein that binds specifically to a specific phospholipid.

9. The chimeric protein according to claim 2, wherein the signal protein remaining active is a full length protein selected from the group consisting of *Arabidopsis* outer envelope membrane protein 7 (AtOEP7), H+-ATPase, Pleckstrin homology domain (PH), and pleckstrin homology domain of FAPP (family A (phosphoinositide binding specific) member 3), or a portion thereof that includes the trafficking signal.

10. The chimeric protein according to claim 1 or 2, wherein the signal masking protein is selected from the group consisting of amino acids, peptides, and proteins.

11. The chimeric protein according to claim 1 or 2 wherein the detectable amino acid sequence is selected from the group consisting of green fluorescent protein (GFP), red fluorescent protein (RFP), mutants thereof, and derivatives thereof.

* * * * *